US012622950B2

(12) United States Patent
Chapman et al.

(10) Patent No.: US 12,622,950 B2
(45) Date of Patent: May 12, 2026

(54) TREATMENT OF PATIENTS WITH SEVERE VON WILLEBRAND DISEASE UNDERGOING ELECTIVE SURGERY BY ADMINISTRATION OF RECOMBINANT VWF

(71) Applicant: Takeda Pharmaceutical Company Limited, Osaka (JP)

(72) Inventors: Miranda Chapman, Wellesley, MA (US); Bruce Ewenstein, Brookline, MA (US); Bettina Ploder, Vienna (AT)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 17/545,870

(22) Filed: Dec. 8, 2021

(65) Prior Publication Data

US 2022/0168397 A1     Jun. 2, 2022

Related U.S. Application Data

(63) Continuation of application No. 16/030,653, filed on Jul. 9, 2018, now abandoned.

(60) Provisional application No. 62/546,999, filed on Aug. 17, 2017, provisional application No. 62/530,024, filed on Jul. 7, 2017.

(51) Int. Cl.
A61K 38/36 (2006.01)
A61P 7/04 (2006.01)

(52) U.S. Cl.
CPC ................ A61K 38/36 (2013.01); A61P 7/04 (2018.01)

(58) Field of Classification Search
None
See application file for complete search history.

(56) References Cited

U.S. PATENT DOCUMENTS

| | | | |
|---|---|---|---|
| 3,941,763 A | 3/1976 | Sarantakis et al. | |
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 5,854,403 A | 12/1998 | Bernhard et al. | |
| 6,531,577 B1 | 3/2003 | Kaergaard et al. | |
| 7,005,502 B1 | 2/2006 | Schwarz et al. | |
| 7,335,634 B2 | 2/2008 | Walter et al. | |
| 8,173,597 B2 | 5/2012 | Schwarz et al. | |
| 8,597,910 B1 | 12/2013 | Ginsburg et al. | |
| 8,852,888 B2 | 10/2014 | Grillberger et al. | |
| 9,409,971 B2 | 8/2016 | Grillberger et al. | |
| 10,632,176 B2 | 4/2020 | Chapman et al. | |
| 12,128,090 B2 | 10/2024 | Mellgard et al. | |
| 2005/0239171 A1 | 10/2005 | Mitterer et al. | |

| | | | |
|---|---|---|---|
| 2006/0094104 A1 | 5/2006 | Grillberger et al. | |
| 2006/0160948 A1 | 7/2006 | Scheiflinger et al. | |
| 2007/0212770 A1 | 9/2007 | Grillberger et al. | |
| 2008/0009040 A1 | 1/2008 | Grillberger et al. | |
| 2010/0099603 A1 | 4/2010 | Schnecker et al. | |
| 2010/0286047 A1 | 11/2010 | Kronthaler | |
| 2012/0035110 A1 | 2/2012 | Grillberger et al. | |
| 2016/0129090 A1 | 5/2016 | Schnecker et al. | |
| 2018/0051067 A1 | 2/2018 | Moses et al. | |
| 2020/0261546 A1 | 8/2020 | Mellgard et al. | |

FOREIGN PATENT DOCUMENTS

| | | | |
|---|---|---|---|
| CA | 2189947 | | 5/1997 |
| EP | 1593390 | * | 11/2005 |
| EP | 1593390 A1 | | 11/2005 |
| JP | H9-221432 | | 8/1997 |
| JP | 2005/320330 A | | 11/2005 |
| RU | 2531493 C2 | | 10/2014 |
| RU | 2563236 C2 | | 9/2015 |
| WO | WO 86/06096 A1 | | 10/1986 |
| WO | WO 96/10584 A1 | | 4/1996 |
| WO | WO 97/34930 A1 | | 9/1997 |
| WO | WO 98/38219 A1 | | 9/1998 |
| WO | WO 2004/039337 | | 5/2004 |
| WO | WO 2005/012354 A1 | | 2/2005 |
| WO | WO 2006/071801 A2 | | 7/2006 |
| WO | WO 2008/151817 | * | 12/2008 |
| WO | WO 2008/151817 A1 | | 12/2008 |
| WO | WO 2009/062100 A1 | | 5/2009 |
| WO | WO 2009/086400 A3 | | 7/2009 |
| WO | WO 2009/156137 A1 | | 12/2009 |
| WO | WO 2010/048275 A2 | | 4/2010 |
| WO | WO 2011/017414 A2 | | 2/2011 |

(Continued)

OTHER PUBLICATIONS

Kahlon et al. (Haemophilia. Sep. 2013; 19(5): 758-764) (Year: 2013).*

Abuchowski, A. et al., "Soluble Polymer-Enzyme Adducts," Chapter 13 in *Enzymes as Drugs*, Holcenberg, J.S. et al., ed., John Wiley and Sons, New York, 1981:367-383.

Andersson, L.-O. et al., "Isolation and characterization of human factor VIII: Molecular forms in commercial factor VIII concentrate, cryoprecipitate, and plasma," *Proc. Natl. Acad. Sci. USA*, May 1986, vol. 83, pp. 2979-2983.

Berntorp, E. et al., "Treatment and prevention of acute bleedings in von Willebrand disease—efficacy and safety of Wilate®, a new generation von Willebrand factor/factor VIII concentrate," Haemophilia, 2009;15(1):122-130.

(Continued)

*Primary Examiner* — Sergio Coffa
(74) *Attorney, Agent, or Firm* — Morgan, Lewis & Bockius LLP; Christina A. MacDougall

(57) ABSTRACT

The present invention relates to method for pretreating a subject with severe von Willebrand disease prior to a surgical procedure comprising administering to the subject a dose ranging from about 20 IU/kg to about 60 IU/kg rVWF between about 12 hours and about 24 hours prior to the surgical procedure, and wherein Factor VIII is not administered with the rVWF prior to the surgical procedure.

27 Claims, 24 Drawing Sheets

Specification includes a Sequence Listing.

(56)                References Cited

FOREIGN PATENT DOCUMENTS

WO     WO 2012/006591 A1     1/2012
WO     WO 2012/171031 A1     12/2012

OTHER PUBLICATIONS

Brown, J.E. et al., "An ELISA test for the binding of von Willebrand antigen to collagen," *Thromb. Res.*, 1986;43:303-311.

Carpenter, J.F. et al., "Interactions of Stabilizing Additives With Proteins During Freeze-Thawing and Freeze-Drying," *Develop. Biol. Standard*, 1991;225-239.

Castaman, G. et al., "von Willebrand's disease in the year 2003: towards the complete identification of gene defects for correct diagnosis and treatment," *Haematological/Journal of Hematology*, Jan. 2003, vol. 88, No. 1, pp. 94-108.

Chang, B.S. et al., "Development of a stable freeze-dried formulation of recombinant human interleukin-1 receptor antagonist," *Pharm Res.*, 1996;13(2):243-249.

Chang, B.S. et al., "Surface-Induced Denaturation of Proteins during Freezing and its Inhibition by Surfactants," *Pharm Sci.*, 1996;85(12):1325-1330.

Chen, B. et al., "Influence of calcium ions on the structure and stability of recombinant human deoxyribonuclease I in the aqueous and lyophilized states," *Pharm. Sci.*, 1999;88(4):477-482.

Chen, B. et al., "Influence of histidine on the stability and physical properties of a fully human antibody in aqueous and solid forms," *Pharm Res.*, 2003;20(12):1952-60.

Chen, T., "Formulation concerns of protein drugs," *Drug Development and Industrial Pharmacy*, 1992;18:1311-1354.

Cumming, A.M. et al., "Analysis of von Willebrand factor multimers using a commercially available enhanced chemiluminescence kit," *J. Clin. Pathol.*, May 1993;46(5):470-473.

Denis, C.V. et al., "Clearance of von Willebrand factor," *Thromb. Haemost.*, 2008, vol. 99, pp. 271-278.

Derrick, T.S. et al., "Effect of metal cations on the conformation and inactivation of recombinant human factor VIII," *Pharm. Sci.*, 2004;93(10):2549-57.

Fatouros, A. et al., "Recombinant factor VIII SQ—influence of oxygen, metal ions, pH and ionic strength on its stability in aqueous solution," *Int. J. Pharm.*, 1997;155:121-131.

Favaloro, E.J. et al., "Collagen binding assay for von Willebrand factor (VWF:CBA) :detection of von Willebrands Disease (VWD), and discrimination of VWD subtypes, depends on collagen source," *Thromb. Haemost.*, 2000;83:127-135.

Favaloro, E.J. et al., "Laboratory assays for von Willebrand factor: relative contribution to the diagnosis of von Willebrand's disease," *Pathology*, 1997;29(4):385-91.

Fernandes, A.I. et al., "Polysialyated asparaginase: preparation, activity and pharmacokinetics," *Biochim. Biophys. Acta.*, 1997;1341:26-34.

Fijnvandraat, K. et al., "Inter-individual variation in half-life of infused recombinant factor VIII is related to pre-infusion von Willebrand factor antigen levels," *British Journal of Haematology*, 1995, vol. 91, pp. 474-476.

Fischer, B.E. et al., "Effect of Multimerization of Human Recombinant von Willebrand Factor on Platelet Aggregation, Binding to Collagen and Binding of Coagulation Factor VIII," Thrombosis Research, 1996, vol. 84, No. 1, pp. 55-66.

Fischer, B.E. et al., "Structural Analysis of Recombinant von Willebrand Factor Produced at Industrial Scale Fermentation of Transformed CHO Cells Co-Expressing Recombinant Furin," *FEBS Letters*, Nov. 20, 1995, vol. 375, pp. 259-262.

Fischer, B.E., "Recombinant von Willebrand factor: potential therapeutic use," *Journal of Thrombosis and Thrombolysis*, Jan. 1, 1999, vol. 8, pp. 197-205.

Franchini, M. et al., "Gastrointestinal angiodysplasia and bleeding in von Willebrand disease," *Thromb Haemost.*, 2014;112(3):427-431.

Franchini, M. et al., "Von Willebrand disease-associated angiodysplasia: a few answers, still many questions," *Br J Haemost.*, 2013; 161(2):177-182.

Franchini, M. et al., "Von Willebrand factor (Vonvendi®): the first recombinant product licensed for the treatment of von Willebrand disease," Expert Rev Hematol., 2016;9(9):825-830.

GenBank Accession No. NM_000543, "*Homo sapiens* sphingomyelin phosphodiesterase 1 (SMPD1), transcript variant 1, mRNA," 2018, 5 pages.

GenBank Accession No. NM_000552, "*Homo sapiens* von Willebrand factor (VWF), mRNA," 2018, 10 pages.

Gill Joan Cox et al: "Recombinant Von Willebrand Factor Administration: Dosing Considerations and Rapid Stabilization of Endogenous Plasma FVIII Levels in Patients with Severe Von Willebrand Disease", XP002784853, Database accession No. REV201800668643 abstract, Blood, vol. 130, Suppl. 1, Dec. 7, 2017 (Dec. 7, 2017), p. 3682, 59th Annual Meeting of the American-Society-of-Hematology (ASH).

Gill, J.C. et al., "Hemostatic efficacy, safety, and pharmacokinetics of a recombinant von Willebrand factor in severe von Willebrand disease," *Blood*, 2015;126(17):2038-2046.

Hollander-Rodriguez, J.C. et al., "Hyperkalemia," *Am. Fam. Physician.*, 2006;73(2):283-90.

International Search Report mailed Sep. 7, 2012, for International Patent Application No. PCT/US2012/041957, 6 pages.

Kappelgaard, A.M. et al., "Liquid Growth Hormone: Preservatives and Buffers," *Horm Res.*, 2004;3(suppl 1):98-103.

Keeling, D. et al., "Guideline on the selection and use of therapeutic products to treat hemophilia and other hereditary bleeding disorders," Haemophilia, 2008, vol. 14, pp. 671-684.

Lam, X.M. et al., "Antioxidants for Prevention of Methionine Oxidation in Recombinant Monoclonal Antibody HER$_2$," *J. Pharm. Sci.*, 1997;86(11):1250-5.

Lankhof, H. et al., "von Willebrand Factor without the A2 Domain Is Resistant to Proteolysis," *Thromb. Haemost.*, 1997;77:1008-1013.

Laursen, T. et al., "Pain Perception after Subcutaneous Injections of Media Containing Different Buffers," *Basic Clin Pharmacol Toxicol.*, 2006;98(2):21821.

MacFarlane, D.E. et al., "Letter: A method for assaying von Willebrand factor (ristocetin cofactor)," *Thromb. Diath. Haemorrh.*, 1975;34:306-308.

MacKenzie, A.P., "Non-equilibrium freezing behavior of aqueous systems," *Phil Trans R Soc London, Ser B, Biol*, 1977;278:167-189.

Mannucci, P.M. et al., "Laboratory monitoring of replacement therapy for major surgery in von Willebrand disease," *Haemophilia*, 2017, 23(2):182-187.

Mannucci, P.M. et al., "Pharmacokinetics and safety of a novel recombinant human von Willebrand factor manufactured with a plasma-free method: a prospective clinical trial," *Blood*, 2013;122(5):648-657.

Meulien, P. et al., "Processing and characterization of recombinant von Willebrand factor expressed in different cell types using a vaccinia virus vector," Thromb. Haemost., Jan. 23, 1992;67(1):154-160.

Migneault, I. et al., "Glutaraldehyde: behavior in aqueous solution, reaction with proteins, and application to enzyme crosslinking," *Biotechniques*, 2004;37:790-802.

Minogue, S.C. et al., "Bacteriostatic Saline Containing Benzyl Alcohol Decreases the Pain Associated with the Injection of Propofol," *Anesth Analg.*, 2005;100(3):683-6.

National Institutes of Health, Lung and Blood Institute, "The Diagnosis, Evaluation, and Management of von Willebrand Disease," NIH Publication No. 08-5832, Dec. 2007, 116 pages.

Piétu, G. et al., "Production in *Escherichia coli* of a biologically active subfragment of von Willebrand factor corresponding to the platelet glycoprotein lb, collagen and heparin binding domains," *Biochem. Biophys. Res. Commun.*, 1989;164:1339-1347.

Randi, A.M. et al., "Von Willebrand factor and angiogenesis: basic and applied issues," J Thromb Haemost., 2017;15(1):13-20.

Randi, A.M., "Endothelial dysfunction in von Willebrand disease: angiogenesis and angiodysplasia," Thromb Res., 2016;141 (suppl 2):S55-58.

(56)            References Cited

OTHER PUBLICATIONS

Remmele, R.L. Jr et al., "Minimization of Recombinant Human Flt3 Ligand Aggregation at the $T_m$ Plateau: A Matter of Thermal Reversibility," *Biochemistry*, 1999;38(16):5241-7.

Remmele, R.L. Jr. et al., "Interleukin-1 receptor (IL-1R) liquid formulation development using differential scanning calorimetry," *Pharm Res.*, 1998;15(2):200-8.

Rodeghiero, F. et al., "Treatment of von Willebrand disease," Semin Heamtol., Jan. 2005;42(1 ):29-35.

Roy, S. et al., "Effects of Benzyl Alcohol on Aggregation of Recombinant Human Interleukin-1-Receptor Antagonist in Reconstituted Lyophilized Formulations," *J Pharm Sci.*, 2005;94(2):382-96.

Sadler, J.E., "Biochemistry and Genetics of von Willebrand Factor," *Annu. Rev. Biochem.*, 1998;67:395-424.

Saenko, E.L. et al., "Strategies towards a longer acting factor VIII," *Haemophilia*, 2006;12:42-51.

Schlokat, E. et al., "Production of Highly Homogenous and Structurally Intact Recombinant von Willebrand Factor Multimers by Furin-Mediated Propeptide Removal in Vitro," Dec. 1, 1996, vol. 24, Part 3, pp. 257-267.

Selvam, S. et al., "Angiodysplasia in von Willibrand Disease: Understanding the Clinical and Basic Science," Semin Thromb Hemost., 2017.

Singal et al., "Recombinant von Willebrand Factor: a first-of-its kind product for von Willebrand disease", Drugs of Today, Dec. 1, 2016 (Dec. 1, 2016), pp. 653-664.

Sobieraj, D.M. et al., "Venous Thromboembolism Prophylaxis in Orthopedic Surgery," Rockville (MD): Agency for Healthcare Research and Quality (US); Mar. 2012, Comparative Effectiveness Reviews, No. 49, 949 pages.

Tang, X. et al., "Design of freeze-drying processes for pharmaceuticals: practical advice," *Pharm. Res.*, 2004;21:191-200.

Tomita, M. et al., "Sensitized photooxidation if histidine and its derivatives. Products and mechanism of the reaction," *Biochemistry*, 1969;8(12):5149-60.

Turecek, P.L. et al., "Biochemical and Functional Characterization of a Serum-Free rVWF Drug Candidate," *Blood*, Nov. 1, 2006, vol. 108, No. 11, p. 303A., Abstract.

Turecek, P.L. et al., "Biochemical and Functional Characterization of Chemically Modified Recombinant von Willebrand Factor (rVWF) as a Carrier Prolonging Survival of RFVIII in Hemophilia a Knock-Out Mice," *J. Thromb. Haemost.*, Aug. 2007; vol. 5 Supplement 2: O-M-018, 3 pages.

Turecek, P.L. et al., "Comparative Study on Collagen-Binding Enzyme-Linked Immunosorbent Assay and Ristocetin Cofactor Activity Assays for Detection of Functional Activity of von Willebrand Factor," *Semin. Thromb. Hemost.*, 2002;28:149-160.

Turecek, P.L. et al., "Development of a plasma- and albumin-free recombinant von Willebrand factor," *Hamostaseologie*, 2009;29(suppl 1):S32-38.

Turecek, P.L. et al., "In Vivo Characterization of Recombinant von Willebrand Factor in Dogs With von Willebrand Disease," Blood, Nov. 1, 1997, vol. 90, No. 9, pp. 3555-3567.

Turecek, P.L. et al., "PEG Modified rVWF Prolongs the Survival of Native rFVIII in Hemophilia A Knock-Out Mice," *Blood*, 2006, vol. 108: Abstract 1002, 1 page.

Turecek, P.L. et al., "Structure and Function of a Recombinant von Willebrand Factor Drug Candidate," *Semin, Thromb. Hemost.*, 2010;36(5):510-521.

Turecek, P.L., "The role of ultralarge multimers in recombinant human von Willebrand factor—a review of physico- and biochemical studies and findings in in vivo models and in humans with von Willebrand disease," *Hämostaseologie*, 2017;37(suppl 1):S15-S25.

Van Wezel, A.L., "Growth of Cell-strains and Primary Cells on Micro-carriers in Homogeneous Culture," *Nature*, Oct. 7, 1967, vol. 216, pp. 64-65.

Varadi, K. et al., "In Vivo Cleavage of Recombinant VWF Upon Intravenous Administration in Preclinical and Clinical Setting," *Blood*, Nov. 1, 2011, vol. 118, No. 21, p. 549.

Veyradier, A. et al., "A Laboratory Phenotype/Genotype Correlation of 1167 French Patients From 670 Families With von Willebrand Disease: A New Epidemiologic Picture," Medicine, Mar. 2016;95(11):1-11.

Vicky Mcdonald: "Inherited bleeding disorders", Medicine, Apr. 1, 2017 (Apr. 1, 2017), XP055507424.

Weiss, H.J.et al., "Quantitative Assay of a Plasma Factor Deficient in von Willebrand's Disease that is Necessary for Platelet Aggregation. Relationship to Factor VIII Procoagulant Activity and Antigen Content," *J. Clin. Invest.*, 1973;52:2708-2716.

Wells, G. et al., "Safety, Effectiveness, and Cost-Effectiveness of New Oral Anticoagulants Compared with Warfarin in Preventing Stroke and Other Cardiovascular Events in Patients with Atrial Fibrillation," Ottawa(ON): Canadian Agency for Drugs and Technologies in Health; Apr. 9, 2012, Clinical Review, 189 pages.

Wen, L.T. et al., "Chemiluminographic Detection of von Willebrand Factor Multimeric Composition," *J. Clin. Lab. Anal.*, 1993;7:317-323.

Castaman, Giancarlo. "Treatment of von Willebrand disease with FVIII/VWF concentrates." Blood transfusion = Trasfusione del sangue vol. 9 Suppl 2,Suppl 2 (2011): s9-13. doi:10.2450/2011.003S.

Suiter, T. et al., "Recombinant Human Von Willebrand Factor (rhVWF): First-In-Human Study Evaluating Pharmacokinetics, Demonstrating Safety and Tolerability In Type 3 Von Willebrand Disease", Blood, vol. 116, Issue 21, 2010, p. 237, ISSN 0006-4971, https://doi.org/10.1182/blood.V116.21.237.237.

Web Archive of "Study NCT02283268 Last updated: Jun. 26, 2015", Oct. 6, 2015, https://web.archive.org/web/20151006100604/https://clinicaltrials.gov/ct2/show/NCT02283268.

"ACOG committee opinion No. 557: Management of acute abnormal uterine bleeding in nonpregnant reproductive-aged women." Obstetrics and gynecology vol. 121,4 (2013): 891-896. doi:10.1097/01.AOG.0000428646.67925.9a.

Adeyemi-Fowode, Oluyemisi A et al. "Levonorgestrel-Releasing Intrauterine Device Use in Female Adolescents with Heavy Menstrual Bleeding and Bleeding Disorders: Single Institution Review." Journal of pediatric and adolescent gynecology vol. 30,4 (2017): 479-483. doi:10.1016/j.jpag.2016.04.001.

Akers et al., Peptides and proteins as parenteral solutions, chapter 8, In: Frokjaer et al. (eds), Pharmaceutical Formulation Development of Peptides and Proteins, CRC Press (2000).

Amesse, Lawrence S et al. "Oral contraceptives and DDAVP nasal spray: patterns of use in managing vWD-associated menorrhagia: a single-institution study." Journal of pediatric hematology/oncology vol. 27,7 (2005): 357-63. doi:10.1097/01.mph.0000173175.95152.95.

Chi, Claudia et al. "Levonorgestrel-releasing intrauterine system for the management of heavy menstrual bleeding in women with inherited bleeding disorders: long-term follow-up." Contraception vol. 83,3 (2011): 242-7. doi:10.1016/j.contraception.2010.07.010.

Connell, Nathan T et al. "ASH ISTH NHF WFH 2021 guidelines on the management of von Willebrand disease." Blood advances vol. 5,1 (2021): 301-325. doi:10.1182/bloodadvances.2020003264.

De Wee, E M et al. "Gynaecological and obstetric bleeding in moderate and severe von Willebrand disease." Thrombosis and haemostasis vol. 106,5 (2011): 885-92. doi:10.1160/TH11-03-0180.

Higgins, Russell A, and Andrew J Goodwin. "Automated assays for von Willebrand factor activity." American journal of hematology vol. 94,4 (2019): 496-503. doi:10.1002/ajh.25393.

James, Paula D et al. "ASH ISTH NHF WFH 2021 guidelines on the diagnosis of von Willebrand disease." Blood advances vol. 5,1 (2021): 280-300. doi:10.1182/bloodadvances.2020003265.

Jennings and Lugowski, J. Immunochemistry of groups A, B, and C meningococcal polysaccharidetetanustoxoid conjugates. 1981; 127:1011-8.

Kadir, R A et al. "The impact of menstrual disorders on quality of life in women with inherited bleeding disorders." Haemophilia : the official journal of the World Federation of Hemophilia vol. 16,5 (2010): 832-9. doi:10.1111/j.1365-2516.2010.02269.x.

Kingman, C E C et al. "The use of levonorgestrel-releasing intrauterine system for treatment of menorrhagia in women with inher-

(56)            References Cited

OTHER PUBLICATIONS ited bleeding disorders." BJOG : an international journal of obstetrics and gynaecology vol. 111,12 (2004): 1425-8. doi:10.1111/j.1471-0528.2004.00305.x.

Kouides, Peter A et al. "Multisite management study of menorrhagia with abnormal laboratory haemostasis: a prospective crossover study of intranasal desmopressin and oral tranexamic acid." *British journal of haematology* vol. 145,2 (2009): 212-20. doi:10.1111/j.1365-2141.2009.07610.x.

Lukes, Andrea S et al. "Use of the levonorgestrel-releasing intrauterine system in women with hemostatic disorders." Fertility and sterility vol. 90,3 (2008): 673-7. doi:10.1016/j.fertnstert.2007.07.1315.

Magnay, Julia L et al. "Pictorial methods to assess heavy menstrual bleeding in research and clinical practice: a systematic literature review." BMC women's health vol. 20,1 24. Feb. 10, 2020, doi:10.1186/s12905-020-0887-y.

Merrifield, *J. Am. Chem. Soc.*, 85:2149 (1963).

Michiels, Jan Jacques et al. "Diagnostic Differentiation of von Willebrand Disease Types 1 and 2 by von Willebrand Factor Multimer Analysis and DDAVP Challenge Test." Clinical and applied thrombosis/hemostasis : official journal of the International Academy of Clinical and Applied Thrombosis/Hemostasis vol. 23,6 (2017): 518-531. doi:10.1177/1076029616647157.

Mohammed, Soma, and Emmanuel J Favaloro. "Laboratory Testing for von Willebrand Factor: Factor VIII Binding (for 2N VWD)." Methods in molecular biology (Clifton, N.J.) vol. 1646 (2017): 461-472. doi:10.1007/978-1-4939-7196-1_34.

Ni, Y et al. "Establishment and characterization of a new and stable collagen-binding assay for the assessment of von Willebrand factor activity." International journal of laboratory hematology vol. 35,2 (2013): 170-6. doi:10.1111/ijlh.12019.

Patzke, Jürgen, and Emmanuel J Favaloro. "Laboratory Testing for von Willebrand Factor Activity by Glycoprotein Ib Binding Assays (VWF:GPIb)." Methods in molecular biology (Clifton, N.J.) vol. 1646 (2017): 453-460. doi:10.1007/978-1-4939-7196-1_33.

Quinn, Stephen D, and Jenny Higham. "Outcome measures for heavy menstrual bleeding." Women's health (London, England) vol. 12,1 (2016): 21-6. doi:10.2217/whe.15.85.

Ragni, M V et al. "Von Willebrand factor for menorrhagia: a survey and literature review." Haemophilia : the official journal of the World Federation of Hemophilia vol. 22,3 (2016): 397-402. doi:10.1111/hae.12898.

Rimmer, E et al. "Malposition and expulsion of the levonorgestrel intrauterine system among women with inherited bleeding disorders." Haemophilia : the official journal of the World Federation of Hemophilia vol. 19,6 (2013): 933-8. doi:10.1111/hae.12184.

Rodeghiero, F et al. "ISTH/SSC bleeding assessment tool: a standardized questionnaire and a proposal for a new bleeding score for inherited bleeding disorders." Journal of thrombosis and haemostasis : JTH vol. 8,9 (2010): 2063-5. doi:10.1111/j.1538-7836.2010.03975.x.

Stufano, Francesca et al. "Evaluation of a fully automated von Willebrand factor assay panel for the diagnosis of von Willebrand disease." Haemophilia : the official journal of the World Federation of Hemophilia vol. 26,2 (2020): 298-305. doi:10.1111/hae.13929.

Yin et al., Effects of antioxidants on the hydrogen peroxide-mediated oxidation of methionine residues in granulocyte colony-stimulating factor and human parathyroid hormone fragment 13-34, *Pharm. Res.*, 21:2377-83 (2004).

Windyga J et al, "P218 | Management of menorrhagia in a phase 3, post-hoc, open-label study of recombinant von Willebrand factor (RVWF) in patients with severe von Willebrand disease (VWD)", Haemophilia, GB, vol. 26 S2, doi:10.1111/hae.13911, ISSN 1351-8216, (Jan. 28, 2020), pp. 138-138, URL: https://onlinelibrary.wiley.com/doi/full-xml/10.1111/hae.13911, XP055799775 [X] 1-39,46-70 * abstract * [I] 40-45.

Srivastava, A et al. "Efficacy and safety of a VWF/FVIII concentrate (wilate® ) in inherited von Willebrand disease patients undergoing surgical procedures." Haemophilia : the official journal of the World Federation of Hemophilia vol. 23,2 (2017): 264-272.

"Willfact 1000 IU Powder and Solvent for Solution for Injection." Willfact 1000 IU Powder and Solvent for Solution for Injection—Summary of Product Characteristics (SmPC)—(EMC) | 3706, www.medicines.org.uk/emc/product/3706/smpc#companyDetails. Accessed Jul. 1, 2025.

Dunkley et al., "Clinical efficacy and safety of the factor VIII/von Willebrand factor concentrate Biostate in patients with von Willebrand's disease: a prospective multicentre study", Haemophilia, vol. 16, 2010, pp. 615-624.

Federici, Augusto B. "Prophylaxis of bleeding episodes in patients with von Willebrand's disease." Blood transfusion = Trasfusione del sangue vol. 6 Suppl 2,Suppl 2 (2008): s26-32. doi:10.2450/2008.0034-08.

Gritsch, Herbert et al. "Structure and Function of Recombinant versus Plasma-Derived von Willebrand Factor and Impact on Multimer Pharmacokinetics in von Willebrand Disease." Journal of blood medicine vol. 13 649-662. Nov. 14, 2022, doi:10.2147/JBM.S377126.

Peyvandi, F et al. "Phase 3 study of recombinant von Willebrand factor in patients with severe von Willebrand disease who are undergoing elective surgery." Journal of thrombosis and haemostasis : JTH vol. 17,1 (2019): 52-62. doi:10.1111/jth.14313.

Peyvandi, Flora et al. "Evolution of replacement therapy for von Willebrand disease: From plasma fraction to recombinant von Willebrand factor." Blood reviews vol. 38 (2019): 100572. doi:10.1016/j.blre.2019.04.001.

Swami, Arjun, and Varinder Kaur. "von Willebrand Disease: A Concise Review and Update for the Practicing Physician." *Clinical and applied thrombosis/hemostasis : official journal of the International Academy of Clinical and Applied Thrombosis/Hemostasis* vol. 23,8 (2017): 900-910. doi:10.1177/1076029616675969.

* cited by examiner

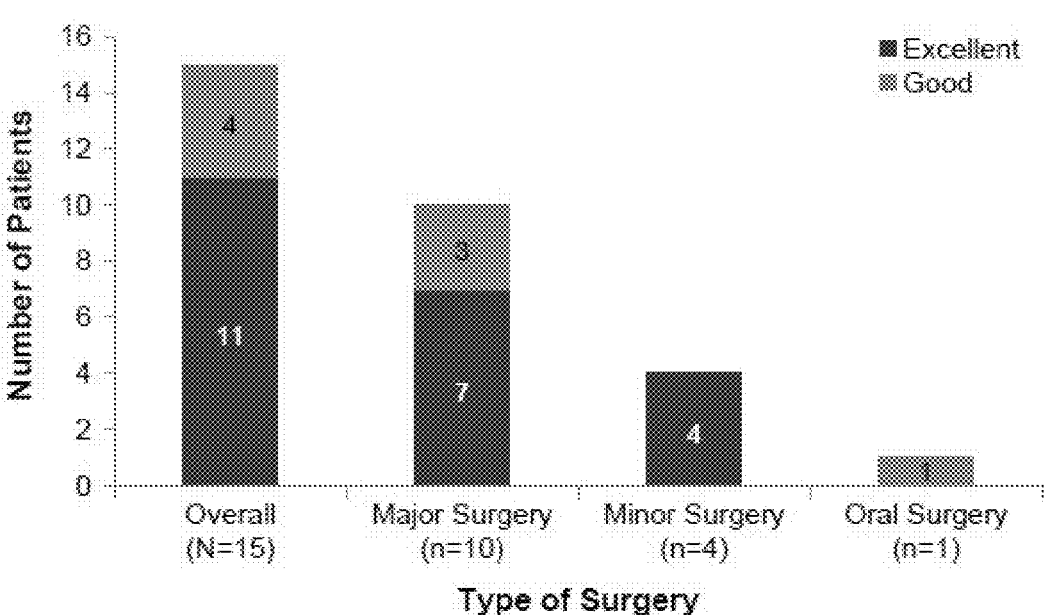
Figure 1. Overall Hemostatic Efficacy (Primary Endpoint)

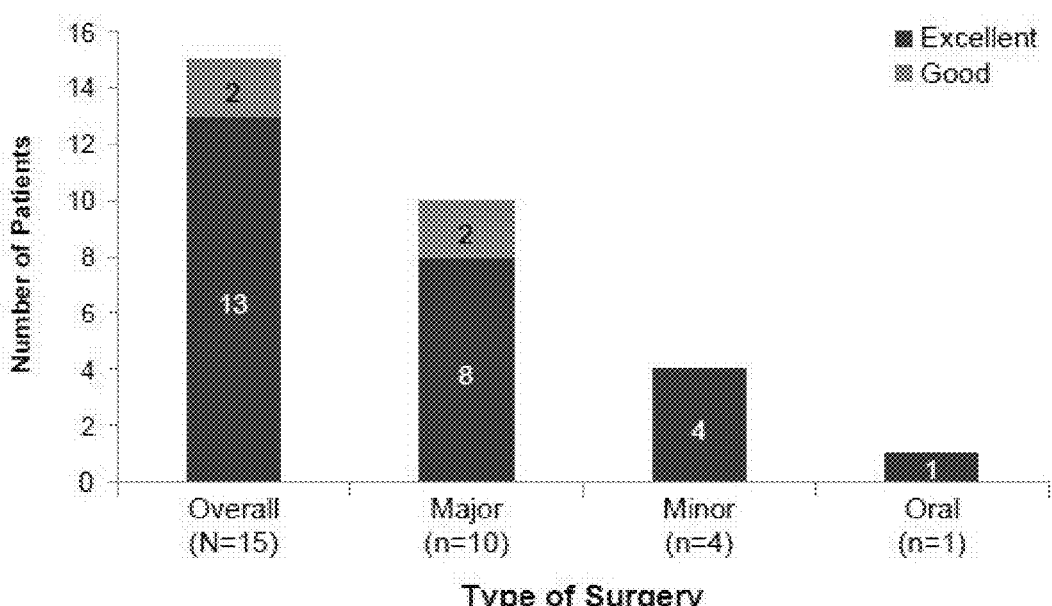
Figure 2. Intraoperative Hemostatic Efficacy (Secondary Endpoint)

FIG. 3

Table 3. Baseline Demographics and Clinical Characteristics

| Parameter | N=15 |
| --- | --- |
| Sex, n (%) | |
| Male | 7 (46.7) |
| Female | 8 (53.3) |
| Median age (range), y | 40 (20–70) |
| Median weight (range), kg | 73.5 (52.0–127.2) |
| Median BMI (range), kg/m$^2$ | 25.6 (17.1–38.0) |
| VWD type, n (%) | |
| 1 | 3 (20.0) |
| 2A | 2 (13.3) |
| 2B | 1 (6.7) |
| 2M | 1 (6.7) |
| 3 | 8 (53.3) |
| Surgery classification, n (%) | |
| Major | 10 (66.7) |
| Minor | 4 (26.7) |
| Oral | 1 (6.7) |
| Mean (SD) FVIII:C, IU/dL | 16.4 (19.9) |
| Mean (SD) VWF:RCo, IU/dL | 10.6 (13.3) |

BMI=body mass index; FVIII:C=factor VIII activity; VWD=von Willebrand disease; VWF:RCo=von Willebrand factor ristocetin cofactor activity.

FIG. 4

Table 4. PK Parameters for VWF:RCo (n=11)

| Parameter | Mean | SD | Range |
|---|---|---|---|
| $AUC_{0-\infty}$/dose, (h*IU/dL)/(IU/kg) | 37.50 | 18.14 | 19.2–83.5 |
| $AUC_{0-72h}$/dose, (h*IU/dL)/(IU/kg) | 34.08 | 14.59 | 18.3–72.6 |
| $C_{max}$, IU/dL | 96.27 | 22.01 | 49.0–118 |
| $T_{1/2}$, h | 17.83 | 7.34 | 9.08–31.6 |
| IR at $C_{max}$, (IU/dL)/(IU/kg) | 1.96 | 0.45 | 1.06–2.48 |

AUC=area under the curve; $C_{max}$=peak concentration; IR=incremental recovery; NC=not calculated; PK=pharmacokinetic; SD=standard deviation; $T_{max}$=time to peak concentration; $T_{1/2}$=terminal half-life; VWF:RCo=von Willebrand factor ristocetin cofactor activity.

FIG. 5A

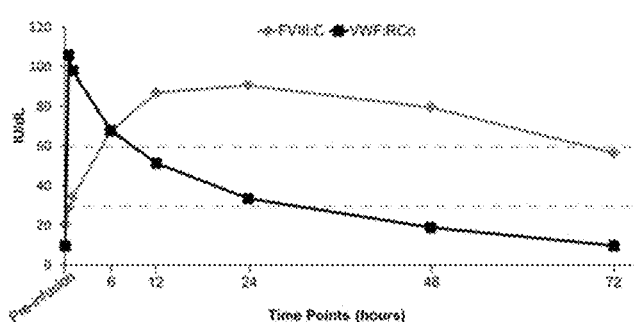

FVIII:C=factor VIII activity; VWF:RCo=von Willebrand factor ristocetin cofactor activity.

Target endogenous FVIII:C levels (30 IU/dL for minor/oral surgery or 60 IU/dL for major surgery) are indicated by dashed horizontal lines.

FIG. 5B

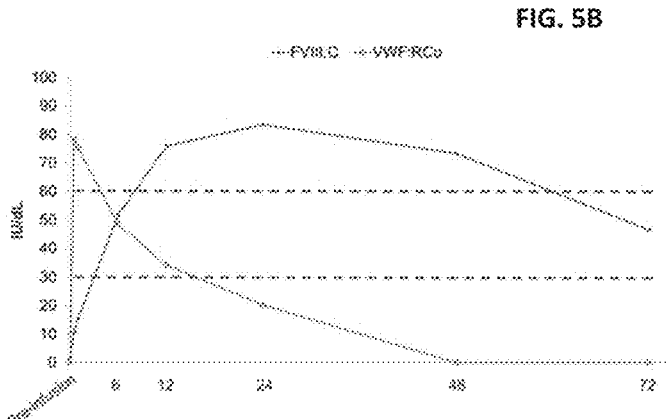

FVIII:C=factor VIII activity; VWF:RCo=von Willebrand factor ristocetin cofactor activity.

Target endogenous FVIII:C levels (30 IU/dL for minor/oral surgery or 60 IU/dL for major surgery) are indicated by dashed horizontal lines.

FIG. 6A-1

SEQ ID NO:1

```
agctcacagc tattgtggtg ggaaagggag ggtggttggt ggatgtcaca gcttgggctt        60
tatctccccc agcagtgggg actccacagc ccctgggcta cataacagca agacagtccg       120
gagctgtagc agacctgatt gagcctttgc agcagctgag agcatggcct agggtgggcg       180
gcaccattgt ccagcagctg agtttcccag ggaccttgga gatagccgca gccctcattt       240
gcagggggaag atgattcctg ccagatttgc cggggtgctg cttgctctgg ccctcatttt       300
gccagggacc ctttgtgcag aaggaactcg cggcaggtca tccacggccc gatgcagcct       360
tttcggaagt gacttcgtca acacctttga tgggagcatg tacagctttg cgggatactg       420
cagttacctc ctggcagggg gctgccagaa acgctccttc tcgattattg gggacttcca       480
gaatggcaag agagtgagcc tctccgtgta tcttggggaa ttttttgaca tccatttgtt       540
tgtcaatggt accgtgacac aggggggacca aagagtctcc atgccctatg cctccaaagg       600
gctgtatcta gaaactgagg ctgggtacta caagctgtcc ggtgaggcct atggctttgt       660
ggccaggatc gatggcagcg gcaactttca agtcctgctg tcagacagat acttcaacaa       720
gacctgcggg ctgtgtggca actttaacat ctttgctgaa gatgactttta tgacccaaga       780
agggaccttg acctcggacc cttatgactt tgccaactca tgggctctga gcagtggaga       840
acagtggtgt gaacgggcat ctcctcccag cagctcatgc aacatctcct ctgggaaat       900
gcagaagggc ctgtgggagc agtgccagct tctgaagagc acctcggtgt ttgcccgctg       960
ccacctctg tgtgaccccg agcctttgt ggccctgtgt gagaagactt tgtgtgagtg      1020
tgctgggggg ctggagtgcg cctgccctgc cctcctggag tacgcccgga cctgtgccca      1080
ggagggaatg gtgctgtacg gctggaccga ccacagcgcg tgcagcccag tgtgccctgc      1140
tggtatggag tataggcagt gtgtgtcccc ttgcgccagg acctgccaga gcctgcacat      1200
caatgaaatg tgtcaggagc gatgcgtgga tggctgcagc tgccctgagg gacagctcct      1260
ggatgaaggc ctctgcgtgg agagcaccga gtgtccctgc gtgcattccg gaaagcgcta      1320
ccctcccggc acctccctct ctcgagactg caacacctgc atttgccgaa acagccagtg      1380
gatctgcagc aatgaagaat gtccagggga gtgccttgtc acaggtcaat cacacttcaa      1440
gagctttgac aacagatact tcaccttcag tgggatctgc cagtacctgc tggcccggga      1500
ttgccaggac cactccttct ccattgtcat tgagactgtc cagtgtgctg atgaccgcga      1560
cgctgtgtgc accccgctccg tcaccgtccg gctgcctggc ctgcacaaca gccttgtgaa      1620
actgaagcat ggggcaggag ttgccatgga tggccaggac gtccagctcc ccctcctgaa      1680
aggtgacctc cgcatccagc atacagtgac ggcctccgtg cgcctcagct acgggaggag      1740
cctgcagatg gactgggatg gccgcggggag gctgctggtg aagctgtccc ccgtctatgc      1800
cgggaagacc tgcggcctgt gtgggaatta caatggcaac cagggcgacg acttccttac      1860
ccctctggg ctggcggagc cccgggtgga ggacttcggg aacgcctgga gctgcacgg      1920
ggactgccag gacctgcaga agcagcacag cgatccctgc gccctcaacc cgcgcatgac      1980
caggttctcc gaggaggcgt gcgcggtcct gacgtccccc acattcgagg cctgccatcg      2040
tgccgtcagc ccgctgccct acctgcggaa ctgccgctac gacgtgtgct cctgctcgga      2100
cggccgcgag tgcctgtgcg gcgccctggc cagctatgcc gcggcctgcg cggggagagg      2160
cgtgcgcgtc gcgtggcgcg agccaggccg ctgtgagctg aactgcccga aaggccaggt      2220
gtacctgcag tgcgggaccc cctgcaacct gacctgccgc tctctctctt acccggatga      2280
ggaatgcaat gaggcctgcc tggaggggctg cttctgcccc ccaggctct acatggatga      2340
gaggggggac tgcgtgccca aggcccagtg ccctgttac tatgacggtg agatcttcca      2400
gccagaagac atcttctcag accatcacac catgtgctac tgtgaggatg gcttcatgca      2460
ctgtaccatg agtggagtcc ccggaagctt gctgcctgac gctgtcctca gcagtccct      2520
gtctcatcgc agcaaaagga gcctatcctg tcggcccccc atggtcaagc tggtgtgtcc      2580
cgctgacaac ctgcgggctg aagggctcga gtgtaccaaa acgtgccaga ctatgacct      2640
ggagtgcatg agcatgggct gtgtctctgg ctgcctctgc cccccgggca tggtccggca      2700
tgagaacaga tgtgtggccc tggaaaggtg tccctgcttc catcagggca aggagtatgc      2760
ccctggagaa acagtgaaga ttggctgcaa cacttgtgtc tgtcgggacc ggaagtggaa      2820
ctgcacagac catgtgtgtg atgccacgtg ctccacgatc ggcatggccc actacctcac      2880
cttcgacggg ctcaaataccc tgttccccgg ggagtgccag tacgttctgg tgcaggatta      2940
ctgcggcagt aaccctggga cctttcggat cctagtgggg aataagggat gcagccaccc      3000
ctcagtgaaa tgcaagaaac gggtcaccat cctggtggag ggaggagaga ttgagctgtt      3060
tgacgggag gtgaatgtga agaggcccat gaaggatgag actcactttg aggtggtgga      3120
gtctggccgg tacatcatc tgctgctggg caaagccctc tccgtggtct gggaccgcca      3180
cctgagcatc tccgtggtcc tgaagcagac ataccaggag aaagtgtgtg gcctgtgtgg      3240
gaattttgat ggcatccaga caatgaccct caccagcagc aacctccaag tggaggaaga      3300
ccctgtggac tttgggaact cctggaaagt gagctcgcag tgtgctgaca ccagaaaagt      3360
gcctctggac tcatcccctg ccacctgcca taacaacatc atgaagcaga cgatggtgga      3420
ttcctcctgt agaatcctta ccagtgacgt cttccaggac tgcaacaagc tggtggaccc      3480
cgagccatat ctggatgtct gcatttacga cacctgctcc tgtgagtcca ttggggactg      3540
```

FIG. 6A-2

```
cgcctgcttc tgcgacacca ttgctgccta tgcccacgtg tgtgcccagc atggcaaggt  3600
ggtgacctgg aggacggcca cattgtgccc ccagagctgc gaggagagga atctccggga  3660
gaacgggtat gagtgtgagt ggcgctataa cagctgtgca cctgcctgtc aagtcacgtg  3720
tcagcaccct gagccactgg cctgccctgt gcagtgtgtg gagggctgcc atgcccactg  3780
ccctccaggg aaaatcctgg atgagctttt gcagacctgc gttgaccctg aagactgtcc  3840
agtgtgtgag gtggctggcc ggcgttttgc ctcaggaaag aaagtcacct tgaatcccag  3900
tgaccctgag cactgccaga tttgccactg tgatgttgtc aacctcacct gtgaagcctg  3960
ccaggagccg ggaggcctgg tggtgcctcc cacagatgcc ccggtgagcc ccaccactct  4020
gtatgtggag gacatctcgg aaccgccgtt gcacgatttc tactgcagca ggctactgga  4080
cctggtcttc ctgctggatg gctcctccag gctgtccgag gctgagtttg aagtgctgaa  4140
ggcctttgtg gtggacatga tggagcggct gcgcatctcc cagaagtggg tccgcgtggc  4200
cgtggtggag taccacgacg gctcccacgc ctacatcggg ctcaaggacc ggaagcgacc  4260
gtcagagctg cggcgcattg ccagccaggt gaagtatgcg ggcagccagg tggcctccac  4320
cagcgaggtc ttgaaataca cactgttcca aatcttcagc aagatcgacc gccctgaagc  4380
ctcccgcatc acctgctcc tgatggccag ccaggagccc caacggatgt ccgggaactt  4440
tgtccgctac gtccagggcc tgaagaagaa gaaggtcatt gtgatcccgg tgggcattgg  4500
gccccatgcc aacctcaagc agatccgcct catcgagaag caggcccctg agaacaaggc  4560
cttcgtgctg agcagtgtgg atgagctgga gcagcaaagg gacgagatcg ttagctacct  4620
ctgtgacctt gcccctgaag ccctcctcc tactctgccc ccgacatgg cacaagtcac  4680
tgtgggcccg gggctcttgg gggtttcgac cctggggccc aagaggaact ccatggttct  4740
ggatgtggcg ttcgtcctgg aaggatcgga caaaattggt gaagccgact tcaacaggag  4800
caaggagttc atggaggagg tgattcagcg gatggatgtg ggccaggaca gcatccacgt  4860
cacggtgctg cagtactcct acatggtgac tgtggagtac cccttcagcg aggcacagtc  4920
caaagggac atcctgcagc gggtgcgaga gatccgctac cagggcggca acaggaccaa  4980
cactgggctg gccctgcggt acctctctga ccacagcttc ttggtcagcc agggtgaccg  5040
ggagcaggcg cccaacctgg tctacatggt caccggaaat cctgcctctg atgagatcaa  5100
gaggctgcct ggagacatcc aggtggtgcc cattggagtg ggccctaatg ccaacgtgca  5160
ggagctggag aggattggct ggcccaatgc ccctatcctc atccaggact ttgagacgct  5220
cccccgagag gctcctgacc tggtgctgca gaggtgctgc tccggagagg ggctgcagat  5280
ccccaccctc tccctgcac ctgactgcag ccagccctg gacgtgatcc ttctcctgga  5340
tggctcctcc agtttcccag cttcttattt tgatgaaatg aagagtttcg ccaaggcttt  5400
catttcaaaa gccaatatag ggcctcgtct cactcaggtg tcagtgctgc agtatggaag  5460
catcaccacc attgacgtgc catggaacgt ggtcccggag aaagcccatt tgctgagcct  5520
tgtggacgtc atgcagcggg agggaggccc cagccaaatc ggggatgcct tgggctttgc  5580
tgtgcgatac ttgacttcag aaatgcatgg tgccaggccg ggagcctcaa aggcggtggt  5640
catcctggtc acggacgtct ctgtggattc agtggatgca gcagctgatg ccgccaggtc  5700
caacagagtg acagtgttcc ctattggaat tggagatcgc tacgatgcag cccagctacg  5760
gatcttggca ggcccagcag gcgactccaa cgtggtgaag ctccagcgaa tcgaagacct  5820
ccctaccatg gtcaccttgg gcaattcctt cctccacaaa ctgtgctctg gatttgttag  5880
gatttgcatg gatgaggatg ggaatgagaa gaggcccggg gacgtctgga ccttgccaga  5940
ccagtgccac accgtgactt gccagccaga tggccagacc ttgctgaaga gtcatcgggt  6000
caactgtgac cgggggctga ggccttcgtg ccctaacagc cagtccctg ttaaagtgga  6060
agagacctgt ggctgccgct ggacctgccc ctgcgtgtgc acaggcagct ccactcggca  6120
catcgtgacc tttgatgggc agaatttcaa gctgactggc agctgttctt atgtcctatt  6180
tcaaaacaag gagcaggacc tggaggtgat tctccataat ggtgcctgca gccctggagc  6240
aaggcagggc tgcatgaaat ccatcgaggt gaagcacagt gccctctccg tcgagctgca  6300
cagtgacatg gaggtgacgg tgaatgggag actggtctct gttccttacg tgggtgggaa  6360
catggaagtc aacgtttatg gtgccatcat gcatgaggtc agattcaatc accttggtca  6420
catcttcaca ttcactccac aaaacaatga gttccaactg cagctcagcc ccaagacttt  6480
tgcttcaaag acgtatggtc tgtgtgggat ctgtgatgag aacggagcca atgacttcat  6540
gctgagggat ggcacagtca ccacagactg gaaaacactt gttcaggaat ggactgtgca  6600
gcggccaggg cagacgtgcc agcccatcct ggaggagcag tgtcttgtcc ccgacagctc  6660
ccactgccag gtcctcctct taccactgtt tgctgaatgc cacaaggtcc tggctccagc  6720
cacattctat gccatctgcc agcaggacag ttgccaccag gagcaagtgt gtgaggtgat  6780
cgcctcttat gcccacctct gtcggaccaa cggggtctgc gttgactgga ggacacctga  6840
tttctgtgct atgtcatgcc caccatctct ggtctacaac cactgtgagc atggctgtcc  6900
ccggcactgt gatggcaacg tgagctcctg tggggaccat ccctccgaag gctgtttctg  6960
ccctccagat aaagtcatgt tggaaggcag ctgtgtccct gaagaggcct gcactcagtg  7020
cattggtgag gatggagtcc agcaccagtt cctggaagcc tgggtcccgg accaccagcc  7080
ctgtcagatc tgcacatgcc tcagcgggcg gaaggtcaac tgcacaacgc agccctgccc  7140
```

FIG. 6A-3

```
cacggccaaa gctcccacgt gtggcctgtg tgaagtagcc cgcctccgcc agaatgcaga    7200
ccagtgctgc cccgagtatg agtgtgtgtg tgacccagtg agctgtgacc tgcccccagt    7260
gcctcactgt gaacgtggcc tccagcccac actgaccaac cctggcgagt gcagacccaa    7320
cttcacctgc gcctgcagga aggaggagtg caaaagagtg tccccaccct cctgcccccc    7380
gcaccgtttg cccacccttc ggaagaccca gtgctgtgat gagtatgagt gtgcctgcaa    7440
ctgtgtcaac tccacagtga gctgtcccct tgggtacttg gcctcaactg ccaccaatga    7500
ctgtggctgt accacaacca cctgccttcc cgacaaggtg tgtgtccacc gaagcaccat    7560
ctaccctgtg ggccagttct gggaggaggg ctgcgatgtg tgcacctgca ccgacatgga    7620
ggatgccgtg atgggcctcc gcgtggccca gtgctcccag aagccctgtg aggacagctg    7680
tcggtcgggc ttcacttacg ttctgcatga aggcgagtgc tgtggaaggt gcctgccatc    7740
tgcctgtgag gtggtgactg gctcaccgcg ggggggactcc cagtcttcct ggaagagtgt    7800
cggctcccag tgggcctccc cggagaaccc ctgcctcatc aatgagtgtg tccgagtgaa    7860
ggaggaggtc tttatacaac aaaggaacgt ctcctgcccc cagctggagg tccctgtctg    7920
ccccctcgggc tttcagctga gctgtaagac ctcagcgtgc tgcccaagct gtcgctgtga    7980
gcgcatggag gcctgcatgc tcaatggcac tgtcattggg cccgggaaga ctgtgatgat    8040
cgatgtgtgc acgacctgcc gctgcatggt gcaggtgggg gtcatctctg gattcaagct    8100
ggagtgcagg aagaccacct gcaacccctg cccctgggt tacaaggaag aaaataacac    8160
aggtgaatgt tgtgggagat gtttgcctac ggcttgcacc attcagctaa gaggaggaca    8220
gatcatgaca ctgaagcgtg atgagacgct ccaggatggc tgtgatactc acttctgcaa    8280
ggtcaatgag agaggagagt acttctggga gaagagggtc acaggctgcc caccctttga    8340
tgaacacaag tgtctggctg agggaggtaa aattatgaaa attccaggca cctgctgtga    8400
cacatgtgag gagcctgagt gcaacgacat cactgccagg ctgcagtatg tcaaggtggg    8460
aagctgtaag tctgaagtag aggtggatat ccactactgc cagggcaaat gtgccagcaa    8520
agccatgtac tccattgaca tcaacgatgt gcaggaccag tgctcctgct gctctccgac    8580
acggacggag cccatgcagg tggccctgca ctgcaccaat ggctctgttg tgtaccatga    8640
ggttctcaat gccatggagt gcaaatgctc ccccaggaag tgcagcaagt gaggctgctg    8700
cagctgcatg ggtgcctgct gctgcctgcc ttggcctgat ggccaggcca gagtgctgcc    8760
agtcctctgc atgttctgct cttgtgccct tctgagccca caataaaggc tgagctctta    8820
tcttgcaaaa ggc                                                       8833
```

FIG. 6B-1

<u>SEQ ID NO:2</u>

```
Met Ile Pro Ala Arg Phe Ala Gly Val Leu Leu Leu Ile Leu Pro Gly
1               5               10              15

Thr Leu Cys Ala Glu Gly Thr Arg Gly Arg Ser Ser Thr Ala Arg Cys
            20              25              30

Ser Leu Phe Gly Ser Asp Phe Val Asn Thr Phe Asp Gly Ser Met Tyr
        35              40              45

Ser Phe Ala Gly Tyr Cys Ser Tyr Leu Leu Ala Gly Gly Cys Gln Lys
        50              55              60

Arg Ser Phe Ser Ile Ile Gly Asp Phe Gln Asn Gly Lys Arg Val Ser
65              70              75              80

Leu Ser Val Tyr Leu Gly Glu Phe Phe Asp Ile His Leu Phe Val Asn
                85              90              95

Gly Thr Val Thr Gln Gly Asp Gln Arg Val Ser Met Pro Tyr Ala Ser
            100             105             110

Lys Leu Glu Thr Glu Ala Gly Tyr Tyr Lys Leu Ser Gly Glu Ala Tyr
        115             120             125

Gly Phe Val Ala Arg Ile Asp Gly Ser Gly Asn Phe Gln Val Leu Leu
        130             135             140
```

FIG. 6B-2

```
Ser Asp Arg Tyr Phe Asn Lys Thr Cys Gly Leu Cys Gly Asn Phe Asn
145             150             155                     160

Ile Phe Ala Glu Asp Asp Phe Met Thr Gln Glu Gly Thr Leu Thr Ser
            165             170                 175

Asp Pro Tyr Asp Phe Ala Asn Ser Trp Ala Leu Ser Ser Gly Glu Gln
            180             185             190

Trp Cys Glu Arg Pro Ser Ser Ser Cys Asn Ile Ser Ser Gly Glu Met
        195             200             205

Gln Lys Gly Leu Trp Glu Gln Cys Gln Leu Leu Lys Ser Thr Ser Val
    210             215             220

Phe Ala Arg Cys His Pro Leu Val Asp Pro Glu Pro Phe Cys Glu Lys
225             230             235             240

Thr Leu Cys Glu Cys Ala Gly Gly Leu Glu Cys Ala Cys Pro Ala Leu
            245             250             255

Leu Glu Tyr Ala Arg Thr Cys Ala Gln Glu Gly Met Val Leu Tyr Gly
            260             265             270

Trp Thr Asp His Ser Ala Cys Ser Pro Val Cys Pro Ala Gly Met Glu
        275             280             285

Tyr Arg Gln Cys Val Ser Pro Cys Ala Arg Thr Cys Gln Ser Leu His
    290             295             300

Ile Asn Glu Met Cys Gln Glu Arg Cys Val Asp Gly Cys Ser Cys Pro
305             310             315             320

Glu Gly Gln Leu Leu Asp Glu Gly Leu Cys Val Glu Ser Thr Glu Cys
            325             330             335

Pro Cys Val His Ser Gly Lys Arg Tyr Pro Pro Gly Thr Ser Leu Ser
        340             345             350

Arg Asp Cys Asn Thr Cys Ile Cys Arg Asn Ser Gln Trp Ile Cys Ser
        355             360             365

Asn Glu Glu Cys Pro Gly Glu Cys Leu Val Thr Gly Gln Ser His Phe
    370             375             380

Lys Ser Phe Asp Asn Arg Tyr Phe Thr Phe Ser Gly Ile Cys Gln Tyr
385             390             395             400

Leu Leu Ala Arg Asp Cys Gln Asp His Ser Phe Ser Ile Val Ile Glu
            405             410             415

Thr Val Gln Cys Ala Asp Asp Arg Asp Ala Val Cys Thr Arg Ser Val
            420             425             430

Thr Val Arg Leu Pro Gly Leu His Asn Ser Leu Val Lys Leu Lys His
    435             440             445
```

FIG. 6B-3

```
Gly Ala Gly Val Ala Met Asp Gly Gln Asp Val Gln Leu Pro Leu Leu
    450             455             460

Lys Gly Asp Leu Arg Ile Gln His Thr Val Thr Ala Ser Val Arg Leu
465             470             475                 480

Ser Tyr Gly Glu Asp Leu Gln Met Asp Trp Asp Gly Arg Gly Arg Leu
            485             490                 495

Leu Val Lys Leu Ser Pro Val Tyr Ala Gly Lys Thr Cys Gly Leu Cys
            500             505             510

Gly Asn Tyr Asn Gly Asn Gln Gly Asp Asp Phe Leu Thr Pro Ser Gly
        515             520             525

Leu Ala Glu Pro Arg Val Glu Asp Phe Gly Asn Ala Trp Lys Leu His
    530             535             540

Gly Asp Cys Gln Asp Leu Gln Lys Gln His Ser Asp Pro Cys Ala Leu
545             550             555                 560

Asn Pro Arg Met Thr Arg Phe Ser Glu Glu Ala Cys Ala Val Leu Thr
            565             570             575

Ser Pro Thr Phe Glu Ala Cys His Arg Ala Val Ser Pro Leu Pro Tyr
            580             585             590

Leu Arg Asn Cys Arg Tyr Asp Val Cys Ser Cys Ser Asp Gly Arg Glu
        595             600             605

Cys Leu Cys Gly Ser Tyr Ala Ala Ala Cys Ala Gly Arg Gly Val Arg
    610             615             620

Val Ala Trp Arg Glu Pro Gly Arg Cys Glu Leu Asn Cys Pro Lys Gly
625             630             635                 640

Gln Val Tyr Leu Gln Cys Gly Thr Pro Cys Asn Leu Thr Cys Arg Ser
            645             650             655

Leu Ser Tyr Pro Asp Glu Glu Cys Asn Glu Ala Cys Leu Glu Gly Cys
            660             665             670

Phe Cys Pro Pro Met Asp Glu Arg Gly Asp Cys Val Pro Lys Ala Gln
        675             680             685

Cys Pro Cys Tyr Tyr Asp Gly Glu Ile Phe Gln Pro Glu Asp Ile Phe
    690             695             700

Ser Asp His His Thr Met Cys Tyr Cys Glu Asp Gly Phe Met His Cys
705             710             715                 720

Thr Met Ser Gly Val Pro Gly Ser Leu Leu Pro Asp Ala Val Leu Ser
            725             730             735

Ser Pro Leu Ser His Arg Ser Lys Arg Ser Leu Ser Cys Arg Pro Pro
            740             745             750
```

FIG. 6B-4

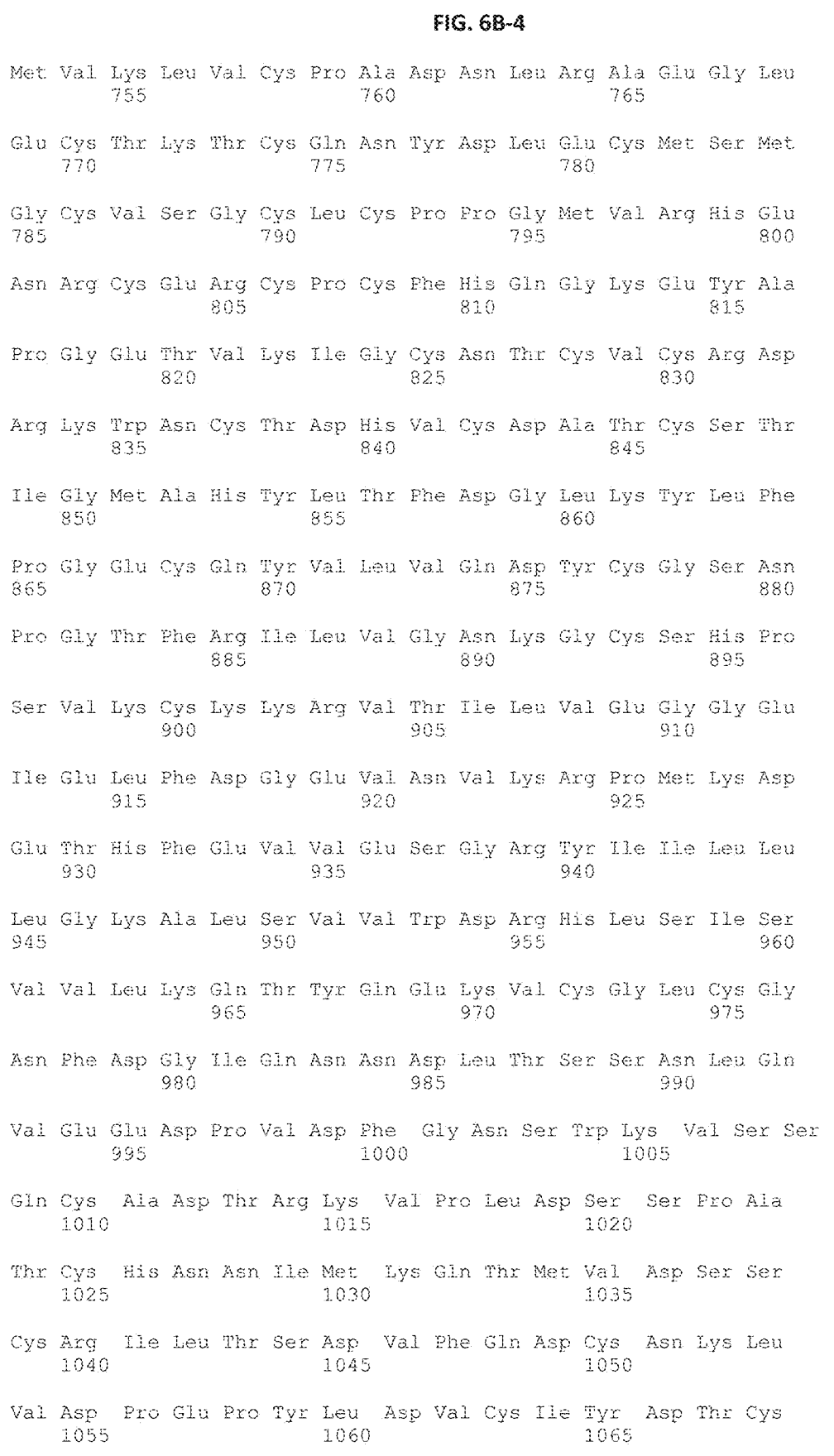

```
Met Val Lys Leu Val Cys Pro Ala Asp Asn Leu Arg Ala Glu Gly Leu
    755             760             765

Glu Cys Thr Lys Thr Cys Gln Asn Tyr Asp Leu Glu Cys Met Ser Met
    770             775             780

Gly Cys Val Ser Gly Cys Leu Cys Pro Pro Gly Met Val Arg His Glu
785             790             795             800

Asn Arg Cys Glu Arg Cys Pro Cys Phe His Gln Gly Lys Glu Tyr Ala
            805             810             815

Pro Gly Glu Thr Val Lys Ile Gly Cys Asn Thr Cys Val Cys Arg Asp
            820             825             830

Arg Lys Trp Asn Cys Thr Asp His Val Cys Asp Ala Thr Cys Ser Thr
            835             840             845

Ile Gly Met Ala His Tyr Leu Thr Phe Asp Gly Leu Lys Tyr Leu Phe
    850             855             860

Pro Gly Glu Cys Gln Tyr Val Leu Val Gln Asp Tyr Cys Gly Ser Asn
865             870             875             880

Pro Gly Thr Phe Arg Ile Leu Val Gly Asn Lys Gly Cys Ser His Pro
            885             890             895

Ser Val Lys Cys Lys Lys Arg Val Thr Ile Leu Val Glu Gly Gly Glu
            900             905             910

Ile Glu Leu Phe Asp Gly Glu Val Asn Val Lys Arg Pro Met Lys Asp
            915             920             925

Glu Thr His Phe Glu Val Val Glu Ser Gly Arg Tyr Ile Ile Leu Leu
    930             935             940

Leu Gly Lys Ala Leu Ser Val Val Trp Asp Arg His Leu Ser Ile Ser
945             950             955             960

Val Val Leu Lys Gln Thr Tyr Gln Glu Lys Val Cys Gly Leu Cys Gly
            965             970             975

Asn Phe Asp Gly Ile Gln Asn Asn Asp Leu Thr Ser Ser Asn Leu Gln
            980             985             990

Val Glu Glu Asp Pro Val Asp Phe  Gly Asn Ser Trp Lys  Val Ser Ser
            995             1000            1005

Gln Cys  Ala Asp Thr Arg Lys  Val Pro Leu Asp Ser  Ser Pro Ala
    1010            1015            1020

Thr Cys  His Asn Asn Ile Met  Lys Gln Thr Met Val  Asp Ser Ser
    1025            1030            1035

Cys Arg  Ile Leu Thr Ser Asp  Val Phe Gln Asp Cys  Asn Lys Leu
    1040            1045            1050

Val Asp  Pro Glu Pro Tyr Leu  Asp Val Cys Ile Tyr  Asp Thr Cys
    1055            1060            1065
```

FIG. 6B-5

```
Ser Cys  Glu Ser Ile Gly Asp  Cys Ala Cys Phe Cys  Asp Thr Ile
    1070             1075              1080

Ala Ala  Tyr Ala His Val Cys  Ala Gln His Gly Lys  Val Val Thr
    1085             1090              1095

Trp Arg  Thr Ala Thr Leu Cys  Pro Gln Ser Cys Glu  Glu Arg Asn
    1100             1105              1110

Leu Arg  Glu Asn Gly Tyr Glu  Cys Glu Trp Arg Tyr  Asn Ser Cys
    1115             1120              1125

Ala Pro  Ala Cys Gln Val Thr  Cys Gln His Pro Glu  Pro Leu Ala
    1130             1135              1140

Cys Pro  Val Gln Cys Val Glu  Gly Cys His Ala His  Cys Pro Pro
    1145             1150              1155

Gly Lys  Ile Leu Asp Glu Leu  Leu Gln Thr Cys Val  Asp Pro Glu
    1160             1165              1170

Asp Cys  Pro Val Cys Glu Val  Ala Gly Arg Arg Phe  Ala Ser Gly
    1175             1180              1185

Lys Lys  Val Thr Leu Asn Pro  Ser Asp Pro Glu His  Cys Gln Ile
    1190             1195              1200

Cys His  Cys Asp Val Val Asn  Leu Thr Cys Glu Ala  Cys Gln Glu
    1205             1210              1215

Pro Gly  Gly Leu Val Val Pro  Pro Thr Asp Ala Pro  Val Ser Pro
    1220             1225              1230

Thr Thr  Leu Tyr Val Glu Asp  Ile Ser Glu Pro Pro  Leu His Asp
    1235             1240              1245

Phe Tyr  Cys Ser Arg Leu Leu  Asp Leu Val Phe Leu  Leu Asp Gly
    1250             1255              1260

Ser Ser  Arg Leu Ser Glu Ala  Glu Phe Glu Val Leu  Lys Ala Phe
    1265             1270              1275

Val Val  Asp Met Met Glu Arg  Leu Arg Ile Ser Gln  Lys Trp Val
    1280             1285              1290

Arg Val  Ala Val Val Glu Tyr  His Asp Gly Ser His  Ala Tyr Ile
    1295             1300              1305

Gly Leu  Lys Asp Arg Lys Arg  Pro Ser Glu Leu Arg  Arg Ile Ala
    1310             1315              1320

Ser Gln  Val Lys Tyr Ala Gly  Ser Gln Val Ala Ser  Thr Ser Glu
    1325             1330              1335

Val Leu  Lys Tyr Thr Leu Phe  Gln Ile Phe Ser Lys  Ile Asp Arg
    1340             1345              1350
```

FIG. 6B-6

```
Pro Glu  Ala Ser Arg Ile Thr  Leu Leu Leu Met Ala  Ser Gln Glu
    1355             1360              1365

Pro Gln  Arg Met Ser Arg Asn  Phe Val Arg Tyr Val  Gln Gly Leu
    1370             1375              1380

Lys Lys  Lys Lys Val Ile Val  Ile Pro Val Gly Ile  Gly Pro His
    1385             1390              1395

Ala Asn  Leu Lys Gln Ile Arg  Leu Ile Glu Lys Gln  Ala Pro Glu
    1400             1405              1410

Asn Lys  Ala Phe Val Leu Ser  Ser Val Asp Glu Leu  Glu Gln Gln
    1415             1420              1425

Arg Asp  Glu Ile Val Ser Tyr  Leu Cys Asp Leu Ala  Pro Glu Ala
    1430             1435              1440

Pro Pro  Pro Thr Leu Pro Pro  Asp Met Ala Gln Val  Thr Val Gly
    1445             1450              1455

Pro Gly  Leu Leu Gly Val Ser  Thr Leu Gly Pro Lys  Arg Asn Ser
    1460             1465              1470

Met Val  Leu Asp Val Ala Phe  Val Leu Glu Gly Ser  Asp Lys Ile
    1475             1480              1485

Gly Glu  Ala Asp Phe Asn Arg  Ser Lys Glu Phe Met  Glu Glu Val
    1490             1495              1500

Ile Gln  Arg Met Asp Val Gly  Gln Asp Ser Ile His  Val Thr Val
    1505             1510              1515

Leu Gln  Tyr Ser Tyr Met Val  Thr Val Glu Tyr Pro  Phe Ser Glu
    1520             1525              1530

Ala Gln  Ser Lys Gly Asp Ile  Leu Gln Arg Val Arg  Glu Ile Arg
    1535             1540              1545

Tyr Gln  Gly Gly Asn Arg Thr  Asn Thr Gly Leu Ala  Leu Arg Tyr
    1550             1555              1560

Leu Ser  Asp His Ser Phe Leu  Val Ser Gln Gly Asp  Arg Glu Gln
    1565             1570              1575

Ala Pro  Asn Leu Val Tyr Met  Val Thr Gly Asn Pro  Ala Ser Asp
    1580             1585              1590

Glu Ile  Lys Arg Leu Pro Gly  Asp Ile Gln Val Val  Pro Ile Gly
    1595             1600              1605

Val Gly  Pro Asn Ala Asn Val  Gln Glu Leu Glu Arg  Ile Gly Trp
    1610             1615              1620

Pro Asn  Ala Pro Ile Leu Ile  Gln Asp Phe Glu Thr  Leu Pro Arg
    1625             1630              1635

Glu Ala  Pro Asp Leu Val Leu  Gln Arg Cys Cys Ser  Gly Glu Gly
    1640             1645              1650
```

FIG. 6B-7

```
Leu Gln  Ile Pro Thr Leu Ser  Pro Ala Pro Asp Cys  Ser Gln Pro
    1655             1660             1665

Leu Asp  Val Ile Leu Leu Leu  Asp Gly Ser Ser Ser  Phe Pro Ala
    1670             1675             1680

Ser Tyr  Phe Asp Glu Met Lys  Ser Phe Ala Lys Ala  Phe Ile Ser
    1685             1690             1695

Lys Ala  Asn Ile Gly Pro Arg  Leu Thr Gln Val Ser  Val Leu Gln
    1700             1705             1710

Tyr Gly  Ser Ile Thr Thr Ile  Asp Val Pro Trp Asn  Val Val Pro
    1715             1720             1725

Glu Lys  Ala His Leu Leu Ser  Leu Val Asp Val Met  Gln Arg Glu
    1730             1735             1740

Gly Gly  Pro Ser Gln Ile Gly  Asp Ala Leu Gly Phe  Ala Val Arg
    1745             1750             1755

Tyr Leu  Thr Ser Glu Met His  Gly Ala Arg Pro Gly  Ala Ser Lys
    1760             1765             1770

Ala Val  Val Ile Leu Val Thr  Asp Val Ser Val Asp  Ser Val Asp
    1775             1780             1785

Ala Ala  Ala Asp Ala Ala Arg  Ser Asn Arg Val Thr  Val Phe Pro
    1790             1795             1800

Ile Gly  Ile Gly Asp Arg Tyr  Asp Ala Ala Gln Leu  Arg Ile Leu
    1805             1810             1815

Ala Gly  Pro Ala Gly Asp Ser  Asn Val Val Lys Leu  Gln Arg Ile
    1820             1825             1830

Glu Asp  Leu Pro Thr Met Val  Thr Leu Gly Asn Ser  Phe Leu His
    1835             1840             1845

Lys Leu  Cys Ser Gly Phe Val  Arg Ile Cys Met Asp  Glu Asp Gly
    1850             1855             1860

Asn Glu  Lys Arg Pro Gly Asp  Val Trp Thr Leu Pro  Asp Gln Cys
    1865             1870             1875

His Thr  Val Thr Cys Gln Pro  Asp Gly Gln Thr Leu  Leu Lys Ser
    1880             1885             1890

His Arg  Val Asn Cys Asp Arg  Gly Leu Arg Pro Ser  Cys Pro Asn
    1895             1900             1905

Ser Gln  Ser Pro Val Lys Val  Glu Glu Thr Cys Gly  Cys Arg Trp
    1910             1915             1920

Thr Cys  Pro Cys Val Cys Thr  Gly Ser Ser Thr Arg  His Ile Val
    1925             1930             1935
```

FIG. 6B-8

```
Thr Phe  Asp Gly Gln Asn Phe  Lys Leu Thr Gly Ser  Cys Ser Tyr
    1940              1945              1950

Val Leu  Phe Gln Asn Lys Glu  Gln Asp Leu Glu Val  Ile Leu His
    1955              1960              1965

Asn Gly  Ala Cys Ser Pro Gly  Ala Arg Gln Gly Cys  Met Lys Ser
    1970              1975              1980

Ile Glu  Val Lys His Ser Ala  Leu Ser Val Glu Leu  His Ser Asp
    1985              1990              1995

Met Glu  Val Thr Val Asn Gly  Arg Leu Val Ser Val  Pro Tyr Val
    2000              2005              2010

Gly Gly  Asn Met Glu Val Asn  Val Tyr Gly Ala Ile  Met His Glu
    2015              2020              2025

Val Arg  Phe Asn His Leu Gly  His Ile Phe Thr Phe  Thr Pro Gln
    2030              2035              2040

Asn Asn  Glu Phe Gln Leu Gln  Leu Ser Pro Lys Thr  Phe Ala Ser
    2045              2050              2055

Lys Thr  Tyr Gly Leu Cys Gly  Ile Cys Asp Glu Asn  Gly Ala Asn
    2060              2065              2070

Asp Phe  Met Leu Arg Asp Gly  Thr Val Thr Thr Asp  Trp Lys Thr
    2075              2080              2085

Leu Val  Gln Glu Trp Thr Val  Gln Arg Pro Gly Gln  Thr Cys Gln
    2090              2095              2100

Pro Glu  Gln Cys Leu Val Pro  Asp Ser Ser His Cys  Gln Val Leu
    2105              2110              2115

Leu Leu  Pro Leu Phe Ala Glu  Cys His Lys Val Leu  Ala Pro Ala
    2120              2125              2130

Thr Phe  Tyr Ala Ile Cys Gln  Gln Asp Ser Cys His  Gln Glu Gln
    2135              2140              2145

Val Cys  Glu Val Ile Ala Ser  Tyr Ala His Leu Cys  Arg Thr Asn
    2150              2155              2160

Gly Val  Cys Val Asp Trp Arg  Thr Pro Asp Phe Cys  Ala Met Ser
    2165              2170              2175

Cys Pro  Pro Ser Leu Val Tyr  Asn His Cys Glu His  Gly Cys Pro
    2180              2185              2190

Arg His  Cys Asp Gly Asn Val  Ser Ser Cys Gly Asp  His Pro Ser
    2195              2200              2205

Glu Gly  Cys Phe Cys Pro Pro  Asp Lys Val Met Leu  Glu Gly Ser
    2210              2215              2220

Cys Val  Pro Glu Glu Ala Cys  Thr Gln Cys Ile Gly  Glu Asp Gly
    2225              2230              2235
```

FIG. 6B-9

```
Val Gln  His Gln Phe Leu Glu  Ala Trp Val Pro Asp  His Gln Pro
    2240                 2245              2250

Cys Gln  Ile Cys Thr Cys Leu  Ser Gly Arg Lys Val  Asn Cys Thr
    2255                 2260              2265

Thr Gln  Pro Cys Pro Thr Ala  Lys Ala Pro Thr Cys  Gly Leu Cys
    2270                 2275              2280

Glu Val  Ala Arg Leu Arg Gln  Asn Ala Asp Gln Cys  Cys Pro Glu
    2285                 2290              2295

Tyr Glu  Cys Val Cys Asp Pro  Val Ser Cys Asp Leu  Pro Pro Val
    2300                 2305              2310

Pro His  Cys Glu Arg Gly Leu  Gln Pro Thr Leu Thr  Asn Pro Gly
    2315                 2320              2325

Glu Cys  Arg Pro Asn Phe Thr  Cys Ala Cys Arg Lys  Glu Glu Cys
    2330                 2335              2340

Lys Arg  Val Ser Pro Pro Ser  Cys Pro Pro His Arg  Leu Pro Thr
    2345                 2350              2355

Leu Arg  Lys Thr Gln Cys Cys  Asp Glu Tyr Glu Cys  Ala Cys Asn
    2360                 2365              2370

Cys Val  Asn Ser Thr Val Ser  Cys Pro Leu Gly Tyr  Leu Ala Ser
    2375                 2380              2385

Thr Ala  Thr Asn Asp Cys Gly  Cys Thr Thr Thr Thr  Cys Leu Pro
    2390                 2395              2400

Asp Lys  Val Cys Val His Arg  Ser Thr Ile Tyr Pro  Val Gly Gln
    2405                 2410              2415

Phe Trp  Glu Glu Gly Cys Asp  Val Cys Thr Cys Thr  Asp Met Glu
    2420                 2425              2430

Asp Ala  Val Met Gly Leu Arg  Val Ala Gln Cys Ser  Gln Lys Pro
    2435                 2440              2445

Cys Glu  Asp Ser Cys Arg Ser  Gly Phe Thr Tyr Val  Leu His Glu
    2450                 2455              2460

Gly Glu  Cys Cys Gly Arg Cys  Leu Pro Ser Ala Cys  Glu Val Val
    2465                 2470              2475

Thr Gly  Ser Pro Arg Gly Asp  Ser Gln Ser Ser Trp  Lys Ser Val
    2480                 2485              2490

Gly Ser  Gln Trp Glu Asn Pro  Cys Leu Ile Asn Glu  Cys Val Arg
    2495                 2500              2505

Val Lys  Glu Glu Val Phe Ile  Gln Gln Arg Asn Val  Ser Cys Pro
    2510                 2515              2520
```

FIG. 6B-10

```
Gln Leu  Glu Val Pro Val Cys  Pro Ser Gly Phe Gln  Leu Ser Cys
    2525                2530                2535

Lys Thr  Ser Ala Cys Cys Pro  Ser Cys Arg Cys Glu  Arg Met Glu
    2540                2545                2550

Ala Cys  Met Leu Asn Gly Thr  Val Ile Gly Pro Gly  Lys Thr Val
    2555                2560                2565

Met Ile  Asp Val Cys Thr Thr  Cys Arg Cys Met Val  Gln Val Gly
    2570                2575                2580

Val Ile  Ser Gly Phe Lys Leu  Glu Cys Arg Lys Thr  Thr Cys Asn
    2585                2590                2595

Pro Cys  Pro Leu Gly Tyr Lys  Glu Glu Asn Asn Thr  Gly Glu Cys
    2600                2605                2610

Cys Gly  Arg Cys Leu Pro Thr  Ala Cys Thr Ile Gln  Leu Arg Gly
    2615                2620                2625

Gly Gln  Ile Met Thr Leu Lys  Arg Asp Glu Thr Leu  Gln Asp Gly
    2630                2635                2640

Cys Asp  Thr His Phe Cys Lys  Val Asn Glu Arg Gly  Glu Tyr Phe
    2645                2650                2655

Trp Glu  Lys Arg Val Thr Gly  Cys Pro Pro Phe Asp  Glu His Lys
    2660                2665                2670

Cys Leu  Ala Glu Gly Gly Lys  Ile Met Lys Ile Pro  Gly Thr Cys
    2675                2680                2685

Cys Asp  Thr Cys Glu Glu Pro  Glu Cys Asn Asp Ile  Thr Ala Arg
    2690                2695                2700

Leu Gln  Tyr Val Lys Val Gly  Ser Cys Lys Ser Glu  Val Glu Val
    2705                2710                2715

Asp Ile  His Tyr Cys Gln Gly  Lys Cys Ala Ser Lys  Ala Met Tyr
    2720                2725                2730

Ser Ile  Asp Ile Asn Asp Val  Gln Asp Gln Cys Ser  Cys Cys Ser
    2735                2740                2745

Pro Thr  Arg Thr Glu Pro Met  Gln His Cys Thr Asn  Gly Ser Val
    2750                2755                2760

Val Tyr  His Glu Val Leu Asn  Ala Met Glu Cys Lys  Cys Ser Pro
    2765                2770                2775

Arg Lys  Cys Ser Lys
    2780
```

FIG. 6C-1

SEQ ID NO:3

```
Ser Leu Ser Cys Arg Pro Pro Met Val Lys Leu Val Cys Pro Ala Asp
1               5               10              15

Asn Leu Arg Ala Glu Gly Leu Glu Cys Thr Lys Thr Cys Gln Asn Tyr
            20              25              30

Asp Leu Glu Cys Met Ser Met Gly Cys Val Ser Gly Cys Leu Cys Pro
        35              40              45

Pro Gly Met Val Arg His Glu Asn Arg Cys Val Ala Leu Glu Arg Cys
    50              55              60

Pro Cys Phe His Gln Gly Lys Glu Tyr Ala Pro Gly Glu Thr Val Lys
65              70              75              80

Ile Gly Cys Asn Thr Cys Val Cys Arg Asp Arg Lys Trp Asn Cys Thr
            85              90              95

Asp His Val Cys Asp Ala Thr Cys Ser Thr Ile Gly Met Ala His Tyr
            100             105             110

Leu Thr Phe Asp Gly Leu Lys Tyr Leu Phe Pro Gly Glu Cys Gln Tyr
        115             120             125

Val Leu Val Gln Asp Tyr Cys Gly Ser Asn Pro Gly Thr Phe Arg Ile
    130             135             140

Leu Val Gly Asn Lys Gly Cys Ser His Pro Ser Val Lys Cys Lys Lys
145             150             155             160

Arg Val Thr Ile Leu Val Glu Gly Gly Glu Ile Glu Leu Phe Asp Gly
            165             170             175

Glu Val Asn Val Lys Arg Pro Met Lys Asp Glu Thr His Phe Glu Val
            180             185             190

Val Glu Ser Gly Arg Tyr Ile Ile Leu Leu Leu Gly Lys Ala Leu Ser
        195             200             205

Val Val Trp Asp Arg His Leu Ser Ile Ser Val Val Leu Lys Gln Thr
    210             215             220

Tyr Gln Glu Lys Val Cys Gly Leu Cys Gly Asn Phe Asp Gly Ile Gln
225             230             235             240

Asn Asn Asp Leu Thr Ser Ser Asn Leu Gln Val Glu Glu Asp Pro Val
            245             250             255

Asp Phe Gly Asn Ser Trp Lys Val Ser Ser Gln Cys Ala Asp Thr Arg
        260             265             270

Lys Val Pro Leu Asp Ser Ser Pro Ala Thr Cys His Asn Asn Ile Met
    275             280             285

Lys Gln Thr Met Val Asp Ser Ser Cys Arg Ile Leu Thr Ser Asp Val
    290             295             300
```

FIG. 6C-2

```
Phe Gln Asp Cys Asn Lys Leu Val Asp Pro Glu Pro Tyr Leu Asp Val
305                 310             315                 320

Cys Ile Tyr Asp Thr Cys Ser Cys Glu Ser Ile Gly Asp Cys Ala Cys
            325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
            405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
            485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
            515                 520                 525

Glu Phe Glu Val Leu Lys Ala Phe Val Val Asp Met Met Glu Arg Leu
    530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
            565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
            595                 600                 605

Ile Asp Arg Pro Glu Ala Ser Arg Ile Thr Leu Leu Leu Met Ala Ser
    610                 615                 620
```

FIG. 6C-3

```
Gln Glu Pro Gln Arg Met Ser Arg Asn Phe Val Arg Tyr Val Gln Gly
625             630         635             640

Leu Lys Lys Lys Lys Val Ile Val Ile Pro Val Gly Ile Gly Pro His
            645         650             655

Ala Asn Leu Lys Gln Ile Arg Leu Ile Glu Lys Gln Ala Pro Glu Asn
            660         665             670

Lys Ala Phe Val Leu Ser Ser Val Asp Glu Leu Glu Gln Gln Arg Asp
        675         680             685

Glu Ile Val Ser Tyr Leu Cys Asp Leu Ala Pro Glu Ala Pro Pro Pro
    690         695             700

Thr Leu Pro Pro Asp Met Ala Gln Val Thr Val Gly Pro Gly Leu Leu
705             710         715             720

Gly Val Ser Thr Leu Gly Pro Lys Arg Asn Ser Met Val Leu Asp Val
            725         730             735

Ala Phe Val Leu Glu Gly Ser Asp Lys Ile Gly Glu Ala Asp Phe Asn
            740         745             750

Arg Ser Lys Glu Phe Met Glu Glu Val Ile Gln Arg Met Asp Val Gly
        755         760             765

Gln Asp Ser Ile His Val Thr Val Leu Gln Tyr Ser Tyr Met Val Thr
    770         775             780

Val Glu Tyr Pro Phe Ser Glu Ala Gln Ser Lys Gly Asp Ile Leu Gln
785             790         795             800

Arg Val Arg Glu Ile Arg Tyr Gln Gly Gly Asn Arg Thr Asn Thr Gly
            805         810             815

Leu Ala Leu Arg Tyr Leu Ser Asp His Ser Phe Leu Val Ser Gln Gly
            820         825             830

Asp Arg Glu Gln Ala Pro Asn Leu Val Tyr Met Val Thr Gly Asn Pro
        835         840             845

Ala Ser Asp Glu Ile Lys Arg Leu Pro Gly Asp Ile Gln Val Val Pro
    850         855             860

Ile Gly Val Gly Pro Asn Ala Asn Val Gln Glu Leu Glu Arg Ile Gly
865             870         875             880

Trp Pro Asn Ala Pro Ile Leu Ile Gln Asp Phe Glu Thr Leu Pro Arg
            885         890             895

Glu Ala Pro Asp Leu Val Leu Gln Arg Cys Cys Ser Gly Glu Gly Leu
        900         905             910

Gln Ile Pro Thr Leu Ser Pro Ala Pro Asp Cys Ser Gln Pro Leu Asp
    915         920             925
```

FIG. 6C-4

```
Val Ile Leu Leu Leu Asp Gly Ser Ser Ser Phe Pro Ala Ser Tyr Phe
    930             935             940

Asp Glu Met Lys Ser Phe Ala Lys Ala Phe Ile Ser Lys Ala Asn Ile
945             950             955             960

Gly Pro Arg Leu Thr Gln Val Ser Val Leu Gln Tyr Gly Ser Ile Thr
            965             970             975

Thr Ile Asp Val Pro Trp Asn Val Val Pro Glu Lys Ala His Leu Leu
            980             985             990

Ser Leu Val Asp Val Met Gln Arg Glu Gly Gly Pro Ser Gln Ile Gly
        995             1000            1005

Asp Ala  Leu Gly Phe Ala Val Arg Tyr Leu Thr  Ser Glu Met His
    1010            1015            1020

Gly Ala  Arg Pro Gly Ala Ser  Lys Ala Val Val Ile  Leu Val Thr
    1025            1030            1035

Asp Val  Ser Val Asp Ser Val  Asp Ala Ala Ala Asp  Ala Ala Arg
    1040            1045            1050

Ser Asn  Arg Val Thr Val Phe  Pro Ile Gly Ile Gly  Asp Arg Tyr
    1055            1060            1065

Asp Ala  Ala Gln Leu Arg Ile  Leu Ala Gly Pro Ala  Gly Asp Ser
    1070            1075            1080

Asn Val  Val Lys Leu Gln Arg  Ile Glu Asp Leu Pro  Thr Met Val
    1085            1090            1095

Thr Leu  Gly Asn Ser Phe Leu  His Lys Leu Cys Ser  Gly Phe Val
    1100            1105            1110

Arg Ile  Cys Met Asp Glu Asp  Gly Asn Glu Lys Arg  Pro Gly Asp
    1115            1120            1125

Val Trp  Thr Leu Pro Asp Gln  Cys His Thr Val Thr  Cys Gln Pro
    1130            1135            1140

Asp Gly  Gln Thr Leu Leu Lys  Ser His Arg Val Asn  Cys Asp Arg
    1145            1150            1155

Gly Leu  Arg Pro Ser Cys Pro  Asn Ser Gln Ser Pro  Val Lys Val
    1160            1165            1170

Glu Glu  Thr Cys Gly Cys Arg  Trp Thr Cys Pro Cys  Val Cys Thr
    1175            1180            1185

Gly Ser  Ser Thr Arg His Ile  Val Thr Phe Asp Gly  Gln Asn Phe
    1190            1195            1200

Lys Leu  Thr Gly Ser Cys Ser  Tyr Val Leu Phe Gln  Asn Lys Glu
    1205            1210            1215

Gln Asp  Leu Glu Val Ile Leu  His Asn Gly Ala Cys  Ser Pro Gly
    1220            1225            1230
```

FIG. 6C-5

```
Ala Arg  Gln Gly Cys Met Lys  Ser Ile Glu Val Lys  His Ser Ala
    1235             1240             1245

Leu Ser  Val Glu Leu His Ser  Asp Met Glu Val Thr  Val Asn Gly
    1250             1255             1260

Arg Leu  Val Ser Val Pro Tyr  Val Gly Gly Asn Met  Glu Val Asn
    1265             1270             1275

Val Tyr  Gly Ala Ile Met His  Glu Val Arg Phe Asn  His Leu Gly
    1280             1285             1290

His Ile  Phe Thr Phe Thr Pro  Gln Asn Asn Glu Phe  Gln Leu Gln
    1295             1300             1305

Leu Ser  Pro Lys Thr Phe Ala  Ser Lys Thr Tyr Gly  Leu Cys Gly
    1310             1315             1320

Ile Cys  Asp Glu Asn Gly Ala  Asn Asp Phe Met Leu  Arg Asp Gly
    1325             1330             1335

Thr Val  Thr Thr Asp Trp Lys  Thr Leu Val Gln Glu  Trp Thr Val
    1340             1345             1350

Gln Arg  Pro Gly Gln Thr Cys  Gln Pro Ile Leu Glu  Glu Gln Cys
    1355             1360             1365

Leu Val  Pro Asp Ser Ser His  Cys Gln Val Leu Leu  Leu Pro Leu
    1370             1375             1380

Phe Ala  Glu Cys His Lys Val  Leu Ala Pro Ala Thr  Phe Tyr Ala
    1385             1390             1395

Ile Cys  Gln Gln Asp Ser Cys  His Gln Glu Gln Val  Cys Glu Val
    1400             1405             1410

Ile Ala  Ser Tyr Ala His Leu  Cys Arg Thr Asn Gly  Val Cys Val
    1415             1420             1425

Asp Trp  Arg Thr Pro Asp Phe  Cys Ala Met Ser Cys  Pro Pro Ser
    1430             1435             1440

Leu Val  Tyr Asn His Cys Glu  His Gly Cys Pro Arg  His Cys Asp
    1445             1450             1455

Gly Asn  Val Ser Ser Cys Gly  Asp His Pro Ser Glu  Gly Cys Phe
    1460             1465             1470

Cys Pro  Pro Asp Lys Val Met  Leu Glu Gly Ser Cys  Val Pro Glu
    1475             1480             1485

Glu Ala  Cys Thr Gln Cys Ile  Gly Glu Asp Gly Val  Gln His Gln
    1490             1495             1500

Phe Leu  Glu Ala Trp Val Pro  Asp His Gln Pro Cys  Gln Ile Cys
    1505             1510             1515
```

FIG. 6C-6

```
Thr Cys  Leu Ser Gly Arg Lys  Val Asn Cys Thr Thr  Gln Pro Cys
    1520                 1525              1530

Pro Thr  Ala Lys Ala Pro Thr  Cys Gly Leu Cys Glu  Val Ala Arg
    1535                 1540              1545

Leu Arg  Gln Asn Ala Asp Gln  Cys Cys Pro Glu Tyr  Glu Cys Val
    1550                 1555              1560

Cys Asp  Pro Val Ser Cys Asp  Leu Pro Pro Val Pro  His Cys Glu
    1565                 1570              1575

Arg Gly  Leu Gln Pro Thr Leu  Thr Asn Pro Gly Glu  Cys Arg Pro
    1580                 1585              1590

Asn Phe  Thr Cys Ala Cys Arg  Lys Glu Glu Cys Lys  Arg Val Ser
    1595                 1600              1605

Pro Pro  Ser Cys Pro Pro His  Arg Leu Pro Thr Leu  Arg Lys Thr
    1610                 1615              1620

Gln Cys  Cys Asp Glu Tyr Glu  Cys Ala Cys Asn Cys  Val Asn Ser
    1625                 1630              1635

Thr Val  Ser Cys Pro Leu Gly  Tyr Leu Ala Ser Thr  Ala Thr Asn
    1640                 1645              1650

Asp Cys  Gly Cys Thr Thr Thr  Thr Cys Leu Pro Asp  Lys Val Cys
    1655                 1660              1665

Val His  Arg Ser Thr Ile Tyr  Pro Val Gly Gln Phe  Trp Glu Glu
    1670                 1675              1680

Gly Cys  Asp Val Cys Thr Cys  Thr Asp Met Glu Asp  Ala Val Met
    1685                 1690              1695

Gly Leu  Arg Val Ala Gln Cys  Ser Gln Lys Pro Cys  Glu Asp Ser
    1700                 1705              1710

Cys Arg  Ser Gly Phe Thr Tyr  Val Leu His Glu Gly  Glu Cys Cys
    1715                 1720              1725

Gly Arg  Cys Leu Pro Ser Ala  Cys Glu Val Val Thr  Gly Ser Pro
    1730                 1735              1740

Arg Gly  Asp Ser Gln Ser Ser  Trp Lys Ser Val Gly  Ser Gln Trp
    1745                 1750              1755

Ala Ser  Pro Glu Asn Pro Cys  Leu Ile Asn Glu Cys  Val Arg Val
    1760                 1765              1770

Lys Glu  Glu Val Phe Ile Gln  Gln Arg Asn Val Ser  Cys Pro Gln
    1775                 1780              1785

Leu Glu  Val Pro Val Cys Pro  Ser Gly Phe Gln Leu  Ser Cys Lys
    1790                 1795              1800

Thr Ser  Ala Cys Cys Pro Ser  Cys Arg Cys Glu Arg  Met Glu Ala
    1805                 1810              1815
```

FIG. 6C-7

```
Cys Met  Leu Asn Gly Thr Val  Ile Gly Pro Gly Lys  Thr Val Met
    1820                 1825             1830

Ile Asp  Val Cys Thr Thr Cys  Arg Cys Met Val Gln  Val Gly Val
    1835                 1840             1845

Ile Ser  Gly Phe Lys Leu Glu  Cys Arg Lys Thr Thr  Cys Asn Pro
    1850                 1855             1860

Cys Pro  Leu Gly Tyr Lys Glu  Glu Asn Asn Thr Gly  Glu Cys Cys
    1865                 1870             1875

Gly Arg  Cys Leu Pro Thr Ala  Cys Thr Ile Gln Leu  Arg Gly Gly
    1880                 1885             1890

Gln Ile  Met Thr Leu Lys Arg  Asp Glu Thr Leu Gln  Asp Gly Cys
    1895                 1900             1905

Asp Thr  His Phe Cys Lys Val  Asn Glu Arg Gly Glu  Tyr Phe Trp
    1910                 1915             1920

Glu Lys  Arg Val Thr Gly Cys  Pro Pro Phe Asp Glu  His Lys Cys
    1925                 1930             1935

Leu Ala  Glu Gly Gly Lys Ile  Met Lys Ile Pro Gly  Thr Cys Cys
    1940                 1945             1950

Asp Thr  Cys Glu Glu Pro Glu  Cys Asn Asp Ile Thr  Ala Arg Leu
    1955                 1960             1965

Gln Tyr  Val Lys Val Gly Ser  Cys Lys Ser Glu Val  Glu Val Asp
    1970                 1975             1980

Ile His  Tyr Cys Gln Gly Lys  Cys Ala Ser Lys Ala  Met Tyr Ser
    1985                 1990             1995

Ile Asp  Ile Asn Asp Val Gln  Asp Gln Cys Ser Cys  Cys Ser Pro
    2000                 2005             2010

Thr Arg  Thr Glu Pro Met Gln  Val Ala Leu His Cys  Thr Asn Gly
    2015                 2020             2025

Ser Val  Val Tyr His Glu Val  Leu Asn Ala Met Glu  Cys Lys Cys
    2030                 2035             2040

Ser Pro  Arg Lys Cys Ser Lys
    2045                 2050
```

1

TREATMENT OF PATIENTS WITH SEVERE VON WILLEBRAND DISEASE UNDERGOING ELECTIVE SURGERY BY ADMINISTRATION OF RECOMBINANT VWF

CROSS REFERENCE TO RELATED APPLICATION

This application is a continuation of U.S. application Ser. No. 16/030,653, filed on Jul. 9, 2018, which claims priority to U.S. Provisional Patent Application No. 62/546,999, filed on Aug. 17, 2017, and U.S. Provisional Patent Application No. 62/530,024, filed on Jul. 7, 2017, which are hereby incorporated by reference in their entirety.

REFERENCE TO A "SEQUENCE LISTING," A TABLE, OR A COMPUTER PROGRAM, LISTING APPENDIX SUBMITTED ON A COMPACT DISK

This disclosure incorporates by reference the Sequence Listing text copy submitted herewith, which was created on Oct. 1, 2018, entitled 008073_5186_US_ST25.txt which is 53 kilobytes in size.

BACKGROUND OF THE INVENTION

Coagulation diseases, such as von Willebrand Disease (VWD) generally result from a deficiency in the coagulation cascade. von Willebrand Disease (VWD) refers to the group of diseases caused by a deficiency of von Willebrand factor. Von Willebrand factor helps blood platelets clump together and stick to the blood vessel wall, which is necessary for normal blood clotting.

von Willebrand disease (VWD) is the most common inherited bleeding disorder, with an estimated prevalence rate of 1% (Veyradier A, et al., Medicine (Baltimore). 2016, 95(11):e3038). However, excluding milder forms of the disease, only about 1/10,000 patients actually require treatment. Current treatment for these coagulopathies includes a replacement therapy using pharmaceutical preparations comprising the normal coagulation factor.

VWF is a glycoprotein circulating in plasma as a series of multimers ranging in size from about 500 to 20,000 kD. The full length of cDNA of VWF has been cloned; the propolypeptide corresponds to amino acid residues 23 to 764 of the full length prepro-VWF (Eikenboom et al (1995) Haemophilia 1, 77 90). Multimeric forms of VWF are composed of 250 kD polypeptide subunits linked together by disulfide bonds. VWF mediates the initial platelet adhesion to the sub-endothelium of the damaged vessel wall, with the larger multimers exhibiting enhanced hemostatic activity. Multimerized VWF binds to the platelet surface glycoprotein Gp1bα, through an interaction in the A1 domain of VWF, facilitating platelet adhesion. Other sites on VWF mediate binding to the blood vessel wall. Thus, VWF forms a bridge between the platelet and the vessel wall that is essential to platelet adhesion and primary hemostasis under conditions of high shear stress. Normally, endothelial cells secrete large polymeric forms of VWF and those forms of VWF that have a lower molecular weight arise from proteolytic cleavage. The multimers of exceptionally large molecular masses are stored in the Weibel-Pallade bodies of the endothelial cells and liberated upon stimulation by agonists such as thrombin and histamine.

For patients with VWD, it is recommended that they be treated with von Willebrand factor (VWF) replacement given the need for prolonged hemostasis, particularly in major surgery (Mannucci P M and Franchini M., Haemophilia, 2017, 23(2):182-187; National Institutes of Health. National Heart, Lung, and Blood Institute. The Diagnosis, Evaluation, and Management of von Willebrand Disease NIH Publication No. 08-5832; December, 2007). Plasma-derived VWF therapies contain factor VIII (FVIII) and have the potential for FVIII accumulation with repeated dosing. VONVENDI® (von Willebrand factor [recombinant], Shire, Westlake Village, CA) is the first and only recombinant VWF (rVWF) concentrate (Turecek P L, et al. Hamostaseologie. 2009; 29(suppl 1):532-38; Mannucci P M, et al. Blood, 2013; 122(5):648-657; Gill J C, et al. Blood, 2015; 126(17):2038-2046).

BRIEF SUMMARY OF THE INVENTION

The present invention provides methods of pre-treatment for a patient with severe von Willebrand disease prior to surgery by administering 20-60 IU/kg recombinant von Willebrand Factor (rVWF) to the patient between 12 hours and 24 hours, e.g., 12 hours, 13 hours, 14 hours, 15 hours, 16 hours, 17 hours, 18 hours, 19 hours, 20 hours, 21 hours, 22 hours, 23 hours, 24 hours, 12 hours and 24 hours, 14 hours and 24 hours, 16 and 24 hours, 18 hours and 24 hours, or 20 hours and 24 hours prior to the surgical procedure, and not administering Factor VIII (FVIII) with the rVWF prior to the surgical procedure. In some embodiments, the method of pre-treating further comprises administering to the subject 5-90 IU/kg rVWF 1 hour prior to surgery. In some embodiments, the subject is administered 70-200 IU rVWF after the surgery, either with or without the pre-treatment described above. In some cases, the surgical procedure is selected from a group consisting of major surgery, minor surgery, and oral surgery.

In some embodiments, the subject is administered 35-60 IU/kg rVWF between 12 hours and 24 hours prior to a major surgical procedure. In other embodiments, the subject is administered 15-90 IU/kg rVWF 1 hour prior to major surgical procedure. In another embodiment, the subject is administered 150-220 IU/kg rVWF after a major surgical procedure. In some instances, the subject undergoing a major surgical procedure is administered a total dosage of 220-320 IU/kg. In some instances, when the surgical procedure is a major surgical procedure and the pre-treatment comprises administering at least two approximately equal doses of rVWF prior to the surgical procedure. By "approximately equal" as used herein refers to doses that have concentrations within 1-15%, 2-14%, 3-13%, 4-12%, 5-11%, 6-10%, 7-9%, 1%, 2%, 3%, 4%, 5%, 6%, 7%, 8%, 9%, 10%, 11%, 12%, 13%, 14%, 15%, 16%, 17%, 18%, 19%, 20% of each other.

In some embodiments, the subject is administered 50-60 IU/kg rVWF between 12 hours and 24 hours prior a minor surgical procedure. In other embodiments, the subject is administered 5-50 IU/kg rVWF 1 hour prior to minor surgery. In another embodiment, the subject is administered 70-150 IU/kg rVWF after a minor surgical procedure. In some instances, the subject undergoing a minor surgical procedure is administered a total dosage of 100-220 IU/kg. In some instances, when the surgical procedure is a minor surgical procedure, the pre-treatment comprises administering at least two doses of rVWF prior to the surgical procedure, wherein the first dose is larger than the second dose.

In some embodiments, the subject is administered 20-40 IU/kg rVWF between 12 hours and 24 hours prior to an oral surgical procedure. In other embodiments, the subject is administered 20-50 IU/kg rVWF 1 hour prior to the oral surgical procedure. In another embodiment, the subject is administered 10-50 IU/kg rVWF during the oral surgical procedure. In another embodiment, the subject is administered 70-150 IU/kg rVWF after an oral surgical procedure. In some instances, the subject undergoing an oral surgical procedure is administered a total dosage of 70-190 IU/kg. In some instances, when the surgical procedure is an oral surgical procedure and the pre-treatment comprises administering at least two approximately equal doses of rVWF prior to the surgical procedure.

Other objects, advantages and embodiments of the invention will be apparent from the detailed description following.

BRIEF DESCRIPTION OF THE DRAWINGS

FIG. 1 shows overall hemostatic efficiency (primary endpoint) in the study patients.

FIG. 2 shows hemostatic efficiency (secondary endpoint) in the study patients.

FIG. 3 shows baseline demographics and clinical characteristics.

FIG. 4 shows PK parameters for VWF:RCo (n=11).

FIG. 5A and FIG. 5B shows mean VWF:RCo and Endogenous FVIII:C Levels in Response to rVWF 50±5 IU rVWF:RCo/kg in all Patients with VWD With PK data analyzed (n=11) (FIG. 5A), and the subset of patients with type 3 VWD (n=5) (FIG. 5B).

FIG. 6A-1-FIG. 6C-7 show VWF nucleic acid and amino acid sequences.

DETAILED DESCRIPTION OF THE INVENTION

Introduction

The present invention provides methods for pretreating a patient with severe von Willebrand disease prior to surgery by administering recombinant von Willebrand Factor (rVWF) to the patient 45-60 IG/kg rVWF without administering Factor VIII with the rVWF prior to the surgical procedure. In some cases, the surgical procedure is selected from a group consisting of major surgery, minor surgery, and oral surgery.

The disclosure of PCT Application Publication No. WO2012/171031 is herein incorporated by reference in its entirety for all purposes.

Definitions

As used herein and in the appended claims, the singular forms "a," "an," and "the" include plural referents unless the context clearly dictates otherwise. Thus, for example, reference to "an antibody" includes a plurality of such antibodies and reference to "a host cell" includes reference to one or more host cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Before the invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

The term "pre-propeptide VWF," "prepro-VWF" or "pro-VWF" refers to a non-mature VWF polypeptide comprising a signal peptide of about 22 amino acid residues, a VWF propeptide of about 741 amino acid residues, and a mature VWF subunit of about 2050 amino acid residues. Pro-VWF subunits can dimerize through disulfide bonds near their carboxyl termini in the endoplasmic reticulum to form tail-to tail dimers which are then transported to the Golgi. In the Golgi, additional head-to-head disulfide bonds are formed near the amino-termini of the subunits, thereby forming multimers. Proteolytic cleavage of the VWF propeptide occurs via the processing protease furin, thus producing a mature VWF/VWF-PP complex. When "r" is included prior to the VWF designation, this refers to the recombinant version. In some embodiments, the methods described herein apply to recombinant VWF (rVWF).

The term "VWF complex" or "mat-VWF/VWF-PP complex" refers to a non-covalently linked heterodimeric structure comprising a mature VWF subunit and VWF propeptide. The VWF complex can be generated as a product of furin cleavage between the propeptide portion and mature VWF portion of the pre-propeptide VWF. When "r" is included prior to the VWF designation, this refers to the recombinant version. In some embodiments, the methods described herein apply to recombinant VWF (rVWF). As used herein. "rVWF" refers to recombinant VWF.

As used herein, "rFVIII" refers to recombinant FVIII.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, "recombinant VWF" includes VWF obtained via recombinant DNA technology. In certain embodiments, VWF proteins of the invention can comprise a construct, for example, prepared as in WO 1986/06096 published on Oct. 23, 1986 and U.S. patent application Ser. No. 07/559,509, filed on Jul. 23, 1990, in the name of Ginsburg et al., which is incorporated herein by reference with respect to the methods of producing recombinant VWF. The VWF in the present invention can include all potential forms, including the monomeric and multimeric forms. It should also be understood that the present invention encompasses different forms of VWF to be used in combination. For example, the VWF of the present invention may include different multimers, different derivatives and both biologically active derivatives and derivatives not biologically active.

In the context of the present invention, the recombinant VWF embraces any member of the VWF family from, for example, a mammal such as a primate, human, monkey, rabbit, pig, rodent, mouse, rat, hamster, gerbil, canine, feline, and biologically active derivatives thereof. Mutant and variant VWF proteins having activity are also embraced, as are functional fragments and fusion proteins of the VWF proteins. Furthermore, the VWF of the invention may further comprise tags that facilitate purification, detection, or both. The VWF described herein may further be modified with a therapeutic moiety or a moiety suitable imaging in vitro or in vivo.

As used herein, "plasma-derived VWF (pdVWF)" includes all forms of the protein found in blood including the mature VWF obtained from a mammal having the property of in vivo-stabilizing, e.g. binding, of at least one FVIII molecule.

The term "highly multimeric VWF" or "high molecular weight VWF" refers to VWF comprising at least 10 subunits, or 12, 14, or 16 subunits, to about 20, 22, 24 or 26 subunits or more. The term "subunit" refers to a monomer of VWF. As is known in the art, it is generally dimers of VWF that polymerize to form the larger order multimers (see Turecek et al., Semin. Thromb. Hemost. 2010, 36(5): 510-521 which is hereby incorporated by reference in its entirety for all purposes and in particular for all teachings regarding multimer analysis of VWF).

As used herein, the term "factor VIII" or "FVIII" refers to any form of factor VIII molecule with the typical characteristics of blood coagulation factor VIII, whether endogenous to a patient, derived from blood plasma, or produced through the use of recombinant DNA techniques, and including all modified forms of factor VIII. Factor VIII (FVIII) exists naturally and in therapeutic preparations as a heterogeneous distribution of polypeptides arising from a single gene product (see, e.g., Andersson et al., Proc. Natl. Acad. Sci. USA, 83:2979-2983 (1986)). Commercially available examples of therapeutic preparations containing Factor VIII include those sold under the trade names of HEMOFIL M, ADVATE, and RECOMBINATE (available from Baxter Healthcare Corporation, Deerfield, Ill., U.S.A.).

As used herein, "plasma FVIII activity" and "in vivo FVIII activity" are used interchangeably. The in vivo FVIII activity measured using standard assays may be endogenous FVIII activity, the activity of a therapeutically administered FVIII (recombinant or plasma derived), or both endogenous and administered FVIII activity. Similarly, "plasma FVIII" refers to endogenous FVIII or administered recombinant or plasma derived FVIII.

As used herein "von Willebrand Disease" refers to the group of diseases caused by a deficiency of von Willebrand factor. Von Willebrand factor helps blood platelets clump together and stick to the blood vessel wall, which is necessary for normal blood clotting. As described in further detail herein, there are several types of Von Willebrand disease including type 1, 2A, 2B, 2M and 3.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. VWF is the predominant species present in a preparation is substantially purified. The term "purified" in some embodiments denotes that a nucleic acid or protein gives rise to essentially one band in an electrophoretic gel. In other embodiments, it means that the nucleic acid or protein is at least 50% pure, more preferably at least 60%, 65%, 70%, 75%, 80%, 85%, 90%, 95%, 96%, 97%, 98%, 99% or more pure. "Purify" or "purification" in other embodiments means removing at least one contaminant from the composition to be purified. In this sense, purification does not require that the purified compound be homogenous, e.g., 100% pure.

As used herein, "administering" (and all grammatical equivalents) includes intravenous administration, intramuscular administration, subcutaneous administration, oral administration, administration as a suppository, topical contact, intraperitoneal, intralesional, or intranasal administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "therapeutically effective amount or dose" or "therapeutically sufficient amount or dose" or "effective or sufficient amount or dose" refer to a dose that produces therapeutic effects for which it is administered. For example, a therapeutically effective amount of a drug useful for treating hemophilia can be the amount that is capable of preventing or relieving one or more symptoms associated with hemophilia. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, the terms "patient" and "subject" are used interchangeably and refer to a mammal (preferably human) that has a disease or has the potential of contracting a disease.

As used herein, the term "about" denotes an approximate range of plus or minus 10% from a specified value. For instance, the language "about 20%" encompasses a range of 18-22%.

As used herein, the term "half-life" refers to the period of time it takes for the amount of a substance undergoing decay (or clearance from a sample or from a patient) to decrease by half.

I. Recombinant von Willebrand Factor (rVWF)

The present invention utilizes compositions comprising von Willebrand Factor (rVWF) for pretreatment of subject with severe VWD who are undergoing a surgical procedure, such as, but not limited to, major surgery, minor surgery, or oral surgery.

In certain embodiments, VWF proteins of the invention may comprise a construct, for example, prepared as in WO 1986/06096 published on Oct. 23, 1986 and U.S. patent application Ser. No. 07/559,509, filed on Jul. 23, 1990, in the name of Ginsburg et al., which is incorporated herein by reference with respect to the methods of producing recombinant VWF. The VWF useful for the present invention includes all potential forms, including the monomeric and multimeric forms. One particularly useful form of VWF are homo-multimers of at least two VWFs. The VWF proteins may be either a biologically active derivative, or when to be used solely as a stabilizer for FVIII the VWF may be of a form not biologically active. It should also be understood that the present invention encompasses different forms of VWF to be used in combination. For example, a composition useful for the present invention may include different multimers, different derivatives and both biologically active derivatives and derivatives not biologically active.

In primary hemostasis VWF serves as a bridge between platelets and specific components of the extracellular matrix, such as collagen. The biological activity of VWF in this process can be measured by different in vitro assays (Turecek et al., Semin. Thromb. Hemost. 28: 149-160, 2002). The ristocetin cofactor assay is based on the agglutination of fresh or formalin-fixed platelets induced by the antibiotic ristocetin in the presence of VWF.

The degree of platelet agglutination depends on the VWF concentration and can be measured by the turbidimetric method, e.g. by use of an aggregometer (Weiss et al., J. Clin. Invest. 52: 2708-2716, 1973; Macfarlane et al., Thromb. Diath. Haemorrh. 34: 306-308, 1975). The second method is the collagen binding assay, which is based on ELISA technology (Brown et Bosak, Thromb. Res. 43: 303-311, 1986; Favaloro, Thromb. Haemost. 83: 127-135, 2000). A microtiter plate is coated with type I or III collagen. Then the VWF is bound to the collagen surface and subsequently detected with an enzyme-labeled polyclonal antibody. The last step is the substrate reaction, which can be photometrically monitored with an ELISA reader. As provided herein, the specific Ristocetin Cofactor activity of the VWF (VWF: RCo) of the present invention is generally described in terms of mU/μg of VWF, as measured using in vitro assays.

An advantage of the rVWF compositions of the present invention over pdVWF is that rVWF exhibits a higher specific activity than pdVWF. In some embodiments, the rVWF of the invention has a specific activity of at least about 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 82.5, 85, 87.5, 90, 92.5, 95, 97.5, 100, 105, 110, 115, 120, 125, 130, 135, 140, 145, 150 or more mU/μg.

The rVWF of the present invention is highly multimeric comprising about 10 to about 40 subunits. In further embodiments, the multimeric rVWF produced using methods of the present invention comprise about 10-30, 12-28, 14-26, 16-24, 18-22, 20-21 subunits. In further embodiments, the rVWF is present in multimers varying in size from dimers to multimers of over 40 subunits (>10 million Daltons). The largest multimers provide multiple binding sites that can interact with both platelet receptors and subendothelial matrix sites of injury, and are the most hemostatically active form of VWF. Application of ADAMTS13 will cleave the ultra-large rVWF multimers over time, but during production (generally through expression in cell culture), rVWF compositions of the present invention are generally not exposed to ADAMTS13 and retain their highly multimeric structure.

In one embodiment, a rVWF composition used in the methods described herein has a distribution of rVWF oligomers characterized in that 95% of the oligomers have between 6 subunits and 20 subunits. In other embodiments, the a rVWF composition has a distribution of rVWF oligomers characterized in that 95% of the oligomers have a range of subunits selected from variations 458 to 641 found in Table 2 of WO 2012/171031, which is herein incorporated by reference in its entirety for all purposes.

In one embodiment, a rVWF composition can be characterized according to the percentage of rVWF molecules that are present in a particular higher order rVWF multimer or larger multimer. For example, in one embodiment, at least 20% of rVWF molecules in a rVWF composition used in the methods described herein are present in an oligomeric complex of at least 10 subunits. In another embodiment, at least 20% of rVWF molecules in a rVWF composition used in the methods described herein are present in an oligomeric complex of at least 12 subunits. In yet other embodiments, a rVWF composition used in the methods provided herein has a minimal percentage (e.g., has at least X %) of rVWF molecules present in a particular higher-order rVWF multimer or larger multimer (e.g., a multimer of at least Y subunits) according to any one of variations 134 to 457 found in Table 3 to Table 5, which is herein incorporated by reference in its entirety for all purposes.

In accordance with the above, the rVWF composition administered to the subject (with or without FVIII) generally comprises a significant percentage of high molecular weight (HMW) rVWF multimers. In further embodiments, the HMW rVWF multimer composition comprises at least 10%-80% rVWF decamers or higher order multimers. In further embodiments, the composition comprises about 10-95%, 20-90%, 30-85%, 40-80%, 50-75%, 60-70% decamers or higher order multimers. In further embodiments, the HMW rVWF multimer composition comprises at least about 10%, 20%, 30%, 40%, 50%, 60%, 70%, 80%, 90% decamers or higher order multimers.

Assessment of the number and percentage of rVWF multimers can be conducted using methods known in the art, including without limitation methods using electrophoresis and size exclusion chromatography methods to separate VWF multimers by size, for example as discussed by Cumming et al, (J Clin Pathol. 1993 May; 46(5): 470-473, which is hereby incorporated by reference in its entirety for all purposes and in particular for all teachings related to assessment of VWF multimers). Such techniques may further include immunoblotting techniques (such as Western Blot), in which the gel is immunoblotted with a radiolabeled antibody against VWF followed by chemiluminescent detection (see for example Wen et al., (1993), J. Clin. Lab. Anal., 7: 317-323, which is hereby incorporated by reference in its entirety for all purposes and in particular for all teachings related to assessment of VWF multimers). Further assays for VWF include VWF:Antigen (VWF:Ag), VWF: Ristocetin Cofactor (VWF:RCof), and VWF:Collagen Binding Activity assay (VWF:CBA), which are often used for diagnosis and classification of Von Willebrand Disease. (see for example Favaloro et al., Pathology, 1997, 29(4): 341-456, which is hereby incorporated by reference in its entirety for all purposes and in particular for all teachings related to assays for VWF).

In further embodiments, higher order rVWF multimers of the invention are stable for about 1 to about 90 hours post-administration. In still further embodiments, the higher order rVWF multimers are stable for about 5-80, 10-70, 15-60, 20-50, 25-40, 30-35 hours post-administration. In yet further embodiments, the higher order rVWF multimers are stable for at least 3, 6, 12, 18, 24, 36, 48, 72 hours post-administration. In certain embodiments the stability of the rVWF multimers is assessed in vitro.

In one embodiment, higher order rVWF multimers used in the compositions and methods provided herein have a half-life of at least 12 hour post administration. In another embodiment, the higher order rVWF multimers have a half-life of at least 24 hour post administration. In yet other embodiments, the higher order rVWF multimers have a half-life selected from variations 642 to 1045 found in Table 6 of WO 2012/171031, which is herein incorporated by reference in its entirety for all purposes.

In specific aspects, the rVWF (recombinant or plasma derived) used in accordance with the present invention are not modified with any conjugation, post-translation or covalent modifications. In particular embodiments, the rVWF of the present invention is not modified with a water soluble polymer, including without limitation, a polyethylene glycol (PEG), a polypropylene glycol, a polyoxyalkylene, a poly-sialic acid, hydroxyl ethyl starch, a poly-carbohydrate moiety, and the like.

In other aspects, the rVWF (recombinant or plasma derived) used in accordance with the present invention is modified through conjugation, post-translation modification, or covalent modification, including modifications of the N- or C-terminal residues as well as modifications of selected side chains, for example, at free sulfhydryl-groups, primary amines, and hydroxyl-groups. In one embodiment, a water soluble polymer is linked to the protein (directly or via a linker) by a lysine group or other primary amine. In one embodiment, the rVWF proteins of the present invention may be modified by conjugation of a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

Water soluble polymers that may be used to modify the rVWF and/or FVIII include linear and branched structures. The conjugated polymers may be attached directly to the coagulation proteins of the invention, or alternatively may be attached through a linking moiety. Non-limiting examples of protein conjugation with water soluble polymers can be found in U.S. Pat. Nos. 4,640,835; 4,496,689; 4,301,144; 4,670,417; 4,791,192, and 4,179,337, as well as in Abuchowski and Davis "Enzymes as Drugs," Holcenberg and Roberts, Eds., pp. 367 383, John Wiley and Sons, New York (1981), and Hermanson G., Bioconjugate Techniques 2nd Ed., Academic Press, Inc. 2008.

Protein conjugation may be performed by a number of well-known techniques in the art, for example, see Hermanson G., Bioconjugate Techniques 2nd Ed., Academic Press, Inc. 2008. Examples include linkage through the peptide bond between a carboxyl group on one of either the coagulation protein or water-soluble polymer moiety and an amine group of the other, or an ester linkage between a carboxyl group of one and a hydroxyl group of the other. Another linkage by which a coagulation protein of the invention could be conjugated to a water-soluble polymer compound is via a Schiff base, between a free amino group on the polymer moiety being reacted with an aldehyde group formed at the non-reducing end of the polymer by periodate oxidation (Jennings and Lugowski, J. Immunol. 1981; 127: 1011-8; Fernandes and Gregonradis, Biochim Biophys Acta. 1997; 1341; 26-34). The generated Schiff Base can be stabilized by specific reduction with NaCNBH3 to form a secondary amine. An alternative approach is the generation of terminal free amino groups on the polymer by reductive amination with NH₄Cl after prior oxidation. Bifunctional reagents can be used for linking two amino or two hydroxyl groups. For example a polymer containing an amino group can be coupled to an amino group of the coagulation protein with reagents like BS3 (Bis(sulfosuccinimidyl)suberate/ Pierce, Rockford, Ill.). In addition heterobifunctional cross linking reagents like Sulfo-EMCS (N-.epsilon.-Maleimido-caproyloxy) sulfosuccinimide ester/Pierce) can be used for instance to link amine and thiol groups. In other embodiments, an aldehyde reactive group, such as PEG alkoxide plus diethyl acetal of bromoacetaldehyde; PEG plus DMSO and acetic anhydride, and PEG chloride plus the phenoxide of 4-hydroxybenzaldehyde, succinimidyl active esters, activated dithiocarbonate PE.G., 2,4,5-trichlorophenylclorofor-mate and P-nitrophenylcloroformate activated PE.G., may be used in the conjugation of a coagulation protein.

In some aspects, the rVWF used in methods of the present invention has been matured in vitro with furin. In further embodiments, the furin is recombinant furin.

In further aspects, the rVWF used in the methods of the present invention are produced by expression in a mammalian cell culture using methods known in the art. In particular embodiments, the mammalian culture comprises CHO cells. In an exemplary embodiment, the rVWF of the invention comprises rVWF protein isolated from a CHO cell expression system. In a further embodiment, the propeptide removal is mediated in vitro through exposure of the pro-VWF to furin—in a still further embodiment, the Furin used for propeptide removal is recombinant furin. In as yet further embodiment, fully glycosylated/ABO blood group glycans are absent.

In yet further embodiments, the rVWF used in methods and compositions of the present invention by expression in a suitable eukaryotic host system. Examples of eukaryotic cells include, without limitation, mammalian cells, such as CHO, COS, HEK 293, BHK, SK-Hep, and HepG2; insect cells, e.g., SF9 cells, SF21 cells, S2 cells, and High Five cells; and yeast cells, e.g., *Saccharomyces* or *Schizosaccha-romyces* cells. In one embodiment, the VWF can be expressed in yeast cells, insect cells, avian cells, mammalian cells, and the like. For example, in a human cell line, a hamster cell line, or a murine cell line. In one particular embodiment, the cell line is a CHO, BHK, or HEK cell line. Typically, mammalian cells, e.g., CHO cell from a continuous cell line, can be used to express the VWF of the present invention.

In certain embodiments, the nucleic acid sequence comprising a sequence coding for VWF can be a vector. The vector can be delivered by a virus or can be a plasmid. The nucleic acid sequence coding for the protein can be a specific gene or a biologically functional part thereof. In one embodiment, the protein is at least a biologically active part of VWF. A wide variety of vectors can be used for the expression of the VWF and can be selected from eukaryotic expression vectors. Examples of vectors for eukaryotic expression include: (i) for expression in yeast, vectors such as pAO, pPIC, pYES, pMET, using promoters such as AOX1, GAP, GAL1, AUG1, etc.; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

In some embodiments of the present invention, the nucleic acid sequence further comprises other sequences suitable for a controlled expression of a protein such as promoter sequences, enhancers, TATA boxes, transcription initiation sites, polylinkers, restriction sites, poly-A-sequences, protein processing sequences, selection markers, and the like which are generally known to a person of ordinary skill in the art.

In certain embodiments, the cell-culture methods of the invention may comprise the use of a microcarrier. In some embodiments, the cell-cultures of the embodiments can be performed in large bioreactors under conditions suitable for providing high volume-specific culture surface areas to achieve high cell densities and protein expression. One means for providing such growth conditions is to use microcarriers for cell-culture in stirred tank bioreactors. The concept of cell-growth on microcarriers was first described by van Wezel (van Wezel, A. L., Nature 216:64-5 (1967)) and allows for cell attachment on the surface of small solid particles suspended in the growth medium. These methods provide for high surface-to-volume ratios and thus allow for efficient nutrient utilization. Furthermore, for expression of secreted proteins in eukaryotic cell lines, the increased surface-to-volume ratio allows for higher levels of secretion and thus higher protein yields in the supernatant of the culture. Finally, these methods allow for the easy scale-up of eukaryotic expression cultures.

The cells expressing VWF can be bound to a spherical or a porous microcarrier during cell culture growth. The microcarrier can be a microcarrier selected from the group of microcarriers based on dextran, collagen, plastic, gelatine and cellulose and others as described in Butler (1988. In: Spier & Griffiths, Animal Cell Biotechnology 3:283-303). It is also possible to grow the cells to a biomass on spherical microcarriers and subculture the cells when they have reached final fermenter biomass and prior to production of the expressed protein on a porous microcarrier or vice versa. Suitable spherical microcarriers can include smooth surface microcarriers, such as Cytodex™ 1, Cytodex™ 2, and Cytode™ 3 (GE Healthcare) and macroporous microcarriers such as Cytopore™. 1, Cytopore™ 2, Cytoline™ 1, and Cytoline™ 2 (GE Healthcare).

In certain embodiments, rVWF is expressed in cells cultured in cell culture media that produces high molecular weight rVWF. The terms "cell culture solution," "cell culture medium or media," and "cell culture supernatant" refer to aspects of cell culture processes generally well known in the art. In the context of the present invention, a cell culture solution can include cell culture media and cell culture supernatant. The cell culture media are externally added to the cell culture solution, optionally together with supplements, to provide nutrients and other components for culturing the cells expressing VWF. The cell culture supernatant refers to a cell culture solution comprising the nutrients and other components from the cell culture medium as well as products released, metabolized, and/or excreted from the cells during culture. In further embodiments, the media can be animal protein-free and chemically defined. Methods of preparing animal protein-free and chemically defined culture media are known in the art, for example in US 2008/0009040 and US 2007/0212770, which are both incorporated herein for all purposes and in particular for all teachings related to cell culture media. "Protein free" and related terms refers to protein that is from a source exogenous to or other than the cells in the culture, which naturally shed proteins during growth. In another embodiment, the culture medium is polypeptide free. In another embodiment, the culture medium is serum free. In another embodiment the culture medium is animal protein free. In another embodiment the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal. The term "chemically defined" as used herein shall mean, that the medium does not comprise any undefined supplements, such as, for example, extracts of animal components, organs, glands, plants, or yeast. Accordingly, each component of a chemically defined medium is accurately defined. In a preferred embodiment, the media are animal-component free and protein free.

In further embodiments, subsequent to purification from a mammalian cell culture, rFVIII is reconstituted prior to administration. In still further embodiments, the rVWF is treated with furin prior to or subsequent to reconstitution. In further embodiments, the Furin is recombinant furin. In still further embodiments, the rVWF of the invention is not exposed to ADAMTS13, with the result that ultra large (i.e., comprising 10 or more subunits) are present in rVWF compositions of the invention.

In specific aspects, the rVWF used in methods of the present invention is contained in a formulation containing a buffer, a sugar and/or a sugar alcohol (including without limitation trehalose and mannitol), a stabilizer (such as glycine), and a surfactant (such as polysorbate 80). In further embodiments, for formulations containing rFVIII, the formulation may further include sodium, histidine, calcium, and glutathione.

In one aspect, the formulations comprising rVWF is lyophilized prior to administration. Lyophilization is carried out using techniques common in the art and should be optimized for the composition being developed [Tang et al., Pharm Res. 21:191-200. (2004) and Chang et al., Pharm Res. 13:243-9 (1996)].

Methods of preparing pharmaceutical formulations can include one or more of the following steps: adding a stabilizing agent as described herein to said mixture prior to lyophilizing, adding at least one agent selected from a bulking agent, an osmolarity regulating agent, and a surfactant, each of which as described herein, to said mixture prior to lyophilization. A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration [Chen, Drug Development and Industrial Pharmacy, 18:1311-1354 (1992)]. Accordingly, methods are provided for preparation of reconstituted recombinant VWF compositions comprising the step of adding a diluent to a lyophilized recombinant VWF composition of the invention.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

In certain embodiments, compositions of the present invention are liquid formulations for administration with the use of a syringe or other storage vessel. In further embodiments, these liquid formulations are produced from lyophilized material described herein reconstituted as an aqueous solution.

In a further aspect, the compositions of the invention further comprise one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

II. Production of Recombinant VWF

The free mature recombinant von Willebrand Factor (rVWF) of the present invention can be produced recombinantly. One skilled in the art recognizes useful methods for expressing a recombinant protein in a host cell. In some instances, the method includes expressing a nucleic acid sequence encoding rVWF in a host cell such as a CHO cell and culturing the resulting host cell under certain conditions to produce rVWF, prepro-VWF, pro-VWF, and the like.

In certain embodiments, the nucleic acid sequence comprising a sequence coding for VWF can be an expression vector. The vector can be delivered by a virus or can be a plasmid. The nucleic acid sequence coding for the protein can be a specific gene or a biologically functional part thereof. In one embodiment, the protein is at least a biologically active part of VWF. The nucleic acid sequence can further comprise other sequences suitable for a controlled expression of a protein such as promoter sequences, enhancers, TATA boxes, transcription initiation sites, polylinkers, restriction sites, poly-A-sequences, protein processing sequences, selection markers, and the like which are generally known to a person of ordinary skill in the art.

A wide variety of vectors can be used for the expression of the VWF and can be selected from eukaryotic expression vectors. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

In some aspects, the rVWF used in the methods of the present invention is produced by expression in a mammalian cell culture using methods known in the art. In particular embodiments, the mammalian culture comprises CHO cells. In further embodiments, the rVWF is co-expressed with recombinant Factor VIII (rFVIII) in the same culture. In such embodiments, the rVWF and the rFVIII are purified together (co-purified) or separately using methods known in the art. In other embodiments, the rVWF is expressed in a culture that does not contain rFVIII.

In some embodiments, rVWF is expressed and isolated from a suitable eukaryotic host system. Examples of eukaryotic cells include, without limitation, mammalian cells, such as CHO, COS, HEK 293, BHK, SK-Hep, and HepG2; insect cells, e.g., SF9 cells, SF21 cells, S2 cells, and High Five cells; and yeast cells, e.g., *Saccharomyces* or *Schizosaccharomyces* cells. In one embodiment, the VWF can be expressed in yeast cells, insect cells, avian cells, mammalian cells, and the like. For example, in a human cell line, a hamster cell line, or a murine cell line. In one particular embodiment, the cell line is a CHO, BHK, or HEK cell line. Typically, mammalian cells, e.g., CHO cell from a continuous cell line, can be used to express the VWF of the present invention. In certain instances, VWF protein is expressed and isolated from a CHO cell expression system.

VWF can be produced in a cell culture system or according to any cell culture method recognized by those in the art. In some embodiments, the cell cultures can be performed in large bioreactors under conditions suitable for providing high volume-specific culture surface areas to achieve high cell densities and protein expression. One means for providing such growth conditions is to use microcarriers for cell-culture in stirred tank bioreactors. The concept of cell-growth on microcarriers was first described by van Wezel (van Wezel, A. L., Nature, 1967, 216:64-5) and allows for cell attachment on the surface of small solid particles suspended in the growth medium. These methods provide for high surface-to-volume ratios and thus allow for efficient nutrient utilization. Furthermore, for expression of secreted proteins in eukaryotic cell lines, the increased surface-to-volume ratio allows for higher levels of secretion and thus higher protein yields in the supernatant of the culture. Finally, these methods allow for the easy scale-up of eukaryotic expression cultures.

The cells expressing VWF can be bound to a spherical or a porous microcarrier during cell culture growth. The microcarrier can be a microcarrier selected from the group of microcarriers based on dextran, collagen, plastic, gelatine and cellulose and others as described in Butler (1988. In: Spier & Griffiths, Animal Cell Biotechnology 3:283-303). It is also possible to grow the cells to a biomass on spherical microcarriers and subculture the cells when they have reached final fermenter biomass and prior to production of the expressed protein on a porous microcarrier or vice versa. Suitable spherical microcarriers can include smooth surface microcarriers, such as Cytodex™ 1, Cytodex™ 2, and Cytodex™ 3 (GE Healthcare) and macroporous microcarriers such as Cytopore™ 1, Cytopore™ 2, Cytoline™ 1, and Cytoline™ 2 (GE Healthcare).

In a further embodiment, the VWF propeptide is cleaved from the non-mature VWF in vitro through exposure of the pro-VWF to furin. In some embodiments, the furin used for propeptide cleavage is recombinant furin.

In certain embodiments, rVWF is expressed in cells cultured in cell culture media that produces high molecular weight rVWF. The terms "cell culture solution," "cell culture medium or media," and "cell culture supernatant" refer to aspects of cell culture processes generally well known in the art. In the context of the present invention, a cell culture solution can include cell culture media and cell culture supernatant. The cell culture media are externally added to the cell culture solution, optionally together with supplements, to provide nutrients and other components for culturing the cells expressing VWF. The cell culture supernatant refers to a cell culture solution comprising the nutrients and other components from the cell culture medium as well as products released, metabolized, and/or excreted from the cells during culture. In further embodiments, the media can be animal protein-free and chemically defined. Methods of preparing animal protein-free and chemically defined culture media are known in the art, for example in US 2006/0094104, US 2007/0212770, and US 2008/0009040, which are both incorporated herein for all purposes and in particular for all teachings related to cell culture media. "Protein free" and related terms refers to protein that is from a source exogenous to or other than the cells in the culture, which naturally shed proteins during growth. In another embodiment, the culture medium is polypeptide free. In another embodiment, the culture medium is serum free. In another embodiment the culture medium is animal protein free. In another embodiment the culture medium is animal component free. In another embodiment, the culture medium contains protein, e.g., animal protein from serum such as fetal calf serum. In another embodiment, the culture has recombinant proteins exogenously added. In another embodiment, the proteins are from a certified pathogen free animal. The term "chemically defined" as used herein shall mean, that the medium does not comprise any undefined supplements, such as, for example, extracts of animal components, organs, glands, plants, or yeast. Accordingly, each component of a chemically defined medium is accurately defined. In a preferred embodiment, the media are animal-component free and protein free.

In certain embodiments, the culture of cells expressing VWF can be maintained for at least about 7 days, or at least about 14 days, 21 days, 28 days, or at least about 5 weeks, 6 weeks, 7 weeks, or at least about 2 months, or 3, 4, 5, 6, 7, 8, 9, 10, 11, 12, 13, 14, 15, 16, 17, 18 months or longer. The cell density at which a cell-culture is maintained at for production of a recombinant VWF protein will depend upon the culture-conditions and medium used for protein expression. One of skill in the art will readily be able to determine the optimal cell density for a cell-culture producing an VWF. In one embodiment, the culture is maintained at a cell density of between about $0.5 \times 10^6$ and $4 \times 10^7$ cells/ml for an extended period of time. In other embodiments, the cell density is maintained at a concentration of between about $1.0 \times 10^6$ and about $1.0 \times 10^7$ cells/ml for an extended period of time. In other embodiments, the cell density is maintained at a concentration of between about $1.0 \times 10^6$ and about $4.0 \times 10^6$ cells/ml for an extended period of time. In other embodiments, the cell density is maintained at a concentration of between about $1.0 \times 10^6$ and about $4.0 \times 10^6$ cells/ml for an extended period of time. In yet other embodiments, the cell density may be maintained at a concentration between about $2.0 \times 10^6$ and about $4.0 \times 10^6$, or between about $1.0 \times 10^6$ and about $2.5 \times 10^6$, or between about $1.5 \times 10^6$ and about $3.5 \times 10^6$, or any other similar range, for an extended period of time. After an appropriate time in cell culture, the rVWF can be isolated from the expression system using methods known in the art.

In a specific embodiment, the cell density of the continuous cell culture for production of rVWF is maintained at a concentration of no more than $2.5 \times 10^6$ cells/mL for an extended period. In other specific embodiments, the cell density is maintained at no more than $2.0 \times 10^6$ cells/mL, $1.5 \times 10^6$ cells/mL, $1.0 \times 10^6$ cells/mL, $0.5 \times 10^6$ cells/mL, or less. In one embodiment, the cell density is maintained at between $1.5 \times 10^6$ cells/mL and $2.5 \times 10^6$ cells/mL.

In one embodiment of the cell cultures described above, the cell culture solution comprises a medium supplement comprising copper. Such cell culture solutions are described, for example, in U.S. Pat. Nos. 8,852,888 and 9,409,971, which is hereby incorporated by reference in its entirety for all purposes and in particular for all teachings related to cell culture methods and compositions for producing recombinant VWF.

The polynucleotide and amino acid sequences of prepro-VWF are set out in SEQ ID NO:1 and SEQ ID NO:2, respectively, and are available at GenBank Accession Nos. NM_000552 (*Homo sapiens* von Willebrand factor (VWF) mRNA) and NP_000543, respectively. The amino acid sequence corresponding to the mature VWF protein is set out in SEQ ID NO: 3 (corresponding to amino acids 764-2813 of the full length prepro-VWF amino acid sequence). In some embodiments, the VWF exhibits at least 80%, at least 85%, at least 90%, at least 95%, at least 96%, at least 97%, at least 98%, at least 99%, or at least 100% identity to the sequence of SEQ ID NO:3. In some embodiments, the rVWF of the invention exhibits at least 80%, at least 85%, at least 90%, at least 95%, at least 96%, at least 97%, at least 98%, at least 99%, or at least 100% identity to the sequence of SEQ ID NO:3. See, for example, U.S. Pat. No. 8,597,910, U.S. Patent Publication No. 2016/0129090, as well as FIG. 6.

One form of useful rVWF has at least the property of in vivo-stabilizing, e.g. binding, of at least one Factor VIII (FVIII) molecule and having optionally a glycosylation pattern which is pharmacologically acceptable. Specific examples thereof include VWF without the A2 domain thus resistant to proteolysis (Lankhof et al., Thromb. Haemost. 77: 1008-1013, 1997), and a VWF fragment from Val 449 to Asn 730 including the glycoprotein lb-binding domain and binding sites for collagen and heparin (Pietu et al., Biochem. Biophys. Res. Commun. 164: 1339-1347, 1989). The determination of the ability of a VWF to stabilize at least one FVIII molecule is, in one aspect, carried out in VWF-deficient mammals according to methods known in the state in the art.

The rVWF of the present invention can be produced by any method known in the art. One specific example is disclosed in WO86/06096 published on Oct. 23, 1986 and U.S. patent application Ser. No. 07/559,509, filed on Jul. 23, 1990, which is incorporated herein by reference with respect to the methods of producing recombinant VWF. Thus, methods are known in the art for (i) the production of recombinant DNA by genetic engineering, e.g. via reverse transcription of RNA and/or amplification of DNA, (ii) introducing recombinant DNA into prokaryotic or eukaryotic cells by transfection, e.g. via electroporation or microinjection, (iii) cultivating the transformed cells, e.g. in a continuous or batchwise manner, (iv) expressing VWF, e.g. constitutively or upon induction, and (v) isolating the VWF, e.g. from the culture medium or by harvesting the transformed cells, in order to (vi) obtain purified rVWF, e.g. via anion exchange chromatography or affinity chromatography. A recombinant VWF is, in one aspect, made in transformed host cells using recombinant DNA techniques well known in the art. For instance, sequences coding for the polypeptide could be excised from DNA using suitable restriction enzymes. Alternatively, the DNA molecule is, in another aspect, synthesized using chemical synthesis techniques, such as the phosphoramidate method. Also, in still another aspect, a combination of these techniques is used.

The invention also provides vectors encoding polypeptides of the invention in an appropriate host. The vector comprises the polynucleotide that encodes the polypeptide operatively linked to appropriate expression control sequences. Methods of effecting this operative linking, either before or after the polynucleotide is inserted into the vector, are well known. Expression control sequences include promoters, activators, enhancers, operators, ribosomal binding sites, start signals, stop signals, cap signals, polyadenylation signals, and other signals involved with the control of transcription or translation. The resulting vector having the polynucleotide therein is used to transform an appropriate host. This transformation may be performed using methods well known in the art.

Any of a large number of available and well-known host cells are used in the practice of this invention. The selection of a particular host is dependent upon a number of factors recognized by the art, including, for example, compatibility with the chosen expression vector, toxicity of the peptides encoded by the DNA molecule, rate of transformation, ease of recovery of the peptides, expression characteristics, biosafety and costs. A balance of these factors must be struck with the understanding that not all host cells are equally effective for the expression of a particular DNA sequence. Within these general guidelines, useful microbial host cells include, without limitation, bacteria, yeast and other fungi, insects, plants, mammalian (including human) cells in culture, or other hosts known in the art.

Transformed host cells are cultured under conventional fermentation conditions so that the desired compounds are expressed. Such fermentation conditions are well known in the art. Finally, the polypeptides are purified from culture media or the host cells themselves by methods well known in the art.

Depending on the host cell utilized to express a compound of the invention, carbohydrate (oligosaccharide) groups are optionally attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids not counting proline. The structures of N-linked and O-linked oligosaccharides and the sugar residues found in each type are different. One type of sugar that is commonly found on both N-linked and O-linked oligosaccharides is N-acetylneuraminic acid (referred to as sialic acid). Sialic acid is usually the terminal residue of both N-linked and O-linked oligosaccharides and, by virtue of its negative charge, in one aspect, confers acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). In other aspects, such sites are glycosylated by synthetic or semi-synthetic procedures known in the art.

In some embodiments, sialysation (also referred to as sialylation), can be performed on the column as part of the purification procedures described herein (including the anion exchange, cation exchange, size exclusion, and/or immunoaffinity methods). In some embodiments, the sialylation results in increased stability of the rVWF as compared to rVWF that has not undergone sialylation. In some embodiments, the sialylation results in increased stability of the rVWF in blood circulation (for example, after administration to a subject) as compared to rVWF that has not undergone sialylation. In some embodiments, the increased stability of salivated rVWF results in an increase of 10%, 20%, 30%, 40%, 50%, 60%, 70%, 80%, 90%, or more as compared rVWF that has not undergone sialylation. In some embodiments, the sialylation results in increased half-life for the rVWF as compared to rVWF that has not undergone sialylation. In some embodiments, the sialylation results in increased half-life for the rVWF in blood circulation (for example, after administration to a subject) as compared to rVWF that has not undergone sialylation. In some embodiments, the increased half-life of sialylated rVWF results in an increase of 10%, 20%, 30%, 40%, 50%, 60%, 70%, 80%, 90%, or more as compared rVWF that has not undergone sialylation. In some embodiments, the increased half-life of sialylated rVWF results in rVWF that is stable for 1 hour, 2 hours, 3 hours, 4 hours, 6 hours, 12 hours, 24 hours or more in blood circulation (for example, after administration to a subject) as compared to rVWF that has not undergone sialylation. In some embodiments, sialylation increases the number of 2,3 sialylation and/or 2,6 sialylation. In some embodiments, sialylation is increased by the addition of 2,3 sialyltransferase and/or 2,6 sialyltransferase and CMP-NANA (Cytidine-5'-monophospho-N-acetylneuraminic acid sodium salt) as an additional buffer step. In some embodiments, sialylation is increased by the addition of 2,3 sialyltransferase and CMP-NANA (Cytidine-5'-monophospho-N-acetylneuraminic acid sodium salt) as an additional buffer step. In some embodiments, 2,3 sialylation is increased by the addition of 2,3 sialyltransferase and CMP-NANA (Cytidine-5'-monophospho-N-acetylneuraminic acid sodium salt) as an additional buffer step.

In some embodiments, 2,6 sialylation is increased by the addition of 2,6 sialyltransferase and CMP-NANA (Cytidine-5'-monophospho-N-acetylneuraminic acid sodium salt) as an additional buffer step. In some embodiments, 2,3 sialylation and/or 2,6 sialylation are increased by the addition of 2,3 sialyltransferase and/or 2,6 sialyltransferase and CMP-NANA (Cytidine-5'-monophospho-N-acetylneuraminic acid sodium salt) as an additional buffer step. In some embodiments, CMP-NANA is chemically or enzymatic modified to transfer modified sialic acid to potential free position. In some embodiments, sialylation is performed by loading rVWF onto the resin, washing with one or more buffers as described herein to deplete unwanted impurities, apply one or more buffers containing sialyltransferase and CMP-NANA at conditions that allow additional sialylation, and washing with one or more buffers to deplete excess of the sialylation reagents, and eluting with one or more buffers the enhanced rVWF (e.g., the rVWF with increased sialylation). In some embodiments, the sialylation process is performed as part of a cation exchange method, an anion exchange method, a size exclusion method, or an immunoaffinity purification method, as described herein.

Alternatively, the compounds are made by synthetic methods using, for example, solid phase synthesis techniques. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941, 763; Finn et al. (1976), The Proteins (3rd ed.) 2: 105-253; and Erickson et al. (1976), The Proteins (3rd ed.) 2: 257-527'. Solid phase synthesis is the preferred technique of making individual peptides since it is the most cost-effective method of making small peptides Fragments, variants and analogs of VWF can be produced according to methods that are well-known in the art. Fragments of a polypeptide can be prepared using, without limitation, enzymatic cleavage (e.g., trypsin, chymotrypsin) and also using recombinant means to generate a polypeptide fragments having a specific amino acid sequence. Polypeptide fragments may be generated comprising a region of the protein having a particular activity, such as a multimerization domain or any other identifiable VWF domain known in the art.

Methods of making polypeptide analogs are also well-known. Amino acid sequence analogs of a polypeptide can be substitutional, insertional, addition or deletion analogs. Deletion analogs, including fragments of a polypeptide, lack one or more residues of the native protein which are not essential for function or immunogenic activity. Insertional analogs involve the addition of, e.g., amino acid(s) at a non-terminal point in the polypeptide. This analog may include, for example and without limitation, insertion of an immunoreactive epitope or simply a single residue. Addition analogs, including fragments of a polypeptide, include the addition of one or more amino acids at either or both termini of a protein and include, for example, fusion proteins. Combinations of the aforementioned analogs are also contemplated.

Substitutional analogs typically exchange one amino acid of the wild-type for another at one or more sites within the protein, and may be designed to modulate one or more properties of the polypeptide without the complete loss of other functions or properties. In one aspect, substitutions are conservative substitutions. "Conservative amino acid substitution" is substitution of an amino acid with an amino acid having a side chain or a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine).

In one aspect, analogs are substantially homologous or substantially identical to the recombinant VWF from which they are derived. Analogs include those which retain at least some of the biological activity of the wild-type polypeptide, e.g. blood clotting activity.

Polypeptide variants contemplated include, without limitation, polypeptides chemically modified by such techniques as ubiquitination, glycosylation, including polysialation (or polysialylation), conjugation to therapeutic or diagnostic agents, labeling, covalent polymer attachment such as pegylation (derivatization with polyethylene glycol), introduction of non-hydrolyzable bonds, and insertion or substitution by chemical synthesis of amino acids such as ornithine, which do not normally occur in human proteins. Variants retain the same or essentially the same binding properties of non-modified molecules of the invention. Such chemical modification may include direct or indirect (e.g., via a linker) attachment of an agent to the VWF polypeptide. In the case of indirect attachment, it is contemplated that the linker may be hydrolyzable or non-hydrolyzable.

Preparing pegylated polypeptide analogs will in one aspect comprise the steps of (a) reacting the polypeptide with polyethylene glycol (such as a reactive ester or aldehyde derivative of PEG) under conditions whereby the binding construct polypeptide becomes attached to one or more PEG groups, and (b) obtaining the reaction product(s). In general, the optimal reaction conditions for the acylation reactions are determined based on known parameters and the desired result. For example, the larger the ratio of PEG:protein, the greater the percentage of poly-pegylated product. In some embodiments, the binding construct has a single PEG moiety at the N-terminus. Polyethylene glycol (PEG) may be attached to the blood clotting factor to, for example, provide a longer half-life in vivo. The PEG group may be of any convenient molecular weight and is linear or branched. The average molecular weight of the PEG ranges from about 2 kiloDalton ("kD") to about 100 kDa, from about 5 kDa to about 50 kDa, or from about 5 kDa to about 10 kDa. In certain aspects, the PEG groups are attached to the blood clotting factor via acylation or reductive alkylation through a natural or engineered reactive group on the PEG moiety (e.g., an aldehyde, amino, thiol, or ester group) to a reactive group on the blood clotting factor (e.g., an aldehyde, amino, or ester group) or by any other technique known in the art.

Methods for preparing polysialylated polypeptide are described in United States Patent Publication 20060160948, Fernandes et Gregoriadis; Biochim. Biophys. Acta 1341: 26-34, 1997, and Saenko et al., Haemophilia 12:42-51, 2006. Briefly, a solution of colominic acid (CA) containing $0.1$ M $NaIO_4$ is stirred in the dark at room temperature to oxidize the CA. The activated CA solution is dialyzed against, e.g., 0.05 M sodium phosphate buffer, pH 7.2 in the dark and this solution was added to a rVWF solution and incubated for 18 h at room temperature in the dark under gentle shaking. Free reagents are optionally be separated from the rVWF-polysialic acid conjugate by, for example, ultrafiltration/diafiltration. Conjugation of rVWF with polysialic acid is achieved using glutaraldehyde as cross-linking reagent (Migneault et al., Biotechniques 37: 790-796, 2004).

It is also contemplated in another aspect that prepro-VWF and pro-VWF polypeptides will provide a therapeutic benefit in the formulations of the present invention. For example, U.S. Pat. No. 7,005,502 describes a pharmaceutical preparation comprising substantial amounts of pro-VWF that induces thrombin generation in vitro. In addition to recombinant, biologically active fragments, variants, or other analogs of the naturally-occurring mature VWF, the present invention contemplates the use of recombinant biologically active fragments, variants, or analogs of the prepro-VWF (set out in SEQ ID NO:2) or pro-VWF polypeptides (amino acid residues 23 to 764 of SEQ ID NO: 2) in the formulations described herein.

Polynucleotides encoding fragments, variants and analogs may be readily generated by a worker of skill to encode biologically active fragments, variants, or analogs of the naturally-occurring molecule that possess the same or similar biological activity to the naturally-occurring molecule. In various aspects, these polynucleotides are prepared using PCR techniques, digestion/ligation of DNA encoding molecule, and the like. Thus, one of skill in the art will be able to generate single base changes in the DNA strand to result in an altered codon and a missense mutation, using any method known in the art, including, but not limited to site-specific mutagenesis. As used herein, the phrase "moderately stringent hybridization conditions" means, for example, hybridization at 42° C. in 50% formamide and washing at 60° C. in 0.1×SSC, 0.1% SDS. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47-9.51 in Molecular Cloning, Cold Spring Harbor Laboratory Press, Cold Spring Harbor, New York (1989).

A. VWF Multimers

Assessment of the number and percentage of rVWF multimers can be conducted using methods known in the art, including without limitation methods using electrophoresis and size exclusion chromatography methods to separate VWF multimers by size, for example as discussed by Cumming et al., (J Clin Pathol., 1993 May; 46(5): 470-473, which is hereby incorporated by reference in its entirety for all purposes and in particular for all teachings related to assessment of VWF multimers). Such techniques may further include immunoblotting techniques (such as Western Blot), in which the gel is immunoblotted with a radiolabeled antibody against VWF followed by chemiluminescent detection (see, for example, Wen et al., J. Clin. Lab. Anal., 1993, 7: 317-323, which is hereby incorporated by reference in its entirety for all purposes and in particular for all teachings related to assessment of VWF multimers). Further assays for VWF include VWF:Antigen (VWF:Ag), VWF: Ristocetin Cofactor (VWF:RCof), and VWF:Collagen Binding Activity assay (VWF:CBA), which are often used for diagnosis and classification of Von Willebrand Disease (see, for example, Favaloro et al., Pathology, 1997, 29(4): 341-456; Sadler, JE, Annu Rev Biochem, 1998, 67:395-424; and Turecek et al., Semin Thromb Hemost, 2010, 36:510-521, which are hereby incorporated by reference in their entirety for all purposes and in particular for all teachings related to assays for VWF). In some embodiments, the rVWF obtained using the present methods includes any multimer pattern present in the loading sample of the rVWF. In some embodiments, the rVWF obtained using the present methods includes physiologically occurring multimer patters as well as ultralarge VWF-multimer patterns.

b. VWF Assays

In primary hemostasis VWF serves as a bridge between platelets and specific components of the extracellular matrix, such as collagen. The biological activity of VWF in this process can be measured by different in vitro assays (Turecek et al., Semin Thromb Hemost, 2010, 36: 510-521).

The VWF:Ristocetin Cofactor (VWF:RCof) assay is based on the agglutination of fresh or formalin-fixed platelets induced by the antibiotic ristocetin in the presence of VWF. The degree of platelet agglutination depends on the VWF concentration and can be measured by the turbidimetric method, e.g., by use of an aggregometer (Weiss et al., J. Clin. Invest., 1973, 52: 2708-2716; Macfarlane et al., Thromb. Diath. Haemorrh., 1975, 34: 306-308). As provided herein, the specific ristocetin cofactor activity of the VWF (VWF:RCo) of the present invention is generally described in terms of mU/μg of VWF, as measured using in vitro assays.

In some embodiments, the rVWF purified according to the methods of the present invention has a specific activity of at least about 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 82.5, 85, 87.5, 90, 92.5, 95, 97.5, 100, 105, 110, 1 15, 120, 125, 130, 135, 140, 145, 150 or more mU/μg. In some embodiments, rVWF used in the methods described herein has a specific activity of from 20 mU/μg to 150 mU/μg. In some embodiments, the rVWF has a specific activity of from 30 mU/μg to 120 mU/μg. In some embodiments, the rVWF has a specific activity from 40 mU/μg to 90 mU/μg. In some embodiments, the rVWF has a specific activity selected from variations 1 to 133 found in Table 3, below.

TABLE 3

| Exemplary embodiments for the specific activity of rVWF found in the compositions and used in the methods provided herein. | |
| --- | --- |
| (mU/μg) | |
| 20 | Var. 1 |
| 22.5 | Var. 2 |
| 25 | Var. 3 |
| 27.5 | Var. 4 |
| 30 | Var. 5 |
| 32.5 | Var. 6 |
| 35 | Var. 7 |
| 37.5 | Var. 8 |
| 40 | Var. 9 |
| 42.5 | Var. 10 |
| 45 | Var. 11 |
| 47.5 | Var. 12 |
| 50 | Var. 13 |
| 52.5 | Var. 14 |
| 55 | Var. 15 |
| 57.5 | Var. 16 |
| 60 | Var. 17 |
| 62.5 | Var. 18 |
| 65 | Var. 19 |
| 67.5 | Var. 20 |
| 70 | Var. 21 |
| 72.5 | Var. 22 |
| 75 | Var. 23 |
| 77.5 | Var. 24 |
| 80 | Var. 25 |
| 82.5 | Var. 26 |
| 85 | Var. 27 |
| 87.5 | Var. 28 |
| 90 | Var. 29 |
| 92.5 | Var. 30 |
| 95 | Var. 31 |
| 97.5 | Var. 32 |
| 100 | Var. 33 |
| 105 | Var. 34 |
| 110 | Var. 35 |
| 115 | Var. 36 |
| 120 | Var. 37 |
| 125 | Var. 38 |
| 130 | Var. 39 |
| 135 | Var. 40 |
| 140 | Var. 41 |
| 145 | Var. 42 |
| 150 | Var. 43 |
| 20-150 | Var. 44 |
| 20-140 | Var. 45 |
| 20-130 | Var. 46 |
| 20-120 | Var. 47 |
| 20-110 | Var. 48 |
| 20-100 | Var. 49 |
| 20-90 | Var. 50 |
| 20-80 | Var. 51 |
| 20-70 | Var. 52 |
| 20-60 | Var. 53 |
| 20-50 | Var. 54 |
| 20-40 | Var. 55 |
| 30-150 | Var. 56 |
| 30-140 | Var. 57 |
| 30-130 | Var. 58 |
| 30-120 | Var. 59 |
| 30-110 | Var. 60 |
| 30-100 | Var. 61 |
| 30-90 | Var. 62 |
| 30-80 | Var. 63 |
| 30-70 | Var. 64 |
| 30-60 | Var. 65 |
| 30-50 | Var. 66 |
| 30-40 | Var. 67 |
| 40-150 | Var. 68 |
| 40-140 | Var. 69 |
| 40-130 | Var. 70 |
| 40-120 | Var. 71 |
| 40-110 | Var. 72 |
| 40-100 | Var. 73 |
| 40-90 | Var. 74 |

TABLE 3-continued

Exemplary embodiments for the specific
activity of rVWF found in the compositions
and used in the methods provided herein.

(mU/µg)

| | |
|---|---|
| 40-80 | Var. 75 |
| 40-70 | Var. 76 |
| 40-60 | Var. 77 |
| 40-50 | Var. 78 |
| 50-150 | Var. 79 |
| 50-140 | Var. 80 |
| 50-130 | Var. 81 |
| 50-120 | Var. 82 |
| 50-110 | Var. 83 |
| 50-100 | Var. 84 |
| 50-90 | Var. 85 |
| 50-80 | Var. 86 |
| 50-70 | Var. 87 |
| 50-60 | Var. 88 |
| 60-150 | Var. 89 |
| 60-140 | Var. 90 |
| 60-130 | Var. 91 |
| 60-120 | Var. 92 |
| 60-110 | Var. 93 |
| 60-100 | Var. 94 |
| 60-90 | Var. 95 |
| 60-80 | Var. 96 |
| 60-70 | Var. 97 |
| 70-150 | Var. 98 |
| 70-140 | Var. 99 |
| 70-130 | Var. 100 |
| 70-120 | Var. 101 |
| 70-110 | Var. 102 |
| 70-100 | Var. 103 |
| 70-90 | Var. 104 |
| 70-80 | Var. 105 |
| 80-150 | Var. 106 |
| 80-140 | Var. 107 |
| 80-130 | Var. 108 |
| 80-120 | Var. 109 |
| 80-110 | Var. 110 |
| 80-100 | Var. 111 |
| 80-90 | Var. 112 |
| 90-150 | Var. 113 |
| 90-140 | Var. 114 |
| 90-130 | Var. 115 |
| 90-120 | Var. 116 |
| 90-110 | Var. 117 |
| 90-100 | Var. 118 |
| 100-150 | Var. 119 |
| 100-140 | Var. 120 |
| 100-130 | Var. 121 |
| 100-120 | Var. 122 |
| 100-110 | Var. 123 |
| 110-150 | Var. 124 |
| 110-140 | Var. 125 |
| 110-130 | Var. 126 |
| 110-120 | Var. 127 |
| 120-150 | Var. 128 |
| 120-140 | Var. 129 |
| 120-130 | Var. 130 |
| 130-150 | Var. 131 |
| 130-140 | Var. 132 |
| 140-150 | Var. 133 |

Var. = Variation

The rVWF of the present invention is highly multimeric comprising about 10 to about 40 subunits. In further embodiments, the multimeric rVWF produced using methods of the present invention comprise about 10-30, 12-28, 14-26, 16-24, 18-22, 20-21 subunits. In some embodiments, the rVWF is present in multimers varying in size from dimers to multimers of over 40 subunits (>10 million Daltons). The largest multimers provide multiple binding sites that can interact with both platelet receptors and subendothelial matrix sites of injury, and are the most hemostatically active form of VWF. In some embodiments, the rVWF of the present invention comprises ultralarge multimers (ULMs). Generally, high and ultralarge multimers are considered to be hemostatically most effective (see, for example, Turecek, P., Hamostaseologie, (Vol. 37): Supplement 1, pages S15-S25 (2017)). In some embodiments, the rVWF is between 500 kDa and 20,000 kDa. In some embodiments, any desired multimer pattern can be obtained using the methods described. In some embodiments, when anion exchange and/or cation exchanger methods are employed, the pH, conductivity, and/or counterion concentration of the buffers in the one or more wash step(s) or the gradient buffers can be manipulated to obtain the desired multimer pattern. In some embodiments, then size exclusion chromatography methods are employed, the collection criteria can be employed to obtain the desired multimer pattern. In some embodiments, the described multimer pattern comprises ultralarge multimers. In some embodiments, the ultralarge multimers are at least 10,000 kDa, at least 11,000 kDa, at least 12,000 kDa, at least 13,000 kDa, at least 14,000 kDa, at least 15,000 kDa, at least 16,000 kDa, at least 17,000 kDa, at least 18,000 kDa, at least 19,000 kDa, at least 20,000 kDa. In some embodiments, the ultralarge multimers are between about 10,000 kDa and 20,000 kDa. In some embodiments, the ultralarge multimers are between about 11,000 kDa and 20,000 kDa. In some embodiments, the ultralarge multimers are between about 12,000 kDa and 20,000 kDa. In some embodiments, the ultralarge multimers are between about 13,000 kDa and 20,000 kDa. In some embodiments, the ultralarge multimers are between about 14,000 kDa and 20,000 kDa. In some embodiments, the ultralarge multimers are between about 15,000 kDa and 20,000 kDa. In some embodiments, the ultralarge multimers are between about 16,000 kDa and 20,000 kDa. In some embodiments, the ultralarge multimers are between about 17,000 kDa and 20,000 kDa. In some embodiments, the ultralarge multimers are between about 18,000 kDa and 20,000 kDa. In some embodiments, the ultralarge multimers are between about 19,000 kDa and 20,000 kDa. In some embodiments, the rVWF obtained using the present methods includes any multimer pattern present in the loading sample of the rVWF. In some embodiments, the rVWF obtained using the present methods includes physiological occurring multimer patters as well as ultra large VWF-multimer patterns.

In some embodiments, the rVWF composition prepared by the purification method described herein has a distribution of rVWF oligomers characterized in that 95% of the oligomers have between 6 subunits and 20 subunits. In some embodiments, the rVWF composition has a distribution of rVWF oligomers characterized in that 95% of the oligomers have a range of subunits selected from variations 458 to 641 found in 4.

TABLE 4

Exemplary embodiments for
the distribution of rVWF
oligomers found in the
compositions and used in
the methods provided herein.

Subunits

| | |
|---|---|
| 2-40 | Var. 458 |
| 2-38 | Var. 459 |
| 2-36 | Var. 460 |
| 2-34 | Var. 461 |
| 2-32 | Var. 462 |
| 2-30 | Var. 463 |
| 2-28 | Var. 464 |

TABLE 4-continued

| Exemplary embodiments for the distribution of rVWF oligomers found in the compositions and used in the methods provided herein. | |
| --- | --- |
| Subunits | |
| 2-26 | Var. 465 |
| 2-24 | Var. 466 |
| 2-22 | Var. 467 |
| 2-20 | Var. 468 |
| 2-18 | Var. 469 |
| 2-16 | Var. 470 |
| 2-14 | Var. 471 |
| 2-12 | Var. 472 |
| 2-10 | Var. 473 |
| 2-8 | Var. 474 |
| 4-40 | Var. 475 |
| 4-38 | Var. 476 |
| 4-36 | Var. 477 |
| 4-34 | Var. 478 |
| 4-32 | Var. 479 |
| 4-30 | Var. 480 |
| 4-28 | Var. 481 |
| 4-26 | Var. 482 |
| 4-24 | Var. 483 |
| 4-22 | Var. 484 |
| 4-20 | Var. 485 |
| 4-18 | Var. 486 |
| 4-16 | Var. 487 |
| 4-14 | Var. 488 |
| 4-12 | Var. 489 |
| 4-10 | Var. 490 |
| 4-8 | Var. 491 |
| 6-40 | Var. 492 |
| 6-38 | Var. 493 |
| 6-36 | Var. 494 |
| 6-34 | Var. 495 |
| 6-32 | Var. 496 |
| 6-30 | Var. 497 |
| 6-28 | Var. 498 |
| 6-26 | Var. 499 |
| 6-24 | Var. 500 |
| 6-22 | Var. 501 |
| 6-20 | Var. 502 |
| 6-18 | Var. 503 |
| 6-16 | Var. 504 |
| 6-14 | Var. 505 |
| 6-12 | Var. 506 |
| 6-10 | Var. 507 |
| 6-8 | Var. 508 |
| 8-40 | Var. 509 |
| 8-38 | Var. 510 |
| 8-36 | Var. 511 |
| 8-34 | Var. 512 |
| 8-32 | Var. 513 |
| 8-30 | Var. 514 |
| 8-28 | Var. 515 |
| 8-26 | Var. 516 |
| 8-24 | Var. 517 |
| 8-22 | Var. 518 |
| 8-20 | Var. 519 |
| 8-18 | Var. 520 |
| 8-16 | Var. 521 |
| 8-14 | Var. 522 |
| 8-12 | Var. 523 |
| 8-10 | Var. 524 |
| 10-40 | Var. 525 |
| 10-38 | Var. 526 |
| 10-36 | Var. 527 |
| 10-34 | Var. 528 |
| 10-32 | Var. 529 |
| 10-30 | Var. 530 |
| 10-28 | Var. 531 |
| 10-26 | Var. 532 |
| 10-24 | Var. 533 |
| 10-22 | Var. 534 |
| 10-20 | Var. 535 |
| 10-18 | Var. 536 |

TABLE 4-continued

| Exemplary embodiments for the distribution of rVWF oligomers found in the compositions and used in the methods provided herein. | |
| --- | --- |
| Subunits | |
| 10-16 | Var. 537 |
| 10-14 | Var. 538 |
| 10-12 | Var. 539 |
| 12-40 | Var. 540 |
| 12-38 | Var. 541 |
| 12-36 | Var. 542 |
| 12-34 | Var. 543 |
| 12-32 | Var. 544 |
| 12-30 | Var. 545 |
| 12-28 | Var. 546 |
| 12-26 | Var. 547 |
| 12-24 | Var. 548 |
| 12-22 | Var. 549 |
| 12-20 | Var. 550 |
| 12-18 | Var. 551 |
| 12-16 | Var. 552 |
| 12-14 | Var. 553 |
| 14-40 | Var. 554 |
| 14-38 | Var. 555 |
| 14-36 | Var. 556 |
| 14-34 | Var. 557 |
| 14-32 | Var. 558 |
| 14-30 | Var. 559 |
| 14-28 | Var. 560 |
| 14-26 | Var. 561 |
| 14-24 | Var. 562 |
| 14-22 | Var. 563 |
| 14-20 | Var. 564 |
| 14-18 | Var. 565 |
| 14-16 | Var. 566 |
| 16-40 | Var. 567 |
| 16-38 | Var. 568 |
| 16-36 | Var. 569 |
| 16-34 | Var. 570 |
| 16-32 | Var. 571 |
| 16-30 | Var. 572 |
| 16-28 | Var. 573 |
| 16-26 | Var. 574 |
| 16-24 | Var. 575 |
| 16-22 | Var. 576 |
| 16-20 | Var. 577 |
| 16-18 | Var. 578 |
| 18-40 | Var. 579 |
| 18-38 | Var. 580 |
| 18-36 | Var. 581 |
| 18-34 | Var. 582 |
| 18-32 | Var. 583 |
| 18-30 | Var. 584 |
| 18-28 | Var. 585 |
| 18-26 | Var. 586 |
| 18-24 | Var. 587 |
| 18-22 | Var. 588 |
| 18-20 | Var. 589 |
| 20-40 | Var. 590 |
| 20-38 | Var. 591 |
| 20-36 | Var. 592 |
| 20-34 | Var. 593 |
| 20-32 | Var. 594 |
| 20-30 | Var. 595 |
| 20-28 | Var. 596 |
| 20-26 | Var. 597 |
| 20-24 | Var. 598 |
| 20-22 | Var. 599 |
| 22-40 | Var. 600 |
| 22-38 | Var. 601 |
| 22-36 | Var. 602 |
| 22-34 | Var. 603 |
| 22-32 | Var. 604 |
| 22-30 | Var. 605 |
| 22-28 | Var. 606 |
| 22-26 | Var. 607 |
| 22-24 | Var. 608 |

TABLE 4-continued

Exemplary embodiments for
the distribution of rVWF
oligomers found in the
compositions and used in
the methods provided herein.

Subunits

| 24-40 | Var. 609 |
| 24-38 | Var. 610 |
| 24-36 | Var. 611 |
| 24-34 | Var. 612 |
| 24-32 | Var. 613 |
| 24-30 | Var. 614 |
| 24-28 | Var. 615 |
| 24-26 | Var. 616 |
| 26-40 | Var. 617 |
| 26-38 | Var. 618 |
| 26-36 | Var. 619 |
| 26-34 | Var. 620 |
| 26-32 | Var. 621 |
| 26-30 | Var. 622 |
| 26-28 | Var. 623 |
| 28-40 | Var. 624 |
| 28-38 | Var. 625 |
| 28-36 | Var. 626 |
| 28-34 | Var. 627 |
| 28-32 | Var. 628 |
| 28-30 | Var. 629 |
| 30-40 | Var. 630 |
| 30-38 | Var. 631 |
| 30-36 | Var. 632 |
| 30-34 | Var. 633 |
| 30-32 | Var. 634 |
| 32-40 | Var. 635 |
| 32-38 | Var. 636 |

TABLE 4-continued

Exemplary embodiments for
the distribution of rVWF
oligomers found in the
compositions and used in
the methods provided herein.

Subunits

| 32-36 | Var. 637 |
| 32-34 | Var. 638 |
| 34-40 | Var. 639 |
| 36-38 | Var. 640 |
| 38-40 | Var. 641 |

Var. = Variation

In some embodiments, the rVWF composition prepared by the methods provided herein can be characterized according to the percentage of rVWF molecules that are present in a particular higher order rVWF multimer or larger multimer. For example, in one embodiment, at least 20% of rVWF molecules in a rVWF composition used in the methods described herein are present in an oligomeric complex of at least 10 subunits. In another embodiment, at least 20% of rVWF molecules in a rVWF composition used in the methods described herein are present in an oligomeric complex of at least 12 subunits. In yet other embodiments, a rVWF composition used in the methods provided herein has a minimal percentage (e.g., has at least X %) of rVWF molecules present in a particular higher-order rVWF multimer or larger multimer (e.g., a multimer of at least Y subunits) according to any one of variations 134 to 457 found in Table 5 to Table 7.

TABLE 5

Exemplary embodiments for the percentage of rVWF molecules that are in multimer
a particular higher order rVWF or larger multimer found in the compositions
present and used in the methods provided herein.

| | | Minimal Number of Subunits in rVWF Multimer | | | | | |
|---|---|---|---|---|---|---|---|
| | | 6 | 8 | 10 | 12 | 14 | 16 |
| Minimal | 10% | Var. 134 | Var. 152 | Var. 170 | Var. 188 | Var. 206 | Var. 224 |
| Percentage | 15% | Var. 135 | Var. 153 | Var. 171 | Var. 189 | Var. 207 | Var. 225 |
| of | 20% | Var. 136 | Var. 154 | Var. 172 | Var. 190 | Var. 208 | Var. 226 |
| | 25% | Var. 137 | Var. 155 | Var. 173 | Var. 191 | Var. 209 | Var. 227 |
| | 30% | Var. 138 | Var. 156 | Var. 174 | Var. 192 | Var. 210 | Var. 228 |
| | 35% | Var. 139 | Var. 157 | Var. 175 | Var. 193 | Var. 211 | Var. 229 |
| | 40% | Var. 140 | Var. 158 | Var. 176 | Var. 194 | Var. 212 | Var. 230 |
| | 45% | Var. 141 | Var. 159 | Var. 177 | Var. 195 | Var. 213 | Var. 231 |
| | 50% | Var. 142 | Var. 160 | Var. 178 | Var. 196 | Var. 214 | Var. 232 |
| | 55% | Var. 143 | Var. 161 | Var. 179 | Var. 197 | Var. 215 | Var. 233 |
| | 60% | Var. 144 | Var. 162 | Var. 180 | Var. 198 | Var. 216 | Var. 234 |
| | 65% | Var. 145 | Var. 163 | Var. 181 | Var. 199 | Var. 217 | Var. 235 |
| | 70% | Var. 146 | Var. 164 | Var. 182 | Var. 200 | Var. 218 | Var. 236 |
| | 75% | Var. 147 | Var. 165 | Var. 183 | Var. 201 | Var. 219 | Var. 237 |
| | 80% | Var. 148 | Var. 166 | Var. 184 | Var. 202 | Var. 220 | Var. 238 |
| | 85% | Var. 149 | Var. 167 | Var. 185 | Var. 203 | Var. 221 | Var. 239 |
| | 90% | Var. 150 | Var. 168 | Var. 186 | Var. 204 | Var. 222 | Var. 240 |
| | 95% | Var. 151 | Var. 169 | Var. 187 | Var. 205 | Var. 223 | Var. 241 |

Var. = Variation

TABLE 6

Exemplary embodiments for the percentage of rVWF molecules that are present in a
particular higher order rVWF multimer or larger multimer found in the compositions
and used in the methods provided herein.

| | | Minimal Number of Subunits in rVWF Multimer | | | | | |
| | | 18 | 20 | 22 | 24 | 26 | 28 |
|---|---|---|---|---|---|---|---|
| Minimal | 10% | Var. 242 | Var. 260 | Var. 278 | Var. 296 | Var. 314 | Var. 332 |
| Percentage | 15% | Var. 243 | Var. 261 | Var. 279 | Var. 297 | Var. 315 | Var. 333 |
| of rVVVF | 20% | Var. 244 | Var. 262 | Var. 280 | Var. 298 | Var. 316 | Var. 334 |
| Molecules | 25% | Var. 245 | Var. 263 | Var. 281 | Var. 299 | Var. 317 | Var. 335 |
| | 30% | Var. 246 | Var. 264 | Var. 282 | Var. 300 | Var. 318 | Var. 336 |
| | 35% | Var. 247 | Var. 265 | Var. 283 | Var. 301 | Var. 319 | Var. 337 |
| | 40% | Var. 248 | Var. 266 | Var. 284 | Var. 302 | Var. 320 | Var. 338 |
| | 45% | Var. 249 | Var. 267 | Var. 285 | Var. 303 | Var. 321 | Var. 339 |
| | 50% | Var. 250 | Var. 268 | Var. 286 | Var. 304 | Var. 322 | Var. 340 |
| | 55% | Var. 251 | Var. 269 | Var. 287 | Var. 305 | Var. 323 | Var. 341 |
| | 60% | Var. 252 | Var. 270 | Var. 288 | Var. 306 | Var. 324 | Var. 342 |
| | 65% | Var. 253 | Var. 271 | Var. 289 | Var. 307 | Var. 325 | Var. 343 |
| | 70% | Var. 254 | Var. 272 | Var. 290 | Var. 308 | Var. 326 | Var. 344 |
| | 75% | Var. 255 | Var. 273 | Var. 291 | Var. 309 | Var. 327 | Var. 345 |
| | 80% | Var. 256 | Var. 274 | Var. 292 | Var. 310 | Var. 328 | Var. 346 |
| | 85% | Var. 257 | Var. 275 | Var. 293 | Var. 311 | Var. 329 | Var. 347 |
| | 90% | Var. 258 | Var. 276 | Var. 294 | Var. 312 | Var. 330 | Var. 348 |
| | 95% | Var. 259 | Var. 277 | Var. 295 | Var. 313 | Var. 331 | Var. 349 |

Var. = Variation

TABLE 7

Exemplary embodiments for the percentage of rVWF
molecules that are present in a particular higher order rVWF
multimer or larger multimer found in the compositions
and used in the methods provided herein.

| | | Minimal Number of Subunits in rVWF Multimer | | | | | |
| | | 30 | 32 | 34 | 36 | 38 | 40 |
|---|---|---|---|---|---|---|---|
| Mi | 10% | Var. 350 | Var. 368 | Var. 386 | Var. 404 | Var. 422 | Var. 440 |
| | 15% | Var. 351 | Var. 369 | Var. 387 | Var. 405 | Var. 423 | Var. 441 |
| | 20% | Var. 352 | Var. 370 | Var. 388 | Var. 406 | Var. 424 | Var. 442 |
| | 25% | Var. 353 | Var. 371 | Var. 389 | Var. 407 | Var. 425 | Var. 443 |
| | 30% | Var. 354 | Var. 372 | Var. 390 | Var. 408 | Var. 426 | Var. 444 |
| | 35% | Var. 355 | Var. 373 | Var. 391 | Var. 409 | Var. 427 | Var. 445 |
| | 40% | Var. 356 | Var. 374 | Var. 392 | Var. 410 | Var. 428 | Var. 446 |
| | 45% | Var. 357 | Var. 375 | Var. 393 | Var. 411 | Var. 429 | Var. 447 |
| | 50% | Var. 358 | Var. 376 | Var. 394 | Var. 412 | Var. 430 | Var. 448 |
| | 55% | Var. 359 | Var. 377 | Var. 395 | Var. 413 | Var. 431 | Var. 449 |
| | 60% | Var. 360 | Var. 378 | Var. 396 | Var. 414 | Var. 432 | Var. 450 |
| | 65% | Var. 361 | Var. 379 | Var. 397 | Var. 415 | Var. 433 | Var. 451 |
| | 70% | Var. 362 | Var. 380 | Var. 398 | Var. 416 | Var. 434 | Var. 452 |
| | 75% | Var. 363 | Var. 381 | Var. 399 | Var. 417 | Var. 435 | Var. 453 |
| | 80% | Var. 364 | Var. 382 | Var. 400 | Var. 418 | Var. 436 | Var. 454 |
| | 85% | Var. 365 | Var. 383 | Var. 401 | Var. 419 | Var. 437 | Var. 455 |
| | 90% | Var. 366 | Var. 384 | Var. 402 | Var. 420 | Var. 438 | Var. 456 |
| | 95% | Var. 367 | Var. 385 | Var. 403 | Var. 421 | Var. 439 | Var. 457 |

Var. = Variation

In accordance with the above, the rVWF comprises a significant percentage of high molecular weight (HMW) rVWF multimers. In further embodiments, the HMW rVWF multimer composition comprises at least 10%-80% rVWF decamers or higher order multimers. In further embodiments, the composition comprises about 10-95%, 20-90%, 30-85%, 40-80%, 50-75%, 60-70% decamers or higher order multimers. In further embodiments, the HMW rVWF multimer composition comprises at least about 10%, 20%, 30%, 40%, 50%, 60%, 70%, 80%, 90% decamers or higher order multimers.

Assessment of the number and percentage of rVWF multimers can be conducted using methods known in the art, including without limitation methods using electrophoresis and size exclusion chromatography methods to separate rVWF multimers by size, for example as discussed by Cumming et al, (J Clin Pathol. 1993 May; 46(5): 470-473, which is hereby incorporated by reference in its entirety for all purposes and in particular for all teachings related to assessment of rVWF multimers). Such techniques may further include immunoblotting techniques (such as Western Blot), in which the gel is immunoblotted with a radiolabeled antibody against VWF followed by chemiluminescent detection (see for example Wen et al., (1993), J. Clin. Lab. Anal., 7: 317-323, which is hereby incorporated by reference in its entirety for all purposes and in particular for all teachings related to assessment of rVWF multimers). Further assays for VWF include VWF:Antigen (VWF:Ag), VWF:Ristocetin Cofactor (VWF:RCof), and VWF:Collagen Binding Activity assay (VWF:CBA), which are often used for diagnosis and classification of Von Willebrand Disease. (see for example Favaloro et al., Pathology, 1997, 29(4): 341-456, which is hereby incorporated by reference in its entirety for all purposes and in particular for all teachings related to assays for VWF).

In some embodiments, the ratio of rFVIII procoagulant activity (IU rFVIII:C) to rVWF Ristocetin cofactor activity (IU rVWF:RCo) for the rVWF prepared according to the methods of the present invention is between 3:1 and 1:5. In further embodiments, the ratio is between 2:1 and 1:4. In still further embodiments, the ratio is between 5:2 and 1:4. In further embodiments, the ratio is between 3:2 and 1:3. In still further embodiments, the ratio is about 1:1, 1:2, 1:3, 1:4, 1:5, 2:1, 2:3, 2:4, 2:5, 3:1, 3:2, 3:4, or 3:5. In further embodiments, the ratio is between 1:1 and 1:2. In yet further embodiments, the ratio is 1.1:1, 1.2:1, 1.3:1, 1.4:1, 1.5:1, 1.6:1, 1.7:1, 1.8:1, 1.9:1, or 2:1. In certain embodiments, the ratio of rFVIII procoagulant activity (IU rFVIII:C) to rVWF Ristocetin cofactor activity (IU rVWF:RCo) in a composition useful for a method described herein is selected from variations 1988 to 2140 found in Table 8.

TABLE 8

Exemplary embodiments for
the ratio of rFVIII procoagulant
activity (IU rFVIII:C) to
rVWF Ristocetin cofactor
activity (IU rVWF:RCo)
in compositions and used in
methods provided herein.

| (IU rFVIII:C) to (IU rVIVF:RCo) | |
|---|---|
| 4:1 | Var. 1988 |
| 3:1 | Var. 1989 |
| 2:1 | Var. 1990 |
| 3:2 | Var. 1991 |
| 4:3 | Var. 1992 |
| 1:1 | Var. 1993 |
| 5:6 | Var. 1994 |
| 4:5 | Var. 1995 |
| 3:4 | Var. 1996 |
| 2:3 | Var. 1997 |
| 3:5 | Var. 1998 |
| 1:2 | Var. 1999 |
| 2:5 | Var. 2000 |
| 1:3 | Var. 2001 |
| 1:4 | Var. 2002 |
| 1:5 | Var. 2003 |
| 1:6 | Var. 2004 |
| 4:1-1:6 | Var. 2005 |
| 4:1-1:5 | Var. 2006 |
| 4:1-1:4 | Var. 2007 |
| 4:1-1:3 | Var. 2008 |
| 4:1-2:5 | Var. 2009 |
| 4:1-1:2 | Var. 2010 |
| 4:1-3:5 | Var. 2011 |
| 4:1-2:3 | Var. 2012 |
| 4:1-3:4 | Var. 2013 |
| 4:1-4:5 | Var. 2014 |
| 4:1-5:6 | Var. 2015 |
| 4:1-1:1 | Var. 2016 |
| 4:1-4:3 | Var. 2017 |
| 4:1-3:2 | Var. 2018 |
| 4:1-2:1 | Var. 2019 |
| 4:1-3:1 | Var. 2020 |
| 3:1-1:6 | Var. 2021 |
| 3:1-1:5 | Var. 2022 |
| 3:1-1:4 | Var. 2023 |
| 3:1-1:3 | Var. 2024 |
| 3:1-2:5 | Var. 2025 |
| 3:1-1:2 | Var. 2026 |
| 3:1-3:5 | Var. 2027 |
| 3:1-2:3 | Var. 2028 |
| 3:1-3:4 | Var. 2029 |
| 3:1-4:5 | Var. 2030 |
| 3:1-5:6 | Var. 2031 |
| 3:1-1:1 | Var. 2032 |
| 3:1-4:3 | Var. 2033 |
| 3:1-3:2 | Var. 2034 |
| 3:1-2:1 | Var. 2035 |
| 2:1-1:6 | Var. 2036 |
| 2:1-1:5 | Var. 2037 |
| 2:1-1:4 | Var. 2038 |
| 2:1-1:3 | Var. 2039 |
| 2:1-2:5 | Var. 2040 |
| 2:1-1:2 | Var. 2041 |
| 2:1-3:5 | Var. 2042 |
| 2:1-2:3 | Var. 2043 |
| 2:1-3:4 | Var. 2044 |
| 2:1-4:5 | Var. 2045 |
| 2:1-5:6 | Var. 2046 |
| 2:1-1:1 | Var. 2047 |
| 2:1-4:3 | Var. 2048 |
| 2:1-3:2 | Var. 2049 |
| 3:2-1:6 | Var. 2050 |
| 3:2-1:5 | Var. 2051 |
| 3:2-1:4 | Var. 2052 |
| 3:2-1:3 | Var. 2053 |
| 3:2-2:5 | Var. 2054 |
| 3:2-1:2 | Var. 2055 |

TABLE 8-continued

Exemplary embodiments for
the ratio of rFVIII procoagulant
activity (IU rFVIII:C) to
rVWF Ristocetin cofactor
activity (IU rVWF:RCo)
in compositions and used in
methods provided herein.

| (IU rFVIII:C) to (IU rVIVF:RCo) | |
|---|---|
| 3:2-3:5 | Var. 2056 |
| 3:2-2:3 | Var. 2057 |
| 3:2-3:4 | Var. 2058 |
| 3:2-4:5 | Var. 2059 |
| 3:2-5:6 | Var. 2060 |
| 3:2-1:1 | Var. 2061 |
| 3:2-4:3 | Var. 2062 |
| 4:3-1:6 | Var. 2063 |
| 4:3-1:5 | Var. 2064 |
| 4:3-1:4 | Var. 2065 |
| 4:3-1:3 | Var. 2066 |
| 4:3-2:5 | Var. 2067 |
| 4:3-1:2 | Var. 2068 |
| 4:3-3:5 | Var. 2069 |
| 4:3-2:3 | Var. 2070 |
| 4:3-3:4 | Var. 2071 |
| 4:3-4:5 | Var. 2072 |
| 4:3-5:6 | Var. 2073 |
| 4:3-1:1 | Var. 2074 |
| 1:1-1:6 | Var. 2075 |
| 1:1-1:5 | Var. 2076 |
| 1:1-1:4 | Var. 2077 |
| 1:1-1:3 | Var. 2078 |
| 1:1-2:5 | Var. 2079 |
| 1:1-1:2 | Var. 2080 |
| 1:1-3:5 | Var. 2081 |
| 1:1-2:3 | Var. 2082 |
| 1:1-3:4 | Var. 2083 |
| 1:1-4:5 | Var. 2084 |
| 1:1-5:6 | Var. 2085 |
| 5:6-1:6 | Var. 2086 |
| 5:6-1:5 | Var. 2087 |
| 5:6-1:4 | Var. 2088 |
| 5:6-1:3 | Var. 2089 |
| 5:6-2:5 | Var. 2090 |
| 5:6-1:2 | Var. 2091 |
| 5:6-3:5 | Var. 2092 |
| 5:6-2:3 | Var. 2093 |
| 5:6-3:4 | Var. 2094 |
| 5:6-4:5 | Var. 2095 |
| 4:5-1:6 | Var. 2096 |
| 4:5-1:5 | Var. 2097 |
| 4:5-1:4 | Var. 2098 |
| 4:5-1:3 | Var. 2099 |
| 4:5-2:5 | Var. 2100 |
| 4:5-1:2 | Var. 2101 |
| 4:5-3:5 | Var. 2102 |
| 4:5-2:3 | Var. 2103 |
| 4:5-3:4 | Var. 2104 |
| 3:4-1:6 | Var. 2105 |
| 3:4-1:5 | Var. 2106 |
| 3:4-1:4 | Var. 2107 |
| 3:4-1:3 | Var. 2108 |
| 3:4-2:5 | Var. 2109 |
| 3:4-1:2 | Var. 2110 |
| 3:4-3:5 | Var. 2111 |
| 3:4-2:3 | Var. 2112 |
| 2:3-1:6 | Var. 2113 |
| 2:3-1:5 | Var. 2114 |
| 2:3-1:4 | Var. 2115 |
| 2:3-1:3 | Var. 2116 |
| 2:3-2:5 | Var. 2117 |
| 2:3-1:2 | Var. 2118 |
| 2:3-3:5 | Var. 2119 |
| 3:5-1:6 | Var. 2120 |
| 3:5-1:5 | Var. 2121 |
| 3:5-1:4 | Var. 2122 |
| 3:5-1:3 | Var. 2123 |

TABLE 8-continued

Exemplary embodiments for the ratio of rFVIII procoagulant activity (IU rFVIII:C) to rVWF Ristocetin cofactor activity (IU rVWF:RCo) in compositions and used in methods provided herein.

| (IU rFVIII:C) to (IU rVIVF:RCo) | |
| --- | --- |
| 3:5-2:5 | Var. 2124 |
| 3:5-1:2 | Var. 2125 |
| 1:2-1:6 | Var. 2126 |
| 1:2-1:5 | Var. 2127 |
| 1:2-1:4 | Var. 2128 |
| 1:2-1:3 | Var. 2129 |
| 1:2-2:5 | Var. 2130 |
| 2:5-1:6 | Var. 2131 |
| 2:5-1:5 | Var. 2132 |
| 2:5-1:4 | Var. 2133 |
| 2:5-1:3 | Var. 2134 |
| 1:3-1:6 | Var. 2135 |
| 1:3-1:5 | Var. 2136 |
| 1:3-1:4 | Var. 2137 |
| 1:4-1:6 | Var. 2138 |
| 1:4-1:5 | Var. 2139 |
| 1:5-1:6 | Var. 2140 |

Var. = Variation

In further embodiments, higher order rVWF multimers of the invention are stable for about 1 to about 90 hours post-administration. In still further embodiments, the higher order rVWF multimers are stable for about 5-80, 10-70, 15-60, 20-50, 25-40, 30-35 hours post-administration. In yet further embodiments, the higher order rVWF multimers are stable for at least 3, 6, 12, 18, 24, 36, 48, 72 hours post-administration. In certain embodiments the stability of the rVWF multimers is assessed in vitro.

In one embodiment, higher order rVWF multimers used in the compositions and methods provided herein have a half-life of at least 12 hour post administration. In another embodiment, the higher order rVWF multimers have a half-life of at least 24 hour post administration. In yet other embodiments, the higher order rVWF multimers have a half-life selected from variations 642 to 1045 found in Table 9.

TABLE 9

Exemplary embodiments for the half-life of higher order rVWF multimers found in the compositions prepared by the methods provided herein.

| Hours | |
| --- | --- |
| at least 1 | Var. 642 |
| at least 2 | Var. 643 |
| at least 3 | Var. 644 |
| at least 4 | Var. 645 |
| at least 5 | Var. 646 |
| at least 6 | Var. 647 |
| at least 7 | Var. 648 |
| at least 8 | Var. 649 |
| at least 9 | Var. 650 |
| at least 10 | Var. 651 |
| at least 11 | Var. 652 |
| at least 12 | Var. 653 |
| at least 14 | Var. 654 |
| at least 16 | Var. 655 |

TABLE 9-continued

Exemplary embodiments for the half-life of higher order rVWF multimers found in the compositions prepared by the methods provided herein.

| Hours | |
| --- | --- |
| at least 18 | Var. 656 |
| at least 20 | Var. 657 |
| at least 22 | Var. 658 |
| at least 24 | Var. 659 |
| at least 27 | Var. 660 |
| at least 30 | Var. 661 |
| at least 33 | Var. 662 |
| at least 36 | Var. 663 |
| at least 39 | Var. 664 |
| at least 42 | Var. 665 |
| at least 45 | Var. 666 |
| at least 48 | Var. 667 |
| at least 54 | Var. 668 |
| at least 60 | Var. 669 |
| at least 66 | Var. 670 |
| at least 72 | Var. 671 |
| at least 78 | Var. 672 |
| at least 84 | Var. 673 |
| at least 90 | Var. 674 |
| 2-90 | Var. 675 |
| 2-84 | Var. 676 |
| 2-78 | Var. 677 |
| 2-72 | Var. 678 |
| 2-66 | Var. 679 |
| 2-60 | Var. 680 |
| 2-54 | Var. 681 |
| 2-48 | Var. 682 |
| 2-45 | Var. 683 |
| 2-42 | Var. 684 |
| 2-39 | Var. 685 |
| 2-36 | Var. 686 |
| 2-33 | Var. 687 |
| 2-30 | Var. 688 |
| 2-27 | Var. 689 |
| 2-24 | Var. 690 |
| 2-22 | Var. 691 |
| 2-20 | Var. 692 |
| 2-18 | Var. 693 |
| 2-16 | Var. 694 |
| 2-14 | Var. 695 |
| 2-12 | Var. 696 |
| 2-10 | Var. 697 |
| 2-8 | Var. 698 |
| 2-6 | Var. 699 |
| 2-4 | Var. 700 |
| 3-90 | Var. 701 |
| 3-84 | Var. 702 |
| 3-78 | Var. 703 |
| 3-72 | Var. 704 |
| 3-66 | Var. 705 |
| 3-60 | Var. 706 |
| 3-54 | Var. 707 |
| 3-48 | Var. 708 |
| 3-45 | Var. 709 |
| 3-42 | Var. 710 |
| 3-39 | Var. 711 |
| 3-36 | Var. 712 |
| 3-33 | Var. 713 |
| 3-30 | Var. 714 |
| 3-27 | Var. 715 |
| 3-24 | Var. 716 |
| 3-22 | Var. 717 |
| 3-20 | Var. 718 |
| 3-18 | Var. 719 |
| 3-16 | Var. 720 |
| 3-14 | Var. 721 |
| 3-12 | Var. 722 |
| 3-10 | Var. 723 |
| 3-8 | Var. 724 |
| 3-6 | Var. 725 |
| 3-4 | Var. 726 |

35

TABLE 9-continued

Exemplary embodiments
for the half-life of higher
order rVWF multimers
found in the compositions
prepared by the methods
provided herein.

| Hours | |
|---|---|
| 4-90 | Var. 727 |
| 4-84 | Var. 728 |
| 4-78 | Var. 729 |
| 4-72 | Var. 730 |
| 4-66 | Var. 731 |
| 4-60 | Var. 732 |
| 4-54 | Var. 733 |
| 4-48 | Var. 734 |
| 4-45 | Var. 735 |
| 4-42 | Var. 736 |
| 4-39 | Var. 737 |
| 4-36 | Var. 738 |
| 4-33 | Var. 739 |
| 4-30 | Var. 740 |
| 4-27 | Var. 741 |
| 4-24 | Var. 742 |
| 4-22 | Var. 743 |
| 4-20 | Var. 744 |
| 4-18 | Var. 745 |
| 4-16 | Var. 746 |
| 4-14 | Var. 747 |
| 4-12 | Var. 748 |
| 4-10 | Var. 749 |
| 4-8 | Var. 750 |
| 4-6 | Var. 751 |
| 6-90 | Var. 752 |
| 6-84 | Var. 753 |
| 6-78 | Var. 754 |
| 6-72 | Var. 755 |
| 6-66 | Var. 756 |
| 6-60 | Var. 757 |
| 6-54 | Var. 758 |
| 6-48 | Var. 759 |
| 6-45 | Var. 760 |
| 6-42 | Var. 761 |
| 6-39 | Var. 762 |
| 6-36 | Var. 763 |
| 6-33 | Var. 764 |
| 6-30 | Var. 765 |
| 6-27 | Var. 766 |
| 6-24 | Var. 767 |
| 6-22 | Var. 768 |
| 6-20 | Var. 769 |
| 6-18 | Var. 770 |
| 6-16 | Var. 771 |
| 6-14 | Var. 772 |
| 6-12 | Var. 773 |
| 6-10 | Var. 774 |
| 6-8 | Var. 775 |
| 8-90 | Var. 776 |
| 8-84 | Var. 777 |
| 8-78 | Var. 778 |
| 8-72 | Var. 779 |
| 8-66 | Var. 780 |
| 8-60 | Var. 781 |
| 8-54 | Var. 782 |
| 8-48 | Var. 783 |
| 8-45 | Var. 784 |
| 8-42 | Var. 785 |
| 8-39 | Var. 786 |
| 8-36 | Var. 787 |
| 8-33 | Var. 788 |
| 8-30 | Var. 789 |
| 8-27 | Var. 790 |
| 8-24 | Var. 791 |
| 8-22 | Var. 792 |
| 8-20 | Var. 793 |
| 8-18 | Var. 794 |
| 8-16 | Var. 795 |
| 8-14 | Var. 796 |
| 8-12 | Var. 797 |

36

TABLE 9-continued

Exemplary embodiments
for the half-life of higher
order rVWF multimers
found in the compositions
prepared by the methods
provided herein.

| Hours | |
|---|---|
| 8-10 | Var. 798 |
| 10-90 | Var. 799 |
| 10-84 | Var. 800 |
| 10-78 | Var. 801 |
| 10-72 | Var. 802 |
| 10-66 | Var. 803 |
| 10-60 | Var. 804 |
| 10-54 | Var. 805 |
| 10-48 | Var. 806 |
| 10-45 | Var. 807 |
| 10-42 | Var. 808 |
| 10-39 | Var. 809 |
| 10-36 | Var. 810 |
| 10-33 | Var. 811 |
| 10-30 | Var. 812 |
| 10-27 | Var. 813 |
| 10-24 | Var. 814 |
| 10-22 | Var. 815 |
| 10-20 | Var. 816 |
| 10-18 | Var. 817 |
| 10-16 | Var. 818 |
| 10-14 | Var. 819 |
| 10-12 | Var. 820 |
| 12-90 | Var. 821 |
| 12-84 | Var. 822 |
| 12-78 | Var. 823 |
| 12-72 | Var. 824 |
| 12-66 | Var. 825 |
| 12-60 | Var. 826 |
| 12-54 | Var. 827 |
| 12-48 | Var. 828 |
| 12-45 | Var. 829 |
| 12-42 | Var. 830 |
| 12-39 | Var. 831 |
| 12-36 | Var. 832 |
| 12-33 | Var. 833 |
| 12-30 | Var. 834 |
| 12-27 | Var. 835 |
| 12-24 | Var. 836 |
| 12-22 | Var. 837 |
| 12-20 | Var. 838 |
| 12-18 | Var. 839 |
| 12-16 | Var. 840 |
| 12-14 | Var. 841 |
| 14-90 | Var. 842 |
| 14-84 | Var. 843 |
| 14-78 | Var. 844 |
| 14-72 | Var. 845 |
| 14-66 | Var. 846 |
| 14-60 | Var. 847 |
| 14-54 | Var. 848 |
| 14-48 | Var. 849 |
| 14-45 | Var. 850 |
| 14-42 | Var. 851 |
| 14-39 | Var. 852 |
| 14-36 | Var. 853 |
| 14-33 | Var. 854 |
| 14-30 | Var. 855 |
| 14-27 | Var. 856 |
| 14-24 | Var. 857 |
| 14-22 | Var. 858 |
| 14-20 | Var. 859 |
| 14-18 | Var. 860 |
| 14-16 | Var. 861 |
| 16-90 | Var. 862 |
| 16-84 | Var. 863 |
| 16-78 | Var. 864 |
| 16-72 | Var. 865 |
| 16-66 | Var. 866 |
| 16-60 | Var. 867 |
| 16-54 | Var. 868 |

TABLE 9-continued

Exemplary embodiments
for the half-life of higher
order rVWF multimers
found in the compositions
prepared by the methods
provided herein.

| Hours | |
|---|---|
| 16-48 | Var. 869 |
| 16-45 | Var. 870 |
| 16-42 | Var. 871 |
| 16-39 | Var. 872 |
| 16-36 | Var. 873 |
| 16-33 | Var. 874 |
| 16-30 | Var. 875 |
| 16-27 | Var. 876 |
| 16-24 | Var. 877 |
| 16-22 | Var. 878 |
| 16-20 | Var. 879 |
| 16-18 | Var. 880 |
| 18-90 | Var. 881 |
| 18-84 | Var. 882 |
| 18-78 | Var. 883 |
| 18-72 | Var. 884 |
| 18-66 | Var. 885 |
| 18-60 | Var. 886 |
| 18-54 | Var. 887 |
| 18-48 | Var. 888 |
| 18-45 | Var. 889 |
| 18-42 | Var. 890 |
| 18-39 | Var. 891 |
| 18-36 | Var. 892 |
| 18-33 | Var. 893 |
| 18-30 | Var. 894 |
| 18-27 | Var. 895 |
| 18-24 | Var. 896 |
| 18-22 | Var. 897 |
| 18-20 | Var. 898 |
| 20-90 | Var. 899 |
| 20-84 | Var. 900 |
| 20-78 | Var. 901 |
| 20-72 | Var. 902 |
| 20-66 | Var. 903 |
| 20-60 | Var. 904 |
| 20-54 | Var. 905 |
| 20-48 | Var. 906 |
| 20-45 | Var. 907 |
| 20-42 | Var. 908 |
| 20-39 | Var. 909 |
| 20-36 | Var. 910 |
| 20-33 | Var. 911 |
| 20-30 | Var. 912 |
| 20-27 | Var. 913 |
| 20-24 | Var. 914 |
| 20-22 | Var. 915 |
| 22-90 | Var. 916 |
| 22-84 | Var. 917 |
| 22-78 | Var. 918 |
| 22-72 | Var. 919 |
| 22-66 | Var. 920 |
| 22-60 | Var. 921 |
| 22-54 | Var. 922 |
| 22-48 | Var. 923 |
| 22-45 | Var. 924 |
| 22-42 | Var. 925 |
| 22-39 | Var. 926 |
| 22-36 | Var. 927 |
| 22-33 | Var. 928 |
| 22-30 | Var. 929 |
| 22-27 | Var. 930 |
| 22-24 | Var. 931 |
| 24-90 | Var. 932 |
| 24-84 | Var. 933 |
| 24-78 | Var. 934 |
| 24-72 | Var. 935 |
| 24-66 | Var. 936 |
| 24-60 | Var. 937 |
| 24-54 | Var. 938 |
| 24-48 | Var. 939 |

TABLE 9-continued

Exemplary embodiments
for the half-life of higher
order rVWF multimers
found in the compositions
prepared by the methods
provided herein.

| Hours | |
|---|---|
| 24-45 | Var. 940 |
| 24-42 | Var. 941 |
| 24-39 | Var. 942 |
| 24-36 | Var. 943 |
| 24-33 | Var. 944 |
| 24-30 | Var. 945 |
| 24-27 | Var. 946 |
| 27-90 | Var. 947 |
| 27-84 | Var. 948 |
| 27-78 | Var. 949 |
| 27-72 | Var. 950 |
| 27-66 | Var. 951 |
| 27-60 | Var. 952 |
| 27-54 | Var. 953 |
| 27-48 | Var. 954 |
| 30-90 | Var. 955 |
| 30-84 | Var. 956 |
| 30-78 | Var. 957 |
| 30-72 | Var. 958 |
| 30-66 | Var. 959 |
| 30-60 | Var. 960 |
| 30-54 | Var. 961 |
| 30-48 | Var. 962 |
| 30-45 | Var. 963 |
| 30-42 | Var. 964 |
| 30-39 | Var. 965 |
| 30-36 | Var. 966 |
| 30-33 | Var. 967 |
| 33-90 | Var. 968 |
| 33-84 | Var. 969 |
| 33-78 | Var. 970 |
| 33-72 | Var. 971 |
| 33-66 | Var. 972 |
| 33-60 | Var. 973 |
| 33-54 | Var. 974 |
| 33-48 | Var. 975 |
| 33-45 | Var. 976 |
| 33-42 | Var. 977 |
| 33-29 | Var. 978 |
| 33-36 | Var. 979 |
| 36-90 | Var. 980 |
| 36-84 | Var. 981 |
| 36-78 | Var. 982 |
| 36-72 | Var. 983 |
| 36-66 | Var. 984 |
| 36-60 | Var. 985 |
| 36-54 | Var. 986 |
| 36-48 | Var. 987 |
| 36-45 | Var. 988 |
| 36-42 | Var. 989 |
| 36-39 | Var. 990 |
| 39-90 | Var. 991 |
| 39-84 | Var. 992 |
| 39-78 | Var. 993 |
| 39-72 | Var. 994 |
| 39-66 | Var. 995 |
| 39-60 | Var. 996 |
| 39-54 | Var. 997 |
| 39-48 | Var. 998 |
| 39-45 | Var. 999 |
| 39-42 | Var. 1000 |
| 42-90 | Var. 1001 |
| 42-84 | Var. 1002 |
| 42-78 | Var. 1003 |
| 42-72 | Var. 1004 |
| 42-66 | Var. 1005 |
| 42-60 | Var. 1006 |
| 42-54 | Var. 1007 |
| 42-48 | Var. 1008 |
| 42-45 | Var. 1009 |
| 45-90 | Var. 1010 |

TABLE 9-continued

Exemplary embodiments
for the half-life of higher
order rVWF multimers
found in the compositions
prepared by the methods
provided herein.

| Hours | |
|---|---|
| 45-84 | Var. 1011 |
| 45-78 | Var. 1012 |
| 45-72 | Var. 1013 |
| 45-66 | Var. 1014 |
| 45-60 | Var. 1015 |
| 45-54 | Var. 1016 |
| 45-48 | Var. 1017 |
| 48-90 | Var. 1018 |
| 48-84 | Var. 1019 |
| 48-78 | Var. 1020 |
| 48-72 | Var. 1021 |
| 48-66 | Var. 1022 |
| 48-60 | Var. 1023 |
| 48-54 | Var. 1024 |
| 54-90 | Var. 1025 |
| 54-84 | Var. 1026 |
| 54-78 | Var. 1027 |
| 54-72 | Var. 1028 |
| 54-66 | Var. 1029 |
| 54-60 | Var. 1030 |
| 60-90 | Var. 1031 |
| 60-84 | Var. 1032 |
| 60-78 | Var. 1033 |
| 60-72 | Var. 1034 |
| 60-66 | Var. 1035 |
| 66-90 | Var. 1036 |
| 66-84 | Var. 1037 |
| 66-78 | Var. 1038 |
| 66-72 | Var. 1039 |
| 72-90 | Var. 1040 |
| 72-84 | Var. 1041 |
| 72-78 | Var. 1042 |
| 78-90 | Var. 1043 |
| 78-84 | Var. 1044 |
| 84-90 | Var. 1045 |

Var. = Variation

In some embodiments, the pro-VWF and/or purified rVWF purified in accordance with the present invention is not modified with any conjugation, post-translation or covalent modifications. In particular embodiments, the pro-VWF and/or purified rVWF of the present invention is not modified with a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

In some embodiments, the pro-VWF and/or purified rVWF purified in accordance with the present invention is modified through conjugation, post-translation modification, or covalent modification, including modifications of the N- or C-terminal residues as well as modifications of selected side chains, for example, at free sulfhydryl-groups, primary amines, and hydroxyl-groups. In one embodiment, a water soluble polymer is linked to the protein (directly or via a linker) by a lysine group or other primary amine. In some embodiments, the pro-VWF and/or purified rVWF of the present invention may be modified by conjugation of a water soluble polymer, including without limitation, a polyethylene glycol (PEG), a polypropylene glycol, a polyoxyalkylene, a polysialic acid, hydroxyl ethyl starch, a poly-carbohydrate moiety, and the like.

Water soluble polymers that may be used to modify the pro-VWF and/or purified rVWF include linear and branched structures. The conjugated polymers may be attached directly to the coagulation proteins of the invention, or alternatively may be attached through a linking moiety. Non-limiting examples of protein conjugation with water soluble polymers can be found in U.S. Pat. Nos. 4,640,835; 4,496,689; 4,301,144; 4,670,417; 4,791,192, and 4,179,337, as well as in Abuchowski and Davis "Enzymes as Drugs," Holcenberg and Roberts, Eds., pp. 367 383, John Wiley and Sons, New York (1981), and Hermanson G., Bioconjugate Techniques 2nd Ed., Academic Press, Inc. 2008.

Protein conjugation may be performed by a number of well-known techniques in the art, for example, see Hermanson G., Bioconjugate Techniques 2nd Ed., Academic Press, Inc. 2008. Examples include linkage through the peptide bond between a carboxyl group on one of either the coagulation protein or water-soluble polymer moiety and an amine group of the other, or an ester linkage between a carboxyl group of one and a hydroxyl group of the other. Another linkage by which a coagulation protein of the invention could be conjugated to a water-soluble polymer compound is via a Schiff base, between a free amino group on the polymer moiety being reacted with an aldehyde group formed at the non-reducing end of the polymer by periodate oxidation (Jennings and Lugowski, J. Immunol. 1981; 127: 1011-8; Femandes and Gregonradis, Biochim Biophys Acta. 1997; 1341; 26-34). The generated Schiff Base can be stabilized by specific reduction with NaCNBH3 to form a secondary amine. An alternative approach is the generation of terminal free amino groups on the polymer by reductive amination with $NH_4Cl$ after prior oxidation. Bifunctional reagents can be used for linking two amino or two hydroxyl groups. For example, a polymer containing an amino group can be coupled to an amino group of the coagulation protein with reagents like BS3 (Bis(sulfosuccinimidyl)suberate/ Pierce, Rockford, Ill.). In addition, heterobifunctional cross linking reagents like Sulfo-EMCS (N-ε-Maleimidocaproyloxy) sulfosuccinimide ester/Pierce) can be used for instance to link amine and thiol groups. In other embodiments, an aldehyde reactive group, such as PEG alkoxide plus diethyl acetal of bromoacetaldehyde; PEG plus DMSO and acetic anhydride, and PEG chloride plus the phenoxide of 4-hydroxybenzaldehyde, succinimidyl active esters, activated dithiocarbonate PE.G., 2,4,5-trichlorophenylcloroformate and P-nitrophenylcloroformate activated PE.G., may be used in the conjugation of a coagulation protein.

Another method for measuring the biological activity of VWF is the collagen binding assay, which is based on ELISA technology (Brown and Bosak, Thromb. Res., 1986, 43:303-311; Favaloro, Thromb. Haemost., 2000, 83 127-135). A microtiter plate is coated with type I or III collagen. Then the VWF is bound to the collagen surface and subsequently detected with an enzyme-labeled polyclonal antibody. The last step is a substrate reaction, which can be photometrically monitored with an ELISA reader.

Immunological assays of von Willebrand factors (VWF: Ag) are immunoassays that measure the concentration of the VWF protein in plasma. They give no indication as to VWF function. A number of methods exist for measuring VWF:Ag and these include both enzyme-linked immunosorbent assay (ELISA) or automated latex immunoassays (LIA.) Many laboratories now use a fully automated latex immunoassay. Historically laboratories used a variety of techniques including Laurell electroimmunoassay 'Laurell Rockets' but these are rarely used in most labs today.

III. Kits

As an additional aspect, the invention includes kits which comprise one or more lyophilized compositions packaged in a manner which facilitates their use for administration to subjects. In one embodiment, such a kit includes pharmaceutical formulation described herein (e.g., a composition comprising a therapeutic protein or peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (e.g., almost none). In one embodiment, the kit contains a first container having a therapeutic protein or peptide composition and a second container having a physiologically acceptable reconstitution solution for the composition. In one aspect, the pharmaceutical formulation is packaged in a unit dosage form. The kit may further include a device suitable for administering the pharmaceutical formulation according to a specific route of administration. Preferably, the kit contains a label that describes use of the pharmaceutical formulations.

IV. rVWF for Methods of Pretreating Subjects with VWD Undergoing Surgery

One of the advantages of administering rVWF to subjects with severe VWD to pretreat for surgery is that the higher specific activity of rVWF as compared to pdVWF allows flexibility in the amount of rVWF administered and the number of times the subject is re-dosed. As will be appreciated and as is discussed in further detail herein, the co-administered FVIII may be recombinant or plasma derived Single or multiple administrations of rVWF are carried out with the dose levels and pattern being selected by the treating physician. For the prevention or treatment of disease, the appropriate dosage depends on the type of disease to be treated (e.g., von Willebrand disease), the severity and course of the disease, whether drug is administered for preventive or therapeutic purposes, previous therapy, the patient's clinical history and response to the drug, and the discretion of the attending physician.

In some aspects, rVWF is administered prior to a surgical procedure to a subject at a range from 20-60 IU/kg, e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 20-60, 35-70, 20-40, 35-60, 45-60, 45-55, 45-50, 50-60, 55-60, or 50-55 IU/kg. In some embodiments, rVWF is administered between 12 hours and 24 hours, e.g., 12 hours, 13 hours, 14 hours, 15 hours, 16 hours, 17 hours, 18 hours, 19 hours, 20 hours, 21 hours, 22 hours, 23 hours, 24 hours, 12 hours and 24 hours, 14 hours and 24 hours, 16 and 24 hours, 18 hours and 24 hours, or 20 hours and 24 hours prior to the surgical procedure. In some aspects, Factor VIII (FVIII) is not administered with the rVWF prior to the surgical procedure.

In some embodiments, rVWF is administered to the subject at a range of 5-90 IU/kg, e.g., 5-90, 5-50, 10-90, 15-90, 20-90, 30-90, 40-90, 50-90, 60-90, 70-90, 80-90, 5-80, 10-70, 20-60, 30-50, 35-60, 5-50, 5-40, 5-30. 5-20, 10-90, 10-50, or 20-40 IU/kg 1 hour prior to surgery. In other embodiments, rVWF is administered at a dose of 70-200 IU/kg, e.g., 70-200, 80-200-, 90-200, 100-200, 110-200, 120-200, 130-200, 130-200, 140-200, 150-200, 160-200, 170-200, 180-200, 190-200, 70-170, 80-180, 60-160, 50-150, 40-140, 30, 130, 20-120, 10-110, 70-100, or 70-90 IU/kg after the surgery. In some cases, the surgical procedure is selected from a group consisting of major surgery, minor surgery, and oral surgery.

In some embodiments, the subject is administered 35-60 IU/kg rVWF between 12 hours and 24 hours prior to major surgery. In other embodiments, the subject is administered 15-90 IU/kg rVWF 1 hour prior to major surgery. In another embodiment, the subject is administered 150-220 IU/kg rVWF after major surgery. In some instances, the subject undergoing major surgery is administered a total dosage of 220-320 IU/kg.

In some embodiments, the subject is administered 50-60 IU/kg rVWF between 12 hours and 24 hours prior to minor surgery. In other embodiments, the subject is administered 5-50 IU/kg rVWF 1 hour prior to minor surgery. In another embodiment, the subject is administered 70-150 IU/kg rVWF after minor surgery. In some instances, the subject undergoing minor surgery is administered a total dosage of 100-220 IU/kg.

In some embodiments, the subject is administered 20-40 IU/kg rVWF between 12 hours and 24 hours prior to oral surgery. In other embodiments, the subject is administered 20-50 IU/kg rVWF 1 hour prior to oral surgery. In another embodiment, the subject is administered 10-50 IU/kg rVWF during oral surgery. In another embodiment, the subject is administered 20-50 IU/kg rVWF after oral surgery. In some instances, the subject undergoing oral surgery is administered a total dosage of 70-190 IU/kg.

Compositions of rVWF can be contained in pharmaceutical formulations, as described herein. Such formulations can be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

In one aspect, formulations of the invention are administered by an initial bolus followed by a continuous infusion to maintain therapeutic circulating levels of drug product. As another example, the inventive compound is administered as a one-time dose. Those of ordinary skill in the art will readily optimize effective dosages and administration regimens as determined by good medical practice and the clinical condition of the individual patient. The route of administration can be, but is not limited to, by intravenous, intraperitoneal, subcutaneous, or intramuscular administration. The frequency of dosing depends on the pharmacokinetic parameters of the agents and the route of administration. The optimal pharmaceutical formulation is determined by one skilled in the art depending upon the route of administration and desired dosage. See for example, Remington's Pharmaceutical Sciences, 18th Ed., 1990, Mack Publishing Co., Easton, Pa. 18042 pages 1435-1712, the disclosure of which is hereby incorporated by reference in its entirety for all purposes and in particular for all teachings related to formulations, routes of administration and dosages for pharmaceutical products. Such formulations influence the physical state, stability, rate of in vivo release, and rate of in vivo clearance of the administered agents. Depending on the route of administration, a suitable dose is calculated according to body weight, body surface area or organ size. Appropriate dosages may be ascertained through use of established assays for determining blood level dosages in conjunction with appropriate dose-response data. The final dosage regimen is determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. By way of example, a typical dose of a recombinant VWF of the present invention is approximately 50 IU/kg, equal to 500 µg/kg. As studies are conducted, further information will emerge regarding the appropriate dosage levels and duration of treatment for various diseases and conditions.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, Highly stabilized York, Gait, "Oligonucleotide Synthesis: A Practical Approach" 1984, IRL Press, London, Nelson and Cox (2000), Lehninger, Principles of Biochemistry 3rd Ed., W. H. Freeman Pub., Highly stabilized York, N.Y. and Berg et al. (2002) Biochemistry, 5th Ed., W. H. Freeman Pub., Highly stabilized York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the above description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive method.

a. Lyophilized VWF Formulations

The present method also provides formulations of rVWF for use in the treatment methods provided herein. In some embodiments, the rVWF composition is used for the production of a pharmaceutical composition. In some embodiments, the rVWF can be formulated into a lyophilized formulation.

In some embodiments, the formulations comprising a VWF polypeptide of the invention are lyophilized after purification and prior to administration to a subject. Lyophilization is carried out using techniques common in the art and should be optimized for the composition being developed (Tang et al., Pharm Res. 21:191-200, (2004) and Chang et al., Pharm Res. 13:243-9 (1996)).

A lyophilization cycle is, in one aspect, composed of three steps: freezing, primary drying, and secondary drying (A. P. Mackenzie, Phil Trans R Soc London, Ser B, Biol 278:167 (1977)). In the freezing step, the solution is cooled to initiate ice formation. Furthermore, this step induces the crystallization of the bulking agent. The ice sublimes in the primary drying stage, which is conducted by reducing chamber pressure below the vapor pressure of the ice, using a vacuum and introducing heat to promote sublimation. Finally, adsorbed or bound water is removed at the secondary drying stage under reduced chamber pressure and at an elevated shelf temperature. The process produces a material known as a lyophilized cake. Thereafter the cake can be reconstituted with either sterile water or suitable diluent for injection.

The lyophilization cycle not only determines the final physical state of excipients but also affects other parameters such as reconstitution time, appearance, stability and final moisture content. The composition structure in the frozen state proceeds through several transitions (e.g., glass transitions, wettings, and crystallizations) that occur at specific temperatures and the structure may be used to understand and optimize the lyophilization process. The glass transition temperature (Tg and/or Tg') can provide information about the physical state of a solute and can be determined by differential scanning calorimetry (DSC). Tg and Tg' are an important parameter that must be taken into account when designing the lyophilization cycle. For example, Tg' is important for primary drying. Furthermore, in the dried state, the glass transition temperature provides information on the storage temperature of the final product.

b. Pharmaceutical Formulations and Excipients in General

Excipients are additives that either impart or enhance the stability and delivery of a drug product (e.g., protein). Regardless of the reason for their inclusion, excipients are an integral component of a formulation and therefore need to be safe and well tolerated by patients. For protein drugs, the choice of excipients is particularly important because they can affect both efficacy and immunogenicity of the drug. Hence, protein formulations need to be developed with appropriate selection of excipients that afford suitable stability, safety, and marketability.

A lyophilized formulation is, in one aspect, at least comprised of one or more of a buffer, a bulking agent, and a stabilizer. In this aspect, the utility of a surfactant is evaluated and selected in cases where aggregation during the lyophilization step or during reconstitution becomes an issue. An appropriate buffering agent is included to maintain the formulation within stable zones of pH during lyophilization. A comparison of the excipient components contemplated for liquid and lyophilized protein formulations is provided in Table 10.

TABLE 1

| Excipient components of lyophilized protein formulations | |
| --- | --- |
| Excipient component | Function in lyophilized formulation |
| Buffer | Maintain pH of formulation during lyophilization and upon reconstitution |
| Tonicity agent/stabilizer | Stabilizers include cryo and lyoprotectants |
| | Examples include Polyols, sugars and polymers |
| | Cryoprotectants protect proteins from freezing stresses |
| | Lyoprotectants stabilize proteins in the freeze-dried state |
| Bulking agent | Used to enhance product elegance and to prevent blowout |
| | Provides structural strength to the lyo cake |
| | Examples include mannitol and glycine |
| Surfactant | Employed if aggregation during the lyophilization process is an issue |
| | May serve to reduce reconstitution times |
| | Examples include polysorbate 20 and 80 |
| Anti-oxidant | Usually not employed, molecular reactions in the lyo cake are greatly retarded |
| Metal ions/chelating agent | May be included if a specific metal ion is included only as a co-factor or where the metal is required for protease activity |
| | Chelating agents are generally not needed in lyo formulations |
| Preservative | For multi-dose formulations only |
| | Provides protection against microbial growth in formulation |
| | Is usually included in the reconstitution diluent (e.g. bWFI) |

The principal challenge in developing formulations for proteins is stabilizing the product against the stresses of manufacturing, shipping and storage. The role of formulation excipients is to provide stabilization against these stresses. Excipients are also be employed to reduce viscosity of high concentration protein formulations in order to enable their delivery and enhance patient convenience. In general, excipients can be classified on the basis of the mechanisms by which they stabilize proteins against various chemical and physical stresses. Some excipients are used to alleviate the effects of a specific stress or to regulate a particular susceptibility of a specific protein. Other excipients have more general effects on the physical and covalent stabilities of proteins. The excipients described herein are organized either by their chemical type or their functional role in formulations. Brief descriptions of the modes of stabilization are provided when discussing each excipient type.

Given the teachings and guidance provided herein, those skilled in the art will know what amount or range of excipient can be included in any particular formulation to achieve a biopharmaceutical formulation of the invention that promotes retention in stability of the biopharmaceutical (e.g., a protein). For example, the amount and type of a salt to be included in a biopharmaceutical formulation of the invention is selected based on the desired osmolality (e.g., isotonic, hypotonic or hypertonic) of the final solution as well as the amounts and osmolality of other components to be included in the formulation.

By way of example, inclusion of about 5% sorbitol can achieve isotonicity while about 9% of a sucrose excipient is needed to achieve isotonicity. Selection of the amount or range of concentrations of one or more excipients that can be included within a biopharmaceutical formulation of the invention has been exemplified above by reference to salts, polyols and sugars. However, those skilled in the art will understand that the considerations described herein and further exemplified by reference to specific excipients are equally applicable to all types and combinations of excipients including, for example, salts, amino acids, other tonicity agents, surfactants, stabilizers, bulking agents, cryoprotectants, lyoprotectants, anti-oxidants, metal ions, chelating agents and/or preservatives.

Further, where a particular excipient is reported in molar concentration, those skilled in the art will recognize that the equivalent percent (%) w/v (e.g., (grams of substance in a solution sample/mL of solution)×100%) of solution is also contemplated.

Of course, a person having ordinary skill in the art would recognize that the concentrations of the excipients described herein share an interdependency within a particular formulation. By way of example, the concentration of a bulking agent may be lowered where, e.g., there is a high protein concentration or where, e.g., there is a high stabilizing agent concentration. In addition, a person having ordinary skill in the art would recognize that, in order to maintain the isotonicity of a particular formulation in which there is no bulking agent, the concentration of a stabilizing agent would be adjusted accordingly (e.g., a "tonicifying" amount of stabilizer would be used). Common excipients are known in the art and can be found in Powell et al., Compendium of Excipients fir Parenteral Formulations (1998), PDA J. Pharm. Sci. Technology, 52:238-311.

c. Pharmaceutical Buffers and Buffering Agents

The stability of a pharmacologically active protein formulation is usually observed to be maximal in a narrow pH range. This pH range of optimal stability needs to be identified early during pre-formulation studies. Several approaches, such as accelerated stability studies and calorimetric screening studies, are useful in this endeavor (Remmele R. L. Jr., et al., Biochemistry, 38(16): 5241-7 (1999)). Once a formulation is finalized, the protein must be manufactured and maintained throughout its shelf-life. Hence, buffering agents are almost always employed to control pH in the formulation.

The buffer capacity of the buffering species is maximal at a pH equal to the pKa and decreases as pH increases or decreases away from this value. Ninety percent of the buffering capacity exists within one pH unit of its pKa. Buffer capacity also increases proportionally with increasing buffer concentration.

Several factors need to be considered when choosing a buffer. First and foremost, the buffer species and its concentration need to be defined based on its pKa and the desired formulation pH. Equally important is to ensure that the buffer is compatible with the protein and other formulation excipients, and does not catalyze any degradation reactions. A third important aspect to be considered is the sensation of stinging and irritation the buffer may induce upon administration. For example, citrate is known to cause stinging upon injection (Laursen T, et al., Basic Clin Pharmacol Toxicol., 98(2): 218-21 (2006)). The potential for stinging and irritation is greater for drugs that are administered via the subcutaneous (SC) or intramuscular (IM) routes, where the drug solution remains at the site for a relatively longer period of time than when administered by the IV route where the formulation gets diluted rapidly into the blood upon administration. For formulations that are administered by direct IV infusion, the total amount of buffer (and any other formulation component) needs to be monitored. One has to be particularly careful about potassium ions administered in the form of the potassium phosphate buffer, which can induce cardiovascular effects in a patient (Hollander-Rodriguez J C, et al., Am. Fam. Physician., 73(2): 283-90 (2006)).

Buffers for lyophilized formulations need additional consideration. Some buffers like sodium phosphate can crystallize out of the protein amorphous phase during freezing resulting in shifts in pH. Other common buffers such as acetate and imidazole may sublime or evaporate during the lyophilization process, thereby shifting the pH of formulation during lyophilization or after reconstitution.

The buffer system present in the compositions is selected to be physiologically compatible and to maintain a desired pH of the pharmaceutical formulation. In one embodiment, the pH of the solution is between pH 2.0 and pH 12.0. For example, the pH of the solution may be 2.0, 2.3, 2.5, 2.7, 3.0, 3.3, 3.5, 3.7, 4.0, 4.3, 4.5, 4.7, 5.0, 5.3, 5.5, 5.7, 6.0, 6.3, 6.5, 6.7, 7.0, 7.3, 7.5, 7.7, 8.0, 8.3, 8.5, 8.7, 9.0, 9.3, 9.5, 9.7, 10.0, 10.3, 10.5, 10.7, 11.0, 11.3, 11.5, 11.7, or 12.0.

The pH buffering compound may be present in any amount suitable to maintain the pH of the formulation at a predetermined level. In one embodiment, the pH buffering concentration is between 0.1 mM and 500 mM (1 M). For example, it is contemplated that the pH buffering agent is at least 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 25, 30, 40, 50, 60, 70, 80, 90, 100, 200, or 500 mM.

Exemplary pH buffering agents used to buffer the formulation as set out herein include, but are not limited to organic acids, glycine, histidine, glutamate, succinate, phosphate, acetate, citrate, Tris, HEPES, and amino acids or mixtures of amino acids, including, but not limited to aspartate, histidine, and glycine. In one embodiment of the present invention, the buffering agent is citrate.

d. Pharmaceutical Stabilizers and Bulking Agents

In one aspect of the present pharmaceutical formulations, a stabilizer (or a combination of stabilizers) is added to prevent or reduce storage-induced aggregation and chemical degradation. A hazy or turbid solution upon reconstitution indicates that the protein has precipitated or at least aggregated. The term "stabilizer" means an excipient capable of preventing aggregation or physical degradation, including chemical degradation (for example, autolysis, deamidation, oxidation, etc.) in an aqueous state. Stabilizers contemplated include, but are not limited to, sucrose, trehalose, mannose, maltose, lactose, glucose, raffinose, cellobiose, gentiobiose, isomaltose, arabinose, glucosamine, fructose, mannitol, sorbitol, glycine, arginine HCL, poly-hydroxy compounds, including polysaccharides such as dextran, starch, hydroxyethyl starch, cyclodextrins, N-methyl pyrollidene, cellulose and hyaluronic acid, sodium chloride, (Carpenter et al., Develop. Biol. Standard 74:225, (1991)). In the present formulations, the stabilizer is incorporated in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM. In one embodiment of the present invention, mannitol and trehalose are used as stabilizing agents.

If desired, the formulations also include appropriate amounts of bulking and osmolality regulating agents. Bulking agents include, for example and without limitation, mannitol, glycine, sucrose, polymers such as dextran, polyvinylpyrolidone, carboxymethylcellulose, lactose, sorbitol, trehalose, or xylitol. In one embodiment, the bulking agent is mannitol. The bulking agent is incorporated in a concentration of about 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, 900, or 1000 mM.

e. Pharmaceutical Surfactants

Proteins have a high propensity to interact with surfaces making them susceptible to adsorption and denaturation at air-liquid, vial-liquid, and liquid-liquid (silicone oil) interfaces. This degradation pathway has been observed to be inversely dependent on protein concentration and results in either the formation of soluble and insoluble protein aggregates or the loss of protein from solution via adsorption to surfaces. In addition to container surface adsorption, surface-induced degradation is exacerbated with physical agitation, as would be experienced during shipping and handling of the product.

Surfactants are commonly used in protein formulations to prevent surface-induced degradation. Surfactants are amphipathic molecules with the capability of out-competing proteins for interfacial positions. Hydrophobic portions of the surfactant molecules occupy interfacial positions (e.g., air/liquid), while hydrophilic portions of the molecules remain oriented towards the bulk solvent. At sufficient concentrations (typically around the detergent's critical micellar concentration), a surface layer of surfactant molecules serves to prevent protein molecules from adsorbing at the interface. Thereby, surface-induced degradation is minimized. Surfactants contemplated herein include, without limitation, fatty acid esters of sorbitan polyethoxylates, e.g., polysorbate 20 and polysorbate 80. The two differ only in the length of the aliphatic chain that imparts hydrophobic character to the molecules, C-12 and C-18, respectively. Accordingly, polysorbate-80 is more surface-active and has a lower critical micellar concentration than polysorbate-20.

Detergents can also affect the thermodynamic conformational stability of proteins. Here again, the effects of a given detergent excipient will be protein specific. For example, polysorbates have been shown to reduce the stability of some proteins and increase the stability of others. Detergent destabilization of proteins can be rationalized in terms of the hydrophobic tails of the detergent molecules that can engage in specific binding with partially or wholly unfolded protein states. These types of interactions could cause a shift in the conformational equilibrium towards the more expanded protein states (e.g. increasing the exposure of hydrophobic portions of the protein molecule in complement to binding polysorbate). Alternatively, if the protein native state exhibits some hydrophobic surfaces, detergent binding to the native state may stabilize that conformation.

Another aspect of polysorbates is that they are inherently susceptible to oxidative degradation. Often, as raw materials, they contain sufficient quantities of peroxides to cause oxidation of protein residue side-chains, especially methionine. The potential for oxidative damage arising from the addition of stabilizer emphasizes the point that the lowest effective concentrations of excipients should be used in formulations. For surfactants, the effective concentration for a given protein will depend on the mechanism of stabilization.

Surfactants are also added in appropriate amounts to prevent surface related aggregation phenomenon during freezing and drying (Chang, B, J. Pharm. Sci. 85:1325, (1996)). Thus, exemplary surfactants include, without limitation, anionic, cationic, nonionic, zwitterionic, and amphoteric surfactants including surfactants derived from naturally-occurring amino acids. Anionic surfactants include, but are not limited to, sodium lauryl sulfate, dioctyl sodium sulfo succinate and dioctyl sodium sulfonate, chenodeoxycholic acid, N-lauroylsarcosine sodium salt, lithium dodecyl sulfate, 1-octanesulfonic acid sodium salt, sodium cholate hydrate, sodium deoxycholate, and glycodeoxycholic acid sodium salt. Cationic surfactants include, but are not limited to, benzalkonium chloride or benzethonium chloride, cetylpyridinium chloride monohydrate, and hexadecyltrimethylammonium bromide. Zwitterionic surfactants include, but are not limited to, CHAPS, CHAPSO, SB3-10, and SB3-12. Non-ionic surfactants include, but are not limited to, digitonin, Triton X-100, Triton X-114, TWEEN-20, and TWEEN-80. Surfactants also include, but are not limited to lauromacrogol 400, polyoxyl 40 stearate, polyoxyethylene hydrogenated castor oil 10, 40, 50 and 60, glycerol monostearate, polysorbate 40, 60, 65 and 80, soy lecithin and other phospholipids such as dioleyl phosphatidyl choline (DOPC), dimyristoylphosphatidyl glycerol (DMPG), dimyristoylphosphatidyl choline (DMPC), and (dioleyl phosphatidyl glycerol) DOPG; sucrose fatty acid ester, methyl cellulose and carboxymethyl cellulose. Compositions comprising these surfactants, either individually or as a mixture in different ratios, are therefore further provided. In one embodiment of the present invention, the surfactant is TWEEN-80. In the present formulations, the surfactant is incorporated in a concentration of about 0.01 to about 0.5 g/L. In formulations provided, the surfactant concentration is 0.005, 0.01, 0.02, 0.03, 0.05, 0.06, 0.07, 0.08, 0.09, 0.1, 0.2, 0.3, 0.4, 0.5, 0.6, 0.7, 0.8, 0.9 or 1.0 g/L.

f. Pharmaceutical Salts

Salts are often added to increase the ionic strength of the formulation, which can be important for protein solubility, physical stability, and isotonicity. Salts can affect the physical stability of proteins in a variety of ways. Ions can stabilize the native state of proteins by binding to charged residues on the protein's surface. Alternatively, salts can stabilize the denatured state by binding to peptide groups along the protein backbone (—CONH—). Salts can also stabilize the protein native conformation by shielding repulsive electrostatic interactions between residues within a protein molecule. Salts in protein formulations can also shield attractive electrostatic interactions between protein molecules that can lead to protein aggregation and insolubility. In formulations provided, the salt concentration is between 0.1, 1, 10, 20, 30, 40, 50, 80, 100, 120, 150, 200, 300, and 500 mM.

g. Other Common Excipient Components: Pharmaceutical Amino Acids

Amino acids have found versatile use in protein formulations as buffers, bulking agents, stabilizers and antioxidants. Thus, in one aspect histidine and glutamic acid are employed to buffer protein formulations in the pH range of 5.5-6.5 and 4.0-5.5 respectively. The imidazole group of histidine has a pKa=6.0 and the carboxyl group of glutamic acid side chain has a pKa of 4.3 which makes these amino acids suitable for buffering in their respective pH ranges. Glutamic acid is particularly useful in such cases. Histidine is commonly found in marketed protein formulations, and this amino acid provides an alternative to citrate, a buffer known to sting upon injection. Interestingly, histidine has also been reported to have a stabilizing effect, with respect to aggregation when used at high concentrations in both liquid and lyophilized presentations (Chen B, et al., Pharm Res., 20(12): 1952-60 (2003)). Histidine was also observed by others to reduce the viscosity of a high protein concentration formulation. However, in the same study, the authors observed increased aggregation and discoloration in histidine containing formulations during freeze-thaw studies of the antibody in stainless steel containers. Another note of caution with histidine is that it undergoes photo-oxidation in the presence of metal ions (Tomita M, et al., Biochemistry, 8(12): 5149-60 (1969)). The use of methionine as an antioxidant in formulations appears promising; it has been observed to be effective against a number of oxidative stresses (Lam X M, et al., J Pharm ScL, 86(11): 1250-5 (1997)).

In various aspects, formulations are provided which include one or more of the amino acids glycine, proline, serine, arginine and alanine have been shown to stabilize proteins by the mechanism of preferential exclusion. Glycine is also a commonly used bulking agent in lyophilized formulations. Arginine has been shown to be an effective agent in inhibiting aggregation and has been used in both liquid and lyophilized formulations.

In formulations provided, the amino acid concentration is between 0.1, 1, 10, 20, 30, 40, 50, 80, 100, 120, 150, 200, 300, and 500 mM. In one embodiment of the present invention, the amino acid is glycine.

h. Other Common Excipient Components: Pharmaceutical Antioxidants

Oxidation of protein residues arises from a number of different sources. Beyond the addition of specific antioxidants, the prevention of oxidative protein damage involves the careful control of a number of factors throughout the manufacturing process and storage of the product such as atmospheric oxygen, temperature, light exposure, and chemical contamination. The invention therefore contemplates the use of the pharmaceutical antioxidants including, without limitation, reducing agents, oxygen/free-radical scavengers, or chelating agents. Antioxidants in therapeutic protein formulations are, in one aspect, water-soluble and remain active throughout the product shelf-life. Reducing agents and oxygen/free-radical scavengers work by ablating active oxygen species in solution. Chelating agents such as EDTA are effective by binding trace metal contaminants that promote free-radical formation. For example, EDTA was utilized in the liquid formulation of acidic fibroblast growth factor to inhibit the metal ion catalyzed oxidation of cysteine residues.

In addition to the effectiveness of various excipients to prevent protein oxidation, the potential for the antioxidants themselves to induce other covalent or physical changes to the protein is of concern. For example, reducing agents can cause disruption of intramolecular disulfide linkages, which can lead to disulfide shuffling. In the presence of transition metal ions, ascorbic acid and EDTA have been shown to promote methionine oxidation in a number of proteins and peptides (Akers M J, and Defelippis M R. Peptides and Proteins as Parenteral Solutions. In: Pharmaceutical Formulation Development of Peptides and Proteins. Sven Frokjaer, Lars Hovgaard, editors. Pharmaceutical Science. Taylor and Francis, UK (1999)); Fransson J. R., /. Pharm. Sci. 86(9): 4046-1050 (1997); Yin J, et al., Pharm Res., 21(12): 2377-83 (2004)). Sodium thiosulfate has been reported to reduce the levels of light and temperature induced methionine-oxidation in rhuMab HER2; however, the formation of a thiosulfate-protein adduct was also reported in this study (Lam X M, Yang J Y, et al., J Pharm Sci. 86(11): 1250-5 (1997)). Selection of an appropriate antioxidant is made according to the specific stresses and sensitivities of the protein. Antioxidants contemplated in certain aspects include, without limitation, reducing agents and oxygen/free-radical scavengers, EDTA, and sodium thiosulfate.

i. Other Common Excipient Components: Pharmaceutical Metal Ions

In general, transition metal ions are undesired in protein formulations because they can catalyze physical and chemical degradation reactions in proteins. However, specific metal ions are included in formulations when they are co-factors to proteins and in suspension formulations of proteins where they form coordination complexes (e.g., zinc suspension of insulin). Recently, the use of magnesium ions (10-120 mM) has been proposed to inhibit the isomerization of aspartic acid to isoaspartic acid (WO 2004039337).

Two examples where metal ions confer stability or increased activity in proteins are human deoxyribonuclease (rhDNase, Pulmozyme®), and Factor VIII. In the case of rhDNase, $Ca^{+2}$ ions (up to 100 mM) increased the stability of the enzyme through a specific binding site (Chen B, et al., /Pharm Sci., 88(4): 477-82 (1999)). In fact, removal of calcium ions from the solution with EGTA caused an increase in deamidation and aggregation. However, this effect was observed only with $Ca^{+2}$ ions; other divalent cations $Mg^{+2}$, $Mn^{+2}$ and $Zn^{+2}$ were observed to destabilize rhDNase. Similar effects were observed in Factor VIII. $Ca^{+2}$ and $Sr^{+2}$ ions stabilized the protein while others like Mg', $Mn^{+2}$ and $Zn^{+2}$, $Cu^{+2}$ and $Fe^{+2}$ destabilized the enzyme (Fatouros, A., et al., Int. J. Pharm., 155, 121-131 (1997). In a separate study with Factor VIII, a significant increase in aggregation rate was observed in the presence of $Al^{+3}$ ions (Derrick T S, et al., I. Pharm. Sci., 93(10): 2549-57 (2004)). The authors note that other excipients like buffer salts are often contaminated with $Al^{+3}$ ions and illustrate the need to use excipients of appropriate quality in formulated products.

j. Other Common Excipient Components: Pharmaceutical Preservatives

Preservatives are necessary when developing multi-use parenteral formulations that involve more than one extraction from the same container. Their primary function is to inhibit microbial growth and ensure product sterility throughout the shelf-life or term of use of the drug product. Commonly used preservatives include, without limitation, benzyl alcohol, phenol and m-cresol. Although preservatives have a long history of use, the development of protein formulations that includes preservatives can be challenging. Preservatives almost always have a destabilizing effect (aggregation) on proteins, and this has become a major factor in limiting their use in multi-dose protein formulations (Roy S, et al., J Pharm ScL, 94(2): 382-96 (2005)).

To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market.

Norditropin® (liquid, Novo Nordisk), Nutropin AQ® (liquid, Genentech) & Genotropin (lyophilized—dual chamber cartridge, Pharmacia & Upjohn) contain phenol while Somatrope® (Eli Lilly) is formulated with m-cresol.

Several aspects need to be considered during the formulation development of preserved dosage forms. The effective preservative concentration in the drug product must be optimized. This requires testing a given preservative in the dosage form with concentration ranges that confer antimicrobial effectiveness without compromising protein stability. For example, three preservatives were successfully screened in the development of a liquid formulation for interleukin-1 receptor (Type I), using differential scanning calorimetry (DSC). The preservatives were rank ordered based on their impact on stability at concentrations commonly used in marketed products (Remmele R L Jr., et al., Pharm Res., 15(2): 200-8 (1998)).

Development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein significantly minimizing the associated stability risks. With liquid formulations, preservative effectiveness and stability have to be maintained over the entire product shelf-life (−18-24 months). An important point to note is that preservative effectiveness has to be demonstrated in the final formulation containing the active drug and all excipient components.

Some preservatives can cause injection site reactions, which is another factor that needs consideration when choosing a preservative. In clinical trials that focused on the evaluation of preservatives and buffers in Norditropin, pain perception was observed to be lower in formulations containing phenol and benzyl alcohol as compared to a formulation containing m-cresol (Kappelgaard A. M., Horm Res. 62 Suppl 3:98-103 (2004)). Interestingly, among the commonly used preservative, benzyl alcohol possesses anesthetic properties (Minogue S C, and Sun D A., Anesth Analg., 100(3): 683-6 (2005)). In various aspects the use of preservatives provide a benefit that outweighs any side effects.

k. Methods of Preparation of Pharmaceutical Formulations

The present invention further contemplates methods for the preparation of pharmaceutical formulations.

The present methods further comprise one or more of the following steps: adding a stabilizing agent as described herein to said mixture prior to lyophilizing, adding at least one agent selected from a bulking agent, an osmolality regulating agent, and a surfactant, each of which as described herein, to said mixture prior to lyophilization.

The standard reconstitution practice for lyophilized material is to add back a volume of pure water or sterile water for injection (WFI) (typically equivalent to the volume removed during lyophilization), although dilute solutions of antibacterial agents are sometimes used in the production of pharmaceuticals for parenteral administration (Chen, Drug Development and Industrial Pharmacy, 18:1311-1354 (1992)). Accordingly, methods are provided for preparation of reconstituted rVWF compositions comprising the step of adding a diluent to a lyophilized rVWF composition of the invention.

The lyophilized material may be reconstituted as an aqueous solution. A variety of aqueous carriers, e.g., sterile water for injection, water with preservatives for multi dose use, or water with appropriate amounts of surfactants (for example, an aqueous suspension that contains the active compound in admixture with excipients suitable for the manufacture of aqueous suspensions). In various aspects, such excipients are suspending agents, for example and without limitation, sodium carboxymethylcellulose, methylcellulose, hydroxypropylmethylcellulose, sodium alginate, polyvinylpyrrolidone, gum tragacanth and gum acacia; dispersing or wetting agents are a naturally-occurring phosphatide, for example and without limitation, lecithin, or condensation products of an alkylene oxide with fatty acids, for example and without limitation, polyoxyethylene stearate, or condensation products of ethylene oxide with long chain aliphatic alcohols, for example and without limitation, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example and without limitation, polyethylene sorbitan monooleate. In various aspects, the aqueous suspensions also contain one or more preservatives, for example and without limitation, ethyl, or n-propyl, p-hydroxybenzoate.

1. Exemplary rVWF Formulation for Administration

In some embodiments, the present methods provide for an enhanced formulation that allows a final product with high potency (high rVWF concentration and enhanced long term stability) in order to reduce the volume for the treatment (100 IU/ml to 10000 IU/ml). In some embodiments, the rVWF concentration in the formulation for administration is about 100 IU/ml to 10000 IU/ml. In some embodiments, the rVWF concentration in the formulation for administration is about 500 IU/ml to 10000 IU/ml. In some embodiments, the rVWF concentration in the formulation for administration is about 1000 IU/ml to 10000 IU/ml. In some embodiments, the rVWF concentration in the formulation for administration is about 2000 IU/ml to 10000 IU/ml. In some embodiments, the rVWF concentration in the formulation for administration is about 3000 IU/ml to 10000 IU/ml. In some embodiments, the rVWF concentration in the formulation for administration is about 4000 IU/ml to 10000 IU/ml. In some embodiments, the rVWF concentration in the formulation for administration is about 5000 IU/ml to 10000 IU/ml. In some embodiments, the rVWF concentration in the formulation for administration is about 6000 IU/ml to 10000 IU/ml. In some embodiments, the rVWF concentration in the formulation for administration is about 7000 IU/ml to 10000 IU/ml. In some embodiments, the rVWF concentration in the formulation for administration is about 8000 IU/ml to 10000 IU/ml. In some embodiments, the rVWF concentration in the formulation for administration is about 9000 IU/ml to 10000 IU/ml.

In some embodiments, the formulation for administration comprises one or more zwitterionic compounds, including for example, amino acids like Histidine, Glycine, Arginine. In some embodiments, the formulation for administration comprises a component with amphipathic characteristic having a minimum of one hydrophobic and one hydrophilic group, including for example polysorbate 80, octylpyranosid, dipeptides, and/or amphipathic peptides. In some embodiments, the formulation for administration comprises a non reducing sugar or sugar alcohol or disaccharides, including for example, sorbitol, mannitol, sucrose, or trehalose. In some embodiments, the formulation for administration comprises a nontoxic water soluble salt, including for example, sodium chloride, that results in a physiological osmolality. In some embodiments, the formulation for administration comprises a pH in a range from 6.0 to 8.0. In some embodiments, the formulation for administration comprises a pH of about 6.0, about 6.5, about 7, about 7.5 or about 8.0. In some embodiments, the formulation for administration comprises one or more bivalent cations that stabilize rVWF, including for example, $Ca2+$, $Mg2+$, $Zn2+$, $Mn2+$ and/or combinations thereof. In some embodiments, the formulation for administration comprises about 1 mM to about 50 mM Glycine, about 1 mM to about 50 mM Histidine, about zero to about 300 mM sodium chloride (e.g., less than 300 mM sodium), about 0.01% to about 0.05% polysorbate 20 (or polysorbate 80), and about 0.5% to about 20% (w/w) sucrose with a pH of about 7.0 and having a physiological osmolarity at the time point of administration.

In some embodiments, the formulation for administration can be freeze dried. In some embodiments, the formulation for administration is stable and can be stored in liquid state at about 2° C. to about 8° C., as well as at about 18° C. to about 25° C. In some embodiments, the formulation for administration is stable and can be stored in liquid state at about 2° C. to about 8° C. In some embodiments, the formulation for administration is stable and can be stored in liquid state at about 18° C. to about 25° C.

m. Administration/Dosing

To administer compositions to human or test animals, in one aspect, the compositions comprises one or more pharmaceutically acceptable carriers. The phrases "pharmaceutically" or "pharmacologically" acceptable refer to molecular entities and compositions that are stable, inhibit protein degradation such as aggregation and cleavage products, and in addition do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like, including those agents disclosed above.

The pharmaceutical formulations are administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramuscular, intramammary, intraperitoneal, intrathecal, retrobulbar, and/or intrapulmonary injection at a particular site is contemplated as well. Generally, compositions are essentially free of pyrogens, as well as other impurities that could be harmful to the recipient.

According to the present invention, rVWF is administered in the absence of Factor VIII (FVIII). In some embodiments, FVIII is not administered.

In some embodiments, the rVWF is administered prior to the surgical procedure, as discussed herein. In some embodiments, the rVWF is administered at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours, prior to the surgical procedure. In some embodiments, the surgical procedure is a minor surgical procedure. In some embodiments, the surgical procedure is a major surgical procedure. In some embodiments, FVIII is not administered.

In some embodiments, 35-60 IU/kg rVWF is administered at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours, prior to the surgical procedure. In some embodiments, 50-60

IU/kg rVWF is administered at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours, prior to the surgical procedure. In some embodiments, 20-40 IU/kg rVWF is administered at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours, prior to the surgical procedure. In some embodiments, the surgical procedure is a major surgical procedure. In some embodiments, the surgical procedure is a minor surgical procedure. In some embodiments, the surgical procedure is an oral surgical procedure. In some embodiments, FVIII is not administered.

In some embodiments, about 50-60 IU/kg rVWF is administered between 12 hours and 24 hours prior to the surgical procedure. In some embodiments, 50-60 IU/kg rVWF is administered between 12 hours and 24 hours prior to the surgical procedure and the surgical procedure is a minor surgical procedure. In some embodiments, about 55-60 IU/kg rVWF is administered between 12 hours and 24 hours prior to the surgical procedure and the surgical procedure is a minor surgical procedure. In some embodiments, about 50-55 IU/kg rVWF is administered between 12 hours and 24 hours prior to the surgical procedure and the surgical procedure is a minor surgical procedure. In some embodiments, about 50 IU/kg, about 52 IU/kg, about 54 IU/kg, about 56 IU/kg, about 58 IU/kg, or about 60 IU/kg rVWF is administered between 12 hours and 24 hours prior to the surgical procedure and the surgical procedure is a minor surgical procedure. In some embodiments, FVIII is not administered.

In some embodiments, about 35-60 IU/kg rVWF is administered between 12 hours and 24 hours prior to the surgical procedure. In some embodiments, about 35-55 IU/kg rVWF is administered between 12 hours and 24 hours prior to the surgical procedure and the surgical procedure is a major surgical procedure. In some embodiments, about 30-60 IU/kg rVWF is administered between 12 hours and 24 hours prior to the surgical procedure and the surgical procedure is a major surgical procedure. In some embodiments, about 40-60 IU/kg rVWF is administered between 12 hours and 24 hours prior to the surgical procedure and the surgical procedure is a major surgical procedure. In some embodiments, about 45-60 IU/kg rVWF is administered between 12 hours and 24 hours prior to the surgical procedure and the surgical procedure is a major surgical procedure. In some embodiments, about 50-60 IU/kg rVWF is administered between 12 hours and 24 hours prior to the surgical procedure and the surgical procedure is a major surgical procedure. In some embodiments, about 35 IU/kg, about 40 IU/kg, about 45 IU/kg, about 50 IU/kg, about 55 IU/kg, or about 60 IU/kg rVWF is administered between 12 hours and 24 hours prior to the surgical procedure and the surgical procedure is a major surgical procedure. In some embodiments, FVIII is not administered.

In some embodiments, about 20-40 IU/kg rVWF between 12 hours and 24 hours prior to said surgical procedure and said surgical procedure is an oral surgical procedure. In some embodiments, about 20 IU/kg rVWF between 12 hours and 24 hours prior to said surgical procedure and said surgical procedure is an oral surgical procedure. In some embodiments, about 25 IU/kg rVWF between 12 hours and 24 hours prior to said surgical procedure and said surgical procedure is an oral surgical procedure. In some embodiments, about 30 IU/kg rVWF between 12 hours and 24 hours prior to said surgical procedure and said surgical procedure is an oral surgical procedure. In some embodiments, about 35 IU/kg rVWF between 12 hours and 24 hours prior to said surgical procedure and said surgical procedure is an oral surgical procedure. In some embodiments, about 40 IU/kg rVWF between 12 hours and 24 hours prior to said surgical procedure and said surgical procedure is an oral surgical procedure. In some embodiments, FVIII is not administered.

In some embodiments, the method comprises a second pre-treatment step of administering rVWF 1 hour prior to the surgical procedure. In some embodiments, about 5-50 IU/kg rVWF is administered 1 hour prior to the surgical procedure when the surgical procedure is a minor surgical procedure. In some embodiments, about 5 IU/kg rVWF is administered 1 hour prior to the surgical procedure when the surgical procedure is a minor surgical procedure. In some embodiments, about 10 IU/kg rVWF is administered 1 hour prior to the surgical procedure when the surgical procedure is a minor surgical procedure. In some embodiments, about 15 IU/kg rVWF is administered 1 hour prior to the surgical procedure when the surgical procedure is a minor surgical procedure. In some embodiments, about 20 IU/kg rVWF is administered 1 hour prior to the surgical procedure when the surgical procedure is a minor surgical procedure. In some embodiments, about 25 IU/kg rVWF is administered 1 hour prior to the surgical procedure when the surgical procedure is a minor surgical procedure. In some embodiments, about 30 IU/kg rVWF is administered 1 hour prior to the surgical procedure when the surgical procedure is a minor surgical procedure. In some embodiments, about 35 IU/kg rVWF is administered 1 hour prior to the surgical procedure when the surgical procedure is a minor surgical procedure. In some embodiments, about 40 IU/kg rVWF is administered 1 hour prior to the surgical procedure when the surgical procedure is a minor surgical procedure. In some embodiments, about 45 IU/kg rVWF is administered 1 hour prior to the surgical procedure when the surgical procedure is a minor surgical procedure. In some embodiments, about 50 IU/kg rVWF is administered 1 hour prior to the surgical procedure when the surgical procedure is a minor surgical procedure. In some embodiments, FVIII is not administered.

In some embodiments, about 15-90 IU/kg rVWF is administered 1 hour prior to the surgical procedure when the surgical procedure is a major surgical procedure. In some embodiments, about 15 IU/kg rVWF is administered 1 hour prior to the surgical procedure when the surgical procedure is a major surgical procedure. In some embodiments, about 20 IU/kg rVWF is administered 1 hour prior to the surgical procedure when the surgical procedure is a major surgical procedure. In some embodiments, about 25 IU/kg rVWF is administered 1 hour prior to the surgical procedure when the surgical procedure is a major surgical procedure. In some embodiments, about 30 IU/kg rVWF is administered 1 hour prior to the surgical procedure when the surgical procedure is a major surgical procedure. In some embodiments, about 35 IU/kg rVWF is administered 1 hour prior to the surgical procedure when the surgical procedure is a major surgical procedure. In some embodiments, about 40 IU/kg rVWF is administered 1 hour prior to the surgical procedure when the surgical procedure is a major surgical procedure. In some embodiments, about 45 IU/kg rVWF is administered 1 hour prior to the surgical procedure when the surgical procedure is a major surgical procedure. In some embodiments, about 50 IU/kg rVWF is administered 1 hour prior to the surgical procedure when the surgical procedure is a major surgical procedure. In some embodiments, about 55 IU/kg rVWF is administered 1 hour prior to the surgical procedure when the surgical procedure is a major surgical procedure. In some embodiments, about 60 IU/kg rVWF is administered 1 hour prior to the surgical procedure when the surgical procedure is a major surgical procedure. In some embodiments, about 65 IU/kg rVWF is administered 1 hour prior to the surgical procedure when the surgical procedure is a major surgical procedure. In some embodiments, about 70 IU/kg rVWF is administered 1 hour prior to the surgical procedure when the surgical procedure is a major surgical procedure. In some embodiments, about 75 IU/kg rVWF is administered 1 hour prior to the surgical procedure when the surgical procedure is a major surgical procedure. In some embodiments, about 80 IU/kg rVWF is administered 1 hour prior to the surgical procedure when the surgical procedure is a major surgical procedure. In some embodiments, about 85 IU/kg rVWF is administered 1 hour prior to the surgical procedure when the surgical procedure is a major surgical procedure. In some embodiments, about 90 IU/kg rVWF is administered 1 hour prior to the surgical procedure when the surgical procedure is a major surgical procedure. In some embodiments, FVIII is not administered.

In some embodiments, about 20-50 IU/kg rVWF is administered 1 hour prior to the surgical procedure when the surgical procedure is an oral surgical procedure. In some embodiments, about 25-50 IU/kg rVWF is administered 1 hour prior to the surgical procedure when the surgical procedure is an oral surgical procedure. In some embodiments, about 30-50 IU/kg rVWF is administered 1 hour prior to the surgical procedure when the surgical procedure is an oral surgical procedure. In some embodiments, about 25-40 IU/kg rVWF is administered 1 hour prior to the surgical procedure when the surgical procedure is an oral surgical procedure. In some embodiments, about 40-50 IU/kg rVWF is administered 1 hour prior to the surgical procedure when the surgical procedure is an oral surgical procedure. In some embodiments, about 20 IU/kg rVWF is administered 1 hour prior to the surgical procedure when the surgical procedure is an oral surgical procedure. In some embodiments, about 25 IU/kg rVWF is administered 1 hour prior to the surgical procedure when the surgical procedure is an oral surgical procedure. In some embodiments, about 30 IU/kg rVWF is administered 1 hour prior to the surgical procedure when the surgical procedure is an oral surgical procedure. In some embodiments, about 35 IU/kg rVWF is administered 1 hour prior to the surgical procedure when the surgical procedure is an oral surgical procedure. In some embodiments, about 40 IU/kg rVWF is administered 1 hour prior to the surgical procedure when the surgical procedure is an oral surgical procedure. In some embodiments, about 45 IU/kg rVWF is administered 1 hour prior to the surgical procedure when the surgical procedure is an oral surgical procedure. In some embodiments, about 50 IU/kg rVWF is administered 1 hour prior to the surgical procedure when the surgical procedure is an oral surgical procedure. In some embodiments, FVIII is not administered.

In some embodiments, the method comprises administration of rVWF during the surgical procedure. In some embodiments, about 10-50 IU/kg rVWF is administered during said surgical procedure and said surgical procedure is an oral surgical procedure. In some embodiments, about 20-50 IU/kg rVWF is administered during said surgical procedure and said surgical procedure is an oral surgical procedure. In some embodiments, about 30-50 IU/kg rVWF is administered during said surgical procedure and said surgical procedure is an oral surgical procedure. In some embodiments, about 40-50 IU/kg rVWF is administered during said surgical procedure and said surgical procedure is an oral surgical procedure. In some embodiments, about 20-40 IU/kg rVWF is administered during said surgical procedure and said surgical procedure is an oral surgical procedure. In some embodiments, about 30-40 IU/kg rVWF is administered during said surgical procedure and said surgical procedure is an oral surgical procedure. In some embodiments, 10 IU/kg rVWF is administered during said surgical procedure and said surgical procedure is an oral surgical procedure. In some embodiments, about 15 IU/kg rVWF is administered during said surgical procedure and said surgical procedure is an oral surgical procedure. In some embodiments, about 20 IU/kg rVWF is administered during said surgical procedure and said surgical procedure is an oral surgical procedure. In some embodiments, about 25 IU/kg rVWF is administered during said surgical procedure and said surgical procedure is an oral surgical procedure. In some embodiments, about 30 IU/kg rVWF is administered during said surgical procedure and said surgical procedure is an oral surgical procedure. In some embodiments, about 35 IU/kg rVWF is administered during said surgical procedure and said surgical procedure is an oral surgical procedure. In some embodiments, about 40 IU/kg rVWF is administered during said surgical procedure and said surgical procedure is an oral surgical procedure. In some embodiments, about 45 IU/kg rVWF is administered during said surgical procedure and said surgical procedure is an oral surgical procedure. In some embodiments, about 50 IU/kg rVWF is administered during said surgical procedure and said surgical procedure is an oral surgical procedure. In some embodiments, FVIII is not administered.

In some embodiments, about 70-220 IU/kg rVWF is administered after the surgical procedure. In some embodiments, about 90-220 IU/kg rVWF is administered after the surgical procedure. In some embodiments, about 110-220 IU/kg rVWF is administered after the surgical procedure. In some embodiments, about 120-220 IU/kg rVWF is administered after the surgical procedure. In some embodiments, about 140-220 IU/kg rVWF is administered after the surgical procedure. In some embodiments, about 150-200 IU/kg rVWF is administered after the surgical procedure. In some embodiments, about 160-220 IU/kg rVWF is administered after the surgical procedure. In some embodiments, about 180-220 IU/kg rVWF is administered after the surgical procedure. In some embodiments, about 180-200 IU/kg rVWF is administered after the surgical procedure. In some embodiments, about 180-190 IU/kg rVWF is administered after the surgical procedure. In some embodiments, about 190-220 IU/kg rVWF is administered after the surgical procedure. In some embodiments, about 190-210 IU/kg rVWF is administered after the surgical procedure. In some embodiments, about 200-220 IU/kg rVWF is administered after the surgical procedure. In some embodiments, about 210-220 IU/kg rVWF is administered after the surgical procedure. In some embodiments, about 80 IU/kg rVWF is administered after the surgical procedure. In some embodiments, about 90 IU/kg rVWF is administered after the surgical procedure. In some embodiments, about 100 IU/kg rVWF is administered after the surgical procedure. In some embodiments, about 110 IU/kg rVWF is administered after the surgical procedure. In some embodiments, about 120 IU/kg rVWF is administered after the surgical procedure. In some embodiments, about 130 IU/kg rVWF is administered after the surgical procedure. In some embodiments, about 140 IU/kg rVWF is administered after the surgical procedure. In some embodiments, about 150 IU/kg rVWF is administered after the surgical procedure. In some embodiments, about 160 IU/kg rVWF is administered after the surgical procedure. In some embodiments, about 170 IU/kg rVWF is administered after the surgical procedure. In some embodiments, about 180 IU/kg rVWF is administered after the surgical procedure. In some embodiments, about 190 IU/kg rVWF is administered after the surgical procedure. In some embodiments, about 200 IU/kg rVWF is administered after the surgical procedure. In some embodiments, about 210 IU/kg rVWF is administered after the surgical procedure. In some embodiments, about 220 IU/kg rVWF is administered after the surgical procedure. In some embodiments, FVIII is not administered.

In some embodiments, about 70-150 IU/kg rVWF is administered after the surgical procedure when the surgical procedure is a minor surgical procedure. In some embodiments, about 80-150 IU/kg rVWF is administered after the surgical procedure when the surgical procedure is a minor surgical procedure. In some embodiments, about 90-150 IU/kg rVWF is administered after the surgical procedure when the surgical procedure is a minor surgical procedure. In some embodiments, about 100-150 IU/kg rVWF is administered after the surgical procedure when the surgical procedure is a minor surgical procedure. In some embodiments, about 110-150 IU/kg rVWF is administered after the surgical procedure when the surgical procedure is a minor surgical procedure. In some embodiments, about 120-150 IU/kg rVWF is administered after the surgical procedure when the surgical procedure is a minor surgical procedure. In some embodiments, about 130-150 IU/kg rVWF is administered after the surgical procedure when the surgical procedure is a minor surgical procedure. In some embodiments, about 100-140 IU/kg rVWF is administered after the surgical procedure when the surgical procedure is a minor surgical procedure. In some embodiments, about 90-140 IU/kg rVWF is administered after the surgical procedure when the surgical procedure is a minor surgical procedure. In some embodiments, about 140-150 IU/kg rVWF is administered after the surgical procedure when the surgical procedure is a minor surgical procedure. In some embodiments, about 70 IU/kg rVWF is administered after the surgical procedure when the surgical procedure is a minor surgical procedure. In some embodiments, about 80 IU/kg rVWF is administered after the surgical procedure when the surgical procedure is a minor surgical procedure. In some embodiments, about 90 IU/kg rVWF is administered after the surgical procedure when the surgical procedure is a minor surgical procedure. In some embodiments, about 100 IU/kg rVWF is administered after the surgical procedure when the surgical procedure is a minor surgical procedure. In some embodiments, about 110 IU/kg rVWF is administered after the surgical procedure when the surgical procedure is a minor surgical procedure. In some embodiments, about 120 IU/kg rVWF is administered after the surgical procedure when the surgical procedure is a minor surgical procedure. In some embodiments, about 130 IU/kg rVWF is administered after the surgical procedure when the surgical procedure is a minor surgical procedure. In some embodiments, about 140 IU/kg rVWF is administered after the surgical procedure when the surgical procedure is a minor surgical procedure. In some embodiments, about 150 IU/kg rVWF is administered after the surgical procedure when the surgical procedure is a minor surgical procedure. In some embodiments, when the surgical procedure is a minor surgical procedure, the pre-treatment comprises administering at least two doses of rVWF prior to the surgical procedure. In some embodiments, when the surgical procedure is a minor surgical procedure, the pre-treatment comprises administering at least two doses of rVWF prior to the surgical procedure, wherein the first dose is larger than the second dose. In some embodiments, FVIII is not administered.

In some embodiments, about 150-220 IU/kg rVWF is administered after the surgical procedure when the surgical procedure is a major surgical procedure. In some embodiments, about 160-220 IU/kg rVWF is administered after the surgical procedure when the surgical procedure is a major surgical procedure. In some embodiments, about 170-220 IU/kg rVWF is administered after the surgical procedure when the surgical procedure is a major surgical procedure. In some embodiments, about 180-220 IU/kg rVWF is administered after the surgical procedure when the surgical procedure is a major surgical procedure. In some embodiments, about 180-210 IU/kg rVWF is administered after the surgical procedure when the surgical procedure is a major surgical procedure. In some embodiments, about 190-220 IU/kg rVWF is administered after the surgical procedure when the surgical procedure is a major surgical procedure. In some embodiments, about 190-210 IU/kg rVWF is administered after the surgical procedure when the surgical procedure is a major surgical procedure. In some embodiments, about 200-220 IU/kg rVWF is administered after the surgical procedure when the surgical procedure is a major surgical procedure. In some embodiments, about 150 IU/kg rVWF is administered after the surgical procedure when the surgical procedure is a major surgical procedure. In some embodiments, about 160 IU/kg rVWF is administered after the surgical procedure when the surgical procedure is a major surgical procedure. In some embodiments, about 170 IU/kg rVWF is administered after the surgical procedure when the surgical procedure is a major surgical procedure. In some embodiments, about 180 IU/kg rVWF is administered after the surgical procedure when the surgical procedure is a major surgical procedure. In some embodiments, about 190 IU/kg rVWF is administered after the surgical procedure when the surgical procedure is a major surgical procedure. In some embodiments, about 200 IU/kg rVWF is administered after the surgical procedure when the surgical procedure is a major surgical procedure. In some embodiments, about 210 IU/kg rVWF is administered after the surgical procedure when the surgical procedure is a major surgical procedure. In some embodiments, about 220 IU/kg rVWF is administered after the surgical procedure when the surgical procedure is a major surgical procedure. In some embodiments, when the surgical procedure is a major surgical procedure, the pre-treatment comprises administering at least two approximately equal doses of rVWF prior to the surgical procedure. In some embodiments, FVIII is not administered.

In some embodiments, about 20-50 IU/kg rVWF is administered after the surgical procedure when the surgical procedure is an oral surgical procedure. In some embodiments, about 25-50 IU/kg rVWF is administered after the surgical procedure when the surgical procedure is an oral surgical procedure. In some embodiments, about 30-50 IU/kg rVWF is administered after the surgical procedure when the surgical procedure is an oral surgical procedure. In some embodiments, about 25-40 IU/kg rVWF is administered after the surgical procedure when the surgical procedure is an oral surgical procedure. In some embodiments, about 30-40 IU/kg rVWF is administered after the surgical procedure when the surgical procedure is an oral surgical procedure. In some embodiments, about 40-50 IU/kg rVWF is administered after the surgical procedure when the surgical procedure is an oral surgical procedure. In some embodiments, about 45-50 IU/kg rVWF is administered after the surgical procedure when the surgical procedure is an oral surgical procedure. In some embodiments, about 20 IU/kg rVWF is administered after the surgical procedure when the surgical procedure is an oral surgical procedure. In some embodiments, about 25 IU/kg rVWF is administered after the surgical procedure when the surgical procedure is an oral surgical procedure. In some embodiments, about 30 IU/kg rVWF is administered after the surgical procedure when the surgical procedure is an oral surgical procedure. In some embodiments, about 35 IU/kg rVWF is administered after the surgical procedure when the surgical procedure is an oral surgical procedure. In some embodiments, about 40 IU/kg rVWF is administered after the surgical procedure when the surgical procedure is an oral surgical procedure. In some embodiments, about 45 IU/kg rVWF is administered after the surgical procedure when the surgical procedure is an oral surgical procedure. In some embodiments, about 50 IU/kg rVWF is administered after the surgical procedure when the surgical procedure is an oral surgical procedure. In some embodiments, the surgical procedure is an oral surgical procedure and the pre-treatment comprises administering at least two approximately equal doses of rVWF prior to the surgical procedure. In some embodiments, FVIII is not administered.

In some embodiments, a total dosage of about 100-220 IU/kg rVWF is administered when the surgical procedure is a minor surgical procedure. In some embodiments, a total dosage of about 110-220 IU/kg rVWF is administered when the surgical procedure is a minor surgical procedure. In some embodiments, a total dosage of about 120-220 IU/kg rVWF is administered when the surgical procedure is a minor surgical procedure. In some embodiments, a total dosage of about 130-220 IU/kg rVWF is administered when the surgical procedure is a minor surgical procedure. In some embodiments, a total dosage of about 140-220 IU/kg rVWF is administered when the surgical procedure is a minor surgical procedure. In some embodiments, a total dosage of about 150-220 IU/kg rVWF is administered when the surgical procedure is a minor surgical procedure. In some embodiments, a total dosage of about 160-220 IU/kg rVWF is administered when the surgical procedure is a minor surgical procedure. In some embodiments, a total dosage of about 170-220 IU/kg rVWF is administered when the surgical procedure is a minor surgical procedure. In some embodiments, a total dosage of about 180-220 IU/kg rVWF is administered when the surgical procedure is a minor surgical procedure. In some embodiments, a total dosage of about 190-220 IU/kg rVWF is administered when the surgical procedure is a minor surgical procedure. In some embodiments, a total dosage of about 180-210 IU/kg rVWF is administered when the surgical procedure is a minor surgical procedure. In some embodiments, a total dosage of about 190-210 IU/kg rVWF is administered when the surgical procedure is a minor surgical procedure. In some embodiments, a total dosage of about 200-220 IU/kg rVWF is administered when the surgical procedure is a minor surgical procedure. In some embodiments, a total dosage of about 210-220 IU/kg rVWF is administered when the surgical procedure is a minor surgical procedure. In some embodiments, a total dosage of about 100 IU/kg rVWF is administered when the surgical procedure is a minor surgical procedure. In some embodiments, a total dosage of about 110 IU/kg rVWF is administered when the surgical procedure is a minor surgical procedure. In some embodiments, a total dosage of about 120 IU/kg rVWF is administered when the surgical procedure is a minor surgical procedure. In some embodiments, a total dosage of about 130 IU/kg rVWF is administered when the surgical procedure is a minor surgical procedure. In some embodiments, a total dosage of about 140 IU/kg rVWF is administered when the surgical procedure is a minor surgical procedure. In some embodiments, a total dosage of about 150 IU/kg rVWF is administered when the surgical procedure is a minor surgical procedure. In some embodiments, a total dosage of about 160 IU/kg rVWF is administered when the surgical procedure is a minor surgical procedure. In some embodiments, a total dosage of about 170 IU/kg rVWF is administered when the surgical procedure is a minor surgical procedure. In some embodiments, a total dosage of about 180 IU/kg rVWF is administered when the surgical procedure is a minor surgical procedure. In some embodiments, a total dosage of about 190 IU/kg rVWF is administered when the surgical procedure is a minor surgical procedure. In some embodiments, a total dosage of about 200 IU/kg rVWF is administered when the surgical procedure is a minor surgical procedure. In some embodiments, a total dosage of about 210 IU/kg rVWF is administered when the surgical procedure is a minor surgical procedure. In some embodiments, a total dosage of about 220 IU/kg rVWF is administered when the surgical procedure is a minor surgical procedure. In some embodiments, FVIII is not administered.

In some embodiments, a total dosage of about 220-320 IU/kg rVWF is administered when the surgical procedure is a major surgical procedure. In some embodiments, a total dosage of about 230-320 IU/kg rVWF is administered when the surgical procedure is a major surgical procedure. In some embodiments, a total dosage of about 240-320 IU/kg rVWF is administered when the surgical procedure is a major surgical procedure. In some embodiments, a total dosage of about 250-320 IU/kg rVWF is administered when the surgical procedure is a major surgical procedure. In some embodiments, a total dosage of about 260-320 IU/kg rVWF is administered when the surgical procedure is a major surgical procedure. In some embodiments, a total dosage of about 270-320 IU/kg rVWF is administered when the surgical procedure is a major surgical procedure. In some embodiments, a total dosage of about 280-320 IU/kg rVWF is administered when the surgical procedure is a major surgical procedure. In some embodiments, a total dosage of about 280-310 IU/kg rVWF is administered when the surgical procedure is a major surgical procedure. In some embodiments, a total dosage of about 290-310 IU/kg rVWF is administered when the surgical procedure is a major surgical procedure. In some embodiments, a total dosage of about 290-320 IU/kg rVWF is administered when the surgical procedure is a major surgical procedure. In some embodiments, a total dosage of about 300-320 IU/kg rVWF is administered when the surgical procedure is a major surgical procedure. In some embodiments, a total dosage of about 300-310 IU/kg rVWF is administered when the surgical procedure is a major surgical procedure. In some embodiments, a total dosage of about 220 IU/kg rVWF is administered when the surgical procedure is a major surgical procedure. In some embodiments, a total dosage of about 230 IU/kg rVWF is administered when the surgical procedure is a major surgical procedure. In some embodiments, a total dosage of about 240 IU/kg rVWF is administered when the surgical procedure is a major surgical procedure. In some embodiments, a total dosage of about 250 IU/kg rVWF is administered when the surgical procedure is a major surgical procedure. In some embodiments, a total dosage of about 260 IU/kg rVWF is administered when the surgical procedure is a major surgical procedure. In some embodiments, a total dosage of about 270 IU/kg rVWF is administered when the surgical procedure is a major surgical procedure. In some embodiments, a total dosage of about 280 IU/kg rVWF is administered when the surgical procedure is a major surgical procedure. In some embodiments, a total dosage of about 290 IU/kg rVWF is administered when the surgical procedure is a major surgical procedure. In some embodiments, a total dosage of about 300 IU/kg rVWF is administered when the surgical procedure is a major surgical procedure. In some embodiments, a total dosage of about 310 IU/kg rVWF is administered when the surgical procedure is a major surgical procedure. In some embodiments, a total dosage of about 320 IU/kg rVWF is administered when the surgical procedure is a major surgical procedure. In some embodiments, FVIII is not administered.

In some embodiments, a total dosage of about 70-190 IU/kg rVWF is administered when the surgical procedure is an oral surgical procedure. In some embodiments, a total dosage of about 80-190 IU/kg rVWF is administered when the surgical procedure is an oral surgical procedure. In some embodiments, a total dosage of 9 about 0-190 IU/kg rVWF is administered when the surgical procedure is an oral surgical procedure. In some embodiments, a total dosage of about 100-190 IU/kg rVWF is administered when the surgical procedure is an oral surgical procedure. In some embodiments, a total dosage of about 110-190 IU/kg rVWF is administered when the surgical procedure is an oral surgical procedure. In some embodiments, a total dosage of about 120-190 IU/kg rVWF is administered when the surgical procedure is an oral surgical procedure. In some embodiments, a total dosage of about 130-190 IU/kg rVWF is administered when the surgical procedure is an oral surgical procedure. In some embodiments, a total dosage of about 140-190 IU/kg rVWF is administered when the surgical procedure is an oral surgical procedure. In some embodiments, a total dosage of about 150-190 IU/kg rVWF is administered when the surgical procedure is an oral surgical procedure. In some embodiments, a total dosage of about 160-190 IU/kg rVWF is administered when the surgical procedure is an oral surgical procedure. In some embodiments, a total dosage of about 170-190 IU/kg rVWF is administered when the surgical procedure is an oral surgical procedure. In some embodiments, a total dosage of about 180-190 IU/kg rVWF is administered when the surgical procedure is an oral surgical procedure. In some embodiments, a total dosage of about 70 IU/kg rVWF is administered when the surgical procedure is an oral surgical procedure. In some embodiments, a total dosage of about 80 IU/kg rVWF is administered when the surgical procedure is an oral surgical procedure. In some embodiments, a total dosage of about 90 IU/kg rVWF is administered when the surgical procedure is an oral surgical procedure. In some embodiments, a total dosage of about 100 IU/kg rVWF is administered when the surgical procedure is an oral surgical procedure. In some embodiments, a total dosage of about 110 IU/kg rVWF is administered when the surgical procedure is an oral surgical procedure. In some embodiments, a total dosage of about 120 IU/kg rVWF is administered when the surgical procedure is an oral surgical procedure. In some embodiments, a total dosage of about 130 IU/kg rVWF is administered when the surgical procedure is an oral surgical procedure. In some embodiments, a total dosage of about 140 IU/kg rVWF is administered when the surgical procedure is an oral surgical procedure. In some embodiments, a total dosage of about 150 IU/kg rVWF is administered when the surgical procedure is an oral surgical procedure. In some embodiments, a total dosage of about 160 IU/kg rVWF is administered when the surgical procedure is an oral surgical procedure. In some embodiments, a total dosage of about 170 IU/kg rVWF is administered when the surgical procedure is an oral surgical procedure. In some embodiments, a total dosage of about 180 IU/kg rVWF is administered when the surgical procedure is an oral surgical procedure. In some embodiments, a total dosage of about 190 IU/kg rVWF is administered when the surgical procedure is an oral surgical procedure. In some embodiments, FVIII is not administered.

In some embodiments, when the surgical procedure is a major surgical procedure, the pre-treatment comprises administering at least two approximately equal doses of rVWF prior to the surgical procedure. In some embodiments, the dosage is a dosage as listed above. In some embodiments, FVIII is not administered. In some embodiments, when the surgical procedure is a minor surgical procedure, the pre-treatment comprises administering at least two doses of rVWF prior to the surgical procedure. In some embodiments, when the surgical procedure is a minor surgical procedure, the pre-treatment comprises administering at least two doses of rVWF prior to the surgical procedure, wherein the first dose is larger than the second dose. In some embodiments, the dosage is a dosage as listed above. In some embodiments, FVIII is not administered. In some embodiments, the surgical procedure is an oral surgical procedure and the pre-treatment comprises administering at least two approximately equal doses of rVWF prior to the surgical procedure. In some embodiments, the dosage is a dosage as listed above. In some embodiments, FVIII is not administered.

Generally, Type 1 VWD is indicated by <30 IU/dL VWF:RCo, <30 IU/dL VWF:Ag, low or normal FVIII, and >0.5-0.7 IU/dLVWF:RCo/VWF:Ag Ratio. Type 2A VWD is indicated by <30 IU/dL VWF:RCo, <30-200 IU/dL VWF:Ag, low or normal FVIII, and <0.5-0.7 IU/dLVWF:RCo/VWF:Ag Ratio. Type 2B VWD is indicated by <30-200 IU/dL VWF:RCo, <30 IU/dL VWF:Ag, low or normal FVIII, and usually <0.5-0.7 IU/dLVWF:RCo/VWF:Ag Ratio. Type 2M VWD is indicated by <30 IU/dL VWF:RCo, <30-200 IU/dL VWF:Ag, low or normal FVIII, and <0.5-0.7 IU/dLVWF:RCo/VWF:Ag Ratio. Type 2N VWD is indicated by 30-2000 IU/dL VWF:RCo, 30-200 IU/dL VWF:Ag, very low FVIII, and >0.5-0.7 IU/dLVWF:RCo/VWF:Ag Ratio. Type 3 VWD is indicated by <3 IU/dL VWF:RCo, <3 IU/dL VWF:Ag, extremely low (<10 IU/dL) FVIII, and the VWF:RCo/VWF:Ag Ratio is not applicable. Normal is indicated by 50-200 IU/dL VWF:RCo, 50-200 IU/dL VWF:Ag, normal FVIII, and >0.5-0.7 IU/dLVWF:RCo/VWF:Ag Ratio. In some embodiments, the subject has Type 3 VWD. In some embodiments, the subject has severe type 1 VWD. In some embodiments, the subject has severe type 2 VWD.

V. Surgical Procedures

The surgical procedure according to the methods of the present invention can be a major surgical procedure or a minor surgical procedure.

Generally, major surgery includes any invasive operative procedure in which a more extensive resection is performed, e.g., a body cavity is entered, organs are removed, or normal anatomy is altered. Generally, if a mesenchymal barrier is opened (for example, pleural cavity, peritoneum, meninges), the surgery is considered major. In some embodiments, a major surgery is one in which there is an expected blood loss of greater than 500 mL, significant fluid shifts and typically, at least one night in hospital. Exemplary major surgical procedures include but are not limited to bariatric surgeries/ gastric bypass, septal myotomy, pancreatectomy, thoracic aortic dissection repair, esophagectomy, bladder cystectomy, coronary revascularization, spinal osteomyelitis surgery, surgical ventricular restoration, craniectomy, laparoscopic surgery (except cholecystectomy and tubal ligation), open resection of organs, large joint replacements, mastectomy with reconstruction, and/or spine, thoracic, vascular, and/or intracranial surgery. Further examples of major surgeries include but are not limited to maxillary or mandibular osteotomy, laryngectomy, resection of large benign or malignant mass and/or lymph node dissection requiring overnight stay in hospital (with or without reconstructive surgery), mastectomy with immediate tissue reconstruction (with or without lymph node biopsy or axillary dissection), laparoscopic or open repair or resection (of, for example, stomach, small bowel, colon, liver, pancreas, spleen, adrenals or liver), open cholecystectomy, large incisional, epigastric or ventral hernia repairs, hysteroscopic resection or ablation, hysterectomy and/or adnexal surgery, laparoscopy for extensive endometriosis, abdominal or transvaginal pelvic floor surgery, intracranial surgery, spinal laminectomy and/or fusion, knee replacement, hip replacement, shoulder replacement, elbow joint replacement, hardware removal or revision for infection or failure, amputation, spinal laminectomy and/or fusion, free flap reconstruction (plastic surgery), panniculectomy, mediastinoscopy, lung resection, esophagus resection, mediastinal mass resection (thoracoscopic or open), hiatal hernia repair (thoracoscopic or open), bladder tumor resection (transurethral or open), prostate tumor (transurethral or open), resection of kidney resection (laparoscopic or open), ureteral resection (laparoscopic or open), resection of testis (transscrotal or abdominal), amputation, peripheral arterial bypass surgery, aortic aneurysm repair (endovascular or open), and/or carotid endarterectomy.

Minor surgery is any invasive operative procedure in which only skin or mucus membranes and connective tissue is resected e.g. vascular cutdown for catheter placement, implanting pumps in subcutaneous tissue. A minor surgical procedure typically includes any procedure that can be safely performed in an outpatient setting, without the use of general anesthesia or the need for respiratory assistance. In some embodiments, a minor surgery is one in which there is an expected blood loss of less than 500 mL, minimal fluid shifts and is typically done on an ambulatory basis (day surgery/same day discharge). Such outpatient surgical procedures can include but are not limited to cataract surgery, breast surgery without reconstruction, laparoscopic cholecystectomy and tubal ligation, and most cutaneous, superficial, endoscopic and arthroscopic procedures. Further examples of minor surgeries include but are not limited to tooth extraction, tonsillectomy, adenoidectomy, septoplasty, turbinectomy, rhinoplasty, pharyngeal biopsy, laryngeal biopsy, minor excision by laser or other means, middle ear surgery, mastoidectomy, cochlear implantation, endoscopic sinus surgery, small resections of benign and malignant masses (done on an ambulatory basis; i.e., mandibular tori, brachial cleft cyst, small tongue cancer), thyroidectomy, breast lumpectomy (with or without lymph node biopsy or axillary dissection), mastectomy (with or without lymph node biopsy or axillary dissection), inguinal hernia repair (laparoscopic or open approach), umbilical hernia repair (laparoscopic or open approach), laparoscopic cholecystectomy, hemorrhoidectomy, dilation, curettage, diagnostic hysteroscopy, laparoscopy, endometrial ablation by thermal balloon, tubal ligation, laparoscopy—limited endometriosis, transvaginal tape insertion, discectomy, cataract extraction, most ophthalmological procedures, arthroscopic surgery (including ACL repair), routine hardware removal (not for infection), tendon surgery, bunionectomy, discectomy, carpal tunnel release, Dupuytren's contracture release, major tendone surgery, minor tendon surgery, small rotational flaps and skin grafts, basal cell carcinoma resection, lipoma excision, reduction mammoplasty and other surgery for benign breast disease, cosmetic breast surgery, bronchoscopy, cystoscopy, ureteroscopy, renoscopy for stone, renoscopy for stricture, renoscopy for biopsy, hydrocele excision, varicocele excision, vasectomy, circumcision, and/or varicose vein excision.

Oral surgical procedures include, but are not limited to, various dental procedures and oral surgeries, including for example tooth extractions.

In some embodiments, the surgical procedure is a major surgical procedure. In some embodiments, the surgical procedure is a minor surgical procedure. In some embodiments, the surgical procedure is an oral surgical procedure.

EXAMPLES

Example 1: Hemostatic Efficacy and Safety of rVWF

This study evaluated the hemostatic efficacy and safety of rVWF with or without ADVATE (antihemophilic factor [recombinant]), Baxalta US Inc., Westlake Village, CA (rFVIII) in patients with severe VWD undergoing elective surgery.

Methods

Phase 3, open-label, uncontrolled, nonrandomized study at 14 sites in 10 countries (NCT02283268) in patients ≥18 y of age who had severe VWD and were scheduled to undergo elective surgery. Patients were monitored for 14 d after surgery.

Treatment 12-24 h before surgery, rVWF 40-60 IU/kg rVWF:RCo was given intravenously to allow endogenous FVIII:C levels to increase to ≥30 IU/dL (minor/oral surgery) or ≥60 IU/dL (major surgery). FVIII:C levels were assessed within 3 h of initiation of surgery. If target FVIII:C levels were achieved, rVWF alone was administered 1 h before surgery to achieve the peak levels described in Table 2. If target FVIII:C levels were achieved, rVWF alone was administered 1 h before surgery to achieve the peak levels described in Table 2. Intraoperative and postoperative dosing were individualized to maintain target trough levels according to pharmacokinetic (PK) and pharmacodynamic (PD) results, as well as the intensity and duration of the hemostatic challenge.

TABLE 2

| VWF:RCo and FVIII:C Target Levels: Recommendations for the Prevention of Excessive Bleeding During and After Surgery | | | |
|---|---|---|---|
| Type of Surgery | VWF:RCo Target Peak Plasma Level (IU/dL) | FVIII:C Target Peak Plasma Level* (IU/dL) | Calculation of rVWF Dose (IU VWF:RCo Required)† |
| Minor/Oral | 50-60 | 40-50 | ΔVWF:RCo × BW (kg)/IR‡ |
| Major | 100 | 80-100 | ΔVWF:RCo × BW (kg)/IR‡ |

BW = body weight;
FVIII:C = factor VIII activity;
IR = incremental recovery;
rVWF = recombinant von Willebrand factor;
VWF:RCo = von Willebrand factor ristocetin cofactor activity.
*Additional rFVIII may be required to attain the recommended FVIII:C target peak plasma levels.
†Administered within 1 h before surgery.
‡If the IR was not available, assume an IR of 2.0 IU/dL per IU/kg.
ΔVWF:RCo = target peak plasma VWF:RCo − baseline plasma VWF:RCo.

Assessment

Overall hemostatic efficacy (primary outcome) was assessed by the investigator at 24 h after the last perioperative infusion or at study completion, whichever occurred earlier (Table 3). Intraoperative hemostatic efficacy was assessed by the surgeon (Table 3), along with intraoperative actual versus predicted blood loss. Safety evaluations included adverse events (AEs) and antibodies to rVWF, rFVIII, Chinese hamster ovary (CHO) proteins, murine immunoglobulin G (IgG), and rFurin.

TABLE 3

| Overall* and Intraoperative† Hemostatic Efficacy Rating Scale | |
| --- | --- |
| Rating | Assessment |
| Excellent | Hemostasis achieved with rVWF with or without rFVIII was as good or better than that expected for the type of surgical procedure performed in a hemostatically normal subject |
| Good | Hemostasis achieved with rVWF with or without rFVIII was probably as good as that expected for the type of surgical procedure performed in a hemostatically normal subject |
| Moderate | Hemostasis with rVWF with or without rFVIII was clearly less than optimal for the type of procedure performed but was maintained without the need to change the rVWF concentrate |
| None | Patient experienced uncontrolled bleeding that was the result of inadequate therapeutic response despite proper dosing, necessitating a change of rVWF concentrate | rFVIII = recombinant factor VIII;
rVWF = recombinant von Willebrand factor.
*As assessed by the investigator.
†As assessed by the surgeon.

Statistics

Descriptive analyses included point estimates and 90% CIs for the number of patients with hemostatic efficacy rated "excellent/good" using a Clopper Pearson test. PK/PD and safety were summarized using descriptive statistics.
Results
Patients

TABLE 4

| Baseline Demographics and Clinical Characteristics | |
| --- | --- |
| Parameter | N = 15 |
| Sex, n (%) | |
| Male | 7 (46.7) |
| Female | 8 (53.3) |
| Median age (range), y | 40 (20-70) |
| Median weight (range), kg | 73.5 (52.0-127.2) |
| Median BMI (range), kg/m2 | 25.6 (17.1-38.0) |

TABLE 4-continued

| Baseline Demographics and Clinical Characteristics | |
| --- | --- |
| Parameter | N = 15 |
| VWD type, n (%) | |
| 1 | 3 (20.0) |
| 2A | 2 (13.3) |
| 2B | 1 (6.7) |
| 2M | 1 (6.7) |
| 3 | 8 (53.3) |
| Surgery classification, n (%) | |
| Major | 10 (66.7) |
| Minor | 4 (26.7) |
| Oral | 1 (6.7) |
| Mean (SD) FVIII:C, IU/dL | |
| All VWD types (n = 11) | 20.6 (23.7) |
| Type 3 VWD (n = 5) | 1.8 (1.1) |
| Mean (SD) VWF:RCo, IU/dL | |
| All VWD types (n = 11) | 9.7 (11.0) |
| Type 3 VWD (n = 5) | <8 (0.0) |

BMI = body mass index;
FVIII:C = factor VIII activity;
VWD = von Willebrand disease;
VWF:RCo = von Willebrand factor ristocetin cofactor activity.

Overall hemostatic efficacy was rated as "excellent" or "good" for all 15 patients (90% CI: 81.9-100.0) (FIG. 1).
Efficacy Overall hemostatic efficacy was rated as "excellent" or "good" for all 15 patients (90% CI: 81.9-100.0) (FIG. 1).

Intraoperative hemostatic efficacy was rated "excellent" or "good" for all 15 patients (90% CI: 81.9-100.0) (FIG. 2). Among the 8 patients with type 3 VWD, overall and intraoperative hemostatic efficacy were both rated "excellent" for 7 patients and "good" for 1 patient. Mean±SD intraoperative actual blood loss relative to predicted blood loss was 70%±45% and was rated "excellent" for 13 patients and "good" for 2 patients.
Exposure Patients received a total of 104 infusions of rVWF to prevent or treat surgical bleeding; the median overall surgical dose of rVWF was 220.4 IU/kg (range, 63.8-648.4 IU/kg) (Table 4). 93 (89.4%) infusions of rVWF alone: 15 (12-24 h before surgery), 12 (1 h before surgery), and 66 (postoperatively). 11 (10.6%) infusions of rVWF with rFVIII: 3 (1 h before surgery), 1 (intraoperatively), and 7 (postoperatively). 5 patients received the 11 infusions of rVWF with rFVIII, and 6 of the 7 postoperative infusions of rVWF with rFVIII were in 1 patient.

Of the 10 patients undergoing major surgery, 7 (70%) did not require coadministration of rFVIII.

TABLE 5

| Median rVWF Exposure Overall and by Surgery Classification | | | | |
| --- | --- | --- | --- | --- |
| | Surgery Classification | | | |
| | Minor (n = 4) | Major (n = 10) | Oral (n = 1) | Overall (N = 15) |
| Median total number of infusions* (range) | 3 (2-4) | 7.5 (4-15) | 5 | 6 (2-15) |
| Median exposure (range), d | 3 (2-4) | 6.5 (4-15) | 4 | 6 (2-15) |
| Median dose 12-24 h before surgery (range), IU/kg | 57.2 (55.0-59.9) | 49.3 (37.4-57.6) | 36.1 55.0 | (36.1-59.9) |

TABLE 5-continued

| Median rVWF Exposure Overall and by Surgery Classification | | | |
|---|---|---|---|
| | Surgery Classification | | |
| | Minor (n = 4) | Major (n = 10) | Oral (n = 1) | Overall (N = 15) |
| Median dose 1 h before surgery (range), IU/kg | 39.3 (8.0-46.4) | 37.6 (15.7-82.7) | 18.1 | 35.8 (8.0-82.7) |
| Median intraoperative dose (range), IU/kg | 0 | 0 | 18.1 | 18.1 |
| Median postoperative dose (range), IU/kg | 79.3 (42.8-115.9) | 214.8 (47.7-533.3) | 36.1 | 189.8 (36.1-533.3) |
| Median total surgical dose (range), IU/kg | 119.9 (63.8-217.3) | 307.6 (125.2-648.4) | 108.4 | 220.4 (63.8-648.4) | rVWF = recombinant von Willebrand factor.
*Total number of preoperative priming infusions, preoperative initial loading doses, preoperative supplemental loading doses, intraoperative doses, and postoperative doses.

Safety 6 patients reported 12 treatment-emergent AEs; none considered related to treatment. patients had serious AEs (diverticulitis and deep vein thrombosis [DVT]; each occurred in 1 patient); neither event was considered related to factor replacement treatment.

The serious DVT occurred on postoperative day 8 (initially reported as a nonserious DVT on postoperative day 4). The event was asymptomatic and observed after routine duplex scan. The event was assessed as unlikely related to rVWF and not related to rFVIII or the study procedures; causally associated with the patient's major surgery (total hip replacement) and ongoing history of obesity. Postoperative levels of FVIII:C never exceeded 150 IU/dL. The event resulted in placement of caval filter and subsequently resolved without sequelae. No severe allergic reactions; neutralizing antibodies to rFVIII, CHO proteins, murine IgG, or rFurin.

One patient with VWD type 3 who had an intraoperative transfusion of packed red blood cells during major total knee replacement surgery tested positive for binding antibodies to VWF on postoperative day 7.

The PK parameters for VWF:RCo for the patients who underwent PK analysis (n=11) are shown in FIG. 4. Mean concentrations of VWF:RCo, VWF:Ag, and VWF collagen binding activity (VWF:CB) reached peak levels by 30 min and gradually declined over a period of 72 h post-infusion (FIG. 4).

Administration of rVWF alone resulted in substantial, rapid stabilization of endogenous FVIII:C levels 6-12 h after infusion, with peak FVIII:C levels reached by 24 h among all patients assessed (n=11; FIG. 5A), as well as in the subset of patients with type 3 VWD (n=5; FIG. 5B). Overall, patients achieved mean FVIII:C >60 IU/dL by 6 h postinfusion (FIG. 5A), and patients with higher baseline FVIII:C (e.g., with type 1 or type 2 VWD) were able to achieve target levels more rapidly. Despite having mean FVIII:C levels <2 IU/dL at baseline, administration of rVWF alone allowed patients with type 3 VWD to achieve target VWF:RCo and FVIII:C levels quickly, with FVIII:C >60 IU/dL achieved by 12 h post-infusion (FIG. 5B).

Conclusions

In this surgery study, overall and intraoperative hemostatic efficacies were rated as "excellent" or "good" for all 15 patients. For major surgeries, overall hemostatic efficacy was "excellent" in 7 patients and "good" in 3 patients, and intraoperative efficacy was "excellent" in 8 patients and "good" in 2 patients. Nearly 90% of infusions to achieve intraoperative and postoperative hemostasis were with rVWF alone; 70% of major surgeries were managed with rVWF alone. rVWF targets the primary dysfunction of VWD and allows physicians to focus on achieving optimal efficacy without concern for FVIII accumulation. These data support the safe and effective use of rVWF in major and minor surgeries.

Example 2: Recombinant Von Willebrand Factor in Subjects with Severe Von Willebrand Disease Undergoing Surgery This example provides the study results from a study examining treatment of subjects with severe von Willebrand Disease (VWD) undergoing surgery.

Outcome Measures:

Primary Outcome Measures:

Overall Hemostatic Efficacy as Assessed by the Investigator (Hemophilia Physician) [Time Frame: 24 hours after last peri-operative infusion or at completion of Day 14 (±2 days) visit, whichever occurs earlier]. Hemostatic efficacy was rated on a scale of excellent-good-moderate-none.

Excellent: Intra-, and postoperative hemostasis achieved with rVWF with or without ADVATE was as good or better than that expected for the type of surgical procedure performed in a hemostatically normal subject.

Good: Intra-, and postoperative hemostasis achieved with rVWF with or without ADVATE was probably as good as that expected for the type of surgical procedure performed in a hemostatically normal subject.

Moderate: Intra-, and postoperative hemostasis with rVWF with or without ADVATE was clearly less than optimal for the type of procedure performed but was maintained without the need to change the rVWF concentrate.

None: Participant experienced uncontrolled bleeding that was the result of inadequate therapeutic response despite proper dosing, necessitating a change of rVWF concentrate.

Secondary Outcome Measures:

1: Intraoperative Actual Versus Predicted Blood Loss as Assessed by the Operating Surgeon [Time Frame: Day 0 (at completion of surgery)]. The predicted blood loss was estimated preoperatively by the operating surgeon based on a hemostatically normal individual of the same sex, age, stature and co-morbidities as the participant. The actual blood loss was assessed consisting of the estimated blood loss, including into swabs, towels and suction during the procedure, per the anesthesiologist's record.

2: Intraoperative Actual Blood Loss Relative to Predicted Blood Loss [Time Frame: Day 0 (at completion of surgery)]. Actual blood loss relative to predicted blood loss was calculated as [Actual Blood loss (mL)] divided by [Predicted Blood loss (mL) multiplied by 100.

3: Intraoperative Actual Versus Predicted Blood Loss Score as Assessed by the Operating Surgeon [Time Frame: Day 0 (at completion of surgery)]

Hemostatic efficacy was rated on a scale of excellent-good-moderate-none.

Excellent: Intraoperative blood loss was less than or equal to the maximum blood loss expected for the type of procedure performed in a hemostatically normal subject (≤100%).

Good: Intraoperative blood loss was up to 50% more than the maximum expected blood loss for the type of procedure performed in a hemostatically normal subject (101-150%) Moderate: Intraoperative blood loss was more than 50% of the maximum expected blood loss for the type of procedure performed in a hemostatically normal subject (>150%).

None: Uncontrolled hemorrhage that was the result of inadequate therapeutic response despite proper dosing, necessitating a change of clotting factor replacement regimen.

4: Intraoperative Hemostatic Efficacy Score as Assessed by the Operating Surgeon [Time Frame: Day 0 (at completion of surgery)]

Hemostatic efficacy was rated on a scale of excellent-good-moderate-none.

Excellent: Intraoperative hemostasis achieved with rVWF with or without ADVATE was as good or better than that expected for the type of surgical procedure performed in a hemostatically normal subject.

Good: Intraoperative hemostasis achieved with rVWF with or without ADVATE was probably as good as that expected for the type of surgical procedure performed in a hemostatically normal subject.

Moderate: Intraoperative hemostasis with rVWF with or without ADVATE was clearly less than optimal for the type of procedure performed but was maintained without the need to change the rVWF concentrate.

None: Participant experienced uncontrolled bleeding that was the result of inadequate therapeutic response despite proper dosing, necessitating a change of rVWF concentrate.

5: Daily Intra- and Postoperative Weight-adjusted Dose of rVWF With or Without ADVATE [Time Frame: Daily, from day of surgery through postoperative Day 14 (±2 days)]

6: Occurrence of Adverse Events [Time Frame: From first infusion of investigational product through study completion (i.e., 14 (±2) days post-surgery)]. Treatment emergent adverse events (TEAEs) and treatment emergent serious adverse events (TESAEs) were evaluated.

7: Occurrence of Thrombotic Events [Time Frame: From first infusion of investigational product through study completion (i.e., 14 (±2) days post-surgery)]. Treatment emergent adverse events (TEAEs) and treatment emergent serious adverse events (TESAEs) were evaluated for thrombotic events.

8: Occurrence of Severe Allergic Reactions (e.g., Anaphylaxis) [Time Frame: From first infusion of investigational product through study completion (i.e., 14 (±2) days post-surgery)]. Treatment emergent adverse events (TEAEs) and treatment emergent serious adverse events (TESAEs) were evaluated for severe allergic reactions.

9: Number of Participants Who Developed Inhibitory and Total Binding Antibodies to Von Willebrand Factor (VWF) and Inhibitory Antibodies to Factor VIII (FVIII) [Time Frame: Testing occurred throughout the study at screening, prior PK infusion, pre-surgery, post-surgery in case of excessive bleeding or unexplained bleeding, at postoperative day 7 and at study completion visit (ie. 14 (±2) days post-surgery)]. Participants were treated with recombinant van Willebrand Factor (rVWF) with or without ADVATE.

10: Number of Participants Who Developed Antibodies to Chinese Hamster Ovary (CHO) Proteins, Mouse Immunoglobulin G (IgG) or Recombinant Furin (rFurin) [Time Frame: Testing occurred throughout the study at screening, prior PK infusion, pre-surgery, post-surgery in case of excessive bleeding or unexplained bleeding, at postoperative day 7 and at study completion visit (ie. 14 (±2) days post-surgery).] Participants were treated with recombinant van Willebrand Factor (rVWF) with or without ADVATE.

11: Pharmacokinetics: Area Under the Plasma Concentration Versus Time Curve From 0 to 72 Hours Post-infusion (AUC 0-72 h/Dose) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.] This assessment was only required for subjects undergoing major surgery. Subjects received a PK infusion at a dose of 50±5 IU/kg rVWF:RCo within 42 days prior to surgery. The area under the plasma concentration/time curve from 0 to 72 hours post-infusion was computed using the linear trapezoidal rule. For the calculation of AUC(0-72 h) the levels at 72 hours was linearly interpolated/extrapolated from the 2 nearest sampling time points. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac), FVIII Coagulation Activity (FVIII:C)

12: Pharmacokinetics: Area Under the Plasma Concentration Versus Time Curve From Time 0 to Infinity (AUC 0-∞/Dose) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.] This assessment was only required for subjects undergoing major surgery. Subjects received a PK infusion at a dose of 50±5 IU/kg rVWF:RCo within 42 days prior to surgery. The area under the plasma concentration/time curve from time 0 to infinity and the area under the first moment curve from time 0 to infinity was calculated as the sum of AUC or AUMC from time 0 to the time of last quantifiable concentration plus a tail area correction calculated as Ct/λz and Ct/λz(t+ 1/λz), respectively, where Ct was the last quantifiable concentration, t was the time of last quantifiable concentration and λz was the terminal or disposition rate constant. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac), FVIII Coagulation Activity (FVIII:C)

13: Pharmacokinetics: Mean Residence Time (MRT) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.] This assessment was only required for subjects undergoing major surgery. Subjects received a PK infusion at a dose of 50±5 IU/kg rVWF:RCo within 42 days prior to surgery. Mean residence time was calculated as area under the first moment curve from time 0 to infinity divided by the area under the curve time 0 to infinity minus T/2 where T was the duration of the infusion. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac)

14: Pharmacokinetics: Clearance (CL) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.] This assessment was only required for subjects undergoing major surgery. Subjects received a PK infusion at a dose of 50±5 IU/kg rVWF:RCo within 42 days prior to surgery. Clearance was calculated as dose (IU/kg) divided by the area under the curve time 0 to infinity. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac)

15: Pharmacokinetics: Incremental Recovery (IR) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.] This assessment was only required for subjects undergoing major surgery. Subjects received a PK infusion at a dose of 50±5 IU/kg rVWF:RCo within 42 days prior to surgery. Incremental recovery was calculated as (Cmax minus Cpreinfusion) divided by the dose (IU/kg) where kg refers to the body weight at the time of dosing and Cmax was the observed maximum concentration before correction for pre-infusion values. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac)

16: Pharmacokinetics: Elimination Phase Half-life (T½) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.] This assessment was only required for subjects undergoing major surgery. Subjects received a PK infusion at a dose of 50±5 IU/kg rVWF:RCo within 42 days prior to surgery. Terminal or disposition half-life (T½) was calculated as ln 2/λz where λz was the terminal elimination rate constant as calculated in WinNonlin NCA using at least three quantifiable concentrations. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac)

17: Pharmacokinetics: Volume of Distribution at Steady State (Vss) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.] This assessment is only required for subjects undergoing major surgery. Subjects received a PK infusion at a dose of 50±5 IU/kg rVWF:RCo within 42 days prior to surgery. Vss was calculated as the clearance multiplied with the mean residence time. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac)

Eligibility Criteria:

Ages Eligible for Study: 18 Years and older; Sexes Eligible for Study: All

Inclusion Criteria:

Diagnosis of severe von Willebrand disease (VWD) as listed below and elective surgical procedure planned:

1. Type 1 (Von Willebrand factor: Ristocetin cofactor activity (VWF:RCo)<20 IU/dL), or
2. Type 2A (as verified by multimer pattern), Type 2B (as diagnosed by genotype), Type 2N (FVIII:C<10% and historically documented genetics), Type 2M, or
3. Type 3 (Von Willebrand factor antigen (VWF:Ag)<3 IU/dL)

VWD with a history of requiring substitution therapy with von Willebrand factor (VWF) concentrate to control bleeding.

If type 3 VWD (VWF Antigen/VWF:Ag≤3 IU/dL), participant has a medical history of at least 20 exposure days to VWF/FVIII coagulation factor concentrates (including cryoprecipitate or fresh frozen plasma).

If type 1 or type 2 VWD, participant has a medical history of 5 exposure days or a past major surgery requiring VWF/FVIII coagulation factor concentrates (including cryoprecipitate or fresh frozen plasma).

Participant was at least 18 years of age.

If female of childbearing potential, participant presents with a negative pregnancy test.

If applicable, participant agrees to employ adequate birth control measures for the duration of the study.

Participant is willing and able to comply with the requirements of the protocol.

Selected Exclusion Criteria:

Diagnosis of pseudo VWD or another hereditary or acquired coagulation disorder (e.g., qualitative and quantitative platelet disorders or elevated prothrombin time [PT]/international normalized ratio [INR]>1.4).

History or presence of a VWF inhibitor at screening.

History or presence of a factor VIII (FVIII) inhibitor with a titer ≥0.4 BU (Nijmegen-modified Bethesda assay) or ≥0.6 BU (by Bethesda assay).

Known hypersensitivity to any of the components of the study drugs, such as to mouse or hamster proteins.

Medical history of immunological disorders, excluding seasonal allergic rhinitis/conjunctivitis, mild asthma, food allergies or animal allergies.

Medical history of a thromboembolic event.

HIV positive with an absolute CD4 count <200/mm³.

Platelet count <100,000/mL.

Diagnosis of significant liver disease, as evidenced by, but not limited to, any of the following: serum alanine aminotransferase (ALT) 5 times the upper limit of normal; hypoalbuminemia; portal vein hypertension (e.g., presence of otherwise unexplained splenomegaly, history of esophageal varices) or liver cirrhosis classified as Child B or C.

Diagnosis of renal disease, with a serum creatinine level ≥2.5 mg/dL.

Participant had been treated with an immunomodulatory drug, excluding topical treatment (e.g., ointments, nasal sprays), within 30 days prior to signing the informed consent.

Participant was pregnant or lactating at the time informed content is obtained.

Participant had participated in another clinical study involving an investigational product (IP), other than rVWF with or without ADVATE, or investigational device within 30 days prior to enrollment or was scheduled to participate in another clinical study involving an IP or investigational device during the course of this study. However, eligible patients participating in the rVWF Prophylaxis Study (071301) may be enrolled.

Progressive fatal disease and/or life expectancy of less than 3 months.

Results:

Enrollment was conducted at 14 study sites in 10 countries (USA, Australia, Taiwan, Germany, Russia, Spain, Ukraine, United Kingdom, Italy, Turkey).

TABLE 6

| Reporting Groups | |
|---|---|
| | Description |
| Recombinant Von Willebrand Factor (rVWF) | Surgery participants treated with Recombinant von Willebrand Factor (rVWF) |

TABLE 6

| Participant: Overall Study | |
|---|---|
| | Recombinant Von Willebrand Factor (rVWF) |
| STARTED | 15 |
| COMPLETED | 14 |
| NOT COMPLETED | 1 |
| Withdrawal by Subject | 1 |

TABLE 7

| Baseline Measures | |
|---|---|
| | Recombinant Von Willebrand Factor (rVWF) |
| Overall Participants Analyzed | |
| [Units: Participants] | 15 |
| Age | |
| [Units: Years] | 40.0 |
| Median (Full Range) | (20.0 to 70.0) |
| Sex: Female, Male | |
| [Units: Participants] | |
| Count of Participants | |
| Female | 8 53.3% |
| Male | 7 46.7% |

Primary Outcome: Outcome #1

TABLE 8

| Outcome Measures |
|---|
| 1. Primary: Overall Hemostatic Efficacy as Assessed by the Investigator (Hemophilia Physician) [Time Frame: 24 hours after last pen-operative infusion or at completion of Day 14 (±2 days) visit, whichever occurred earlier]. |

TABLE 9

| Primary Outcome #1 | |
|---|---|
| Measure Type | Primary |
| Measure Title | Overall Hemostatic Efficacy as Assessed by the Investigator (Hemophilia Physician) |
| Measure Description | Hemostatic efficacy was rated on a scale of excellent - good - moderate - none. |
| | Excellent: Intra-, and postoperative hemostasis achieved with rVWF with our without ADVATE was as good or better than that expected for the type of surgical procedure performed in a hemostatically normal subject. |
| | Good: Intra-, and postoperative hemostasis achieved with rVWF with or without ADVATE was probably as good as that expected for the type of surgical procedure performed in a hemostatically normal subject. |
| | Moderate: Intra-, and postoperative hemostasis with rVWF with or without ADVATE was clearly less than optimal for the type of procedure performed but was maintained without the need to change the rVWF concentrate. |
| | None: Participant experienced uncontrolled bleeding that was the result of inadequate therapeutic response despite proper dosing, necessitating a change of rVWF concentrate. |
| Time Frame | 24 hours after last pen-operative infusion or at completion of Day 14 (±2 days) visit, whichever occurs earlier |

Population Description Outcome #1

Number of participants with major, minor and oral surgery and number of participant with Von Willebrand Type 1, 2A, 2B, 2M and 3 do sum up to the overall number of participants analyzed. The full analysis data set, including all participants who received investigational product and have at least 1 hemostatic assessment, was used for analysis.

TABLE 10

| Reporting Groups Outcome #1 | |
|---|---|
| | Description |
| Recombinant Von Willebrand Factor (rVWF) | Surgery participants treated with Recombinant von Willebrand Factor (rVWF) |
| Minor Surgery | All participants who underwent minor surgery. |
| Major Surgery | All participants who underwent major surgery. |
| Oral Surgery | All participants who underwent oral surgery. |
| Von Willebrand Disease Type 1 | All participants with von Willebrand Disease Type 1. |
| Von Willebrand Disease Type 2A | All participants with von Willebrand Disease Type 2A. |
| Von Willebrand Disease Type 2B | All participants with von Willebrand Disease Type 2B. |
| Von Willebrand Disease Type 2M | All participants with von Willebrand Disease Type 2M. |
| Von Willebrand Disease Type 3 | All participants with von Willebrand Disease Type 3. |

TABLE 11

| | Recombinant Von Willebrand Factor (rVNVF) | Minor Surgery | Major Surgery | Oral Surgery | Von Willebrand Disease Type 1 | Von Willebrand Disease Type 2A | Von Willebrand Disease Type 2B | Von Willebrand Disease Type 2M | Von Willebrand Disease Type 3 |
|---|---|---|---|---|---|---|---|---|---|
| Participants Analyzed | 15 | 4 | 10 | 1 | 3 | 2 | 1 | 1 | 8 |

Measured Values Outcome #1

Overall Hemostatic Efficacy as Assessed by the Investigator (Hemophilia Physician) [Units: Participants] Count of Participants

| | rVNVF | | Minor Surgery | | Major Surgery | | Oral Surgery | | Type 1 | | Type 2A | | Type 2B | | Type 2M | | Type 3 | |
|---|---|---|---|---|---|---|---|---|---|---|---|---|---|---|---|---|---|---|
| Excellent | 11 | 73.3% | 4 | 100.0% | 7 | 70.0% | 0 | 0.0% | 2 | 66.7% | 1 | 50.0% | 1 | 100.0% | 0 | 0.0% | 7 | 87.5% |
| Good | 4 | 26.7% | 0 | 0.0% | 3 | 30.0% | 1 | 100.0% | 1 | 33.3% | 1 | 50.0% | 0 | 0.0% | 1 | 100.0% | 1 | 12.5% |
| Moderate | 0 | 0.0% | 0 | 0.0% | 0 | 0.0% | 0 | 0.0% | 0 | 0.0% | 0 | 0.0% | 0 | 0.0% | 0 | 0.0% | 0 | 0.0% |
| None | 0 | 0.0% | 0 | 0.0% | 0 | 0.0% | 0 | 0.0% | 0 | 0.0% | 0 | 0.0% | 0 | 0.0% | 0 | 0.0% | 0 | 0.0% |

Secondary Outcome: Outcome #2

2. Secondary: Intraoperative Actual Versus Predicted Blood Loss as Assessed by the Operating Surgeon [Time Frame: Day 0 (at completion of surgery)]

TABLE 12

Primary Outcome #2

| Measure Type | Secondary |
|---|---|
| Measure Title | Intraoperative Actual Versus Predicted Blood Loss as Assessed by the Operating Surgeon |
| Measure Description | The predicted blood loss was estimated preoperatively by the operating surgeon based on a hemostatically normal individual of the same sex, age, stature and co-morbidities as the participant. The actual blood loss was assessed consisting of the estimated blood loss, including into swabs, towels and suction during the procedure, per the anesthesiologist's record. |
| Time Frame | Day 0 (at completion of surgery) |

Population Description Outcome #2

For predicted blood loss the number of participants analyzed was 14 as for one participant (included in the major surgery reporting group) the predicted blood loss was not collected. The full analysis data set, including all participants who received investigational product and had at least 1 hemostatic assessment, was used for analysis.

TABLE 13

Reporting Groups Outcome #2

| | Description |
|---|---|
| Recombinant Von Willebrand Factor (rVWF) | Surgery participants treated with Recombinant von Willebrand Factor (rVWF) |
| Minor Surgery | All participants who underwent minor surgery. |
| Major Surgery | All participants who underwent major surgery. |
| Oral Surgery | All participants who underwent oral surgery. |
| Von Willebrand Disease Type 1 | All participants with von Willebrand Disease Type 1. |
| Von Willebrand Disease Type 2A | All participants with von Willebrand Disease Type 2A. |
| Von Willebrand Disease Type 2B | All participants with von Willebrand Disease Type 2B. |
| Von Willebrand Disease Type 2M | All participants with von Willebrand Disease Type 2M. |
| Von Willebrand Disease Type 3 | All participants with von Willebrand Disease Type 3. |

TABLE 26

Measured Values Outcome #2

| Recombinant Von Willebrand Factor (rVWF) | Minor Surgery | Major Surgery | Oral Surgery | Von Willebrand Disease Type 1 | Von Willebrand Disease Type 2A | Von Willebrand Disease Type 2B | Von Willebrand Disease Type 2M | Von Willebrand Disease Type 3 |
|---|---|---|---|---|---|---|---|---|
| Participants Analyzed | | | | | | | | |
| 15 | 4 | 10 | 1 | 3 | 2 | 1 | 1 | 8 |

Intra-operative Actual Versus

TABLE 26-continued

| | Recombinant Von Willebrand Factor (rVWF) | Minor Surgery | Major Surgery | Oral Surgery | Von Willebrand Disease Type 1 | Von Willebrand Disease Type 2A | Von Willebrand Disease Type 2B | Von Willebrand Disease Type 2M | Von Willebrand Disease Type 3 |
|---|---|---|---|---|---|---|---|---|---|
| | | | | | Measured Values Outcome #2 | | | | |
| Predicted BloodLoss as Assessed by the Operating Surgeon [Units: mL] Mean (Standard Deviation) Actual blood loss | | | | | | | | | |
| | | | | | Participants Analyzed | | | | |
| | 15 | 4 | 10 | 1 | 3 | 2 | 1 | 1 | 8 |
| Actual blood loss Predicted blood loss | 94.3 (177.88) | 0.0 (0.00) | 127.0 (209.27) | 145.0 [1] | 115.0 (103.32) | 42.5 (53.03) | 50.0 [1] | 50.0 [1] | 110.6 (240.87) |
| | | | | | Participants Analyzed | | | | |
| | 14 | 4 | 9 | 1 | 3 | 1 | 1 | 1 | 8 |
| Predicted blood loss | 106.1 (161.82) | 2.5 (5.00) | 152.8 (186.33) | 100.0 [1] | 100.0 (100.00) | 10.0 [1] | 50.0 [1] | 50.0 [1] | 134.4 (206.46) |

[1] No standard deviation possible as only one participant was analyzed.
No statistical analysis provided for Intraoperative Actual Versus Predicted Blood Loss as Assessed by the Operating Surgeon Secondary Outcome: Outcome #3

3. Secondary: Intraoperative Actual Blood Loss Relative to Predicted Blood Loss [Time Frame: Day 0 (at completion of surgery)]

TABLE 14

| | Outcome #3 |
|---|---|
| Measure Type | Secondary |
| Measure Title | Intraoperative Actual Blood Loss Relative to Predicted Blood Loss |
| Measure Description | Actual blood loss relative to predicted blood loss was calculated as [Actual Blood loss (mL)] divided by [Predicted Blood Loss (mL) multiplied by 100. |
| Time Frame | Day 0 (at completion of surgery) |

Population Description Outcome #3

Number of participants analyzed was 11, as for 3 participants the actual and the predicted blood loss was zero and for 1 participant the predicted blood loss was not collected. Therefore 'actual blood loss relative to predicted blood loss' could not be calculated. The full analysis data set was used for the analysis of this outcome measure.

TABLE 15

| Reporting Groups Outcome #3 | |
|---|---|
| | Description |
| Recombinant Von Willebrand Factor (rVWF) | Surgery participants treated with Recombinant von Willebrand Factor (rVWF) |
| Minor Surgery | All participants who underwent minor surgery. |
| Major Surgery | All participants who underwent major surgery. |
| Oral Surgery | All participants who underwent oral surgery. |
| Von Willebrand Disease Type 1 | All participants with von Willebrand Disease Type 1. |
| Von Willebrand Disease Type 2A | All participants with von Willebrand Disease Type 2A. |
| Von Willebrand Disease Type 2B | All participants with von Willebrand Disease Type 2B. |
| Von Willebrand Disease Type 2M | All participants with von Willebrand Disease Type 2M. |
| Von Willebrand Disease Type 3 | All participants with von Willebrand Disease Type 3. |

TABLE 16

| | Measured Values | | | | | | | | |
|---|---|---|---|---|---|---|---|---|---|
| | Recombinant Von Willebrand Factor (rVIVF) | Minor Surgery | Major Surgery | Oral Surgery | Von Willebrand Disease Type 1 | Von Willebrand Disease Type 2A | Von Willebrand Disease Type 2B | Von Willebrand Disease Type 2M | Von Willebrand Disease Type 3 |
| | | | | | Participants Analyzed | | | | |
| | 11 | 1 | 9 | 1 | 2 | 1 | 1 | 1 | 6 |
| Intraoperative Actual Blood Loss Relative to Predicted Blood Loss [Units: Percent] Mean (Standard Deviation) | 69.6 (44.77) | 0.0 [1] | 68.9 (34.48) | 145.0 [1] | 122.5 (31.82) | 50.0 [1] | 100.0 [1] | 100.0 [1] | 45.0 (38.92) |

[1] No standard deviation possible as only one participant was analyzed.
No statistical analysis provided for Intraoperative Actual Blood Loss Relative to Predicted Blood Loss

Secondary Outcome: Outcome #4

4. Secondary: Intraoperative Actual Versus Predicted Blood Loss Score as Assessed by the Operating Surgeon [Time Frame: Day 0 (at completion of surgery)]

TABLE 17

| Outcome #4 | |
|---|---|
| Measure Type | Secondary |
| Measure Title | Intraoperative Actual Versus Predicted Blood Loss Score as Assessed by the Operating Surgeon |
| Measure Description | Hemostatic efficacy was rated on a scale of excellent - good - moderate - none. Excellent: Intraoperative blood loss was less than or equal to the maximum blood loss expected for the type of procedure performed in a hemostatically normal subject (≤100%). Good: Intraoperative blood loss was up to 50% more than the maximum expected blood loss for the type of procedure performed in a hemostatically normal subject (101-150%) Moderate: Intraoperative blood loss was more than 50% of the maximum expected blood loss for the type of procedure performed in a hemostatically normal subject (>150%). None: Uncontrolled hemorrhage that was the result of inadequate therapeutic response despite proper dosing, necessitating a change of clotting factor replacement regimen. |
| Time Frame | Day 0 (at completion of surgery) |

TABLE 18

| Population Description Outcome #4 |
|---|
| Number of participants with major, minor and oral surgery and number of participant with Von Willebrand Type 1, 2A, 2B, 2M and 3 do sum up to the overall number of participants analyzed. The full analysis data set, including all participants who received investigational product and have at least 1 hemostatic assessment, was used for analysis. |

TABLE 19

| Reporting Groups Outcome #4 | |
|---|---|
| | Description |
| Recombinant Von Willebrand Factor (rVWF) | Surgery participants treated with Recombinant von Willebrand Factor (rVWF) |
| Minor Surgery | All participants who underwent minor surgery. |
| Major Surgery | All participants who underwent major surgery. |
| Oral Surgery | All participants who underwent oral surgery. |
| Von Willebrand Disease Type 1 | All participants with von Willebrand Disease Type 1. |
| Von Willebrand Disease Type 2A | All participants with von Willebrand Disease Type 2A. |
| Von Willebrand Disease Type 2B | All participants with von Willebrand Disease Type 2B. |
| Von Willebrand Disease Type 2M | All participants with von Willebrand Disease Type 2M. |
| Von Willebrand Disease Type 3 | All participants with von Willebrand Disease Type 3. |

TABLE 20

| | Measured Values Outcome #4 | | | | | | | | |
|---|---|---|---|---|---|---|---|---|---|
| | Recombinant Von Willebrand Factor (rVNVF) | Minor Surgery | Major Surgery | Oral Surgery | Von Willebrand Disease Type 1 | Von Willebrand Disease Type 2A | Von Willebrand Disease Type 2B | Von Willebrand Disease Type 2M | Von Willebrand Disease Type 3 |
| | | | | | Participants Analyzed | | | | |
| | 15 | 4 | 10 | 1 | 3 | 2 | 1 | 1 | 8 |
| Intraoperative Actual Versus Predicted Blood Loss Score as | | | | | | | | | |

TABLE 20-continued

| | Recombinant Von Willebrand Factor (rVNVF) | Minor Surgery | Major Surgery | Oral Surgery | Von Willebrand Disease Type 1 | Von Willebrand Disease Type 2A | Von Willebrand Disease Type 2B | Von Willebrand Disease Type 2M | Von Willebrand Disease Type 3 |
|---|---|---|---|---|---|---|---|---|---|
| | | | | | Participants Analyzed | | | | |
| | 15 | 4 | 10 | 1 | 3 | 2 | 1 | 1 | 8 |

Measured Values Outcome #4

Assessed by the Operating Surgeon [Units: Participants] Count of Participants

| | rVNVF | | Minor Surgery | | Major Surgery | | Oral Surgery | | Type 1 | | Type 2A | | Type 2B | | Type 2M | | Type 3 | |
|---|---|---|---|---|---|---|---|---|---|---|---|---|---|---|---|---|---|---|
| Excellent | 13 | 86.7% | 4 | 100.0% | 8 | 80.0% | 1 | 100.0% | 3 | 100.0% | 1 | 50.0% | 1 | 100.0% | 1 | 100.0% | 7 | 87.5% |
| Good | 2 | 13.3% | 0 | 0.0% | 2 | 20.0% | 0 | 0.0% | 0 | 0.0% | 1 | 50.0% | 0 | 0.0% | 0 | 0.0% | 1 | 12.5% |
| Moderate | 0 | 0.0% | 0 | 0.0% | 0 | 0.0% | 0 | 0.0% | 0 | 0.0% | 0 | 0.0% | 0 | 0.0% | 0 | 0.0% | 0 | 0.0% |
| None | 0 | 0.0% | 0 | 0.0% | 0 | 0.0% | 0 | 0.0% | 0 | 0.0% | 0 | 0.0% | 0 | 0.0% | 0 | 0.0% | 0 | 0.0% |

No statistical analysis provided for Intraoperative Actual Versus Predicted Blood Loss Score as Assessed by the Operating Surgeon Secondary Outcome: Outcome #5

5. Secondary: Intraoperative Hemostatic Efficacy Score as Assessed by the Operating Surgeon [Time Frame: Day 0 (at completion of surgery)]

Table 21

Outcome #5

| Measure Type | Secondary |
|---|---|
| Measure Title | Intraoperative Hemostatic Efficacy Score as Assessed by the Operating Surgeon |
| Measure Description | Hemostatic efficacy was rated on a scale of excellent - good - moderate - none. Excellent: Intraoperative hemostasis achieved with rVWF with our without ADVATE was as good or better than that expected for the type of surgical procedure performed in a hemostatically normal subject. Good: Intraoperative hemostasis achieved with rVWF with or without ADVATE was probably as good as that expectedfor the type of surgical procedure performed in a hemostatically normal subject. Moderate: Intraoperative hemostasis with rVWF with or without ADVATE was clearly less than optimal for the type of procedure performed but was maintained without the need to change the rVWF concentrate. None: Participant experienced uncontrolled bleeding that was the result of inadequate therapeutic response despite proper dosing, necessitating a change of rVWF concentrate. |
| Time Frame | Day 0 (at completion of surgery) |

TABLE 22

Population Description Outcome #5

Number of participants with major, minor and oral surgery and number of participant with Von Willebrand Type 1, 2A, 2B, 2M and 3 do sum up to the overall number of participants analyzed. The full analysis data set, including all participants who received investigational product and have at least 1 hemostatic assessment, was used for analysis.

TABLE 23

Reporting Groups Outcome #5

| | Description |
|---|---|
| Recombinant Von Willebrand Factor (rVWF) | Surgery participants treated with Recombinant von Willebrand Factor (rVWF) |
| Minor Surgery | All participants who underwent minor surgery. |
| Major Surgery | All participants who underwent major surgery. |
| Oral Surgery | All participants who underwent oral surgery. |
| Von Willebrand Disease Type 1 | All participants with von Willebrand Disease Type 1. |
| Von Willebrand Disease Type 2A | All participants with von Willebrand Disease Type 2A. |
| Von Willebrand Disease Type 2B | All participants with von Willebrand Disease Type 2B. |
| Von Willebrand Disease Type 2M | All participants with von Willebrand Disease Type 2M. |
| Von Willebrand Disease Type 3 | All participants with von Willebrand Disease Type 3. |

TABLE 24

MeasuredValues Outcome #5

| | Recombinant Von Willebrand Factor (rVNVF) | Minor Surgery | Major Surgery | Oral Surgery | Von Willebrand Disease Type 1 | Von Willebrand Disease Type 2A | Von Willebrand Disease Type 2B | Von Willebrand Disease Type 2M | Von Willebrand Disease Type 3 |
|---|---|---|---|---|---|---|---|---|---|
| | | | | | Participants Analyzed | | | | |
| | 15 | 4 | 10 | 1 | 3 | 2 | 1 | 1 | 8 |

Intraoperative Hemostatic Efficacy Score as

TABLE 24-continued

| | MeasuredValues Outcome #5 | | | | | | | | |
|---|---|---|---|---|---|---|---|---|---|
| | Recombinant Von Willebrand Factor (rVNVF) | Minor Surgery | Major Surgery | Oral Surgery | Von Willebrand Disease Type 1 | Von Willebrand Disease Type 2A | Von Willebrand Disease Type 2B | Von Willebrand Disease Type 2M | Von Willebrand Disease Type 3 |
| | | | | | Participants Analyzed | | | | |
| | 15 | 4 | 10 | 1 | 3 | 2 | 1 | 1 | 8 |
| Assessed by the Operating Surgeon [Units: Participants] Count of Participants | | | | | | | | | |
| Excellent | 13 86.7% | 4 100.0% | 8 80.0% | 1 100.0% | 3 100.0% | 1 50.0% | 1 100.0% | 1 100.0% | 7 87.5% |
| Good | 2 13.3% | 0 0.0% | 2 20.0% | 0 0.0% | 0 0.0% | 1 50.0% | 0 0.0% | 0 0.0% | 1 12.5% |
| Moderate | 0 0.0% | 0 0.0% | 0 0.0% | 0 0.0% | 0 0.0% | 0 0.0% | 0 0.0% | 0 0.0% | 0 0.0% |
| None | 0 0.0% | 0 0.0% | 0 0.0% | 0 0.0% | 0 0.0% | 0 0.0% | 0 0.0% | 0 0.0% | 0 0.0% |

No statistical analysis provided for Intraoperative Hemostatic Efficacy Score as Assessed by the Operating Surgeon

Secondary Outcome: Outcome #6

6. Secondary: Daily Intra- and Postoperative Weight-adjusted Dose of rVWF With or Without ADVATE [Time Frame: Daily, from day of surgery through postoperative Day 14 (±2 days)]

TABLE 25

| Outcome #6 | |
|---|---|
| Measure Type | Secondary |
| Measure Title | Daily Intra- and Postoperative Weight-adjusted Dose of rVWF With or Without ADVATE |
| Measure Description | No text entered. |
| Time Frame | Daily, from day of surgery through postoperative Day 14 (±2 days) |

TABLE 25

| Population Description Outcome #6 |
|---|
| Number of participants analyzed was different for the time points according to individual treatment. The full analysis data set, including all participants who received investigational product and have at least 1 hemostatic assessment, was used for analysis. |

TABLE 40

| Reporting Groups Outcome #6 | |
|---|---|
| | Description |
| Recombinant Von Willebrand Factor (rVWF) | Surgery participants treated with Recombinant von Willebrand Factor (rVWF) |

TABLE 26

| Measured Values Outcome #6 | |
|---|---|
| | Recombinant Von Willebrand Factor (rVVVF) |
| Participants Analyzed Daily Intra- and Postoperative Weight-adjusted Dose of rVWF With or Without ADVATE [Units: IU/kg] Median (Inter-Quartile Range) intraoperative | 15 |
| Participants Analyzed intraoperative | 1 18.1 (18.1 to 18.1) |
| postoperative day 1 | |
| Participants Analyzed postoperative day 1 | 3 23.5 (16.9 to 47.2) |
| postoperative day 2 | |
| Participants Analyzed postoperative day 2 | 11 42.3 (23.2 to 50.6) |
| postoperative day 3 | |
| Participants Analyzed postoperative day 3 | 12 28.6 (20.6 to 48.9) |
| postoperative day 4 | |
| Participants Analyzed postoperative day 4 | 9 33.9 (23.2 to 44.3) |
| postoperative day 5 | |
| Participants Analyzed postoperative day 5 | 7 31.5 (18.8 to 47.2) |
| postoperative day 6 | |
| Participants Analyzed postoperative day 6 | 5 23.2 (18.8 to 23.6) |
| postoperative day 7 | |
| Participants Analyzed postoperative day 7 | 5 23.8 (23.6 to 50.8) |

TABLE 26-continued

| Measured Values Outcome #6 | |
| --- | --- |
| | Recombinant Von Willebrand Factor (rVVVF) |
| postoperative day 8 | |
| Participants Analyzed postoperative day 8 | 7 33.9 (23.6 to 53.6) |
| postoperative day 9 | |
| Participants Analyzed postoperative day 9 | 3 23.6 (16.3 to 53.6) |
| postoperative day 10 | |
| Participants Analyzed postoperative day 10 | 3 23.6 (16.3 to 34.8) |
| postoperative day 11 | |
| Participants Analyzed postoperative day 11 | 3 23.6 (16.3 to 53.6) |
| postoperative day 12 | |
| Participants Analyzed postoperative day 12 | 4 29.3 (20.1 to 44.2) |
| postoperative day 13 | |
| Participants Analyzed postoperative day 13 | 1 16.3 (16.3 to 16.3) |
| postoperative day 14 | |
| Participants Analyzed postoperative day 14 | 2 25.5 (16.3 to 34.8) |
| postoperative day 15 | |
| Participants Analyzed postoperative day 15 | 1 16.3 (16.3 to 16.3) |

No statistical analysis provided for Daily Intra- and Postoperative Weight-adjusted Dose of rVWF With or Without ADVATE Secondary Outcome: Outcome #7

7. Secondary: Occurrence of Adverse Events [Time Frame: From first infusion of investigational product through study completion (i.e., 14 (±2) days post-surgery)].

TABLE 27

| Outcome #7 | |
| --- | --- |
| Measure Type | Secondary |
| Measure Title | Occurrence of Adverse Events |
| Measure Description | Treatment emergent adverse events (TEAEs) and treatment emergent serious adverse events (TESAEs) was evaluated. |
| Time Frame | From first infusion of investigational product through study completion (i.e., 14 (±2) days post-surgery) |

TABLE 28

| Population Description Outcome #7 |
| --- |
| The safety analysis data set, including all participants who received any amount of investigational product, was used for analysis of this outcome measure. |

TABLE 29

| Reporting Groups Outcome #7 | |
| --- | --- |
| | Description |
| Recombinant Von Willebrand Factor (rVWF) | Surgery participants treated with Recombinant von Willebrand Factor (rVWF) |

TABLE 30

| Measured Values | |
| --- | --- |
| | Recombinant Von Willebrand Factor (rVWF) |
| Participants Analyzed Occurrence of Adverse Events [Units: Adverse Events] | 15 |
| Treatment emergent Adverse Events (TEAEs) | 12 |
| Severe TEAEs | 1 |
| TEAEs related to rVWF | 0 |
| TEAEs related to ADVATE | 0 |
| TEAEs related to both rVWF and ADVATE | 0 |
| Treatment emergent Serious Adverse Events (TESAEs) SAE s) | 2 |
| TESAEs related to rVWF | 0 |
| TESAEs related to ADVATE | 0 |
| TESAEs related to both rVWF and ADVATE | 0 |
| TEAEs leading to discontinuation F of rVW | 0 |
| TEAEs leading to discontinuation of ADVATE | 0 |
| TEAEs leading to discontinuation of study | 0 |
| TEAEs leading to death | 0 |
| TEAEs related to study procedure | 0 |
| TESAEs related to study procedure | 0 |

No statistical analysis provided for Occurrence of Adverse Events

Secondary Outcome: Outcome #8

8. Secondary: Occurrence of Thrombotic Events [Time Frame: From first infusion of investigational product through study completion (i.e., 14 (±2) days post-surgery)]

TABLE 31

| Outcome #8 | |
| --- | --- |
| Measure Type | Secondary |
| Measure Title | Occurrence of Thrombotic Events |
| Measure Description | Treatment emergent adverse events (TEAEs) and treatment emergent serious adverse events (TESAEs) were evaluated for thrombotic events. |
| Time Frame | From first infusion of investigational product through study completion (i.e., 14 (±2) days post-surgery) |

TABLE 32

| Population Description Outcome #8 |
| --- |
| The safety analysis data set, including all participants who received any amount of investigational product, was used for analysis of this outcome measure. |

TABLE 33

Reporting Groups

| | Description |
|---|---|
| Recombinant Von Willebrand Factor (rVWF) | Surgery participants treated with Recombinant von Willebrand Factor (rVWF) |

TABLE 34

Measured Values Outcome #8

| | Recombinant Von Willebrand Factor (rVWF) |
|---|---|
| Participants Analyzed | 15 |
| Occurrence of Thrombotic Events [Units: Adverse Events] | |
| Thrombotic TEAEs | 2 |
| Thrombotic TESAEs | 1 |

No statistical analysis provided for Occurrence of Thrombotic Events

Secondary Outcome: Outcome #9

9. Secondary: Occurrence of Severe Allergic Reactions (e.g., Anaphylaxis) [Time Frame: From first infusion of investigational product through study completion (i.e., 14 (±2) days post-surgery)]

TABLE 35

Outcome #9

| Measure Type | Secondary |
|---|---|
| Measure Title | Occurrence of Severe Allergic Reactions (e.g., Anaphylaxis) |
| Measure Description | Treatment emergent adverse events (TEAEs) and treatment emergent serious adverse events (TESAEs) were evaluated for severe allergic reactions. |
| Time Frame | From first infusion of investigational product through study completion (i.e., 14 (±2) days post-surgery) |

TABLE 36

Population Description Outcome #9

The safety analysis data set, including all participants who received any amount of investigational product, was used for analysis of this outcome measure.

TABLE 37

Reporting Groups Outcome #9

| | Description |
|---|---|
| Recombinant Von Willebrand Factor (rVWF) | Surgery participants treated with Recombinant von Willebrand Factor (rVWF) |

TABLE 38

Measured Values Outcome #9

| | Recombinant Von Willebrand Factor (rVWF) |
|---|---|
| Participants Analyzed | 15 |
| Occurrence of Severe Allergic Reactions (e.g., Anaphylaxis) [Units: Adverse Events] | |
| Severe allergic reaction TEAEs | 0 |
| Severe allergic reaction TESAEs | 0 |

No statistical analysis provided for Occurrence of Severe Allergic Reactions (e.g., Anaphylaxis)

Secondary Outcome: Outcome #10

10. Secondary: Number of Participants Who Developed Inhibitory and Total Binding Antibodies to Von Willebrand Factor (VWF) and Inhibitory Antibodies to Factor VIII (FVIII) [Time Frame: Testing occurred throughout the study at screening, prior PK infusion, pre-surgery, post-surgery in case of excessive bleeding or unexplained bleeding, at postoperative day 7 and at study completion visit (ie. 14 (±2) days post-surgery).]

TABLE 39

Population Description Outcome #10

| Measure Type | Secondary |
|---|---|
| Measure Title | Number of Participants Who Developed Inhibitory and Total Binding Antibodies to Von Willebrand Factor (VWF) and Inhibitory Antibodies to Factor VIII (FVIII) |
| Measure Description | Participants were treated with recombinant van Willebrand Factor (rVWF) with or without ADVATE. |
| Time Frame | Testing occurred throughout the study at screening, prior PK infusion, pre-surgery, post-surgery in case of excessive bleeding or unexplained bleeding, at postoperative day 7 and at study completion visit (ie. 14 (±2) days post-surgery). |

TABLE 40

Population Description Outcome #10

The safety analysis data set, including all participants who received any amount of investigational product, was used for analysis of this outcome measure.

TABLE 41

Reporting Groups Outcome #10

| | Description |
|---|---|
| Recombinant Von Willebrand Factor (rVWF) | Surgery participants treated with Recombinant von Willebrand Factor (rVWF) |

TABLE 55

| Measured Values Outcome #10 | |
| --- | --- |
| | Recombinant Von Willebrand Factor (rVWF) |
| Participants Analyzed Number of Participants Who Developed Inhibitory and Total Binding Antibodies to Von Willebrand Factor (VWF) and Inhibitory Antibodies to Factor VIII (FVIII) [Units: Participants] Count of Participants | 15 |
| Development of inhibitory antibodies to VWF | 0 |
| Development of total binding antibodies to VWF | 1 |
| Development of inhibitory antibodies to FVIII | 0 |

No statistical analysis provided for Number of Participants Who Developed Inhibitory and Total Binding Antibodies to Von Willebrand Factor (VWF) and Inhibitory Antibodies to Factor VIII (FVIII)

Secondary Outcome: Outcome #11

11. Secondary: Number of Participants Who Developed Antibodies to Chinese Hamster Ovary (CHO) Proteins, Mouse Immunoglobulin G (IgG) or Recombinant Furin (rFurin) [Time Frame: Testing occurred throughout the study at screening, prior PK infusion, pre-surgery, post-surgery in case of excessive bleeding or unexplained bleeding, at postoperative day 7 and at study completion visit (ie. 14 (±2) days post-surgery).]

TABLE 42

| Outcome #11 | |
| --- | --- |
| Measure Type | Secondary |
| Measure Title | Number of Participants Who Developed Antibodies to Chinese Hamster Ovary (CHO) Proteins, Mouse Immunoglobulin G (IgG) or Recombinant Furin (rFurin) |
| Measure Description | Participants were treated with recombinant von Willebrand Factor (rVWF) with or without ADVATE. |
| Time Frame | Testing occurred throughout the study at screening, prior PK infusion, pre-surgery, post-surgery in case of excessive bleeding or unexplained bleeding, at postoperative day 7 and at study completion visit (ie. 14 (±2) days post-surgery). |

TABLE 43

| Population Description Outcome #11 |
| --- |
| The safety analysis data set, including all participants who received any amount of investigational product, was used for analysis of this outcome measure. |

TABLE 44

| Reporting Groups Outcome #11 | |
| --- | --- |
| | Description |
| Recombinant Von Willebrand Factor (rVWF) | Surgery participants treated with Recombinant von Willebrand Factor (rVWF) |

TABLE 59

| Measured Values Outcome #11 | |
| --- | --- |
| | Recombinant Von Willebrand Factor (rVWF) |
| Participants Analyzed Number of Participants Who Developed Anti-bodies to Chinese Hamster Ovary (CHO) Proteins, Mouse Immunoglobulin G (IgG) or Recombinant Furin (rFurin) [Units: Participants] Count of Participants | 15 |
| | 0 |

No statistical analysis provided for Number of Participants Who Developed Antibodies to Chinese Hamster Ovary (CHO) Proteins, Mouse Immunoglobulin G (IgG) or Recombinant Furin (rFurin)

Secondary Outcome: Outcome #12

12. Secondary: Pharmacokinetics: Area Under the Plasma Concentration Versus Time Curve From 0 to 72 Hours Post-infusion (AUC 0-72 h/Dose) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.]

TABLE 45

| Outcome #12 | |
| --- | --- |
| Measure Type | Secondary |
| Measure Title | Pharmacokinetics: Area Under the Plasma Concentration Versus Time Curve From 0 to 72 Hours Post-infusion (AUC 0-72 h/Dose) |
| Measure Description | This assessment was only required for subjects undergoing major surgery. Subjects received a PK infusion at a dose of 50 ± 5 IU/kg rVWF:RCo within 42 days prior to surgery. The area under the plasma concentration/time curve from 0 to 72 hours post-infusion was computed using the linear trapezoidal rule. For the calculation of AUC(0-72 h) the levels at 72 hours was linearly interpolated/extrapolated from the 2 nearest sampling time points. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac), FVIII Coagulation Activity (FVIII:C) |
| Time Frame | PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours. |

TABLE 46

| Population Description Outcome #12 |
| --- |
| The PK analysis data set, including all participants who underwent PK assessment with data collected at the relevant time points, was used for analysis of this outcome measure. |

TABLE 47

| Reporting Groups Outcome #12 | |
| --- | --- |
| | Description |
| Recombinant Von Willebrand Factor (rVWF) | Surgery participants treated with Recombinant von Willebrand Factor (rVWF) |

TABLE 48

| Measured Values Outcome #12 | |
| --- | --- |
| | Recombinant Von Willebrand Factor (rVWF) |
| Participants Analyzed Pharmacokinetics: Area Under the Plasma Concentration Versus Time Curve From 0 to 72 Hours Post-infusion (AUC 0-72 h/Dose) [Units hours * IU/dL] Geometric Mean (Geometric Coefficient of Variation) VWF:RCo | 11 |
| Participants Analyzed VWF:RCo VWF:Ag | 11 31.91 (37.5%) |
| Participants Analyzed VWF:Ag VWF:CB | 11 57.08 (25.6%) |
| Participants Analyzed VWF:CB VWF:Ac | 11 63.91 (29.4%) |
| Participants Analyzed VWF:Ac FVIII:C | 11 54.61 (28.1%) |
| Participants Analyzed FVIII:C | 5 67.49 (31.1%) |

No statistical analysis provided for Pharmacokinetics: Area Under the Plasma Concentration Versus Time Curve From 0 to 72 Hours Post-infusion (AUC 0-72 h/Dose)

Secondary Outcome: Outcome #13

13. Secondary: Pharmacokinetics: Area Under the Plasma Concentration Versus Time Curve From Time 0 to Infinity (AUC 0-∞/Dose) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.]

TABLE 49

| Outcome #13 | |
| --- | --- |
| Measure Type | Secondary |
| Measure Title | Pharmacokinetics: Area Under the Plasma Concentration Versus Time Curve From Time 0 to Infinity (AUC 0-∞/Dose) |
| Measure Description | This assessment was only required for subjects undergoing major surgery. Subjects received a PK infusion at a dose of 50 ± 5 IU/kg rVWF:RCo within 42 days prior to surgery. The area under the plasma concentration/time curve from time 0 to infinity and the area under the first moment curve from time 0 to infinity was calculated as the sum of AUC or AUMC from time 0 to the time of last quantifiable concentration plus a tail area correction calculated as $Ct/\lambda z$ and $Ct/\lambda z(t + 1/\lambda z)$, respectively, where Ct was the last quantifiable concentration, t was the time of last quantifiable concentration and $\lambda z$ was the terminal or disposition rate constant. PK analysis was performed for the following analytes: |

TABLE 49-continued

| Outcome #13 | |
| --- | --- |
| | VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac), FVIII Coagulation Activity (FVIII:C) |
| Time Frame | PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours. |

TABLE 50

| Population Description Outcome #13 |
| --- |
| The PK analysis data set, including all participants who underwent PK assessment with data collected at the relevant time points, was used for analysis of this outcome measure. |

TABLE 51

| Reporting Groups Outcome #13 | |
| --- | --- |
| | Description |
| Recombinant Von Willebrand Factor (rVWF) | Surgery participants treated with Recombinant von Willebrand Factor (rVWF) |

TABLE 52

| Measured Values | |
| --- | --- |
| | Recombinant Von Willebrand Factor (rVWF) |
| Participants Analyzed Pharmacokinetics: Area Under the Plasma Concentration Versus Time Curve From Time 0 to Infinity (AUC 0-∞/Dose) [Units: hours * IU/dL] Geometric Mean (Geometric Coefficient of Variation) VWF:RCo | 11 |
| Participants Analyzed VWF:RCo VWF:Ag | 11 34.43 (43.3%) |
| Participants Analyzed VWF:Ag VWF:CB | 11 68.87 (31.5%) |
| Participants Analyzed VWF:CB VWF:Ac | 11 71.82 (34.1%) |
| Participants Analyzed VWF:Ac FVIII:C | 11 61.90 (32.2%) |
| Participants Analyzed FVIII:C | 3 75.00 (30.9%) |

No statistical analysis provided for Pharmacokinetics: Area Under the Plasma Concentration Versus Time Curve From Time 0 to Infinity (AUC 0-∞/Dose)

Secondary Outcome: Outcome #14

14. Secondary: Pharmacokinetics: Mean Residence Time (MRT) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.]

TABLE 53

| Outcome #14 | |
| --- | --- |
| Measure Type | Secondary |
| Measure Title | Pharmacokinetics: Mean Residence Time (MRT) |
| Measure Description | This assessment was only required for subjects undergoing major surgery. Subjects received a PK infusion at a dose of 50 ± 5 IU/kg rVWF:RCo within 42 days prior to surgery. Mean residence time was calculated as area under the first moment curve from time 0 to infinity divided by the area under the curve time 0 to infinity minus T/2 where T was the duration of the infusion. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNO-VANCE VWF Ac Assay (VWF:Ac) |
| Time Frame | PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours. |

TABLE 54

| Population Description Outcome #14 |
| --- |
| The PK analysis data set, including all participants who underwent PK assessment with data collected at the relevant time points, was used for analysis of this outcome measure. |

TABLE 55

| Reporting Groups Outcome #14 | |
| --- | --- |
| | Description |
| Recombinant Von Willebrand Factor (rVWF) | Surgery participants treated with Recombinant von Willebrand Factor (rVWF) |

TABLE 56

| Measured Values | |
| --- | --- |
| | Recombinant Von Willebrand Factor (rVWF) |
| Participants Analyzed | 11 |
| Pharmacokinetics: Mean Residence Time (MRT) [Units: Hours] Geometric Mean (Geometric Coefficient of Variation) | |
| VWF:RCo | 22.69 (41.3%) |
| VWF:Ag | 37.92 (28.4%) |
| VWF:CB | 29.35 (31.1%) |
| VWF:Ac | 29.75 (28.6%) |

No statistical analysis provided for Pharmacokinetics: Mean Residence Time (MRT)

Secondary Outcome: Outcome #15

15. Secondary: Pharmacokinetics: Clearance (CL) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.]

TABLE 57

| Outcome #15 | |
| --- | --- |
| Measure Type | Secondary |
| Measure Title | Pharmacokinetics: Clearance (CL) |
| Measure Description | This assessment was only required for subjects undergoing major surgery. Subjects received a PK infusion at a dose of 50 ± 5 IU/kg rVWF:RCo within 42 days prior to surgery. Clearance was calculated as dose (IU/kg) divided by the area under the curve time 0 to infinity. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac) |
| Time Frame | PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours. |

TABLE 58

| Population Description Outcome #15 |
| --- |
| The PK analysis data set, including all participants who underwent PK assessment with data collected at the relevant time points, was used for analysis of this outcome measure. |

TABLE 59

| Reporting Groups Outcome #15 | |
| --- | --- |
| | Description |
| Recombinant Von Willebrand Factor (rVWF) | Surgery participants treated with Recombinant von Willebrand Factor (rVWF) |

TABLE 60

| Measured Values | |
| --- | --- |
| | Recombinant Von Willebrand Factor (rVWF) |
| Participants Analyzed Pharmacokinetics: Clearance (CL) [Units: dL/hour/kg] | 11 |

TABLE 60-continued

| Measured Values | |
| --- | --- |
| | Recombinant Von Willebrand Factor (rVWF) |
| Geometric Mean (Geometric Coefficient of Variation) | |
| VWF:RCo | 0.02904 |
| | (43.3%) |
| VWF:Ag | 0.01452 |
| | (31.5%) |
| VWF: CB | 0.01392 |
| | (34.1%) |
| VVVF:Ac | 0.01616 |
| | (32.2%) |

No statistical analysis provided for Pharmacokinetics: Clearance (CL)

Secondary Outcome: Outcome #16

16. Secondary: Pharmacokinetics: Incremental Recovery (IR) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.]

TABLE 61

| Outcome #16 | |
| --- | --- |
| Measure Type | Secondary |
| Measure Title | Pharmacokinetics: Incremental Recovery (IR) |
| Measure Description | This assessment was only required for subjects undergoing major surgery. Subjects received a PK infusion at a dose of 50 ± 5 IU/kg rVWF:RCo within 42 days prior to surgery. Incremental recovery was calculated as (Cmax minus Cpreinfusion) divided by the dose (IU/kg) where kg refers to the body weight at the time of dosing and Cmax was the observed maximum concentration before correction for pre-infusion values. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac) |
| Time Frame | PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours. |

TABLE 77

| Population Description Outcome #16 |
| --- |
| The PK analysis data set, including all participants who underwent PK assessment with data collected at the relevant time points, was used for analysis of this outcome measure. |

TABLE 62

| Reporting Groups Outcome #16 | |
| --- | --- |
| | Description |
| Recombinant Von Willebrand Factor (rVWF) | Surgery participants treated with Recombinant von Willebrand Factor (rVWF) |

TABLE 63

| Measured Values Outcome #16 | |
| --- | --- |
| | Recombinant Von Willebrand Factor (rVWF) |
| Participants Analyzed | 11 |
| Pharmacokinetics: Incremental Recovery (IR) [Units: IU/dL] Mean (Standard Deviation) | |
| VWF:RCo | 1.961 (0.45445) |
| VWF:Ag | 1.991 (0.38395) |
| VWF:CB | 2.780 (0.56640) |
| VWF:Ac | 2.635 (0.38050) |

No statistical analysis provided for Pharmacokinetics: Incremental Recovery (IR)

Secondary Outcome: Outcome #17

17. Secondary: Pharmacokinetics: Elimination Phase Half-life (T½) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.]

TABLE 64

| Outcome #17 | |
| --- | --- |
| Measure Type | Secondary |
| Measure Title | Pharmacokinetics: Elimination Phase Half-life (T½) |
| Measure Description | This assessment was only required for subjects undergoing major surgery. Subjects received a PK infusion at a dose of 50 ± 5 IU/kg rVWF:RCo within 42 days prior to surgery. Terminal or disposition half-life (T½) was calculated as $\ln2/\lambda z$ where $\lambda z$ was the terminal elimination rate constant as calculated in WinNonlin NCA using at least three quantifiable concentrations. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac) |
| Time Frame | PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours. |

TABLE 65

| Population Description Outcome #17 |
| --- |
| The PK analysis data set, including all participants who underwent PK assessment with data collected at the relevant time points, was used for analysis of this outcome measure. |

TABLE 66

| Reporting Groups Outcome #17 | |
| --- | --- |
| | Description |
| Recombinant Von Willebrand Factor (rVWF) | Surgery participants treated with Recombinant von Willebrand Factor (rVWF) |
| Measured Values | |
| | Recombinant Von Willebrand Factor (rVWF) |
| Participants Analyzed | 11 |
| Pharmacokinetics: Elimination Phase Half-life (T½) | |

TABLE 66-continued

| Reporting Groups Outcome #17 | |
| --- | --- |
| | Description |
| [Units: Hours] Geometric Mean (Geometric Coefficient of Variation) | |
| VWF:RCo | 16.52 (42.7%) |
| VWF:Ag | 26.88 (26.5%) |
| VWF:CB | 21.07 (33.2%) |
| VVVF:Ac | 22.19 (28.5%) |

No statistical analysis provided for Pharmacokinetics: Elimination Phase Half-life (T½)

Secondary Outcome: Outcome #18

18. Secondary: Pharmacokinetics: Volume of Distribution at Steady State (Vss) [Time Frame: PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours.]

TABLE 67

| Outcome #18 | |
| --- | --- |
| Measure Type | Secondary |
| Measure Title | Pharmacokinetics: Volume of Distribution at Steady State (Vss) |
| Measure Description | This assessment was only required for subjects undergoing major surgery. Subjects received a PK infusion at a dose of 50 ± 5 IU/kg rVWF:RCo within 42 days prior to surgery. Vss was calculated as the clearance multiplied with the mean residence time. PK analysis was performed for the following analytes: VWF Ristocetin Cofactor Activity (VWF:RCo), VWF Antigen Activity (VWF:Ag), VWF Collagen Binding Activity (VWF:CB), VWF Activity Measured INNOVANCE VWF Ac Assay (VWF:Ac) |
| Time Frame | PK measurements were done within 30 minutes pre-infusion, and post infusion at 30 (±5) minutes, 60 (±5) minutes, 6 (±1) hours, 12 (±1) hours, 24 (±2) hours, 48 (±2) hours and 72 (±2) hours. |

TABLE 68

| Population Description Outcome #18 |
| --- |
| The PK analysis data set, including all participants who underwent PK assessment with data collected at the relevant time points, was used for analysis of this outcome measure. |

TABLE 69

| Reporting Groups Outcome #18 | |
| --- | --- |
| | Description |
| Recombinant Von Willebrand Factor (rVWF) | Surgery participants treated with Recombinant von Willebrand Factor (rVWF) |
| Measured Values Outcome #18 | |
| | Recombinant Von Willebrand Factor (rVWF) |
| Participants Analyzed | 11 |
| Pharmacokinetics: Volume of Distribution at Steady State (Vss) [Units: dL/kg] Geometric Mean (Geometric Coefficient of Variation) | |
| VWF:RCo | 0.6591 (28.8%) |

TABLE 69-continued

| Reporting Groups Outcome #18 | |
| --- | --- |
| | Description |
| VWF:Ag | 0.5506 |
| | (18.4%) |
| VWF:CB | 0.4086 |
| | (24.0%) |
| VVVF:Ac | 0.4806 |
| | (21.5%) |

No statistical analysis provided for Pharmacokinetics: Volume of Distribution at Steady State (Vss)

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method for pre-treatment of a subject with severe von Willebrand disease (VWD) prior to a surgical procedure, wherein said pre-treatment comprises the following steps:

(i) administering 40-60 IU/kg of recombinant Von Willebrand Factor (rVWF) to said subject between 12 hours and 24 hours prior to said surgical procedure, wherein Factor VIII (FVIII) is not administered with the rVWF prior to the surgical procedure, wherein the rVWF comprises ultra-large multimers (ULMs), wherein the ULMs comprise over 40 subunits and are at least 10,000 kDa;

(ii) measuring the subject's FVIII: C level within 3 hours prior to said procedure; and (iii) administering 5-90 IU/kg rVWF to said subject within 1 hour prior to said surgical procedure.

2. The method of claim 1, wherein FVIII is not administered after said surgical procedure.

3. The method of claim 1, wherein said surgical procedure is selected from the group consisting of major surgery, minor surgery, and oral surgery.

4. The method of claim 1, wherein said subject is administered 50-60 IU/kg rVWF between 12 hours and 24 hours prior to said surgical procedure and said surgical procedure is a minor surgical procedure.

5. The method of claim 1, wherein said subject is administered 45-60 IU/kg rVWF between 12 hours and 24 hours prior to said surgical procedure and said surgical procedure is a major surgical procedure.

6. The method of claim 1, wherein said subject is administered 5-50 IU/kg rVWF 1 hour prior to the surgical procedure and said surgical procedure is a minor surgical procedure.

7. The method of claim 1, wherein said subject is administered 15-90 IU/kg rVWF 1 hour prior to said surgical procedure and said surgical procedure is a major surgical procedure.

8. The method of claim 1, wherein said subject is administered 20-50 IU/kg rVWF 1 hour prior to said surgical procedure and said surgical procedure is an oral surgical procedure.

9. The method of claim 1, wherein said subject is administered 10-50 IU/kg rVWF during said surgical procedure and said surgical procedure is an oral surgical procedure.

10. The method of claim 1, wherein said subject is administered 70-220 IU/kg rVWF after said surgical procedure.

11. The method of claim 1, wherein said subject is administered 70-150 IU/kg rVWF after said surgical procedure and said surgical procedure is a minor surgical procedure.

12. The method of claim 1, wherein said subject is administered 150-220 IU/kg rVWF after said surgical procedure and said surgical procedure is a major surgical procedure.

13. The method of claim 1, wherein said subject is administered 20-50 IU/kg rVWF after said surgical procedure and said surgical procedure is an oral surgical procedure.

14. The method of claim 1, wherein said subject is administered a total dosage of 100-220 IU/kg rVWF and said surgical procedure is a minor surgical procedure.

15. The method of claim 1, wherein said subject is administered a total dosage of 220-320 IU/kg rVWF and said surgical procedure is a major surgical procedure.

16. The method of claim 1, wherein said subject is administered a total dosage of 70-190 IU/kg rVWF and said surgical procedure is an oral surgical procedure.

17. The method of claim 1, wherein said surgical procedure is a major surgical procedure and said pre-treatment comprises administering at least two approximately equal doses of rVWF prior to the surgical procedure.

18. The method of claim 1, wherein said surgical procedure is a minor surgical procedure and said pre-treatment comprises administering at least two doses of rVWF prior to the surgical procedure, wherein the first dose is larger than the second dose.

19. The method of claim 1, wherein said surgical procedure is an oral surgical procedure and said pre-treatment comprises administering at least two approximately equal doses of rVWF prior to the surgical procedure.

20. The method of claim 1, wherein said surgical procedure further comprises step (iv) administering recombinant factor VIII immediately after said administration of 5-90 IU/kg of rVWF if the subject's measured FVIII: C level is below 30 IU/dL for a minor/oral surgical procedure or below 60 IU/dL for a major surgical procedure.

21. The method of claim 1, wherein the rVWF comprises a percentage of high molecular weight (HMW) rVWF multimers, wherein the HMW rVWF multimers comprise 10%-40% rVWF decamers or higher order multimers.

22. The method of claim 1, wherein the FVIII: C level when measured is increased to at least 30 IU/dL, wherein said surgical procedure is a minor surgical procedure.

23. The method of claim 1, wherein the FVIII: C level is increased to at least 60 IU/dL, wherein said surgical procedure is a major surgical procedure.

24. A method for pre-treatment of a subject with severe von Willebrand disease (VWD) prior to surgical procedure, wherein said pre-treatment comprises the following steps:

(i) administering 40-60 IU/kg of recombinant Von Willebrand Factor (rVWF) to said subject between 12 hours and 24 hours prior to said surgical procedure, wherein Factor VIII (FVIII) is not administered with the rVWF prior to the surgical procedure, wherein the rVWF comprises ultra-large multimers (ULMs), wherein the ULMs comprise over 40 subunits and are at least 10,000 kDa;

(ii) measuring the subject's FVIII: C level within 3 hours prior to said procedure; and (iii) administering 5-90 IU/kg rVWF to said subject within 1 hour prior to said surgical procedure, wherein said surgical procedure is an oral surgical procedure.

25. The method of claim 24, wherein the rVWF comprises a percentage of high molecular weight (HMW) rVWF multimers, wherein the HMW rVWF multimers comprise 10%-40% rVWF decamers or higher order multimers.

26. The method of claim 24, wherein the FVIII: C level when measured is increased to at least 30 IU/dL, wherein said surgical procedure is a minor surgical procedure.

27. The method of claim 24, wherein the FVIII: C level is increased to at least 60 IU/dL, wherein said surgical procedure is a major surgical procedure.

\* \* \* \* \*

SEQUENCE LISTING

```
<160> NUMBER OF SEQ ID NOS: 3

<210> SEQ ID NO 1
<211> LENGTH: 8833
<212> TYPE: DNA
<213> ORGANISM: Artificial Sequence
<220> FEATURE:
<223> OTHER INFORMATION: prepro-VWF

<400> SEQUENCE: 1
agctcacagc tattgtggtg ggaaagggag ggtggttggt ggatgtcaca gcttgggctt      60
tatctccccc agcagtgggg actccacagc ccctgggcta cataacagca agacagtccg     120
gagctgtagc agacctgatt gagcctttgc agcagctgag agcatggcct agggtgggcg     180
gcaccattgt ccagcagctg agtttcccag ggaccttgga gatagccgca gccctcattt     240 gcagggggaag atgattcctg ccagatttgc cggggtgctg cttgctctgg ccctcatttt     300
gccagggacc ctttgtgcag aaggaactcg cggcaggtca tccacggccc gatgcagcct     360
tttcggaagt gacttcgtca acacctttga tgggagcatg tacagctttg cgggatactg     420
cagttacctc ctggcagggg gctgccagaa acgctccttc tcgattattg gggacttcca     480
gaatggcaag agagtgagcc tctccgtgta tcttggggaa tttttttgaca tccatttgtt     540 tgtcaatggt accgtgacac aggggggacca aagagtctcc atgccctatg cctccaaagg     600
gctgtatcta gaaactgagg ctgggtacta caagctgtcc ggtgaggcct atggctttgt     660
ggccaggatc gatggcagcg gcaactttca agtcctgctg tcagacagat acttcaacaa     720
gacctgcggg ctgtgtggca actttaacat ctttgctgaa gatgacttta tgacccaaga     780
agggaccttg acctcggacc cttatgactt tgccaactca tgggctctga gcagtggaga     840
acagtggtgt gaacgggcat ctcctcccag cagctcatgc aacatctcct ctgggggaaat     900
```

-continued

```
gcagaagggc ctgtgggagc agtgccagct tctgaagagc acctcggtgt ttgcccgctg    960
ccaccctctg gtggaccccg agcctttttgt ggccctgtgt gagaagactt tgtgtgagtg   1020 tgctggggggg ctggagtgcg cctgccctgc cctcctggag tacgcccgga cctgtgccca   1080
ggagggaatg gtgctgtacg gctggaccga ccacagcgcg tgcagcccag tgtgccctgc   1140
tggtatggag tataggcagt gtgtgtcccc ttgcgccagg acctgccaga gcctgcacat   1200
caatgaaatg tgtcaggagc gatgcgtgga tggctgcagc tgccctgagg acagctcct   1260 ggatgaaggc ctctgcgtgg agagcaccga gtgtccctgc gtgcattccg gaaagcgcta   1320 ccctccccggc acctccctct ctcgagactg caacacctgc atttgccgaa acagccagtg   1380
gatctgcagc aatgaagaat gtccaggggga gtgccttgtc acaggtcaat cacacttcaa   1440
gagctttgac aacagatact tcaccttcag tgggatctgc cagtacctgc tggcccggga   1500
ttgccaggac cactccttct ccattgtcat tgagactgtc cagtgtgctg atgaccgcga   1560
cgctgtgtgc acccgctccg tcaccgtccg gctgcctggc ctgcacaaca gccttgtgaa   1620
actgaagcat ggggcaggag ttgccatgga tggccaggac gtccagctcc ccctcctgaa   1680
aggtgacctc cgcatccagc atacagtgac ggcctccgtg cgcctcagct acggggagga   1740
cctgcagatg gactgggatg gccgcgggag gctgctggtg aagctgtccc ccgtctatgc   1800
cgggaagacc tgcggcctgt gtgggaatta caatggcaac cagggcgacg acttccttac   1860
cccctctggg ctggcggagc cccgggtgga ggacttcggg aacgcctgga agctgcacgg   1920
ggactgccag gacctgcaga agcagcacag cgatccctgc gccctcaacc cgcgcatgac   1980
caggttctcc gaggaggcgt gcgcggtcct gacgtccccc acattcgagg cctgccatcg   2040
tgccgtcagc ccgctgccct acctgcggaa ctgccgctac gacgtgtgct cctgctcgga   2100
cggccgcgag tgcctgtgcg gcgccctggc cagctatgcc gcggcctgcg cggggagagg   2160
cgtgcgcgtc gcgtggcgcg agccaggccg ctgtgagctg aactgcccga aaggccaggt   2220
gtacctgcag tgcgggaccc cctgcaacct gacctgccgc tctctctctt acccggatga   2280
ggaatgcaat gaggcctgcc tggaggggctg cttctgcccc ccagggctct acatggatga   2340
gaggggggac tgcgtgccca aggcccagtg ccctgttac tatgacggtg agatcttcca   2400
gccagaagac atcttctcag accatcacac catgtgctac tgtgaggatg gcttcatgca   2460
ctgtaccatg agtggagtcc ccggaagctt gctgcctgac gctgtcctca gcagtccccc   2520
gtctcatcgc agcaaaagga gcctatcctg tcggcccccc atggtcaagc tggtgtgtcc   2580
cgctgacaac ctgcgggctg aagggctcga gtgtaccaaa acgtgccaga actatgacct   2640
ggagtgcatg agcatgggct gtgtctctgg ctgcctctgc cccccgggca tggtccggca   2700
tgagaacaga tgtgtggccc tggaaaggtg tccctgcttc catcagggca aggagtatgc   2760
ccctggagaa acagtgaaga ttggctgcaa cacttgtgtc tgtcgggacc ggaagtggaa   2820
ctgcacagac catgtgtgtg atgccacgtg ctccacgatc ggcatggccc actacctcac   2880
cttcgacggg ctcaaatacc tgttcccccgg ggagtgccag tacgttctgg tgcaggatta   2940
ctgcggcagt aaccctggga cctttcggat cctagtgggg aataagggat gcagccaccc   3000
ctcagtgaaa tgcaagaaac gggtcaccat cctggtggag ggaggagaga ttgagctgtt   3060
tgacggggag gtgaatgtga agaggcccat gaaggatgag actcactttg aggtggtgga   3120
gtctggccgg tacatcattc tgctgctggg caaagccctc tccgtggtct gggaccgcca   3180
cctgagcatc tccgtggtcc tgaagcagac ataccaggag aaagtgtgtg gcctgtgtgg   3240
```

```
gaattttgat ggcatccaga acaatgacct caccagcagc aacctccaag tggaggaaga      3300
ccctgtggac tttgggaact cctggaaagt gagctcgcag tgtgctgaca ccagaaaagt      3360
gcctctggac tcatcccctg ccacctgcca taacaacatc atgaagcaga cgatggtgga      3420
ttcctcctgt agaatcctta ccagtgacgt cttccaggac tgcaacaagc tggtggaccc      3480
cgagccatat ctggatgtct gcatttacga cacctgctcc tgtgagtcca ttggggactg      3540
cgcctgcttc tgcgacacca ttgctgccta tgcccacgtg tgtgcccagc atggcaaggt      3600
ggtgacctgg aggacggcca cattgtgccc ccagagctgc gaggagagga atctccggga      3660
gaacgggtat gagtgtgagt ggcgctataa cagctgtgca cctgcctgtc aagtcacgtg      3720
tcagcaccct gagccactgg cctgccctgt gcagtgtgtg gagggctgcc atgcccactg      3780
ccctccaggg aaaatcctgg atgagctttt gcagacctgc gttgaccctg aagactgtcc      3840
agtgtgtgag gtggctggcc ggcgttttgc ctcaggaaag aaagtcacct tgaatcccag      3900
tgaccctgag cactgccaga tttgccactg tgatgttgtc aacctcacct gtgaagcctg      3960
ccaggagccg ggaggcctgg tggtgcctcc cacagatgcc ccggtgagcc ccaccactct      4020
gtatgtggag gacatctcgg aaccgccgtt gcacgatttc tactgcagca ggctactgga      4080
cctggtcttc ctgctggatg gctcctccag gctgtccgag gctgagtttg aagtgctgaa      4140
ggcctttgtg gtggacatga tggagcggct gcgcatctcc cagaagtggg tccgcgtggc      4200
cgtggtggag taccacgacg gctcccacgc ctacatcggg ctcaaggacc ggaagcgacc      4260
gtcagagctg cggcgcattg ccagccaggt gaagtatgcg ggcagccagg tggcctccac      4320
cagcgaggtc ttgaaataca cactgttcca aatcttcagc aagatcgacc gccctgaagc      4380
ctcccgcatc accctgctcc tgatggccag ccaggagccc caacggatgt cccggaactt      4440
tgtccgctac gtccagggcc tgaagaagaa gaaggtcatt gtgatcccgg tgggcattgg      4500
gccccatgcc aacctcaagc agatccgcct catcgagaag caggcccctg agaacaaggc      4560
cttcgtgctg agcagtgtgg atgagctgga gcagcaaagg gacgagatcg ttagctacct      4620
ctgtgacctt gcccctgaag cccctcctcc tactctgccc cccgacatgg cacaagtcac      4680
tgtgggcccg gggctcttgg gggtttcgac cctggggccc aagaggaact ccatggttct      4740
ggatgtggcg ttcgtcctgg aaggatcgga caaaattggt gaagccgact tcaacaggag      4800
caaggagttc atggaggagg tgattcagcg gatggatgtg ggccaggaca gcatccacgt      4860
cacggtgctg cagtactcct acatggtgac tgtggagtac cccttcagcg aggcacagtc      4920
caaaggggac atcctgcagc gggtgcgaga gatccgctac cagggcggca acaggaccaa      4980
cactgggctg gccctgcggt acctctctga ccacagcttc ttggtcagcc agggtgaccg      5040
ggagcaggcg cccaacctgg tctacatggt caccggaaat cctgcctctg atgagatcaa      5100
gaggctgcct ggagacatcc aggtggtgcc cattggagtg ggccctaatg ccaacgtgca      5160
ggagctggag aggattggct ggcccaatgc ccctatcctc atccaggact ttgagacgct      5220
cccccgagag gctcctgacc tggtgctgca gaggtgctgc tccggagagg ggctgcagat      5280
ccccaccctc tcccctgcac ctgactgcag ccagcccctg gacgtgatcc ttctcctgga      5340
tggctcctcc agtttcccag cttcttattt tgatgaaatg aagagtttcg ccaaggcttt      5400
catttcaaaa gccaatatag ggcctcgtct cactcaggtg tcagtgctgc agtatggaag      5460
catcaccacc attgacgtgc catggaacgt ggtcccggag aaagcccatt gctgagcct       5520 tgtggacgtc atgcagcggg agggaggccc cagccaaatc ggggatgcct gggctttgc       5580 tgtgcgatac ttgacttcag aaatgcatgg tgccaggccg ggagcctcaa aggcggtggt      5640
```

```
catcctggtc acggacgtct ctgtggattc agtggatgca gcagctgatg ccgccaggtc    5700
caacagagtg acagtgttcc ctattggaat tggagatcgc tacgatgcag cccagctacg    5760
gatcttggca ggcccagcag gcgactccaa cgtggtgaag ctccagcgaa tcgaagacct    5820
ccctaccatg gtcaccttgg gcaattcctt cctccacaaa ctgtgctctg gatttgttag    5880
gatttgcatg gatgaggatg ggaatgagaa gaggcccggg gacgtctgga ccttgccaga    5940
ccagtgccac accgtgactt gccagccaga tggccagacc ttgctgaaga gtcatcgggt    6000
caactgtgac cgggggctga ggccttcgtg ccctaacagc cagtcccctg ttaaagtgga    6060
agagacctgt ggctgccgct ggacctgccc ctgcgtgtgc acaggcagct ccactcggca    6120
catcgtgacc tttgatgggc agaatttcaa gctgactggc agctgttctt atgtcctatt    6180
tcaaaacaag gagcaggacc tggaggtgat tctccataat ggtgcctgca gccctggagc    6240
aaggcagggc tgcatgaaat ccatcgaggt gaagcacagt gccctctccg tcgagctgca    6300
cagtgacatg gaggtgacgg tgaatgggag actggtctct gttccttacg tgggtgggaa    6360
catggaagtc aacgtttatg gtgccatcat gcatgaggtc agattcaatc accttggtca    6420
catcttcaca ttcactccac aaaacaatga gttccaactg cagctcagcc ccaagacttt    6480
tgcttcaaag acgtatggtc tgtgtgggat ctgtgatgag aacggagcca atgacttcat    6540
gctgagggat ggcacagtca ccacagactg gaaaacactt gttcaggaat ggactgtgca    6600
gcggccaggg cagacgtgcc agcccatcct ggaggagcag tgtcttgtcc ccgacagctc    6660
ccactgccag gtcctcctct taccactgtt tgctgaatgc cacaaggtcc tggctccagc    6720
cacattctat gccatctgcc agcaggacag ttgccaccag gagcaagtgt gtgaggtgat    6780
cgcctcttat gcccacctct gtcggaccaa cgggggtctgc gttgactgga ggacacctga    6840
tttctgtgct atgtcatgcc caccatctct ggtctacaac cactgtgagc atggctgtcc    6900
ccggcactgt gatggcaacg tgagctcctg tggggaccat ccctccgaag gctgtttctg    6960
ccctccagat aaagtcatgt tggaaggcag ctgtgtccct gaagaggcct gcactcagtg    7020
cattggtgag gatggagtcc agcaccagtt cctggaagcc tgggtcccgg accaccagcc    7080
ctgtcagatc tgcacatgcc tcagcgggcg gaaggtcaac tgcacaacgc agccctgccc    7140
cacggccaaa gctcccacgt gtggcctgtg tgaagtagcc cgcctccgcc agaatgcaga    7200
ccagtgctgc cccgagtatg agtgtgtgtg tgacccagtg agctgtgacc tgccccagt     7260 gcctcactgt gaacgtggcc tccagcccac actgaccaac cctggcgagt gcagacccaa    7320
cttcacctgc gcctgcagga aggaggagtg caaaagagtg tccccaccct cctgcccccc    7380
gcaccgtttg cccacccttc ggaagaccca gtgctgtgat gagtatgagt gtgcctgcaa    7440
ctgtgtcaac tccacagtga gctgtccccct tgggtacttg gcctcaactg ccaccaatga    7500
ctgtggctgt accacaacca cctgccttcc cgacaaggtg tgtgtccacc gaagcaccat    7560
ctaccctgtg ggccagttct gggaggaggg ctgcgatgtg tgcacctgca ccgacatgga    7620
ggatgccgtg atgggcctcc gcgtggccca gtgctcccag aagccctgtg aggacagctg    7680
tcggtcgggc ttcacttacg ttctgcatga aggcgagtgc tgtggaaggt gcctgccatc    7740
tgcctgtgag gtggtgactg gctcaccgcg ggggactcc cagtcttcct ggaagagtgt     7800
cggctcccag tgggcctccc cggagaaccc ctgcctcatc aatgagtgtg tccgagtgaa    7860
ggaggaggtc tttatacaac aaaggaacgt ctcctgcccc cagctggagg tccctgtctg    7920
cccctcgggc tttcagctga gctgtaagac ctcagcgtgc tgcccaagct gtcgctgtga    7980
```

```
gcgcatggag gcctgcatgc tcaatggcac tgtcattggg cccgggaaga ctgtgatgat   8040
cgatgtgtgc acgacctgcc gctgcatggt gcaggtgggg gtcatctctg gattcaagct   8100
ggagtgcagg aagaccacct gcaacccctg cccctgggt tacaaggaag aaaataacac    8160
aggtgaatgt tgtgggagat gtttgcctac ggcttgcacc attcagctaa gaggaggaca   8220
gatcatgaca ctgaagcgtg atgagacgct ccaggatggc tgtgatactc acttctgcaa   8280
ggtcaatgag agaggagagt acttctggga agagggtc acaggctgcc cacccttttga    8340 tgaacacaag tgtctggctg agggaggtaa aattatgaaa attccaggca cctgctgtga   8400
cacatgtgag gagcctgagt gcaacgacat cactgccagg ctgcagtatg tcaaggtggg   8460
aagctgtaag tctgaagtag aggtggatat ccactactgc cagggcaaat gtgccagcaa   8520
agccatgtac tccattgaca tcaacgatgt gcaggaccag tgctcctgct gctctccgac   8580
acggacggag cccatgcagg tggccctgca ctgcaccaat ggctctgttg tgtaccatga   8640
ggttctcaat gccatggagt gcaaatgctc ccccaggaag tgcagcaagt gaggctgctg   8700
cagctgcatg ggtgcctgct gctgcctgcc ttggcctgat ggccaggcca gagtgctgcc   8760
agtcctctgc atgttctgct cttgtgccct tctgagccca caataaaggc tgagctctta   8820
tcttgcaaaa ggc                                                      8833
```

```
<210> SEQ ID NO 2
<211> LENGTH: 2783
<212> TYPE: PRT
<213> ORGANISM: Artificial Sequence
<220> FEATURE:
<223> OTHER INFORMATION: prepro-VWF

<400> SEQUENCE: 2

Met Ile Pro Ala Arg Phe Ala Gly Val Leu Leu Leu Ile Leu Pro Gly
1               5                   10                  15

Thr Leu Cys Ala Glu Gly Thr Arg Gly Arg Ser Ser Thr Ala Arg Cys
            20                  25                  30

Ser Leu Phe Gly Ser Asp Phe Val Asn Thr Phe Asp Gly Ser Met Tyr
        35                  40                  45

Ser Phe Ala Gly Tyr Cys Ser Tyr Leu Leu Ala Gly Gly Cys Gln Lys
    50                  55                  60

Arg Ser Phe Ser Ile Ile Gly Asp Phe Gln Asn Gly Lys Arg Val Ser
65                  70                  75                  80

Leu Ser Val Tyr Leu Gly Glu Phe Phe Asp Ile His Leu Phe Val Asn
                85                  90                  95

Gly Thr Val Thr Gln Gly Asp Gln Arg Val Ser Met Pro Tyr Ala Ser
            100                 105                 110

Lys Leu Glu Thr Glu Ala Gly Tyr Tyr Lys Leu Ser Gly Glu Ala Tyr
        115                 120                 125

Gly Phe Val Ala Arg Ile Asp Gly Ser Gly Asn Phe Gln Val Leu Leu
    130                 135                 140

Ser Asp Arg Tyr Phe Asn Lys Thr Cys Gly Leu Cys Gly Asn Phe Asn
145                 150                 155                 160

Ile Phe Ala Glu Asp Asp Phe Met Thr Gln Glu Gly Thr Leu Thr Ser
                165                 170                 175

Asp Pro Tyr Asp Phe Ala Asn Ser Trp Ala Leu Ser Ser Gly Glu Gln
            180                 185                 190

Trp Cys Glu Arg Pro Ser Ser Ser Cys Asn Ile Ser Ser Gly Glu Met
        195                 200                 205
```

```
Gln Lys Gly Leu Trp Glu Gln Cys Gln Leu Leu Lys Ser Thr Ser Val
    210             215             220

Phe Ala Arg Cys His Pro Leu Val Asp Pro Glu Pro Phe Cys Glu Lys
225             230             235             240

Thr Leu Cys Glu Cys Ala Gly Gly Leu Glu Cys Ala Cys Pro Ala Leu
            245             250             255

Leu Glu Tyr Ala Arg Thr Cys Ala Gln Glu Gly Met Val Leu Tyr Gly
            260             265             270

Trp Thr Asp His Ser Ala Cys Ser Pro Val Cys Pro Ala Gly Met Glu
            275             280             285

Tyr Arg Gln Cys Val Ser Pro Cys Ala Arg Thr Cys Gln Ser Leu His
    290             295             300

Ile Asn Glu Met Cys Gln Glu Arg Cys Val Asp Gly Cys Ser Cys Pro
305             310             315             320

Glu Gly Gln Leu Leu Asp Glu Gly Leu Cys Val Glu Ser Thr Glu Cys
            325             330             335

Pro Cys Val His Ser Gly Lys Arg Tyr Pro Pro Gly Thr Ser Leu Ser
            340             345             350

Arg Asp Cys Asn Thr Cys Ile Cys Arg Asn Ser Gln Trp Ile Cys Ser
            355             360             365

Asn Glu Glu Cys Pro Gly Glu Cys Leu Val Thr Gly Gln Ser His Phe
    370             375             380

Lys Ser Phe Asp Asn Arg Tyr Phe Thr Phe Ser Gly Ile Cys Gln Tyr
385             390             395             400

Leu Leu Ala Arg Asp Cys Gln Asp His Ser Phe Ser Ile Val Ile Glu
            405             410             415

Thr Val Gln Cys Ala Asp Asp Arg Asp Ala Val Cys Thr Arg Ser Val
            420             425             430

Thr Val Arg Leu Pro Gly Leu His Asn Ser Leu Val Lys Leu Lys His
            435             440             445

Gly Ala Gly Val Ala Met Asp Gly Gln Asp Val Gln Leu Pro Leu Leu
    450             455             460

Lys Gly Asp Leu Arg Ile Gln His Thr Val Thr Ala Ser Val Arg Leu
465             470             475             480

Ser Tyr Gly Glu Asp Leu Gln Met Asp Trp Asp Gly Arg Gly Arg Leu
            485             490             495

Leu Val Lys Leu Ser Pro Val Tyr Ala Gly Lys Thr Cys Gly Leu Cys
            500             505             510

Gly Asn Tyr Asn Gly Asn Gln Gly Asp Asp Phe Leu Thr Pro Ser Gly
            515             520             525

Leu Ala Glu Pro Arg Val Glu Asp Phe Gly Asn Ala Trp Lys Leu His
    530             535             540

Gly Asp Cys Gln Asp Leu Gln Lys Gln His Ser Asp Pro Cys Ala Leu
545             550             555             560

Asn Pro Arg Met Thr Arg Phe Ser Glu Glu Ala Cys Ala Val Leu Thr
            565             570             575

Ser Pro Thr Phe Glu Ala Cys His Arg Ala Val Ser Pro Leu Pro Tyr
            580             585             590

Leu Arg Asn Cys Arg Tyr Asp Val Cys Ser Cys Ser Asp Gly Arg Glu
            595             600             605

Cys Leu Cys Gly Ser Tyr Ala Ala Ala Cys Ala Gly Arg Gly Val Arg
    610             615             620

Val Ala Trp Arg Glu Pro Gly Arg Cys Glu Leu Asn Cys Pro Lys Gly
```

```
625             630             635             640

Gln Val Tyr Leu Gln Cys Gly Thr Pro Cys Asn Leu Thr Cys Arg Ser
            645             650             655

Leu Ser Tyr Pro Asp Glu Glu Cys Asn Glu Ala Cys Leu Glu Gly Cys
            660             665             670

Phe Cys Pro Pro Met Asp Glu Arg Gly Asp Cys Val Pro Lys Ala Gln
            675             680             685

Cys Pro Cys Tyr Tyr Asp Gly Glu Ile Phe Gln Pro Glu Asp Ile Phe
    690             695             700

Ser Asp His His Thr Met Cys Tyr Cys Glu Asp Gly Phe Met His Cys
705             710             715             720

Thr Met Ser Gly Val Pro Gly Ser Leu Leu Pro Asp Ala Val Leu Ser
            725             730             735

Ser Pro Leu Ser His Arg Ser Lys Arg Ser Leu Ser Cys Arg Pro Pro
            740             745             750

Met Val Lys Leu Val Cys Pro Ala Asp Asn Leu Arg Ala Glu Gly Leu
            755             760             765

Glu Cys Thr Lys Thr Cys Gln Asn Tyr Asp Leu Glu Cys Met Ser Met
    770             775             780

Gly Cys Val Ser Gly Cys Leu Cys Pro Pro Gly Met Val Arg His Glu
785             790             795             800

Asn Arg Cys Glu Arg Cys Pro Cys Phe His Gln Gly Lys Glu Tyr Ala
            805             810             815

Pro Gly Glu Thr Val Lys Ile Gly Cys Asn Thr Cys Val Cys Arg Asp
            820             825             830

Arg Lys Trp Asn Cys Thr Asp His Val Cys Asp Ala Thr Cys Ser Thr
            835             840             845

Ile Gly Met Ala His Tyr Leu Thr Phe Asp Gly Leu Lys Tyr Leu Phe
    850             855             860

Pro Gly Glu Cys Gln Tyr Val Leu Val Gln Asp Tyr Cys Gly Ser Asn
865             870             875             880

Pro Gly Thr Phe Arg Ile Leu Val Gly Asn Lys Gly Cys Ser His Pro
            885             890             895

Ser Val Lys Cys Lys Lys Arg Val Thr Ile Leu Val Glu Gly Gly Glu
            900             905             910

Ile Glu Leu Phe Asp Gly Glu Val Asn Val Lys Arg Pro Met Lys Asp
            915             920             925

Glu Thr His Phe Glu Val Val Glu Ser Gly Arg Tyr Ile Ile Leu Leu
    930             935             940

Leu Gly Lys Ala Leu Ser Val Val Trp Asp Arg His Leu Ser Ile Ser
945             950             955             960

Val Val Leu Lys Gln Thr Tyr Gln Glu Lys Val Cys Gly Leu Cys Gly
            965             970             975

Asn Phe Asp Gly Ile Gln Asn Asn Asp Leu Thr Ser Ser Asn Leu Gln
            980             985             990

Val Glu Glu Asp Pro Val Asp Phe  Gly Asn Ser Trp Lys  Val Ser Ser
            995             1000            1005

Gln Cys  Ala Asp Thr Arg Lys  Val Pro Leu Asp Ser  Ser Pro Ala
    1010            1015            1020

Thr Cys  His Asn Asn Ile Met  Lys Gln Thr Met Val  Asp Ser Ser
    1025            1030            1035

Cys Arg  Ile Leu Thr Ser Asp  Val Phe Gln Asp Cys  Asn Lys Leu
    1040            1045            1050
```

-continued

```
Val Asp Pro Glu Pro Tyr Leu Asp Val Cys Ile Tyr Asp Thr Cys
1055              1060              1065

Ser Cys Glu Ser Ile Gly Asp Cys Ala Cys Phe Cys Asp Thr Ile
1070              1075              1080

Ala Ala Tyr Ala His Val Cys Ala Gln His Gly Lys Val Val Thr
1085              1090              1095

Trp Arg Thr Ala Thr Leu Cys Pro Gln Ser Cys Glu Glu Arg Asn
1100              1105              1110

Leu Arg Glu Asn Gly Tyr Glu Cys Glu Trp Arg Tyr Asn Ser Cys
1115              1120              1125

Ala Pro Ala Cys Gln Val Thr Cys Gln His Pro Glu Pro Leu Ala
1130              1135              1140

Cys Pro Val Gln Cys Val Glu Gly Cys His Ala His Cys Pro Pro
1145              1150              1155

Gly Lys Ile Leu Asp Glu Leu Leu Gln Thr Cys Val Asp Pro Glu
1160              1165              1170

Asp Cys Pro Val Cys Glu Val Ala Gly Arg Arg Phe Ala Ser Gly
1175              1180              1185

Lys Lys Val Thr Leu Asn Pro Ser Asp Pro Glu His Cys Gln Ile
1190              1195              1200

Cys His Cys Asp Val Val Asn Leu Thr Cys Glu Ala Cys Gln Glu
1205              1210              1215

Pro Gly Gly Leu Val Val Pro Pro Thr Asp Ala Pro Val Ser Pro
1220              1225              1230

Thr Thr Leu Tyr Val Glu Asp Ile Ser Glu Pro Pro Leu His Asp
1235              1240              1245

Phe Tyr Cys Ser Arg Leu Leu Asp Leu Val Phe Leu Leu Asp Gly
1250              1255              1260

Ser Ser Arg Leu Ser Glu Ala Glu Phe Glu Val Leu Lys Ala Phe
1265              1270              1275

Val Val Asp Met Met Glu Arg Leu Arg Ile Ser Gln Lys Trp Val
1280              1285              1290

Arg Val Ala Val Val Glu Tyr His Asp Gly Ser His Ala Tyr Ile
1295              1300              1305

Gly Leu Lys Asp Arg Lys Arg Pro Ser Glu Leu Arg Arg Ile Ala
1310              1315              1320

Ser Gln Val Lys Tyr Ala Gly Ser Gln Val Ala Ser Thr Ser Glu
1325              1330              1335

Val Leu Lys Tyr Thr Leu Phe Gln Ile Phe Ser Lys Ile Asp Arg
1340              1345              1350

Pro Glu Ala Ser Arg Ile Thr Leu Leu Leu Met Ala Ser Gln Glu
1355              1360              1365

Pro Gln Arg Met Ser Arg Asn Phe Val Arg Tyr Val Gln Gly Leu
1370              1375              1380

Lys Lys Lys Lys Val Ile Val Ile Pro Val Gly Ile Gly Pro His
1385              1390              1395

Ala Asn Leu Lys Gln Ile Arg Leu Ile Glu Lys Gln Ala Pro Glu
1400              1405              1410

Asn Lys Ala Phe Val Leu Ser Ser Val Asp Glu Leu Glu Gln Gln
1415              1420              1425

Arg Asp Glu Ile Val Ser Tyr Leu Cys Asp Leu Ala Pro Glu Ala
1430              1435              1440
```

-continued

```
Pro Pro  Pro Thr Leu Pro Pro  Asp Met Ala Gln Val  Thr Val Gly
    1445             1450             1455

Pro Gly  Leu Leu Gly Val Ser  Thr Leu Gly Pro Lys  Arg Asn Ser
    1460             1465             1470

Met Val  Leu Asp Val Ala Phe  Val Leu Glu Gly Ser  Asp Lys Ile
    1475             1480             1485

Gly Glu  Ala Asp Phe Asn Arg  Ser Lys Glu Phe Met  Glu Glu Val
    1490             1495             1500

Ile Gln  Arg Met Asp Val Gly  Gln Asp Ser Ile His  Val Thr Val
    1505             1510             1515

Leu Gln  Tyr Ser Tyr Met Val  Thr Val Glu Tyr Pro  Phe Ser Glu
    1520             1525             1530

Ala Gln  Ser Lys Gly Asp Ile  Leu Gln Arg Val Arg  Glu Ile Arg
    1535             1540             1545

Tyr Gln  Gly Gly Asn Arg Thr  Asn Thr Gly Leu Ala  Leu Arg Tyr
    1550             1555             1560

Leu Ser  Asp His Ser Phe Leu  Val Ser Gln Gly Asp  Arg Glu Gln
    1565             1570             1575

Ala Pro  Asn Leu Val Tyr Met  Val Thr Gly Asn Pro  Ala Ser Asp
    1580             1585             1590

Glu Ile  Lys Arg Leu Pro Gly  Asp Ile Gln Val Val  Pro Ile Gly
    1595             1600             1605

Val Gly  Pro Asn Ala Asn Val  Gln Glu Leu Glu Arg  Ile Gly Trp
    1610             1615             1620

Pro Asn  Ala Pro Ile Leu Ile  Gln Asp Phe Glu Thr  Leu Pro Arg
    1625             1630             1635

Glu Ala  Pro Asp Leu Val Leu  Gln Arg Cys Cys Ser  Gly Glu Gly
    1640             1645             1650

Leu Gln  Ile Pro Thr Leu Ser  Pro Ala Pro Asp Cys  Ser Gln Pro
    1655             1660             1665

Leu Asp  Val Ile Leu Leu Leu  Asp Gly Ser Ser Ser  Phe Pro Ala
    1670             1675             1680

Ser Tyr  Phe Asp Glu Met Lys  Ser Phe Ala Lys Ala  Phe Ile Ser
    1685             1690             1695

Lys Ala  Asn Ile Gly Pro Arg  Leu Thr Gln Val Ser  Val Leu Gln
    1700             1705             1710

Tyr Gly  Ser Ile Thr Thr Ile  Asp Val Pro Trp Asn  Val Val Pro
    1715             1720             1725

Glu Lys  Ala His Leu Leu Ser  Leu Val Asp Val Met  Gln Arg Glu
    1730             1735             1740

Gly Gly  Pro Ser Gln Ile Gly  Asp Ala Leu Gly Phe  Ala Val Arg
    1745             1750             1755

Tyr Leu  Thr Ser Glu Met His  Gly Ala Arg Pro Gly  Ala Ser Lys
    1760             1765             1770

Ala Val  Val Ile Leu Val Thr  Asp Val Ser Val Asp  Ser Val Asp
    1775             1780             1785

Ala Ala  Ala Asp Ala Ala Arg  Ser Asn Arg Val Thr  Val Phe Pro
    1790             1795             1800

Ile Gly  Ile Gly Asp Arg Tyr  Asp Ala Ala Gln Leu  Arg Ile Leu
    1805             1810             1815

Ala Gly  Pro Ala Gly Asp Ser  Asn Val Val Lys Leu  Gln Arg Ile
    1820             1825             1830

Glu Asp  Leu Pro Thr Met Val  Thr Leu Gly Asn Ser  Phe Leu His
```

-continued

```
          1835                 1840                 1845

Lys Leu  Cys Ser Gly Phe Val  Arg Ile Cys Met Asp  Glu Asp Gly
    1850                 1855                 1860

Asn Glu  Lys Arg Pro Gly Asp  Val Trp Thr Leu Pro  Asp Gln Cys
    1865                 1870                 1875

His Thr  Val Thr Cys Gln Pro  Asp Gly Gln Thr Leu  Leu Lys Ser
    1880                 1885                 1890

His Arg  Val Asn Cys Asp Arg  Gly Leu Arg Pro Ser  Cys Pro Asn
    1895                 1900                 1905

Ser Gln  Ser Pro Val Lys Val  Glu Glu Thr Cys Gly  Cys Arg Trp
    1910                 1915                 1920

Thr Cys  Pro Cys Val Cys Thr  Gly Ser Ser Thr Arg  His Ile Val
    1925                 1930                 1935

Thr Phe  Asp Gly Gln Asn Phe  Lys Leu Thr Gly Ser  Cys Ser Tyr
    1940                 1945                 1950

Val Leu  Phe Gln Asn Lys Glu  Gln Asp Leu Glu Val  Ile Leu His
    1955                 1960                 1965

Asn Gly  Ala Cys Ser Pro Gly  Ala Arg Gln Gly Cys  Met Lys Ser
    1970                 1975                 1980

Ile Glu  Val Lys His Ser Ala  Leu Ser Val Glu Leu  His Ser Asp
    1985                 1990                 1995

Met Glu  Val Thr Val Asn Gly  Arg Leu Val Ser Val  Pro Tyr Val
    2000                 2005                 2010

Gly Gly  Asn Met Glu Val Asn  Val Tyr Gly Ala Ile  Met His Glu
    2015                 2020                 2025

Val Arg  Phe Asn His Leu Gly  His Ile Phe Thr Phe  Thr Pro Gln
    2030                 2035                 2040

Asn Asn  Glu Phe Gln Leu Gln  Leu Ser Pro Lys Thr  Phe Ala Ser
    2045                 2050                 2055

Lys Thr  Tyr Gly Leu Cys Gly  Ile Cys Asp Glu Asn  Gly Ala Asn
    2060                 2065                 2070

Asp Phe  Met Leu Arg Asp Gly  Thr Val Thr Thr Asp  Trp Lys Thr
    2075                 2080                 2085

Leu Val  Gln Glu Trp Thr Val  Gln Arg Pro Gly Gln  Thr Cys Gln
    2090                 2095                 2100

Pro Glu  Gln Cys Leu Val Pro  Asp Ser Ser His Cys  Gln Val Leu
    2105                 2110                 2115

Leu Leu  Pro Leu Phe Ala Glu  Cys His Lys Val Leu  Ala Pro Ala
    2120                 2125                 2130

Thr Phe  Tyr Ala Ile Cys Gln  Gln Asp Ser Cys His  Gln Glu Gln
    2135                 2140                 2145

Val Cys  Glu Val Ile Ala Ser  Tyr Ala His Leu Cys  Arg Thr Asn
    2150                 2155                 2160

Gly Val  Cys Val Asp Trp Arg  Thr Pro Asp Phe Cys  Ala Met Ser
    2165                 2170                 2175

Cys Pro  Pro Ser Leu Val Tyr  Asn His Cys Glu His  Gly Cys Pro
    2180                 2185                 2190

Arg His  Cys Asp Gly Asn Val  Ser Ser Cys Gly Asp  His Pro Ser
    2195                 2200                 2205

Glu Gly  Cys Phe Cys Pro Pro  Asp Lys Val Met Leu  Glu Gly Ser
    2210                 2215                 2220

Cys Val  Pro Glu Glu Ala Cys  Thr Gln Cys Ile Gly  Glu Asp Gly
    2225                 2230                 2235
```

Val Gln His Gln Phe Leu Glu Ala Trp Val Pro Asp His Gln Pro
2240              2245              2250

Cys Gln Ile Cys Thr Cys Leu Ser Gly Arg Lys Val Asn Cys Thr
2255              2260              2265

Thr Gln Pro Cys Pro Thr Ala Lys Ala Pro Thr Cys Gly Leu Cys
2270              2275              2280

Glu Val Ala Arg Leu Arg Gln Asn Ala Asp Gln Cys Cys Pro Glu
2285              2290              2295

Tyr Glu Cys Val Cys Asp Pro Val Ser Cys Asp Leu Pro Pro Val
2300              2305              2310

Pro His Cys Glu Arg Gly Leu Gln Pro Thr Leu Thr Asn Pro Gly
2315              2320              2325

Glu Cys Arg Pro Asn Phe Thr Cys Ala Cys Arg Lys Glu Glu Cys
2330              2335              2340

Lys Arg Val Ser Pro Pro Ser Cys Pro Pro His Arg Leu Pro Thr
2345              2350              2355

Leu Arg Lys Thr Gln Cys Cys Asp Glu Tyr Glu Cys Ala Cys Asn
2360              2365              2370

Cys Val Asn Ser Thr Val Ser Cys Pro Leu Gly Tyr Leu Ala Ser
2375              2380              2385

Thr Ala Thr Asn Asp Cys Gly Cys Thr Thr Thr Cys Leu Pro
2390              2395              2400

Asp Lys Val Cys Val His Arg Ser Thr Ile Tyr Pro Val Gly Gln
2405              2410              2415

Phe Trp Glu Glu Gly Cys Asp Val Cys Thr Cys Thr Asp Met Glu
2420              2425              2430

Asp Ala Val Met Gly Leu Arg Val Ala Gln Cys Ser Gln Lys Pro
2435              2440              2445

Cys Glu Asp Ser Cys Arg Ser Gly Phe Thr Tyr Val Leu His Glu
2450              2455              2460

Gly Glu Cys Cys Gly Arg Cys Leu Pro Ser Ala Cys Glu Val Val
2465              2470              2475

Thr Gly Ser Pro Arg Gly Asp Ser Gln Ser Ser Trp Lys Ser Val
2480              2485              2490

Gly Ser Gln Trp Glu Asn Pro Cys Leu Ile Asn Glu Cys Val Arg
2495              2500              2505

Val Lys Glu Glu Val Phe Ile Gln Gln Arg Asn Val Ser Cys Pro
2510              2515              2520

Gln Leu Glu Val Pro Val Cys Pro Ser Gly Phe Gln Leu Ser Cys
2525              2530              2535

Lys Thr Ser Ala Cys Cys Pro Ser Cys Arg Cys Glu Arg Met Glu
2540              2545              2550

Ala Cys Met Leu Asn Gly Thr Val Ile Gly Pro Gly Lys Thr Val
2555              2560              2565

Met Ile Asp Val Cys Thr Thr Cys Arg Cys Met Val Gln Val Gly
2570              2575              2580

Val Ile Ser Gly Phe Lys Leu Glu Cys Arg Lys Thr Thr Cys Asn
2585              2590              2595

Pro Cys Pro Leu Gly Tyr Lys Glu Glu Asn Asn Thr Gly Glu Cys
2600              2605              2610

Cys Gly Arg Cys Leu Pro Thr Ala Cys Thr Ile Gln Leu Arg Gly
2615              2620              2625

-continued

```
Gly Gln  Ile Met Thr Leu Lys  Arg Asp Glu Thr Leu  Gln Asp Gly
    2630                2635                2640

Cys Asp  Thr His Phe Cys Lys  Val Asn Glu Arg Gly  Glu Tyr Phe
    2645                2650                2655

Trp Glu  Lys Arg Val Thr Gly  Cys Pro Pro Phe Asp  Glu His Lys
    2660                2665                2670

Cys Leu  Ala Glu Gly Gly Lys  Ile Met Lys Ile Pro  Gly Thr Cys
    2675                2680                2685

Cys Asp  Thr Cys Glu Glu Pro  Glu Cys Asn Asp Ile  Thr Ala Arg
    2690                2695                2700

Leu Gln  Tyr Val Lys Val Gly  Ser Cys Lys Ser Glu  Val Glu Val
    2705                2710                2715

Asp Ile  His Tyr Cys Gln Gly  Lys Cys Ala Ser Lys  Ala Met Tyr
    2720                2725                2730

Ser Ile  Asp Ile Asn Asp Val  Gln Asp Gln Cys Ser  Cys Cys Ser
    2735                2740                2745

Pro Thr  Arg Thr Glu Pro Met  Gln His Cys Thr Asn  Gly Ser Val
    2750                2755                2760

Val Tyr  His Glu Val Leu Asn  Ala Met Glu Cys Lys  Cys Ser Pro
    2765                2770                2775

Arg Lys  Cys Ser Lys
    2780

<210> SEQ ID NO 3
<211> LENGTH: 2050
<212> TYPE: PRT
<213> ORGANISM: Artificial Sequence
<220> FEATURE:
<223> OTHER INFORMATION: mature-VWF

<400> SEQUENCE: 3

Ser Leu Ser Cys Arg Pro Pro Met Val Lys Leu Val Cys Pro Ala Asp
1               5               10              15

Asn Leu Arg Ala Glu Gly Leu Glu Cys Thr Lys Thr Cys Gln Asn Tyr
            20              25              30

Asp Leu Glu Cys Met Ser Met Gly Cys Val Ser Gly Cys Leu Cys Pro
        35              40              45

Pro Gly Met Val Arg His Glu Asn Arg Cys Val Ala Leu Glu Arg Cys
    50              55              60

Pro Cys Phe His Gln Gly Lys Glu Tyr Ala Pro Gly Glu Thr Val Lys
65              70              75              80

Ile Gly Cys Asn Thr Cys Val Cys Arg Asp Arg Lys Trp Asn Cys Thr
            85              90              95

Asp His Val Cys Asp Ala Thr Cys Ser Thr Ile Gly Met Ala His Tyr
            100             105             110

Leu Thr Phe Asp Gly Leu Lys Tyr Leu Phe Pro Gly Glu Cys Gln Tyr
        115             120             125

Val Leu Val Gln Asp Tyr Cys Gly Ser Asn Pro Gly Thr Phe Arg Ile
    130             135             140

Leu Val Gly Asn Lys Gly Cys Ser His Pro Ser Val Lys Cys Lys Lys
145             150             155             160

Arg Val Thr Ile Leu Val Glu Gly Gly Glu Ile Glu Leu Phe Asp Gly
            165             170             175

Glu Val Asn Val Lys Arg Pro Met Lys Asp Glu Thr His Phe Glu Val
            180             185             190
```

```
Val Glu Ser Gly Arg Tyr Ile Ile Leu Leu Leu Gly Lys Ala Leu Ser
    195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
    275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
    355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
    435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
                500                 505                 510

Leu Asp Leu Val Phe Leu Leu Asp Gly Ser Ser Arg Leu Ser Glu Ala
    515                 520                 525

Glu Phe Glu Val Leu Lys Ala Phe Val Val Asp Met Met Glu Arg Leu
    530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
                580                 585                 590

Ser Thr Ser Glu Val Leu Lys Tyr Thr Leu Phe Gln Ile Phe Ser Lys
    595                 600                 605

Ile Asp Arg Pro Glu Ala Ser Arg Ile Thr Leu Leu Leu Met Ala Ser
```

```
          610                 615                 620

Gln Glu Pro Gln Arg Met Ser Arg Asn Phe Val Arg Tyr Val Gln Gly
625                 630                 635                 640

Leu Lys Lys Lys Lys Val Ile Val Ile Pro Val Gly Ile Gly Pro His
                    645                 650                 655

Ala Asn Leu Lys Gln Ile Arg Leu Ile Glu Lys Gln Ala Pro Glu Asn
                    660                 665                 670

Lys Ala Phe Val Leu Ser Ser Val Asp Glu Leu Glu Gln Gln Arg Asp
                    675                 680                 685

Glu Ile Val Ser Tyr Leu Cys Asp Leu Ala Pro Glu Ala Pro Pro Pro
                    690                 695                 700

Thr Leu Pro Pro Asp Met Ala Gln Val Thr Val Gly Pro Gly Leu Leu
705                 710                 715                 720

Gly Val Ser Thr Leu Gly Pro Lys Arg Asn Ser Met Val Leu Asp Val
                    725                 730                 735

Ala Phe Val Leu Glu Gly Ser Asp Lys Ile Gly Glu Ala Asp Phe Asn
                    740                 745                 750

Arg Ser Lys Glu Phe Met Glu Glu Val Ile Gln Arg Met Asp Val Gly
                    755                 760                 765

Gln Asp Ser Ile His Val Thr Val Leu Gln Tyr Ser Tyr Met Val Thr
                    770                 775                 780

Val Glu Tyr Pro Phe Ser Glu Ala Gln Ser Lys Gly Asp Ile Leu Gln
785                 790                 795                 800

Arg Val Arg Glu Ile Arg Tyr Gln Gly Gly Asn Arg Thr Asn Thr Gly
                    805                 810                 815

Leu Ala Leu Arg Tyr Leu Ser Asp His Ser Phe Leu Val Ser Gln Gly
                    820                 825                 830

Asp Arg Glu Gln Ala Pro Asn Leu Val Tyr Met Val Thr Gly Asn Pro
                    835                 840                 845

Ala Ser Asp Glu Ile Lys Arg Leu Pro Gly Asp Ile Gln Val Val Pro
                    850                 855                 860

Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                    885                 890                 895

Glu Ala Pro Asp Leu Val Leu Gln Arg Cys Cys Ser Gly Glu Gly Leu
                    900                 905                 910

Gln Ile Pro Thr Leu Ser Pro Ala Pro Asp Cys Ser Gln Pro Leu Asp
                    915                 920                 925

Val Ile Leu Leu Leu Asp Gly Ser Ser Ser Phe Pro Ala Ser Tyr Phe
                    930                 935                 940

Asp Glu Met Lys Ser Phe Ala Lys Ala Phe Ile Ser Lys Ala Asn Ile
945                 950                 955                 960

Gly Pro Arg Leu Thr Gln Val Ser Val Leu Gln Tyr Gly Ser Ile Thr
                    965                 970                 975

Thr Ile Asp Val Pro Trp Asn Val Val Pro Glu Lys Ala His Leu Leu
                    980                 985                 990

Ser Leu Val Asp Val Met Gln Arg Glu Gly Gly Pro Ser Gln Ile Gly
                    995                 1000                1005

Asp Ala  Leu Gly Phe Ala Val Arg Tyr Leu Thr  Ser Glu Met His
     1010                1015                1020

Gly Ala  Arg Pro Gly Ala Ser  Lys Ala Val Val Ile  Leu Val Thr
     1025                1030                1035
```

-continued

```
Asp Val Ser Val Asp Ser Val Asp Ala Ala Ala Asp Ala Ala Arg
    1040            1045            1050

Ser Asn Arg Val Thr Val Phe Pro Ile Gly Ile Gly Asp Arg Tyr
    1055            1060            1065

Asp Ala Ala Gln Leu Arg Ile Leu Ala Gly Pro Ala Gly Asp Ser
    1070            1075            1080

Asn Val Val Lys Leu Gln Arg Ile Glu Asp Leu Pro Thr Met Val
    1085            1090            1095

Thr Leu Gly Asn Ser Phe Leu His Lys Leu Cys Ser Gly Phe Val
    1100            1105            1110

Arg Ile Cys Met Asp Glu Asp Gly Asn Glu Lys Arg Pro Gly Asp
    1115            1120            1125

Val Trp Thr Leu Pro Asp Gln Cys His Thr Val Thr Cys Gln Pro
    1130            1135            1140

Asp Gly Gln Thr Leu Leu Lys Ser His Arg Val Asn Cys Asp Arg
    1145            1150            1155

Gly Leu Arg Pro Ser Cys Pro Asn Ser Gln Ser Pro Val Lys Val
    1160            1165            1170

Glu Glu Thr Cys Gly Cys Arg Trp Thr Cys Pro Cys Val Cys Thr
    1175            1180            1185

Gly Ser Ser Thr Arg His Ile Val Thr Phe Asp Gly Gln Asn Phe
    1190            1195            1200

Lys Leu Thr Gly Ser Cys Ser Tyr Val Leu Phe Gln Asn Lys Glu
    1205            1210            1215

Gln Asp Leu Glu Val Ile Leu His Asn Gly Ala Cys Ser Pro Gly
    1220            1225            1230

Ala Arg Gln Gly Cys Met Lys Ser Ile Glu Val Lys His Ser Ala
    1235            1240            1245

Leu Ser Val Glu Leu His Ser Asp Met Glu Val Thr Val Asn Gly
    1250            1255            1260

Arg Leu Val Ser Val Pro Tyr Val Gly Gly Asn Met Glu Val Asn
    1265            1270            1275

Val Tyr Gly Ala Ile Met His Glu Val Arg Phe Asn His Leu Gly
    1280            1285            1290

His Ile Phe Thr Phe Thr Pro Gln Asn Asn Glu Phe Gln Leu Gln
    1295            1300            1305

Leu Ser Pro Lys Thr Phe Ala Ser Lys Thr Tyr Gly Leu Cys Gly
    1310            1315            1320

Ile Cys Asp Glu Asn Gly Ala Asn Asp Phe Met Leu Arg Asp Gly
    1325            1330            1335

Thr Val Thr Thr Asp Trp Lys Thr Leu Val Gln Glu Trp Thr Val
    1340            1345            1350

Gln Arg Pro Gly Gln Thr Cys Gln Pro Ile Leu Glu Glu Gln Cys
    1355            1360            1365

Leu Val Pro Asp Ser Ser His Cys Gln Val Leu Leu Leu Pro Leu
    1370            1375            1380

Phe Ala Glu Cys His Lys Val Leu Ala Pro Ala Thr Phe Tyr Ala
    1385            1390            1395

Ile Cys Gln Gln Asp Ser Cys His Gln Glu Gln Val Cys Glu Val
    1400            1405            1410

Ile Ala Ser Tyr Ala His Leu Cys Arg Thr Asn Gly Val Cys Val
    1415            1420            1425
```

-continued

```
Asp Trp  Arg Thr Pro Asp Phe  Cys Ala Met Ser Cys  Pro Pro Ser
    1430             1435              1440

Leu Val  Tyr Asn His Cys Glu  His Gly Cys Pro Arg  His Cys Asp
    1445             1450              1455

Gly Asn  Val Ser Ser Cys Gly  Asp His Pro Ser Glu  Gly Cys Phe
    1460             1465              1470

Cys Pro  Pro Asp Lys Val Met  Leu Glu Gly Ser Cys  Val Pro Glu
    1475             1480              1485

Glu Ala  Cys Thr Gln Cys Ile  Gly Glu Asp Gly Val  Gln His Gln
    1490             1495              1500

Phe Leu  Glu Ala Trp Val Pro  Asp His Gln Pro Cys  Gln Ile Cys
    1505             1510              1515

Thr Cys  Leu Ser Gly Arg Lys  Val Asn Cys Thr Thr  Gln Pro Cys
    1520             1525              1530

Pro Thr  Ala Lys Ala Pro Thr  Cys Gly Leu Cys Glu  Val Ala Arg
    1535             1540              1545

Leu Arg  Gln Asn Ala Asp Gln  Cys Cys Pro Glu Tyr  Glu Cys Val
    1550             1555              1560

Cys Asp  Pro Val Ser Cys Asp  Leu Pro Pro Val Pro  His Cys Glu
    1565             1570              1575

Arg Gly  Leu Gln Pro Thr Leu  Thr Asn Pro Gly Glu  Cys Arg Pro
    1580             1585              1590

Asn Phe  Thr Cys Ala Cys Arg  Lys Glu Glu Cys Lys  Arg Val Ser
    1595             1600              1605

Pro Pro  Ser Cys Pro Pro His  Arg Leu Pro Thr Leu  Arg Lys Thr
    1610             1615              1620

Gln Cys  Cys Asp Glu Tyr Glu  Cys Ala Cys Asn Cys  Val Asn Ser
    1625             1630              1635

Thr Val  Ser Cys Pro Leu Gly  Tyr Leu Ala Ser Thr  Ala Thr Asn
    1640             1645              1650

Asp Cys  Gly Cys Thr Thr Thr  Thr Cys Leu Pro Asp  Lys Val Cys
    1655             1660              1665

Val His  Arg Ser Thr Ile Tyr  Pro Val Gly Gln Phe  Trp Glu Glu
    1670             1675              1680

Gly Cys  Asp Val Cys Thr Cys  Thr Asp Met Glu Asp  Ala Val Met
    1685             1690              1695

Gly Leu  Arg Val Ala Gln Cys  Ser Gln Lys Pro Cys  Glu Asp Ser
    1700             1705              1710

Cys Arg  Ser Gly Phe Thr Tyr  Val Leu His Glu Gly  Glu Cys Cys
    1715             1720              1725

Gly Arg  Cys Leu Pro Ser Ala  Cys Glu Val Val Thr  Gly Ser Pro
    1730             1735              1740

Arg Gly  Asp Ser Gln Ser Ser  Trp Lys Ser Val Gly  Ser Gln Trp
    1745             1750              1755

Ala Ser  Pro Glu Asn Pro Cys  Leu Ile Asn Glu Cys  Val Arg Val
    1760             1765              1770

Lys Glu  Glu Val Phe Ile Gln  Gln Arg Asn Val Ser  Cys Pro Gln
    1775             1780              1785

Leu Glu  Val Pro Val Cys Pro  Ser Gly Phe Gln Leu  Ser Cys Lys
    1790             1795              1800

Thr Ser  Ala Cys Cys Pro Ser  Cys Arg Cys Glu Arg  Met Glu Ala
    1805             1810              1815

Cys Met  Leu Asn Gly Thr Val  Ile Gly Pro Gly Lys  Thr Val Met
```

-continued

```
        1820            1825            1830

Ile Asp Val Cys Thr Thr Cys  Arg Cys Met Val Gln  Val Gly Val
    1835            1840            1845

Ile Ser Gly Phe Lys Leu Glu  Cys Arg Lys Thr Thr  Cys Asn Pro
    1850            1855            1860

Cys Pro Leu Gly Tyr Lys Glu  Glu Asn Asn Thr Gly  Glu Cys Cys
    1865            1870            1875

Gly Arg Cys Leu Pro Thr Ala  Cys Thr Ile Gln Leu  Arg Gly Gly
    1880            1885            1890

Gln Ile Met Thr Leu Lys Arg  Asp Glu Thr Leu Gln  Asp Gly Cys
    1895            1900            1905

Asp Thr His Phe Cys Lys Val  Asn Glu Arg Gly Glu  Tyr Phe Trp
    1910            1915            1920

Glu Lys Arg Val Thr Gly Cys  Pro Pro Phe Asp Glu  His Lys Cys
    1925            1930            1935

Leu Ala Glu Gly Gly Lys Ile  Met Lys Ile Pro Gly  Thr Cys Cys
    1940            1945            1950

Asp Thr Cys Glu Glu Pro Glu  Cys Asn Asp Ile Thr  Ala Arg Leu
    1955            1960            1965

Gln Tyr Val Lys Val Gly Ser  Cys Lys Ser Glu Val  Glu Val Asp
    1970            1975            1980

Ile His Tyr Cys Gln Gly Lys  Cys Ala Ser Lys Ala  Met Tyr Ser
    1985            1990            1995

Ile Asp Ile Asn Asp Val Gln  Asp Gln Cys Ser Cys  Cys Ser Pro
    2000            2005            2010

Thr Arg Thr Glu Pro Met Gln  Val Ala Leu His Cys  Thr Asn Gly
    2015            2020            2025

Ser Val Val Tyr His Glu Val  Leu Asn Ala Met Glu  Cys Lys Cys
    2030            2035            2040

Ser Pro Arg Lys Cys Ser Lys
    2045            2050
```